US007442784B2

(12) United States Patent
Barbas, III et al.

(10) Patent No.: US 7,442,784 B2
(45) Date of Patent: *Oct. 28, 2008

(54) LIGAND ACTIVATED TRANSCRIPTIONAL REGULATOR PROTEINS

(75) Inventors: Carlos F. Barbas, III, Del Mar, CA (US); Michael Joseph Kadan, Adams Town, MD (US); Roger Beerli, San Diego, CA (US)

(73) Assignees: The Scripps Research Institute, La Jolla, CA (US); Novartis AG, Basel (CH)

( * ) Notice: Subject to any disclaimer, the term of this patent is extended or adjusted under 35 U.S.C. 154(b) by 656 days.

This patent is subject to a terminal disclaimer.

(21) Appl. No.: 10/422,934

(22) Filed: Apr. 23, 2003

(65) Prior Publication Data

US 2003/0186841 A1 Oct. 2, 2003

Related U.S. Application Data

(63) Continuation of application No. 09/586,625, filed on Jun. 2, 2000, which is a continuation-in-part of application No. 09/433,042, filed on Oct. 25, 1999, now abandoned.

(51) Int. Cl.

| | |
|---|---|
| ***C07H 21/04*** | (2006.01) |
| ***C12P 21/06*** | (2006.01) |
| ***C12P 21/04*** | (2006.01) |
| ***C12N 15/00*** | (2006.01) |
| ***C12N 5/00*** | (2006.01) |
| ***C12N 5/02*** | (2006.01) |

(52) U.S. Cl. .................... 536/23.4; 536/23.5; 536/24.1; 435/69.1; 435/69.7; 435/320.1; 435/325

(58) Field of Classification Search ....................... None
See application file for complete search history.

(56) References Cited

U.S. PATENT DOCUMENTS

| | | | | |
|---|---|---|---|---|
| 4,394,443 | A | 7/1983 | Weissman et al. | 435/6 |
| 4,446,235 | A | 5/1984 | Seeburg | 435/91 |
| 4,990,607 | A | 2/1991 | Katagiri et al. | 536/27 |
| 5,198,346 | A | 3/1993 | Ladner et al. | 435/69.1 |
| 5,217,867 | A | 6/1993 | Evans et al. | |
| 5,364,791 | A | 11/1994 | Vegeto et al. | 435/320.1 |
| 5,376,530 | A | 12/1994 | De The et al. | 435/6 |
| 5,578,483 | A | 11/1996 | Evans et al. | 435/240.2 |
| 5,789,538 | A | 8/1998 | Rebar et al. | 530/324 |
| 5,874,534 | A | 2/1999 | Vegeto et al. | 530/350 |
| 5,935,934 | A | 8/1999 | Vegeto et al. | 514/44 |
| 6,140,081 | A | 10/2000 | Barbas | 435/69.1 |
| 6,140,466 | A | 10/2000 | Barbas, III et al. | 530/350 |
| 6,242,568 | B1 | 6/2001 | Barbas, III et al. | 530/350 |
| 6,416,998 | B1 | 7/2002 | O'Malley et al. | 435/325 |
| 6,534,261 | B1 | 3/2003 | Cox, III et al. | 435/6 |
| 6,610,512 | B1 | 8/2003 | Barbas | 435/69.1 |
| 6,723,531 | B2 * | 4/2004 | Evans et al. | 435/69.1 |
| 6,790,941 | B2 | 9/2004 | Barbas, III et al. | 530/400 |
| 2002/0081614 | A1 | 6/2002 | Case et al. | 435/6 |
| 2002/0147327 | A1 | 10/2002 | O'Malley et al. | 536/23.5 |
| 2002/0165356 | A1 | 11/2002 | Barbas, III et al. | 530/350 |
| 2002/0168714 | A1 | 11/2002 | Barbas, III et al. | 435/69.1 |
| 2002/0182698 | A1 | 12/2002 | O'Malley et al. | 435/199 |
| 2003/0037355 | A1 | 2/2003 | Barbas, III et al. | 800/278 |
| 2003/0059767 | A1 | 3/2003 | Barbas, III et al. | 435/6 |
| 2003/0143559 | A1 | 7/2003 | Bracken et al. | 705/1 |
| 2004/0224385 | A1 | 11/2004 | Barbas et al. | 435/69.1 |
| 2005/0084885 | A1 | 4/2005 | Barbas, III et al. | 435/6 |
| 2005/0148075 | A1 | 7/2005 | Barbas | 435/455 |

FOREIGN PATENT DOCUMENTS

| | | | |
|---|---|---|---|
| EP | 0540065 | | 5/1993 |
| WO | 9323431 | | 11/1993 |
| WO | 9401548 | | 1/1994 |
| WO | 9519431 | | 7/1995 |
| WO | 9640911 | | 12/1996 |
| WO | 9818925 | | 5/1998 |
| WO | WO9818925 | * | 5/1998 |
| WO | 9854311 | | 12/1998 |
| WO | 9945132 | | 9/1999 |
| WO | 0023464 | | 5/2000 |
| WO | 0130843 | | 5/2001 |
| WO | 01/52620 | | 7/2001 |
| WO | 02/06463 | | 1/2002 |

(Continued)

OTHER PUBLICATIONS

Beerli et al 1998. PNAS. 95:14628-14633.*

(Continued)

*Primary Examiner*—Lorraine Spector
*Assistant Examiner*—Shulamith H Shafer
(74) *Attorney, Agent, or Firm*—Bell, Boyd & Lloyd LLP; Stephanie Seidman

(57) ABSTRACT

Fusion proteins for use as ligand-dependent transcriptional regulators are provided. The fusion proteins include a nucleotide binding domain operatively linked to a ligand-binding domain. They also can include a transcription regulating domain. The nucleotide binding domain is a zinc-finger peptide that binds to a targeted contiguous nucleotide sequence of from 3 to about 18 nucleotides are provided. The fusion proteins are used for gene therapy. Also provided are polynucleotides encoding the fusion proteins, expression vectors, and transfected cells.

34 Claims, 27 Drawing Sheets

FOREIGN PATENT DOCUMENTS

| | | |
|---|---|---|
| WO | WO 02/066640 | 8/2002 |
| WO | 02/097050 | 12/2002 |
| WO | WO 03/016496 | 2/2003 |
| WO | WO 03/066828 | 8/2003 |
| WO | WO 03/104414 | 12/2003 |

OTHER PUBLICATIONS

Robbins et al. 1998. Pharmacol. Ther. 80:35-47.*

Clackson 2000. Gene Therapy. 7:120-125.*

Kay et al., "Viral vectors for gene therapy: the art of turning infectious agents into vehicles of therapeutics," Nature Medicine 7(1):33-40, Jan. 2001.

Phillips, A. J., "The challenge of gene therapy and DNA delivery," Journal of Pharmacy and Pharmacology 53(9):1169-1174, May 2001.

Thomas et al., "Progress and problems with the use of viral vectors for gene therapy," Nature Reviews-Genetics 4:346-358, May 2003.

Eck, S.L. and J.M. Wilson, "Gene-based Therapy," Chapter 5 in *Goodman and Gilson's: The Pharmacological Basis of Therapeutics*, 9th Edition, New York: McGraw-Hill, pp. 77-101 (1996).

Mikayama et al., "Molecular cloning and functional expression of a cDNA encoding glycosylation-inhibiting factor," Proc. Natl. Acad. Sci. USA 90: 10056-10060 (1993).

Voet, D. and J.G Voet, *Biochemistry*, New York: John Wiley & Sons, pp. 126-128 and 228-234 (1990).

Alwin et al., "Custom zinc-finger nucleases for use in human cells," Mol. Ther. 12(4): 610-617 (2005).

Beerli, R.R.and C.F. Barbas III, "Engineering polydactyl zinc-finger transcription factors," Nature Biotechnology 20(2): 135-41 (2002).

Blancafort et al., "Designing transcription factor architectures for drug discovery," Mol. Pharmacol. 66(6): 1361-71 (2004).

Blancafort et al., "Genetic reprogramming of tumor cells by zinc finger transcription factors," Proc. Natl. Acad. Sci. USA 102(33): 11716-21 (2005).

Blancafort et al., "Scanning the human genome with combinatorial transcription factor libraries," Nature Biotechnol. 31(3):269-274 (2003).

Blau et al., "γ-globin gene expression in CID-dependent multi-potential cells established from beta-YAC transgenic mice," J. Biol. Chem. Aug. 30, 2005.

Dreier et al., "Development of zinc finger domains for recognition of the 5'-ANN-3' family of DNA sequences and their use in the construction of artificial transcription factors," J. Biol. Chem. 276(31): 29466-78 (2001).

Dreier et al., "Development of zinc finger domains for recognition of the 5'-CNN-3' family DNA sequences and their use in the construction of artificial transcription factors," J. Biol. Chem. 280(42):35588-35597 (2005).

Graslund et al., "Exploring strategies for the design of artificial transcription factors: targeting sites proximal to known regulatory regions for the induction of γ-globin expression and the treatment of sickle cell disease," J. Biol. Chem. 280(5): 3707-14 (2005).

Guan et al., "Heritable endogenous gene regulation in plants with designed polydactyl zinc finger transcription factors," Proc. Natl. Acad. Sci. USA 99(20): 13296-301 (2002).

Lin et al., "Small-molecule switches for zinc finger transcription factors," J. Am Chem. Soc. 125(3):612-3 (2003).

Lund et al., "Promoter-targeted phage display selections with preassembled synthetic zinc finger libraries for endogenous gene regulation," J. Mol. Biol. 340(3): 599-613 (2004).

Lund et al., "Zinc Finger Transcription Factors Designed for Bispecific Coregulation of ErB2 and ErbB3 Receptors: Insights into ErbB Receptor Biology," Mol. Cell. Biol. 25(20): 9082-91 (2005).

Magnenat et al., "In vivo selection of combinatorial libraries and designed affinity maturation of polydactyl zinc finger transcription factors for ICAM-1 provides new insights into gene regulation," J. Mol. Biol. 341(3): 635-49 (2004).

Ordiz et al., "Regulation of transgene expression in plants with polydactyl zinc finger transcription factors," Proc. Natl. Acad. Sci. USA 99(20): 13290-5 (2002).

Segal et al., "Custom DNA-binding proteins come of age: polydactyl zinc-finger proteins," Curr. Opin. Biotechnol. 12(6): 632-7 (2001).

Segal et al., "Evaluation of a modular strategy for the construction of novel polydactyl zinc finger DNA-binding proteins," Biochemistry 42(7): 2137-2148 (2003).

Segal et al., "Attenuation of HIV-1 replication in primary human cells with a designed zinc finger transcription factor," J. Biol. Chem. 279(15): 14509-19 (2004).

Segal et all., "Zinc fingers and a green thumb: manipulating gene expression in plants," Curr. Opin. Plant Biol. 6(2): 163-8 (2003).

Stege et al., "Controlling gene expression in plants using synthetic zinc finger transcription factors," Plant J. 32(6): 1077-86 (2002).

Tan et al. , "Fusion proteins consisting of human immunodeficiency virus type 1 integrase and the designed polydactyl zinc finger protein E2C direct integration of viral DNA into specific sites," J. Virol. 78(3): 1301-13 (2004).

Xu et al., "A versatile framework for the design of ligand-dependent, transgene-specific transcription factors," Mol. Ther. 3(2): 262-73 (2001).

Agarwal et al. Stimulation of Transcript Elongation Requires both the Zinc Fingers and RNA Polymerase II Binding Domains of Human TFIIS, *Biochemistry* 30:7842-51 (1991).

Altschul et al., Basic Local Alignment Search Tool, *J. Mol. Biol.* 215:403-410 (1990).

Aumais et al., elective Interaction of hsp90 with an Estrogen Receptor Ligand-binding Domain Containing a Point Mutation, *J. Biol. Chem.* 272(18):12229-35 (1997).

Ayer et al., Mad Proteins Contain a Dominant Transcription Repression Domain, *Mol. Cell. Biol.* 16(10):5772-5781 (1996).

Barbas et al., From Catalytic Asymmetric Synthesis to the Transcriptioanl Regulation of Genes: In Vivo and In Vitro Evolution of Proteins, *Adv. Protein Chem.* 55:317-66 (2000).

Barbas et al., Semisynthetic combinatorial antibody libraries: A chemical solution to the diversity problem, *TITLE????*89:4457-61 (1992). PNAS.

Barbas et al., Assembly of combinatorial antibody libraries on phage surfaces: The gene III site, *Proc. Natl. Acad. Sci. USA*, 88:7978-82 (1991).

Barbas et al., Combinatorial Immunoglobulin Libraries on the Surface of Phage (Phabs): Rapid Selection of Antigen-Specific Fabs, *Methods* 2:119-24 (1991).

Baron et al., Tetracycline-controlled transcription in eukaryotes: novel transactivators with graded transactivation potential, *Nucl. Acids. Res.* 25(14):2723-9 (1997).

Beerli et al., Positive and Negative Regulation of Endogenous Genes by Designed Transcription Factors, *Proc. Natl. Acad. Sci. USA* 97(4):1495-500 (2000).

Beerli et al., Chemically Regulated Zinc Finger Transcription Factors, *J. Biol. Chem.* 275(42):32617-27 (2000).

Beerli et al., Chemically Regulated Zinc Finger Transcription Factors, Journal of Biological Chemistry Papers in Press. Live on the JBC's website on Aug. 2, 2000 as Manuscript MO05108200.

Beerli et al., Toward controlling gene expression at will: Specific regulation of *erbB-2/HER-2* promoter by using polydactyl zinc finger proteins constructed from modular building blocks, *Proc. Natl. Acad. Sci. USA* 95:14628-33 (1998).

Bergqvist et al. Loss of DNA-binding and new transcriptional *trans*-activation function in polyomavirus large T-antigen with mutation of zinc finger motif, *Nucl. Acids Res.* 18(9):2715-20 (1990).

Better et al., *Esherichia coli* Secretion of an Active Chimeric Antibody Fragment, *Science* 240:1041-3 (1988).

Burcin et al., Adenovirus-mediated regulable target gene expression *in vivo*, *Proc. Natl. Acad. Sci. USA* 96:355-60 (1999).

Carrillo, et al., The Multiple Sequence Alignment Problem in Biology, *SIAM J Applied Math* 48(5):1073 (1988).

Choo et al., Toward a code for the interaction of zinc fingers with DNA: Selection of randomized fingers displayed on phage, *Proc. Natl. Acad. Sci. USA* 91:11163-7 (1994).

Corsaro et al., Enhancing the Efficiency of DNA-Mediated Gene Transfer in Mammalian Cells, *Somatic Cell Genetics* 7(5):603-616 (1981).

Danielian et al., Identification of Residues in the Estrogen Receptor That Confer Differential Sensitivity to Estrogen and Hydroxytamoxifen, *Mol. Endocrinol*. 7:234-40 (1993).
Debs et al. Regulation of Gene Expression *in Vivo* by Lipsome-mediated Delivery of a Purified Transcription Factor, *J. Biol. Chem.* 265(18):10189-92 (1990).
Desjarlais, et al., Use of zinc-finger consensus framework and specificity rules to design specific DNA binding proteins, *Proc. Natl. Acad. Sci. USA* 90:2256-60 (1993).
Devereux et al., A comprehensive set of sequence analysis programs for the VAX, *Nucleic Acids Research* 129(1):387-395 (1984).
Drier et al., Insights into the Molecular Recognition of the 5'-GNN-3' Family of DNA Sequences by Zinc Finger Domains, *J. Mol. Biol.* 303(4):489-502 (2000).
Elrod-Erickson et al., High-resolution structures of variant Zif268-DNA complexes: implications for understanding zinc finger-DNA recognition, *Structure* 6:451-64 (1998).
Elrod-Erickson et al., Zif268 protein-DNA complex refined at 1.6 Angstroms: a model system for understanding zinc finger-DNA interactions, *Structure* 4:1171-80 (1996).
Fraley et al., New generation liposomes: the engineering of an efficient vehicle for intracellular delivery of nucleic acids, *Trends Biochem. Sci*. 6:77-80 (1981).
Friedman et al., Kap-1, a novel corepressor for the highly conserved KRAB repression domain, *Genes & Dev.* 10:2067-78 (1996).
Gorziglia et al., Elimination of both E1 and E2a from Adenovirus Vectors Further Improves Prospects for In Vivo Human Gene Therapy, *J. Virol*. 70(6):4173-78 (1996).
Gossen et al., Tight control of gene expression in mammalain cells by tetracycline-responsive promoters, *Proc. Natl. Acad. Sci. USA* 89:5547-51 (1992).
Greisman et al., A General Strategy for Selecting High-Affinity Zinc Finger Proteins for Diverse DNA Target Sites, *Science* 275:657-61 (1997).
Gribskov, et al., Sigma factors from *E. coli, B. subtilis*, phage SP01, and phage T4 are homologous proteins, *Nucl. Acids Res*. 14:6745-63 (1986).
Grignani et al. Formation of PML/RARα high molecular weight complexes through the PML coiled-coil region is essential for the PML/RARα-mediated retinoic acid response, *Oncogene* 18:6313-21 (1999).
Hall et al., Efficient sequence-specific cleavage of RNA using novel europium complexes conjugated to oligonucleotides, *Chemistry and Biology* 1:185-190 (1994).
He et al., A simplified system for generating recombinant adenoviruses, *Proc. Natl. Acad. Sci. USA* 95:2509-14 (1998).
Heinzel et al., A complex containing N-CoR, mSin3 and histone deacetylase mediates transcriptional repression, *Nature* 387:43-6 (1997).
Isalan et al., Comprehensive DNA Recognition through Concerted Interactions from Adjacent, *Biochemistry* 37:12026-33 (1998).
Ishii et al., Characterization of the promoter region of the human *c-erbB*-2 protooncogene, *Proc. Natl. Acad. Sci. USA* 84:4374-8 (1987).
Jacobs et al. Determination of the base recognition positions of zinc fingers from sequence analysis, *The EMBO Journal* 11(12):4507-17 (1992).
Jamieson et al., A zinc finger directory for high-affinity DNA recognition, *Proc. Natl. Acad. Sci. USA* 93:12834-9 (1996).
Jamieson et al., In Vitro Selection of Zinc Fingers with Altered DNA-Binding Specificity, *Biochemistry* 33:5689-95 (1994).
Jaye et al., Isolation of a human anti-haemophilic factor IX cDNA clone using a unique 52-base synthetic oligonucleotide probe deduced from the amino acids sequence of bovine factor IX, *Nucl. Acids. Res*. 11: 2325-35 (1983).
Julian et al. Replacement of His(23) by Cys in a zinc finger of HiV-1 NCp7 led to a change in 1H NMR-derived 3D structure and to a loss of biological activity, *FEBS* 331(1-2):43-8 (1993).
Kalderon et al. A Short Amino Acid Sequence Able to Specify Nuclear Location, *Cell* 39:499-509 (1984).
Lai et al., Conserved organization of the human and murine T-cell receptor β-gene families, *Nature* 331:543-6 (1988).
Landschulz et al. The Leucine Zipper: A Hypothetical Structure Common to a New Class of DNA Binding Proteins, *Science* 240:1759-64 (1988).
Littlewood et al., A modified oestrogen receptor ligand-binding domain as a improved switch for the regulation of heterologous proteins, *Nucl. Acids. Res*. 23: 1686-90 (1995).
Liu et al., Design of Polydactyl Zinc-finger Proteins for Unique Addressing within Complex Genomes, *Proc. Natl. Acad. Sci. USA* 94(11):5525-30 (1997).
Mack et al., Design and Chemical Synthesis of a Sequence-Specific DNA-Cleavage Protein, *J. Am. Chem. Soc*. 110:7572-4 (1988).
Maniatis et al., Molecular Cloning-A Laboratory Manual, *Cold Spring Harbor Laboratory* (1982), Table of Contents.
Mannino et al., Liposome Mediated Gene Transfer, *BioTechniques* 6(7):682-690 (1988).
Margolin et al., Kruppel-associated Boxes are Potent Transcriptional Repression Domains, *Proc. Natl. Acad. Sci USA* 91:4509-4513 (1994).
Mullinax et al., Identification of Human Antibody Fragment Clones Specific for Tetanus Toxoid in a Bacteriophage λ Immunoexpression Library, *Proc. Natl. Acad. Sci USA* 87:8095-8099 (1990).
Needleman and Wunsch, A General Method Applicable to the Search for Similarities in the Amino Acid Sequence of Two Proteins, *J. Mol. Biol*. 48:443-453 (1970).
O'Shea et al., X-Ray Structure of the GCN4 Leucine Zipper, a Two-Stranded, Parallel Coiled Coil, *Science* 254:539-544 (1991).
Pavletich and Pabo, Zinc Finger-DNA Recognition: Crystal Structure of a Zif268-DNA Complex at 2.1 A, *Science* 252:809-817 (1991).
Pearson and Lipman, Improved Tools for Biological Sequence Comparison, *Proc. Natl. Acad. Sci. USA* 85:2444-2448 (1988).
Penque and Lania, Kruppel-Associated Box-Mediated Repression of RNA Polymerase II Promoters is Influenced by the Arrangment of Basal Promoter Elements, *Proc. Natl. Acad. Sci. USA* 93:1015-1020 (1996).
Quigley et al. Complete Androgen Insensitivity Due to Deletion of Exon C of the Androgen Receptor Gene Highlights the Functional Importance of the Second zinc Finger of the Androgen Receptor in Vivo, *Molecular Endocrinology* 6:1103-12 (1992).
Rader and Barbas III, Phage Display of Combinatorial Antibody Libraries, *Current Opinion in Biotechnology* 8:503-508 (1997).
Rauscher et al. Binding of the Wilms' Tumor Locus Zinc Finger Protein to the EGR-1 Consensus Sequence, *Science* 250:1259-61 (1990).
Ray et al. Repressor to activator switch by mutations in the first Zn finger of the glucocorticoid receptor: Is direct DNA binding necessary? *Proc. Natl. Acad. Sci. USA* 88:7086-90 (1991).
Rebar and Pabo, Zinc Finger Phage: Affinity Selection of Fingers with New DNA-Binding Specificities, *Science* 263:671-673 (1994).
Regulatory Issues: Future Meetings of the NIH Recombinant DNA Advisory Committee, *Human Gene Therapy* 5:541-563 (1994).
Rollins et al. Role of TFIIIA Zinc Fingers In Vivo: Analysis of Single-Finger Function in Developing *Xenopus* Embryos, *Molecular and Cellular Biology* 13(8):4776-83 (1993).
Sadowski et al., GAL4-VP16 is an Unusually Potent Transcriptional Activator, *Nature* 335:563-564 (1988).
Sadowski et al., GAL4 Fusion Vectors for Expression in Yeast or Mammalian Cells, *Gene* 118:137-141 (1992).
Sastry et al., Cloning of the Immunological Repertoire in *Escherichia coli* for Generation of Monoclonal Catalytic Antibodies: Construction of a Heavy Chain Variable Region-Specific cDNA Library, *Proc. Natl. Acad Sci USA* 86:5728-5732 (1989).
Schnaith et al., Double-Stranded Cleavage of pBR322 by a Diiron Complex Via a "hydrolytic" Mechanism, *Proc. Natl. Acad. Sci USA* 91:569-573 (1994).
Segal et al., Toward Controlling Gene Expression at Will: Selection and Design Of Zinc Finger Domains Recognizing Each of the 5'-GNN-3' DNA Target Sequences, *Proc. Natl. Acad. Sci. USA* 96(6):2758-63 (1999).
Segal et al., Design of Novel Sequence-Specific DNA-Binding Proteins, *Curr. Opin. Chem. Biol*. 4(1):34-9 (2000).

Seipel et al., Different Activation Domains Stimulate Transcription from Remote ('Enhancer') and Proximal ('Promoter') Position, *The EMBO J.* 11(13):4961-4968 (1992).
Sgouras et al., ERF: an ETS Domain Protein with Strong Transcriptional Repressor Activity, Can Suppress etsOassociated Tumorigenesis and is Regulated by Phosphorylation During Cell Cycle and Mitotgenic Stimulation, *The EMBO J.* 14(19):4781-4793 (1995).
Sigman, D., Chemical Nucleases, *Biochemistry* 29(39):9097-9105 (1990).
Smith, et al., Single Step purification of polypeptides expressed in *Escherichia coli* as fusions with glutathione S-transferase, *Gene* 67:31-40 (1988).
Smith, et al., Comparison of Biosequences, *Adv. Appl. Math.* 2:482 (1981).
South et al. The Nucleocapsid Protein Isolated from HIV-1 Particles Binds Zinc and Forms Retroviral-Type Zinc Fingers, *Biochemistry* 29:7786-89 (1990).
Steinberger et al., Generation and characterization of a recombinant human CCR5-specific Antibody: A phage display approach for rabbit antibody humanization, *J. Biol. Chem.* 275(46): 36073-36078 (2000).
Swirnoff and Milbrandt, DNA-Binding Specificity of NGF-A and Related Zinc Finger Transcription Factors, *Mol. Cell. Biol.* 15(4):2275-2287 (1995).
Takasaki and Chin, Cleavage of the Phosphate Diester Backbone of DNA with Cerium (III) and Molecular Oxygen, *J. Am. Chem. Soc.* 116:1121-1122 (1994).
Thiesen an Bach, Target Detection Assay (TDA): a Versatile Procedure to Determine DNA Binding Sites as Demonstrated on SP1 Protein, *Nucleic Acids Res.* 18(11): 3203-3209 (1990).
Thukral et al., Mutations in the Zinc Fingers of ADR1 That Change the Specificity of DNA Binding and Transactivation, *Molecular and Cellular Biology* 12(6):2784-92 (1992).
Tora et al., The Cloned Human Oestrogen Receptor Contains a Mutation which alters its Hormone Binding Properties, *The EMBO J.* 8(7):1981-1986 (1989).
Vinson et al. Scissors-Grip Model for DNA Recognition by a Family of Leucine Zipper Proteins, *Science* 246:911-6 (1989).
Wallace et al., The Use of Synthetic Oligonucleotides as Hybridization Probes, *Nucleic Acids Research* 9(4):879-895 (1981).
Wang et al., A Regulatory System for Use in Gene Transfer, *Proc. Natl. Acad. Sci. USA* 91:8180-8184 (1994).
White, J., Modified Steroid Receptors and Steroid-Inducible Promoters as Genetic Switches for Gene Therapy, *Adv. in Pharmacology* 40:339-367 (1997).
Wright et al. Expression of a Zinc Finger Gene in HTLV-1- and HTLV-11- Transformed Cells, *Science* 248:588-91 (1990).
Wu et al., Building Zinc Fingers by Selection: Toward a Therapeutic Application, *Proc. Natl. Acad. Sci USA* 92:344-248 (1995).
Yang et al., Surface Plasmon Resonance Based Kinetics Studies of Zinc Finger-DNA interactions, *J. Immunol Methods* 183(1):175-82 (1995).
Yu et al. A hairpin ribozyme inhibits expression of diverse strains of human immunodeficiency virus type 1, *Proc. Natl. Acad. Sci. USA* 90:6340-44 (1993).
Choo et al., "In vivo repression by a site-specific DNA-binding protein designed against an oncogenic sequence", *Nature* 372:642-645 (1994).
Clemens et al., "Molecular basis for specific recognition of both RNA and DNA by zinc finger protein", *Science* 260:530-533 (1993).
Rhodes and Klug, "Zinc Fingers", *Scientific American* , pp. 56-65 (Feb. 1993).
Shi and Berg, "Specific DNA-RNA hybrid binding by zinc finger proteins", *Science* 268:282-284 (1995).
Scheller et al., "Multiple receptor domains interact to permit, or restrict, androgen-specific gene activation", *J. Biol. Chem.* 273(37):24216-24222 (1998).
Israeli Office Action, issued Apr. 16, 2007, in connection with corresponding Israeli Patent Application No. 149142.
Barbas, NIH Grant GM53910, "Zinc finger proteins as anti-HIV therapeutics" funding period from Feb. 1, 1996 to Jan. 31, 2000.
Burcin et al. "A regulatory system for target gene expression" Frontiers in Bioscience 3:1-7 (1998).
Pengue et al. "Repression of transcriptional activity at a distance by the evolutionarily conserved KRAB domain present in a subfamily of zinc finger proteins" Nucleic Acids Research 22(15):2908-2914 (1994).
Pomerantz et al. "Structure based design of transcription factors" Science 267:93-96 (1995).

* cited by examiner

Domains of a Steroid Nuclear Receptor
ex. Human Estrogen Receptor (ER)

Cloning Stategy for DNA binding domain Replacement

Plasmid construction

| ZFP | Binding Sequence | Chimerics Constructed |
|---|---|---|
| C7 | GCG TGG GCG | AS, BS, CS, AL, BL, CL |
| E2C | GGG GCC GGA g | AS, BS |
| 2C7 | GCG TGG GCG GCG TGG GCG | AS, BS, CS |

Left end shuttle plasmid for adenovirus vector construction

Right End Vector Genome-containing plasmid

LIGAND ACTIVATED TRANSCRIPTIONAL REGULATOR PROTEINS

RELATED APPLICATIONS

This application is a continuation of U.S. application Ser. No. 09/586,625, filed Jun. 2, 2000, which is a continuation-in-part of U.S. application Ser. No. 09/433,042, filed Oct. 25, 1999, now abandoned. The subject matter of each of U.S. application Ser. Nos. 09/433,042 and 09/586,625 is herein incorporated by reference in its entirety.

Work described herein was supported by National Institutes of Health NIH Contract No. GM53910. The United States Government has certain rights in such subject matter.

FIELD OF THE INVENTION

The field of this invention is the regulation of gene expression. In particular, ligand-activated fusion proteins (also referred to herein as chimeric regulators) and the use thereof for regulation of gene expression are provided. The fusion polypeptides contain a DNA binding domain containing one or a plurality of zinc finger polypeptide domains and a ligand binding domain (LBD) derived from an intracellular receptor.

BACKGROUND OF THE INVENTION

Intracellular receptors are a superfamily of related proteins that mediate the nuclear effects of a variety of hormones and effector molecules, including steroid hormones, thyroid hormones and vitamins A and D. Members of this family of intracellular receptors are prototypical ligand activated transcription factors. These receptors contain two primary functional domains: a DNA binding domain (DBD) that contains about sixty-six amino acids and a ligand-binding domain (LBD) located in the carboxyl-terminal half of the receptor that has about 300 amino acids. The receptors are inactive in the absence of hormone (ligand) by virtue of association with inactivating factors, such as heat shock proteins. Upon ligand binding, the receptors dissociate from the inactivating complex and dimerize, which renders them able to bind to DNA and modulate transcription.

For example, for the steroid receptors, binding of a steroid hormone to its receptor results in receptor protein homodimerization and subsequent binding to the "steroid response element" (SRE) DNA sequence in nuclear DNA. Conformational changes in the receptor associated with ligand binding results in the recruitment of other transcriptional regulatory proteins, called co-activators, that regulate the transcription from promoters adjacent to the SRE binding sites.

Modified steroid hormone receptors have been developed for use for regulated expression of transgenes (see, e.g., U.S. Pat. No. 5,874,534 and published International PCT application No. WO 98/18925, which is based on U.S. provisional application Ser. No. 60/029,964) by modifying the ligand specificity of the LBD. In addition, the DNA binding domain of the receptor has been replaced with a non-mammalian DNA binding domain selected from yeast GAL4 DBD, a viral DBD and an insect DBD to provide for regulated expression of a co-administered gene containing a region recognized by the non-mammalian DBD. These constructs, however, have several drawbacks. The non-mammalian DBD is potentially immunogenic and the array of sequences recognized by these DBD is limited, thereby severely restricting gene targets.

Therefore, there remains a need for more versatile gene regulators. It is an object herein to provide polypeptides that function as versatile regulators of gene expression.

SUMMARY OF THE INVENTION

Polypeptides that function as ligand activated transcriptional regulators and nucleic acid molecules encoding such polypeptides are provided. The polypeptides are fusion proteins that are ligand activated transcriptional regulators that can be targeted to any desired endogenous or exogenous gene. Variants of the fusion protein can be designed to have different selectivity and sensitivity for endogenous and exogenous ligands.

Nucleic acid molecules encoding the fusion proteins, expression vectors containing the nucleic acids and cells containing the expression vectors are provided. The fusion protein or nucleic acids, particularly vectors, that encode the fusion protein can be introduced into a cell and, when expressed in the cell, regulate gene expression in a ligand-dependent manner.

Fusion Proteins

The fusion proteins provided herein contain a ligand binding domain (designated herein LBD) from an intracellular receptor, preferably a LBD that has modified ligand specificity compared to the native intracellular receptor from which the LBD originates, and a nucleic acid binding domain (designated herein DBD) that can be tailored for any desired specificity. The fusion proteins may also include a transcriptional regulating domain (designated herein TRD), particularly a repressor or activator domain. The domains are operatively linked whereby the resulting fusion protein functions as a ligand-regulated targeted transcription factor.

When delivered to the nucleus of a cell, the domains, which are operatively linked, together act to modulate the expression of a targeted gene, which may be a native gene in a cell or a gene that also is delivered to a cell. Hence the targeted gene can be an endogenous cellular gene or an exogenously supplied recombinant polynucleotide construct. The fusion protein may also include a transcriptional regulating domain that is selected to activate, enhance or suppress transcription of a targeted gene.

In one embodiment, the fusion protein is constructed from components highly similar to human proteins, preferably components that are about 80% more preferably about 85%, most preferably at least about 90% identical in amino acid sequence to the corresponding human domain. In another embodiment, the fusion protein binds to a naturally occurring gene and modulates the transcription of the naturally occurring gene in a ligand-dependent way. In another embodiment, the fusion protein binds to an exogenously supplied recombinant construct and modulates the transcription of the exogenously supplied recombinant construct in a ligand-dependent way.

In a preferred embodiment, the isolated recombinant fusion protein forms a dimer when bound to a polynucleotide. The dimer can be a homodimer or a heterodimer. In one embodiment, the dimer includes at least one DNA binding domain, at least one, preferably two, ligand binding domains and at least one transcription modulating domain. In heterodimers, the dimer can include two different DNA binding domains, two different ligand binding domains or two different transcription modulating domains. One exemplary heterodimer includes at least three zinc finger modular units, two different ligand binding sites and a transcription modulating domain.

Exemplary fusion proteins containing zinc fingers and LBD that are non-responsive to estrogen, and that are induced by synthetic non-steroidal drugs that are routinely used for clinical treatments are described; these regulators provide ligand-dependent gene activation. Exemplary fusion proteins comprise the sequence of amino acids encoded by the open reading frame set forth in each of SEQ ID Nos. 1-18.

The fusion proteins can be used in plant species as well as animals. Transgenic plants resistant to particular bacterial or viral pathogens can be produced.

Ligan Binding Domain (LBD)

The LBD is derived from an intracellular receptor, particularly a steroid hormone receptor. The receptors from which the LBD is derived include, but is not limited to, glucocorticoid receptors, mineralocorticoid receptors, thyroid hormone receptors, retinoic acid receptors, retinoid X receptors, Vitamin D receptors, COUP-TF receptors, ecdysone receptors, Nurr-I receptors, orphan receptors and variants thereof. Receptors of these types include, but are not limited to, estrogen receptors, progesterone receptors, glucocorticoid-α receptors, glucocorticoid-β receptors, androgen receptors and thyroid hormone receptors. LBDs preferably are modified to alter ligand specificity so that they preferentially bind to an exogenous ligand, such as a drug, compared to an endogenous ligand.

When intended for human gene therapy, the ligand binding domain preferably retain sufficient identity, typically at least about 90% sequence identity to a human ligand binding domain, to avoid substantial immunological response. A single amino acid change in the LBD can dramatically alter performance of the protein.

The LBD is preferably modified so that it does not bind to the endogenous ligand for the receptor from which the LBD is derived, but to a selected ligand to permit fine tuned regulation of targeted genes. Hence, in certain embodiments, the ligand-binding domain has been modified to change its ligand selectivity compared to its selectivity in the native receptor. Preferably the modified ligand-binding domain is not substantially activated by endogenous ligands. Any method for altering ligand specificity, including systematic sequence alteration and testing for specificity, and selection protocols (see, e.g., U.S. Pat. No. 5,874,534 and Wang et al. (1994) *Proc. Natl. Acad. Sci. U.S.A.* 91:8180-8184) can be used.

Nucleic Acid Binding Domain (DBD)

To achieve targeted and specific transcriptional regulation the DBD includes at least one zinc finger modular unit and is engineered to bind to targeted genes. The zinc finger nucleic acid binding domain contains at least two zinc finger modules that bind to selected sequences of nucleotides. Any zinc finger or modular portions thereof can be used. The DBD replaces or supplements the naturally-occurring zinc finger domain in the receptor from which the ligand binding domain is derived.

The nucleic acid binding domain (DBD) includes at least one, preferably at least two, modular units of a zinc finger nucleic acid binding polypeptide, each modular unit specifically recognizing a three nucleotide sequence of bases. The resulting DBD binds to a contiguous sequence of nucleotides of from 3 to about 18 nucleotides.

As noted, the DBD contains modular zinc-finger units, where each unit is specific for a trinucleotide. Modular zinc protein units can be combined so that the resulting domain specifically binds to any targeted sequence, generally DNA, such that upon binding of the fusion protein to the targeted sequence transcription of the targeted gene is modulated.

The zinc finger-nucleotide binding portion of the fusion protein can be derived or produced from a wild type zinc finger protein by truncation or expansion, or as a variant of a wild type-derived polypeptide by a process of site directed mutagenesis, or by combination of a variety of modular units or by a combination of procedures.

$Cys_2His_2$ (C2H2) type zinc finger proteins are exemplary of the zinc fingers that can replace the naturally occurring DNA binding domain in an intracellular receptor, such as the C4-C4 type domain in a steroid receptor, to form a functional ligand-responsive transcription factor fusion protein. By virtue of the zinc finger, the resulting fusion protein exhibits altered DNA binding specificity compared to the unmodified intracellular receptor.

The optimal portion of the ligand binding domain (LBD) of the receptor to use, the zinc finger array and extent thereof and the stoichiometry and orientation of DNA binding can be empirically determined as exemplified herein for a steroid receptor.

In preferred embodiments the zinc-finger portion of the fusion protein binds to a nucleotide sequence of the formula $(GNN)_n$, where G is guanidine, N is any nucleotide and n is an integer from 1 to 6, and typically n is 3 to 6. Preferably, the zinc-finger modular unit is derived from C2H2 zinc-finger peptide. More preferably, the zinc-finger peptide is a C2H2 zinc-finger peptide and has at least 90% sequence identity to a human zinc-finger peptide.

Transcription Regulating Domain (TRD)

The fusion proteins also can include transcription regulating domains. In preferred embodiments, the transcription regulating domain includes a transcription activation domain. Preferably, the transcription regulating domain has at least 90% sequence identity to a mammalian, including human if the fusion protein is intended for human gene therapy, transcription regulating domain to avoid inducing undesirable immunological responses.

The transcription regulating domain can be any such domain known to regulate or prepared to regulate eukaryotic transcription. Such TRDs are known, and include, but are not limited to, VP16, VP64, TA2, STAT-6, p65, and derivatives, multimers and combinations thereof that exhibit transcriptional regulation properties. The transcription regulating domain can be derived from an intracellular receptor, such as a nuclear hormone receptor transcription activation (or repression) domain, and is preferably a steroid hormone receptor transcription activation domain or variant thereof that exhibits transcriptional regulation properties. Transcription domains include, but are not limited to, TAF-1, TAF-2, TAU-1, TAU-2, and variants thereof.

The transcription regulating domain may be a viral transcription activation domain or variant thereof. Preferably, the viral transcription regulating domain comprises a VP16 transcription activation domain or variant thereof.

The transcription regulating domain can include a transcription repression domain. Such domains are known, and include, but are not limited to, transcription repression domains selected from among ERD, KRAB, SID, Deacetylase, and derivatives, multimers and combinations thereof, such as KRAB-ERD, SID-ERD, $(KRAB)_2$, $(KRAB)_3$, KRAB-A, $(KRAB\text{-}A)_2$, $(SID)_2$ (KRAB-A)-SID and SID-(KRAB-A).

Nucleic acid constructs

Also provided are nucleic acid molecules that encode the resulting fusion proteins. The nucleic acids can be included in vectors, suitable for expression of the proteins and/or vectors suitable for gene therapy. Cells containing the vectors are also provided. Typically the cell is a eukaryotic cell. In other embodiments, the cell is a prokaryotic cell.

Also provided are expression cassettes that contain a gene of interest, particularly a gene encoding a therapeutic product, such as an angiogenesis inhibitor, operatively linked to a transcriptional regulatory region or response element, including sequences of nucleic acids to which a fusion protein provided herein binds and controls transcription, particularly upon binding of a ligand to the LBD of the fusion polypeptide.

Such expression cassettes can be included in a vector for gene therapy, and are intended for administration with, before or after, administration of the fusion protein or nucleic acid encoding the fusion protein. Genes of interest for exogenous delivery typically encode therapeutic proteins, such as growth factors, growth factor inhibitors or antagonists, tumor necrosis factor (TNF) inhibitors, anti-tumor agents, angiogenesis agents, anti-angiogenesis agents, clotting factors, apoptotic and other suicide genes.

Compositions, combinations and kits

Also provided are compositions that contain the fusion proteins or the vectors that encode the fusion proteins. Combinations of the fusion proteins or nucleic acids encoding the proteins and nucleic acid encoding a targeted gene with regulatory regions selected for activation by the fusion protein are also provided.

Methods

Methods for regulating expression of endogenous and exogenous genes are provided. The methods are practiced by administering to a cell a composition that contains an effective amount or concentration of the fusion protein or of nucleic acid molecule, such as a vector that encodes the fusion protein. The nucleic acid binding domain (DBD) of the fusion protein is selected to bind to a targeted nucleic acid sequence in the genome of the cell or in an exogenously administered nucleic acid molecule, and the transcription regulating domain (TRD) is selected to regulate transcription from a selected promoter, which typically is operatively linked to the targeted nucleic acid binding domain. The exogenously administered nucleic acid molecule comprises an expression cassette encoding a gene of interest and operatively linked to a regulatory region that contains elements, such as a promoter and response elements.

As noted the targeted regulatory region and gene of interest may be endogenously present in the cell or separately administered as part of an expression cassette encoding the gene of interest. If separately administered, it is administered as part of a regulatable expression cassette that includes a gene and at least one response element for the gene recognized by the nucleotide binding domain of the fusion protein.

At the same time or at a later time, a composition comprising a ligand that binds to the ligand binding domain of the fusion protein is also administered. The ligand can be administered in the same composition as the fusion protein (or encoding nucleic acid molecule) or in a separate composition. The ligand and fusion protein may be administered sequentially, simultaneously or intermittently.

Hence gene therapy is effected by administering a ligand that binds to the LBD of the fusion protein. Preferably the ligand is a non-natural ligand and the LBD has been modified from the native form present in native intracellular receptors to preferentially and selectively interact with the non-natural ligand. Upon administration, the ligand binds to the ligand binding domain of the fusion protein, whereby the DBD of the fusion protein, either as a monomer or dimer, interacts with a targeted gene and transcription of the targeted gene is repressed or activated. As noted, the targeted gene may be an endogenous gene or an exogenously administered gene.

In other embodiments, the methods for regulating gene expression in a cell are effected by administering to the cell a composition containing an effective amount of the nucleic acid molecule that encodes the ligand activated transcriptional regulatory fusion protein, a regulatable expression cassette containing a gene operatively linked to at least one response element for the gene recognized by the nucleotide binding domain of the polypeptide encoded by the polynucleotide, and a pharmaceutically acceptable excipient; and administering to the cell a ligand that binds to the ligand binding domain of the encoded polypeptide, where the nucleotide binding domain of the encoded polypeptide binds to the response element and activates or represses transcription of the gene.

Methods for treating a cellular proliferative disorder by the ex vivo introduction of a recombinant expression vector encoding the fusion protein are provided. Cellular proliferative disorders include disorders associated with transcription of a gene at reduced or increased levels.

Administration of the composition(s) can be effected in vitro, in vivo or ex vivo. One such method includes the removal of a tissue sample from a subject with a disorder, such as a cell proliferative disorder, isolating hematopoietic or other cells from the tissue sample, and contacting isolated cells with the fusion protein or a nucleic acid molecule encoding the fusion protein, and, optionally, a target specific gene. Optionally, the cells can be treated with a growth factor, such as interleukin-2 for example, to stimulate cell growth, before reintroducing the cells into the subject. When reintroduced, the cells specifically target the cell population from which they were originally isolated. In this way, the trans-repressing activity of the zinc finger-nucleotide binding polypeptide may be used to inhibit or suppress undesirable cell proliferation in a subject. Preferably, the subject is a human.

Methods for treating a cellular proliferative disorder by the ex vivo introduction of a recombinant expression vector encoding the fusion protein are provided. Cellular proliferative disorder include disorders associated with transcription of a gene at reduced or increased levels.

Administration can of the composition(s) can be effected in vitro, in vivo or ex vivo. One such method includes the removal of a tissue sample from a subject with a disorder, such as a cell proliferative disorder, isolating hematopoietic or other cells from the tissue sample, and contacting isolated cells with the fusion protein or a nucleic acid molecule encoding the fusion protein, and, optionally, a target specific gene. Optionally, the cells can be treated with a growth factor, such as interleukin-2 for example, to stimulate cell growth, before reintroducing the cells into the subject. When reintroduced, the cells specifically target the cell population from which they were originally isolated. In this way, the trans-repressing activity of the zinc finger-nucleotide binding polypeptide may be used to inhibit or suppress undesirable cell proliferation in a subject. Preferably, the subject is a human.

Results exemplified herein demonstrate ligand activated transcription of a targeted gene and demonstrate the utility of the fusion protein containing a zinc finger DNA binding domain, such as a mammalian C2H2 DNA binding domain, a ligand binding domain from an intracellular receptor, such as an estrogen receptor, and, optionally, a heterologous transcription regulating domain for the purpose of obtaining ligand-dependent control of expression of a transgene introduced into mammalian cells. Hence it is shown herein that heterologous zinc finger domains can be combined with an intracellular receptor to achieve ligand-dependent gene expression of a targeted gene.

DESCRIPTION OF THE DRAWINGS

In the drawings, which form a portion of the specification.

DETAILED DESCRIPTION

I. Definitions

Figure 1:
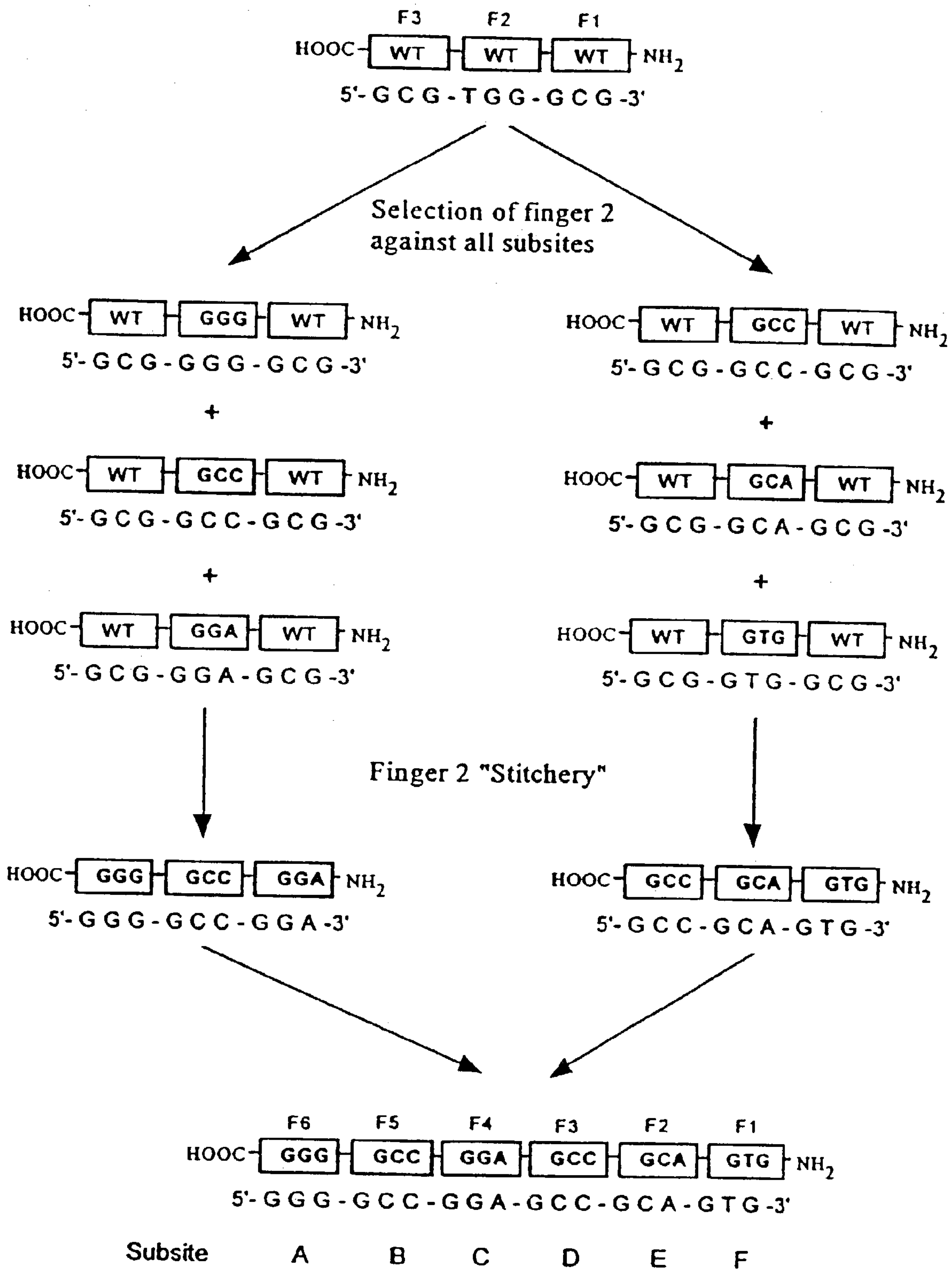
FIG. 1 is a schematic for the selection strategy for the in vitro evolution of the 3 finger protein Zif268, recognizing its natural 9 bp target site (top), into a 6 finger protein, recognizing a desired 18 bp target sequence (bottom).

Unless defined otherwise, all technical and scientific terms used herein have the same meaning as is commonly understood by one of skill in the art to which this invention belongs. All patents, applications, published applications and other publications and sequences from GenBank and other data bases referred to anywhere in the disclosure herein are incorporated by reference in their entirety.

As used herein, the ligand binding domain (LBD) of the fusion proteins provided herein refers to the portion of the fusion protein responsible for binding to a selected ligand. The LBD optionally and preferably includes dimerization and inactivation functions. The LBDs in the proteins herein are derived from the 300 amino acid carboxyl-terminal half of intracellular receptors, particularly those that are members of the steroid hormone nuclear receptor superfamily. It is the portion of the receptor protein with which a ligand interacts thereby inducing a cascade of events leading to the specific association of an activated receptor with regulatory elements of target genes. In these receptors the LDB includes the hormone binding function, the inactivation function, such as through interactions with heat shock proteins (hsp), and dimerization function. The LBDs used herein include such LBDs and modified derivatives thereof, particularly forms with altered ligand specificity.

As used herein, the transcription regulating domain (TRD) refers to the portion of the fusion polypeptide provided herein that functions to regulate gene transcription. Exemplary and preferred transcription repressor domains are ERD, KRAB, SID, Deacetylase, and derivatives, multimers and combinations thereof such as KRAB-ERD, SID-ERD, $(KRAB)_2$, $(KRAB)_3$, KRAB-A, $(KRAB-A)_2$, $(SID)_2$ (KRAB-A)-SID and SID-(KRAB-A).

As used herein, the DNA binding domain (DBD), or alternatively the nucleic acid (or nucleotide) binding domain, refers to the portion of the fusion polypeptide provided herein that provides specific nucleic acid binding capability. The use of the abbreviation DBD is not meant to limit it to DNA binding domains, but is also intended to include polypeptides that bind to RNA. The nucleic acid binding domain functions to target the protein to specific genes by virtue of the specificity of the interaction of the TRD region for nucleotide sequences operatively linked to the transcriptional apparatus of a gene. The DBD targets the fusion protein to the selected targeted gene or genes, which gene(s) may be endogenous or exogenously added.

As used herein, operatively linked means that elements of the fusion polypeptide, for example, are linked such that each perform or function as intended. For example, the repressor is attached to the binding domain in such a manner that, when bound to a target nucleotide via that binding domain, the repressor acts to inhibit or prevent transcription. Linkage between and among elements may be direct or indirect, such as via a linker. The elements are not necessarily adjacent. Hence a repressor domain of a TRD can be linked to a DNA binding domain using any linking procedure well known in the art. It may be necessary to include a linker moiety between the two domains. Such a linker moiety is typically a short sequence of amino acid residues that provides spacing between the domains. So long as the linker does not interfere with any of the functions of the binding or repressor domains, any sequence can be used.

As used herein, a fusion protein is a protein that contains portions or fragments of two or more naturally-occurring proteins operatively joined or linked to form the fusion protein in which each fragment retains a function or a modified function exhibited by the naturally occurring proteins. The fragments from the naturally occurring protein may be modified to alter the original properties.

As used herein, modified, modification, mutant or other such terms refers to an alteration of the domain in question from its naturally occurring wild-type form, and includes primary sequence changes.

As used herein, "modulating" envisions the inhibition or suppression of expression from a promoter containing a zinc finger-nucleotide binding motif when it is over-activated, or augmentation or enhancement of expression from such a promoter when it is under-activated.

As used herein, steroid hormone receptor superfamily refers to the superfamily of intracellular receptors that are steroid receptors. Representative examples of such receptors include, but are not limited to, the estrogen, progesterone, glucocorticoid-α, glucocorticoid-β, mineralocorticoid, androgen, thyroid hormone, retinoic acid, retinoid X, Vitamin D, COUP-TF, ecdysone, Nurr-I and orphan receptors.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224).

As used herein, a delivery plasmid is a plasmid vector that carries or delivers nucleic acids encoding a therapeutic gene or gene that encodes a therapeutic product or a precursor thereof or a regulatory gene or other factor that results in a therapeutic effect when delivered in vivo in or into a cell line, such as, but not limited to a packaging cell line, to propagate therapeutic viral vectors.

As used herein, "recombinant expression vector" or "expression vector" refers to a plasmid, virus or other vehicle known in the art that has been manipulated by insertion or incorporation of heterologous DNA, such as nucleic acid encoding the fusion proteins herein or expression cassettes provided herein. Such expression vectors contain a promoter sequence for efficient transcription of the inserted nucleic acid in a cell. The expression vector typically contains an origin of replication, a promoter, as well as specific genes that permit phenotypic selection of transformed cells.

As used herein, a DNA or nucleic acid homolog refers to a nucleic acid that includes a preselected conserved nucleotide sequence, such as a sequence encoding a therapeutic polypeptide. By the term "substantially homologous" is meant having at least 80%, preferably at least 90%, most preferably at least 95% homology therewith or a less percentage of homology or identity and conserved biological activity or function.

As used herein, "host cells" are cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

The terms "homology" and "identity" are often used interchangeably. In this regard, percent homology or identity may be determined, for example, by comparing sequence information using a GAP computer program. The GAP program uses the alignment method of Needleman and Wunsch ((1970) *J. Mol. Biol.* 48:443), as revised by Smith and Waterman ((1981) *Adv. Appl. Math.* 2:482). Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358(1979); (2) a penalty of 3.0 for each gap and an additional 0.10 penalty for each symbol in each gap; and (3) no penalty for end gaps.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson et al. (1988) *Proc. Natl. Acad. Sci. USA* 85:2444. Alternatively the BLAST function of the National Center for Biotechnology Information database may be used to determine identify.

In general, sequences are aligned so that the highest order match is obtained. "Identity" per se has an art-recognized meaning and can be calculated using published techniques (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo et al. (1988) *SIAM J Applied Math* 48:1073). Methods commonly employed to determine identity or similarity between two sequences include, but are not limited to, those disclosed in Guide to Huge Computers, Martin J. Bishop, ed., Academic Press, San Diego, 1994, and Carillo et al. (1988) *SIAM J Applied Math* 48:1073. Methods to determine identity and similarity are codified in computer programs. Preferred computer program methods to determine identity and similarity between two sequences include, but are not limited to, GCG program package (Devereux, J., et al., *Nucleic Acids Research* 12(I):387 (1984)), BLASTP, BLASTN, and FASTA (Atschul, S. F., et al., *J Molec Biol* 215:403 (1990)).

Therefore, as used herein, the term "identity" represents a comparison between a test and a reference polypeptide or polynucleotide. For example, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions.

As used herein, primer refers to an oligonucleotide containing two or more deoxyribonucleotides or ribonucleotides, preferably more than three, from which synthesis of a primer extension product can be initiated. For purposes herein, a primer of interest is one that is substantially complementary to a zinc finger-nucleotide binding protein strand, but also can introduce mutations into the amplification products at selected residue sites. Experimental conditions conducive to synthesis include the presence of nucleoside triphosphates and an agent for polymerization and extension, such as DNA polymerase, and a suitable buffer, temperature and pH.

As used herein, genetic therapy involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease.

Typically, DNA encoding a desired gene product is cloned into a plasmid vector and introduced by routine methods, such as calcium-phosphate mediated DNA uptake (see, (1981) *Somat. Cell. Mol. Genet* 7:603-616) or microinjection, into producer cells, such as packaging cells. After amplification in producer cells, the vectors that contain the heterologous DNA are introduced into selected target cells.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors." Also included are vectors that allow cloning of cDNA (complementary DNA) from mRNAs produced using reverse transcriptase.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, isolated with reference to a nucleic acid molecule or polypeptide or other biomolecule means that the nucleic acid or polypeptide has separated from the genetic environment from which the polypeptide or nucleic acid were obtained. It may also mean altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) *Gene* 67:31-40. The terms isolated and purified are sometimes used interchangeably.

Thus, by "isolated" the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Isolated or purified as it refers to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange chromatography, affinity chromatography, density gradient centrifugation and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, "modulate" refers to the suppression, enhancement or induction of a function. For example, zinc finger-nucleic acid binding domains and variants thereof may modulate a promoter sequence by binding to a motif within the promoter, thereby enhancing or suppressing transcription of a gene operatively linked to the promoter cellular nucleotide sequence. Alternatively, modulation may include inhibition of transcription of a gene where the zinc finger-nucleotide binding polypeptide variant binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

As used herein, "inhibit" refers to the suppression of the level of activation of transcription of a structural gene operably linked to a promoter. For example, for the methods herein the gene includes a zinc finger-nucleotide binding motif.

As used herein, a transcriptional regulatory region refers to a region that drives gene expression in the target cell. Transcriptional regulatory regions suitable for use herein include but are not limited to the human cytomegalovirus (CMV) immediate-early enhancer/promoter, the SV40 early enhancer/promoter, the JC polyomavirus promoter, the albumin promoter, PGK and the $\alpha$-actin promoter coupled to the CMV enhancer.

As used herein, a promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or, for example, an onco-promoter. An onco-promoter is generally a virus-derived promoter. Viral promoters to which zinc finger binding polypeptides may be targeted include, but are not limited to, retroviral long terminal repeats (LTRs), and Lentivirus promoters, such as promoters from human T-cell lymphotrophic virus (HTLV) 1 and 2 and human immunodeficiency virus (HIV) 1 or 2.

As used herein, "effective amount" includes that amount that results in the deactivation of a previously activated promoter or that amount that results in the inactivation of a promoter containing a zinc finger-nucleotide binding motif, or that amount that blocks transcription of a structural gene or translation of RNA. The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or "contacting" the cellular nucleotide sequence containing the zinc finger-nucleotide binding protein motif, can be accomplished by one of the mechanisms described herein, such as by retroviral vectors or liposomes, or other methods well known in the art.

As used herein, "truncated" refers to a zinc finger-nucleotide binding polypeptide derivative that contains less than the full number of zinc fingers found in the native zinc finger binding protein or that has been deleted of non-desired sequences. For example, truncation of the zinc finger-nucleotide binding protein TFIIIA, which naturally contains nine zinc fingers, might be a polypeptide with only zinc fingers one through three. Expansion refers to a zinc finger polypeptide to which additional zinc finger modules have been added. For example, TFIIIA may be extended to 12 fingers by adding 3 zinc finger domains. In addition, a truncated zinc finger-nucleotide binding polypeptide may include zinc finger modules from more than one wild type polypeptide, thus resulting in a "hybrid" zinc finger-nucleotide binding polypeptide.

As used herein, "mutagenized" refers to a zinc finger derived-nucleotide binding polypeptide that has been obtained by performing any of the known methods for accomplishing random or site-directed mutagenesis of the DNA encoding the protein. For instance, in TFIIIA, mutagenesis can be performed to replace nonconserved residues in one or more of the repeats of the consensus sequence. Truncated zinc finger-nucleotide binding proteins can also be mutagenized.

As used herein, a polypeptide "variant" or "derivative" refers to a polypeptide that is a mutagenized form of a polypeptide or one produced through recombination but that still retains a desired activity, such as the ability to bind to a ligand or a nucleic acid molecule or to modulate transcription.

As used herein, a zinc finger-nucleotide binding polypeptide "variant" or "derivative" refers to a polypeptide that is a mutagenized form of a zinc finger protein or one produced through recombination. A variant may be a hybrid that contains zinc finger domain(s) from one protein linked to zinc finger domain(s) of a second protein, for example. The domains may be wild type or mutagenized. A "variant" or "derivative" includes a truncated form of a wild type zinc finger protein, which contains less than the original number of fingers in the wild type protein. Examples of zinc finger-nucleotide binding polypeptides from which a derivative or variant may be produced include TFIIIA and zif268. Similar terms are used to refer to "variant" or "derivative" nuclear hormone receptors and "variant" or "derivative" transcription effector domains.

As used herein a "zinc finger-nucleotide binding motif" refers to any two or three-dimensional feature of a nucleotide segment to which a zinc finger-nucleotide binding derivative polypeptide binds with specificity. Included within this definition are nucleotide sequences, generally of five nucleotides or less, as well as the three dimensional aspects of the DNA double helix, such as, but are not limited to, the major and minor grooves and the face of the helix. The motif is typically any sequence of suitable length to which the zinc finger polypeptide can bind. For example, a three finger polypeptide binds to a motif typically having about 9 to about 14 base pairs. Preferably, the recognition sequence is at least about 16 base pairs to ensure specificity within the genome. Therefore, zinc finger-nucleotide binding polypeptides of any specificity are provided. The zinc finger binding motif can be any sequence designed empirically or to which the zinc finger protein binds. The motif may be found in any DNA or RNA sequence, including regulatory sequences, exons, introns, or any non-coding sequence.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to nucleic acid molecules, including DNA fragments, the phrase "operatively linked" means the sequences or segments have been covalently joined, preferably by conventional phosphodiester bonds, into one strand of DNA, whether in single or double stranded form such that operatively linked portions function as intended. The choice of vector to which a transcription unit or a cassette provided herein is operatively linked depends directly, as is well known in the art, on the functional properties desired, e.g., vector replication and protein expression, and the host cell to be transformed, these being limitations inherent in the art of constructing recombinant DNA molecules.

As used herein, a sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

As used herein, a secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei, et al. (*Nature,* 331:543-546, 1988). The leader sequence of the pelB protein has previously been used as a secretion signal for fusion proteins (Better et al. (1988) *Science* 240:1041-1043;Sastry et al. (1989) *Proc. Natl. Acad. Sci. USA* 86:5728-5732; and Mullinax et al. (1990) *Proc. Natl. Acad. Sci. USA,* 87:8095-8099). Amino acid residue sequences for other secretion signal polypeptide domains from *E. coli* are known (see, e.g.,Oliver, In Neidhard, F. C. (ed.), *Escherichia coli* and *Salmonella Typhimurium*, American Society for Microbiology, Washington, D.C., 1:56-69 (1987)).

As used herein, ligand refers to any compound that interacts with the ligand binding domain of a receptor and modulates its activity; ligands typically activate receptors. Ligand can also include compounds that activate the receptor without binding. A natural ligand is a compound that normally interacts with the receptor.

As used herein, anti-hormones are compounds that are antagonists of the naturally-occurring receptor. The anti-hormone is opposite in activity to a hormone.

As used herein, non-natural ligands or non-native ligands refer to compounds that are normally not found in mammals, such as humans, that bind to or interact with the ligand binding domain of a receptor. Hence, the term "non-native ligands" refers to those ligands that are not naturally found in the specific organism (man or animal) in which gene therapy is contemplated. For example, certain insect hormones such as ecdysone are not found in humans. As such ecdysone is non-native hormone to an animal, such as a human.

As used herein, non-natural ligands or non-native ligands refer to compounds that are normally are not found in mammals, such as humans, that bind to or interact with the ligand binding domain of a receptor. Hence, the term "non-native ligands" refers to those ligands that are not naturally found in the specific organism (man or animal) in which gene therapy is contemplated. For example, certain insect hormones such as ecdysone are not found in humans. As such ecdysone is non-native hormone to an animal, such as a human.

As used herein, "cell-proliferative disorder" denotes malignant as well as non-malignant disorders in which cell populations morphologically appear to differ from the surrounding tissue. The cell-proliferative disorder may be a transcriptional disorder that results in an increase or a decrease in gene expression level. The cause of the disorder may be of cellular origin or viral origin. Gene therapy using a zinc finger-nucleotide binding polypeptide can be used to treat a virus-induced cell proliferative disorder in a human, for example, as well as in a plant. Treatment can be prophylactic in order to make a plant cell, for example, resistant to a virus, or therapeutic, in order to ameliorate an established infection in a cell, by preventing production of viral products.

As used herein, "cellular nucleotide sequence" refers to a nucleotide sequence that is present within a cell. It is not necessary that the sequence be a naturally occurring sequence of the cell. For example, a retroviral genome that is integrated within a host's cellular DNA, would be considered a "cellular nucleotide sequence". The cellular nucleotide sequence can be DNA or RNA and includes introns and exons, DNA and RNA. The cell and/or cellular nucleotide sequence can be prokaryotic or eukaryotic, including a yeast, virus, or plant nucleotide sequence.

As used herein, administration of a therapeutic composition can be effected by any means, and includes, but is not limited to, subcutaneous, intravenous, intramuscular, intrasternal, infusion techniques, intraperitoneal administration and parenteral administration.

II. Fusion Protein

A. General

The fusion protein is constructed to include a ligand binding domain and a nucleic acid binding domain; the nucleic acid binding domain is not derived from the same receptor as the ligand binding domain. Inclusion of these two domains permits sequence specific binding to target nucleic acid sequences present in endogenous or exogenous nucleic acid molecules. It also provides ligand-dependent control of such sequence-specific binding. The fusion protein can also include a transcription regulating domain that serves to enhance, suppress or activate expression of an endogenous or exogenous gene. Such transcriptional control is also ligand dependent.

The nucleic acid binding domain (the DBD) includes one or more zinc finger peptide modular units, and typically a plurality of such units joined to provide a peptide designed to bind to the regulatory region in a targeted gene. Zinc fingers provide a means to design DBDs of a desired specificity.

The fusion protein also includes a LBD that is derived from an intracellular receptor, preferably a hormone receptor, more preferably a steroid receptor. The LBD can be modified to have altered ligand specificity so that endogenous or natural ligands do not interact with it, but non-natural ligands do. The fusion protein also can include a transcription regulating domain (TRD) that regulates transcription of the targeted gene(s). In some embodiments, the TRD can repress transcription of an endogenous gene; in others it can activate expression of an endogenous or exogenous gene.

Hence the fusion protein is made by operably linking a LBD domain from an intracellular receptor to one or more zinc finger domains, selected to bind to a targeted gene. A transcription regulating domain can also be operably linked. This is accomplished by any method known to those of skill in the art. Generally the fusion protein is produced by expressing nucleic acid encoding the fusion protein.

1. Ligand Binding Domain (LBD)

The ligand binding domain is derived from an intracellular receptor, and is preferably derived from a nuclear hormone receptor. The LBD of an intracellular receptor includes the approximately 300 amino acids from the carboxy terminus, which can be used with or without modification.

By mutation of a small number of residues ligand specificity can be altered. The ligand binding domain can be modified, such as by truncation or point mutation to alter its ligand specificity permitting gene regulation by non-natural or non-native ligands.

Exemplary hormone receptors are steroid receptors, which are well known in the art. Exemplary and preferred steroid receptors include estrogen and progesterone receptors and variants thereof. Of particular interest are ligand binding domains that exhibit altered ligand specificity so that the LBD does not respond to the natural hormone, but rather to a drug, such as RU486, or other inducer. Means to modify and test the specificity of ligand binding domains and to identify ligands therefor are known (see, U.S. Pat. No. 5,874,534; U.S. Pat. No. 5,935,934; and International PCT application No. 98/18925, which is based on U.S. provisional application Ser. No. 60/029,964; International PCT application No. 96/40911, which is based on U.S. application Ser. No. 08/479,913).

The LBD can be modified by deletion of from about 1 up to about 150, typically 120, amino acids on the carboxyl terminal end of the receptor from which the LBD derives. Systematic deletion of amino acids and subsequent testing of the ligand specificity and of the resulting LBD can be used to empirically identify mutations that lead to modified LBDs that have desired properties, such as preferential interaction with non-natural ligands. Exemplary mutations are described in the Examples herein, and also are known to those of skill in the art (see, e.g., U.S. Pat. No. 5,874,534; U.S. Pat. No. 5,935,934; U.S. Pat. No. 5,364,791; and International PCT application No. 98/18925, which is based on U.S. provisional application Ser. No. 60/029,964; International PCT application No. 96/40911, which is based on U.S. application Ser. No. 08/479,913) and references cited therein. Hence a LBD or modified form thereof prepared by known methods is obtained and operably linked to a DBD; a TRD is also linked as needed.

2. Nucleic Acid Binding Domain (DBD)

Zinc fingers are modular nucleic acid binding peptides. The zinc fingers, or modules thereof, or variants thereof can be used to construct fusion proteins that specifically interact with targeted sequences. Zinc fingers are ubiquitous proteins, and many are well-characterized. For example, methods and rules for preparation and selection of zinc fingers based upon the C2H2 class of zinc fingers with unique specificity are known (see, e.g., International PCT application No. WO 98/54311 and International PCT application No. 95/19431; see, also U.S. Pat. No. 5,789,538; Beerli et al. (1999) *Proc. Natl. Acad. Sci. U.S.A.* 96:2758-2763; Beerli et al. (1995) *Proc. Natl. Acad. Sci. U.S.A.* 95:14628-14633; see, also U.S. application Ser. No. 09/173,941, filed 16 Oct., 1998, published as International PCT application No. WO 00/23464). Exemplary targeting sequences are provided herein.

Furthermore, other zinc fingers can be similarly identified and the rules known for the C2H2 can be applied to modification of the specificity of such zinc fingers or alternative rules unique to each class can be deduced in a similar manner.

The advantage of using zinc fingers for targeting of the ligand-dependent transcription regulating fusion proteins provided herein is the ability to construct zinc fingers with unique specificity. This permits targeting and ligand-dependent control of expression of specific endogenous genes and also ligand-dependent control of exogenously administered genes, such as genes that encode therapeutic products.

Zinc fingers and modular units thereof can be obtained or prepared by any method known to those of skill in the art. As discussed herein, a plethora of zinc fingers, including synthetic zinc fingers having a variety of sequence specificities are known, as are means for combining the modular domains to produce a resulting peptide that binds to any desired target sequence of nucleic acids. Rules for creating zinc fingers of desired specificity are known and can be deduced by methods used by those of skill in the art (see, e.g., (see, e.g., International PCT application No. WO 98/54311, which is based on U.S. application Ser. No. 08/863,813; International PCT application No. 95/19431, which is based on U.S. application Ser. Nos. 08/183,119 and 08/312,604).

For example, zinc finger variants can be prepared by identifying a zinc finger or modular unit thereof, creating an expression library, such as a phage display library (see, e.g., International PCT application No. WO 98/54311, Barbas et al. (1991) *Methods* 2:119; Barbas et al. (1992) *Proc. Natl. Acad. Sci. U.S.A.* 89:4457), encoding polypeptide variants of the zinc finger or modular units thereof, expressing the library in a host and screening for variant peptides having a desired specificity. Zinc fingers may also be constructed by combining amino acids (or encoding nucleic acids) according to the known rules of binding specificity and, if necessary, testing or screening the resulting peptides to ensure the peptide has a desired specificity. Because of the modular nature of zinc fingers, where each module can be prepared to bind to a three nucleotide sequence, peptides of any specificity can be prepared from the modules. The number of modules used depends upon the specificity of gene targeting desired. Modular units are combined; spacers (i.e. TGEKP, TGQKP) required to maintain spacing and conformational features of the modular domains are included in the peptide (see, e.g., WO 98/54311).

a. Zinc Fingers as DBDs and Zinc Finger Modular Units

The nucleic acid binding domain in the fusion protein includes zinc finger modular domains and is designed to bind to a target nucleic acid sequence present in an endogenous gene or in an exogenous gene that is administered in combination with the fusion protein or nucleic acid encoding the fusion protein.

Zinc fingers are among the most common and ubiquitous nucleic acid binding proteins. Any zinc finger polypeptide or modular unit thereof is contemplated; preferably the domain is non-immunogenic in the host for which the fusion protein is intended. For human therapy, the zinc finger DBD preferably is selected from human zinc protein modular units or variants thereof.

For purposes herein, the zinc finger used generally is other than the naturally-occurring zinc finger present in the intracellular receptor from which the ligand binding domain is derived. Typically the fusion protein is produced by replacing the native zinc finger present in the receptor with the selected zinc finger designed to interact with a targeted nucleic acid regulatory region. In addition, the zinc fingers can be designed by selection of appropriate modular units to have specificity for a targeted gene, thereby providing a precise means to modulate expression of a targeted gene.

Naturally occurring zinc finger proteins generally contain multiple repeats of the zinc finger motif. This modular nature is unique among the different classes of DNA binding proteins. Wild type zinc finger proteins are made up of from two to as many as 37 modular tandem repeats, with each repeat forming a “finger” holding a zinc atom in tetrahedral coordination by means of a pair of conserved cysteines and a pair of conserved histidines. Generally each finger also contains conserved hydrophobic amino acids that interact to form a hydrophobic core that helps the module maintain its shape. Polydactyl arrays of as many as 37 zinc finger domains allow this recognition domain to recognize extended asymmetric sequences. Any such zinc finger or combinations of modular units thereof is intended for use herein.

A zinc finger-nucleotide binding peptide domain contains a unique heptamer (contiguous sequence of 7 amino acid residues) within the α-helical domain of the polypeptide, which heptameric sequence determines binding specificity to a target nucleotide. The heptameric sequence can be located anywhere within the α-helical domain but it is preferred that the heptamer extend from position −1 to position 6 as the residues are conventionally numbered in the art. A peptide nucleotide-binding domain can include any β-sheet and framework sequences known in the art to function as part of a zinc finger protein.

Studies of natural zinc finger proteins have shown that three zinc finger domains can bind 9 bp of contiguous DNA sequence (Pavletich et al. (1991) *Science* 252:809-817; Swirnoff et al. (1995) *Mol. Cell. Biol.* 15:2275-2287). While recognition of 9 bp of sequence is insufficient to specify a unique site in a complex genome, proteins containing six zinc finger domains can specify 18-bp recognition (Liu et al. (1997) *Proc. Natl. Acad. Sci. USA* 94:5525-5530). An 18-bp address made up of modular units is of sufficient complexity to specify a single site within all known genomes (see, published International PCT application No. WO 98/54311). Rules for constructing Zinc finger arrays that bind to a particular DNA sequence are known (see, e.g., International PCT application No. WO 98/54311, which is based on U.S. application Ser. No. 08/863,813; International PCT application No. 95/19431, which is based on U.S. application Ser. Nos. 08/183,119 and 08/312,604).

Zinc finger-nucleotide binding polypeptide variants can be constructed from known motifs. The variants include at least two and preferably at least about four zinc finger modules that bind to a cellular nucleotide sequence, such as DNA, RNA or both, and specifically bind to and modulate the function of a cellular nucleotide sequence.

For purposes herein, it is not necessary that the zinc finger-nucleotide binding motif be known in order to obtain a zinc-finger nucleotide binding variant polypeptide. It is contemplated that zinc finger-nucleotide binding motifs can be identified in non-eukaryotic DNA or RNA, especially in the native promoters of bacteria and viruses by the binding thereto of the modified nucleic acid binding peptides. Modified nucleic acid binding peptides should preserve the well known structural characteristics of the zinc finger, but differ from zinc finger proteins found in nature by their amino acid sequences and three-dimensional structures.

A variety of zinc finger proteins are known. Among these, the $Cys_2$-$His_2$ (also referred to as “C2H2”) zinc fingers are preferred for use in the fusion proteins. There are well-defined rules for C2H2 zinc finger binding to DNA that allow the DNA binding specificity of the fusion proteins containing the zinc fingers to be adjusted in order to reduce non-specific interactions with genes other than the targeted genes. These proteins can be selected or engineered to bind to diverse sequences. Further, the sequence specificity of these proteins can be modified to be different from their naturally occurring targets. Examples of zinc finger proteins from which a polypeptide can be produced include TFIIIA and Zif268.

The murine $Cys_2$-$His_2$ zinc finger protein Zif268 has been used for construction of phage display libraries (Wu et al. (1995) *Proc. Natl. Acad. Sci. U.S.A.* 92:344-348). Zif268 is structurally the most well characterized of the zinc-finger proteins (Pavletich, et al. (1991) *Science* 252:809-817; Elrod-Erickson et al. (1996) *Structure* 4:1171-1180; Swirnoff et al. (1995) *Mol. Cell. Biol.* 15:2275-2287). DNA recognition in each of the three zinc finger domains of this protein is mediated by residues in the N-terminus of the α-helix contacting primarily three nucleotides on a single strand of the DNA. The operator binding site for this three finger protein is 5'-GCGTGGGCG-'3 (finger-2 subsite is underlined). Structural studies of Zif268 and other related zinc finger-DNA complexes have shown that residues from primarily three positions on the α-helix, −1, 3, and 6, are involved in specific base contacts. Typically, the residue at position −1 of the α-helix contacts the 3' base of that finger's subsite while positions 3 and 6 contact the middle base and the 5' base, respectively.

b. Construction and Isolation of Zinc Finger DBD Peptides

A zinc finger-nucleotide binding polypeptide that binds to DNA, and specifically, the zinc finger domains that bind to DNA, can be identified by examination of the "linker" region between two zinc finger domains. The linker amino acid sequence TGEK(P) (SEQ ID NO: 19) is typically indicative of zinc finger domains that bind to a DNA. Therefore, one can determine whether a particular zinc finger-nucleotide binding polypeptide preferably binds to DNA or RNA by examination of the linker amino acids.

c. Synthetic Zinc Fingers

Synthetic zinc fingers can be assembled based upon known sequence specificities. A large number of zinc finger-nucleotide binding polypeptides were made and tested for binding specificity against target nucleotides containing a GNN triplet. The data show that a striking conservation of all three of the primary DNA contact positions (−1, 3, and 6) was observed for virtually all the clones of a given target (see, Example 1, see, also U.S. application Ser. No. 09/173,941, filed 16 Oct., 1998, published as International PCT application No. WO 00/23464).

In order to select a family of zinc finger domains recognizing the 5'-GNN-3' subset of sequences, two highly diverse zinc finger libraries were constructed in the phage display vector pComb3H (Barbas et al. (1991) *Proc. Natl. Acad. Sci. USA* 88:7978-7982; Rader et al. (1997) *Curr. Opin. Biotechnol.* 8:503-508). Both libraries involved randomization of residues within the α-helix of finger 2 of C7, a variant of Zif268 (Wu et al. (1995) *Proc. Natl. Acad. Sci. U.S.A.* 92:344-348). Library 1 was constructed by randomization of positions −1,1,2,3,5,6 using a NNK doping strategy while library 2 was constructed using a VNS doping strategy with randomization of positions −2,−1,1,2,3,5,6. The NNK doping strategy allows for all amino acid combinations within 32 codons while VNS precludes Tyr, Phe, Cys and all stop codons in its 24 codon set. The libraries contained $4.4\times10^9$ and $3.5\times10^9$ members, respectively, each capable of recognizing sequences of the 5'-GCGNNNGCG-3' type. The size of the NNK library ensured that it could be surveyed with 99% confidence while the VNS library was highly diverse but somewhat incomplete. These libraries are, however, significantly larger than previously reported zinc finger libraries (International PCT application No. WO 09/54311; Choo et al. (1994) *Proc Natl Acad Sci U S A* 91:11163-7; Greisman et al. (1997) *Science* 275:657-661; Rebar et al. (1994) *Science* 263:671-673; Jamieson et al. (1994) *Biochemistry* 33:5689-5695; Jamieson et al. 1996) *Proc. Natl. Acad. Sci. U.S.A.* 93:12834-12839; Isalan et al. (1998) *Biochemistry* 37:12026-12033; and U.S. Pat. No. 5,789,538). Seven rounds of selection were performed on the zinc finger displaying-phage with each of the 16 5'-GCGGNNGCG-3' biotinylated hairpin DNAs targets using a solution binding protocol. Stringency was increased in each round by the addition of competitor DNA. Sheared herring sperm DNA was provided for selection against phage that bound non-specifically to DNA. Stringent selective pressure for sequence specificity was obtained by providing DNAs of the 5'-GCGNNNGCG-3' types as specific competitors. Excess DNA of the 5'-GCGGNNGCG-3' type was added to provide even more stringent selection against binding to DNAs with single or double base changes as compared to the biotinylated target. Phage binding to the single biotinylated DNA target sequence were recovered using streptavidin coated beads. In some cases the selection process was repeated. The data show that these domains are functionally modular and can be recombined with one another to create proteins capable of binding to 18-bp sequences with subnanomolar affinity. The resulting family of zinc finger domains described herein is sufficient for the construction of 17 million proteins that bind to the 5'-$(GNN)_6$-3' family of DNA sequences.

Also impressive amino acid conservation was been observed for recognition of the same nucleotide in different targets. For example, Asn in position 3 (Asn3) virtually always selects to recognize adenine in the middle position, whether in the context of GAG, GAA, GAT, or GAC. Gln-1 and Arg-1 were always selected to recognize adenine or guanine, respectively, in the 3' position regardless of context. Amide side chain based recognition of adenine by Gln or Asn is well documented in structural studies as is the Arg guanidinium side chain to guanine contact with a 3' or 5' guanine (see, e.g., Elrod-Erickson et al. (1998) *Structure* 6:451-464).

More often, however, two or three amino acids are selected for nucleotide recognition. His3 or Lys3 (and to a lesser extent, Gly3) are selected for the recognition of a middle guanine. Ser3 and Ala3 are selected to recognize a middle thymine. Thr3, Asp3, and Glu3 are selected to recognize a middle cytosine. Asp and Glu are selected in position −1 to recognize a 3' cytosine, while Thr-1 and Ser-1 are selected to recognize a 3' thymine.

Specific recognition of many nucleotides can best accomplished using motifs, rather than a single amino acid. For example, the best specification of a 3' guanine is achieved using the combination of Arg-1, Ser1, and Asp2 (the RSD motif). By using Val5 and Arg6 to specify a 5' guanine, recognition of subsites GGG, GAG, GTG, and GCG can be accomplished using a common helix structure (SRSD-X-LVR) differing only in the position 3 residue (Lys3 for GGG, Asn3 for GAG, Glu3 for GTG, and Asp3 for GCG). Similarly, 3' thymine is specified using Thr-1, Ser1, and Gly2 in the final clones(the TSG motif). Further, a 3' cytosine can be specified using Asp-1, Pro1, and Gly2 (the DPG motif) except when the subsite is GCC; Pro1 is not tolerated by this subsite. Specification of a 3' adenine is with Gln-1, Ser1, Ser2 in two clones (QSS motif).

The data (see, Table 1 in Example) show that all possible GNN triplet sequences can be recognized with exquisite specificity by zinc finger domains. Optimized zinc finger domains can discriminate single base differences by greater than 100-fold loss in affinity. While many of the amino acids found in the optimized proteins at the key contact positions −1,3, and 6 are those that are consistent with a simple code of recognition, it has been discovered that optimal specific recognition is sensitive to the context in which these residues are presented. Residues at positions 1,2, and 5 have been found to be critical for specific recognition.

Further the data demonstrate that sequence motifs at positions −1,1, and 2 rather than the simple identity of the position 1 residue are required for highly specific recognition of the 3' base. These residues likely provide the proper stereo-chemical context for interactions of the helix in terms of recognition of specific bases and in the exclusion of other bases, the net result being highly specific interactions. Ready recombination of the disclosed domains then allows for the creation of proteins, typically polydactyl proteins, of defined specificity precluding the need to develop phage display libraries in their generation. Such family of zinc finger domains is sufficient for the construction of 16 or 17 million proteins that bind to the 5'-$(GNN)_6$-3' family of DNA sequences.

d. Modification of Zinc Finger Peptides

The zinc finger-nucleotide binding peptide domain can be derived or produced from a wild type zinc finger protein by truncation or expansion, or as a variant of the wild type-derived polypeptide by a process of site directed mutagenesis, or by a combination of the procedures (see, e.g., U.S. Pat. No. 5,789,538, which describes methods for design and construction of zinc finger peptides). Mutagenesis can be performed to replace non-conserved residues in one or more of the repeats of the consensus sequence. Truncated zinc finger-nucleotide binding proteins can also be mutagenized.

DNA encoding the zinc finger-nucleotide binding proteins, including native, truncated, and expanded polypeptides, can be obtained by several methods. For example, the DNA can be isolated using hybridization procedures which are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA can be obtained by methods known in the art (seem e.g., *Current Protocols in Molecular Biology,* 1988, Ed. Ausubel, et al., Greene Publish. Assoc. & Wiley lnterscience).

DNA encoding zinc finger-nucleotide binding proteins also can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods the isolation of genomic DNA is the least common. This is especially true when it is desirable to obtain the microbial expression of mammalian polypeptides due to the presence of introns.

For obtaining zinc finger derived-DNA binding polypeptides, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucleic Acid Research,* 11:2325, 1983).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981; Maniatis, et al., *Molecular Cloning: A Laboratory Manual,* Cold Spring Harbor Laboratory, 1982).

Screening procedures that rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

A cDNA expression library, such as lambda gt11, can be screened indirectly for zinc finger-nucleotide binding protein or for the zinc finger derived polypeptide having at least one epitope, using antibodies specific for the zinc finger-nucleotide binding protein. Such antibodies can be either polyclonally or monoclonally derived and used to detect expression product indicative of the presence of zinc finger-nucleotide binding protein cDNA. Alternatively, binding of the derived polypeptides to DNA targets can be assayed by incorporated radiolabeled DNA into the target site and testing for retardation of electrophoretic mobility as compared with unbound target site.

A preferred vector used for identification of truncated and/or mutagenized zinc finger-nucleotide binding polypeptides is a recombinant DNA molecule containing a nucleotide sequence that codes for and is capable of expressing a fusion polypeptide containing, in the direction of amino- to carboxy-terminus, (1) a prokaryotic secretion signal domain, (2) a heterologous polypeptide, and (3) a filamentous phage membrane anchor domain. The vector includes DNA expression control sequences for expressing the fusion polypeptide, preferably prokaryotic control sequences.

Since the DNA sequences provided herein encode essentially all or part of an zinc finger-nucleotide binding protein, it is routine to prepare, subclone, and express the truncated polypeptide fragments of DNA from this or corresponding DNA sequences. Alternatively, by using the DNA fragments disclosed herein, which define the zinc finger-nucleotide binding polypeptides, it is possible, in conjunction with known techniques, to determine the DNA sequences encoding the entire zinc finger-nucleotide binding protein. Such techniques are described in U.S. Pat. No. 4,394,443 and U.S. Pat. No. 4,446,235, which are incorporated herein by reference.

In addition to modifications in the amino acids making up the zinc finger, the zinc finger derived polypeptide can contain more or less than the full amount of fingers contained in the wild type protein from which it is derived. Minor modifications of the primary amino acid sequence may result in proteins which have substantially equivalent activity compared to the zinc finger derived-binding protein described herein. Such modifications may be deliberate, as by site-directed mutagenesis, or may be spontaneous. All proteins produced by these modifications are included herein as long as zinc finger-nucleotide binding protein activity exists.

e. Screening of Variant Zinc Finger and Other DBD Peptides

Any method known to those of skill in the art for identification of functional modular domains derived from zinc fingers and combinations thereof can be employed. An exemplary method for identifying variants of zinc fingers or other polypeptides that bind to zinc finger binding motifs is provided. Components used in the method include a nucleic acid molecule encoding a putative or modified zinc finger peptide operably linked to a first inducible promoter and a reporter gene operably linked to a second inducible promoter and a zinc finger-nucleotide binding motif, wherein the incubating is carried out under conditions sufficient to allow the components to interact, and measuring the affect of the putative DBD peptide on the expression of the reporter gene is provided.

For example, a first inducible promoter, such as the arabinose promoter, is operably linked to the nucleotide sequence encoding the putative DBD polypeptide. A second inducible promoter, such as the lactose promoter, is operably linked to a zinc finger derived-DNA binding motif followed by a reporter gene, such as β-galactosidase. Incubation of the components may be in vitro or in vivo. In vivo incubation may include prokaryotic or eukaryotic systems, such as *E.coli* or COS cells, respectively. Conditions that allow the assay to proceed include incubation in the presence of a substance, such as arabinose and lactose, which activate the first and second inducible promoters, respectively, thereby allowing expression of the nucleotide sequence encoding the putative trans-modulating protein nucleotide sequence. Determination of whether the putative modulating protein binds to the zinc finger-nucleotide binding motif, which is operably linked to the second inducible promoter, and affects its activity is measured by the expression of the reporter gene. For example, if the reporter gene is β-galactosidase, the presence of blue or white plaques indicates whether the putative modulating protein enhances or inhibits, respectively, gene expression from the promoter. Other commonly used assays to assess the function from a promoter, including chloramphenicol acetyl transferase (CAT) assay, are known to those of skill in the art. Prokaryote and eukaryote systems can be used.

As discussed above, Example 1 provides an illustration of modification of Zif268 as described above. Therefore, in another embodiment, a ligand activated transcriptional regulator polypeptide variant containing at least two zinc finger modules that bind to an HIV sequence and modulates the function of the HIV sequence, for example, the HIV promoter sequence is provided.

In another embodiment, zinc finger proteins can be manipulated to recognize and bind to extended target sequences. For example, zinc finger proteins containing from about 2 to 20 zinc fingers Zif(2) to Zif(20), and preferably from about 2 to 12 zinc fingers, may be fused to the leucine zipper domains of the Jun/Fos proteins, prototypical members of the bZIP family of proteins (O'Shea et al. (1991) *Science* 254:539). Alternatively, zinc finger proteins can be fused to other proteins which are capable of forming heterodimers and contain dimerization domains. Such proteins are known to those of skill in the art.

The Jun/Fos leucine zippers are described for illustrative purposes and preferentially form heterodimers and allow for the recognition of 12 to 72 base pairs. Henceforth, Jun/Fos refer to the leucine zipper domains of these proteins. Zinc finger proteins are fused to Jun, and independently to Fos by methods commonly used in the art to link proteins. Following purification, the Zif-Jun and Zif-Fos constructs, the proteins are mixed to spontaneously form a Zif-Jun/Zif-Fos heterodimer. Alternatively, coexpression of the genes encoding these proteins results in the formation of Zif-Jun/Zif-Fos heterodimers in vivo. Fusion of the heterodimer with an N-terminal nuclear localization signal allows for targeting of expression to the nucleus (Kalderon, et al, *Cell,* 39:499-509, 1984). Activation domains may also be incorporated into one or each of the leucine zipper fusion constructs to produce activators of transcription (Sadowski et al. (1992) *Gene* 118: 137). These dimeric constructs then allow for specific activation or repression of transcription. These heterodimeric Zif constructs are advantageous since they allow for recognition of palindromic sequences (if the fingers on Jun and Fos recognize the same DNA/RNA sequence) or extended asymmetric sequences (if the fingers on Jun and Fos recognize different DNA/RNA sequences). For example the palindromic sequence 5'-GGC CCA CGC $\{N\}_x$ GCG TGG GCG-3' (SEQ ID NO:20)

3'-GCG GGT GCG $\{N\}_x$ CGC ACC CGC-5' is recognized by the Zif268-Fos/Zif268 Jun dimer (x is any number). The spacing between subsites is determined by the site of fusion of Zif with the Jun or Fos zipper domains and the length of the linker between the Zif and zipper domains. Subsite spacing is determined by a binding site selection method as is common to those skilled in the art (Thiesen et al. (1990) *Nucleic Acids Research,* 18:3203, 1990). Example of the recognition of an extended asymmetric sequence is shown by the Zif(C7)$_6$-Jun/Zif-268-Fos dimer. This protein includes 6 fingers of the C7 type (EXAMPLE 11) linked to Jun and three fingers of Zif268 linked to Fos, and recognizes the extended sequence:

(SEQ ID NO:21)

5'-CGC CGC CGC CGC CGC CGC $\{N\}_x$ GCG TGG GCG-3'

3'-GCG GCG GCG GCG GCG GCG $\{N\}_x$ CGC ACC CGC-5'

In another embodiment, attachment of chelating groups to Zif proteins is preferably facilitated by the incorporation of a Cysteine (Cys) residue between the initial Methionine (Met) and the first Tyrosine (Tyr) of the protein. The Cys is then alkylated with chelators known to those skilled in the art, for example, EDTA derivatives as described (Sigman (1990) *Biochemistry,* 29:9097). Alternatively the sequence Gly-Gly-His can be made as the most amino terminal residues since an amino terminus composed of the residues has been described to chelate $Cu^{+2}$ (Mack et al. (1988) *J. Am. Chem. Soc.* 110: 7572). Preferred metal ions include $Cu^{+2}$, $Ce^{+3}$ (Takasaki and Chin (1994) *J. Am. Chem. Soc.* 116:1121, 1994) $Zn^{+2}$, $Cd^{+2}$, $Pb^{+2}$, $Fe^{+2}$ (Schnaith et al. (1994) *Proc. Natl. Acad. Sci., USA* 91:569, 1994), $Fe^{+3}$, $Ni^{+2}$, $Ni^{+3}$, $La^{+3}$, $Eu^{+3}$ (Hall et al. (1994) *Chemistry and Biology* 1:185), $Gd^{+3}$, $Tb^{+3}$, $Lu^{+3}$, $Mn^{+2}$, $Mg^{+2}$. Cleavage with chelated metals is generally performed in the presence of oxidizing agents such as $O_2$, hydrogen peroxide $H_2O_2$ and reducing agents such as thiols and ascorbate. The site and strand (+ or − site) of cleavage is determined empirically (Mack et al. (1988) *J. Am. Chem. Soc* 110:7572, 1988) and is dependent on the position of the Cys between the Met and the Tyr preceding the first finger. In the protein Met (AA) Tyr-(Zif)$_{1-12}$, the chelate becomes Met-(AA)$_{x1}$ Cys-Chelate-(AA)$_{x2}$-Tyr-(Zif)$_{1-12}$, where AA=any amino acid and x=the number of amino acids. Dimeric zif constructs of the type Zif-Jun/Zif-Fos are preferred for cleavage at two sites within the target oligonucleotide or at a single long target site.

In the case where double stranded cleavage is desired, Jun and Fos containing proteins are labelled with chelators and cleavage is performed by methods known to those skilled in the art. In this case, a staggered double-stranded cut analogous to that produced by restriction enzymes is generated.

Following mutagenesis and selection of variants of the Zif268 protein in which the finger 1 specificity or affinity is modified, proteins carrying multiple copies of the finger may be constructed using the TGEKP linker sequence by methods known in the art. For example, the C7 finger may be constructed according to the scheme: MKLLEPYACPVESCDRRFSKSADLKRHIRHTGEKP- (SEQ ID NO: 22) (YACPVESCDRRFSKSADLKHIRIHTGEKP)$_{1-11}$, (SEQ ID NO: 23) where the sequence of the last linker is subject to change since it is at the terminus and not involved in linking two fingers together. This protein binds the designed target sequence GCG-GCG-GCG in the oligonucleotide hairpin CCT-CGC-CGC-CGC-GGG-TTT-TCC-CGC-GCC-CCC GAG G (SEQ ID NO: 24) with an affinity of 9 nM, as compared to an affinity of 300 nM for an oligonucleotide encoding the GCG-TGG-GCG sequence (as determined by surface plasmon resonance studies). Fingers used need not be identical and may be mixed and matched to produce proteins which recognize a desired target sequence. These may also be used with leucine zippers (e.g., Fos/Jun) or other heterodimers to produce proteins with extended sequence recognition.

In addition to producing polymers of finger 1, the entire three finger Zif268 and modified versions therein may be fused using the consensus linker TGEKP to produce proteins with extended recognition sites. For example, the protein Zif268-Zif268 can be produced in which the natural protein has been fused to itself using the TGEKP linker. This protein now binds the sequence GCG-TGG-GCG-GCG-TGG-GCG. Therefore modifications within the three fingers of Zif268 or other zinc finger proteins known in the art may be fused together to form a protein which recognizes extended sequences. These new zinc proteins may also be used in combination with leucine zippers if desired.

3. Transcription Regulating Domain (TRD)

Any TRD known to those of skill in the art can be selected, including those present in intracellular receptors. The TRD is selected to regulate transcription of the gene targeted by the DBD and to effect regulation of expression thereof. The TRD can be selected to regulate expression of an endogenous gene in a cell or in an exogenously added construct. For exogenously added genes, the regulatory region of the gene can be selected to interact with a desired TRD. Identification, preparation and testing of TRDs in combination with DBDs is exemplified herein for ERB-2 and integrin $\beta_3$.

a. Selection of the TRD

Transcription regulating domains are well known in the art. Exemplary and preferred transcription repressor domains are ERD, KRAB, SID, Deacetylase, and derivatives, multimers and combinations thereof such as KRAB-ERD, SID-ERD, $(KRAB)_2$, $(KRAB)_3$, KRAB-A, $(KRAB-A)_2$, $(SID)_2$ (KRAB-A)-SID and SID-(KRAB-A).

b. Repressors

Transcriptional repressors are well known in the art, and any such repressor can be used herein. The repressor is a polypeptide that is operatively linked to the nucleic acid binding domain as set forth above. The repressor is operatively linked to the binding domain in that it is attached to the binding domain in such a manner that, when bound to a target nucleotide via that binding domain, the repressor acts to inhibit or prevent transcription. The repressor domain can be linked to the binding domain using any linking procedure well known in the art. It may be necessary to include a linker moiety between the two domains. Such a linker moiety is typically a short sequence of amino acid residues that provides spacing between the domains. So long as the linker does not interfere with any of the functions of the binding or repressor domains, any sequence can be used.

Transcriptional repressors have been generated by attaching either of three human-derived repressor domains to the zinc finger protein. The first repressor protein was prepared using the ERF repressor domain (ERD) (Sgouras et al. (1995) *EMBO J.* 14:4781-4793), defined by amino acids 473 to 530 of the ets2 repressor factor (ERF). This domain mediates the antagonistic effect of ERF on the activity of transcription factors of the ets family. A synthetic repressor was constructed by fusion of this domain to the C-terminus of the zinc finger protein.

The second repressor protein was prepared using the Krüppel-associated box (KRAB) domain (Margolin et al. (1994) *Proc. Natl. Acad. Sci. USA* 91:4509-4513). This repressor domain is commonly found at the N-terminus of zinc finger proteins and presumably exerts its repressive activity on TATA-dependent transcription in a distance- and orientation-independent manner (Pengue et al. (1996) *Proc. Natl. Acad. Sci. USA* 93:1015-1020), by interacting with the RING finger protein KAP-1(Friedman et al. (1996) *Genes & Dev.* 10:2067-2078). The KRAB domain found between amino acids 1 and 97 of the zinc finger protein KOX1 (Margolin et al. (1994) *Proc. Natl. Acad. Sci. USA* 91:4509-4513) was used. In this case an N-terminal fusion with the six-finger protein was constructed.

Histone deacetylation as a means for repression can be employed. For example, amino acids 1 to 36 of the Mad mSIN3 interaction domain (SID) have been fused to the N-terminus of a zinc finger protein (Ayer et al. (1996) *Mol. Cell. Biol.* 16:5772-5781). This small domain is found at the N-terminus of the transcription factor Mad and is responsible for mediating its transcriptional repression by interacting with mSIN3, which in turn interacts the co-repressor N-CoR and with the histone deacetylase mRPD1 (Heinzel et al. (1997) *Nature* 387:43-46).

c. Activators

Exemplary and preferred transcription activation domains include any protein or factor that regulates transcription. Exemplary transcriptional regulation domains include, but are not limited to, VP16, TA2, VP64, STAT6 and relA.

4. Exemplary Construct Based on Human Integrin β3 and erbB-2 Target Sequences

To exemplify the generation of zinc finger modular domains and peptides containing one or more of such domains to produce peptides with DNA binding specificity and therapeutic potential, target sequences have been identified based on human integrin β3 and erbB-2 (Ishii et al. (1987) *Proc. Natl. Acad. Sci. U.S.A.* 84:4374-4378) genomic sequences.

Integrin β3 as a Target for Cancer Gene Therapy

Integrin $\alpha_v\beta3$ is the most promiscuous member of the integrin family and has been identified as a marker of angiogenic vascular tissue. For instance, integrin $\alpha_v\beta3$ shows enhanced expression on blood vessels in human wound granulation tissue but not in normal skin. Following the induction of angiogenesis, blood vessels show a four-fold increase in $\alpha_v\beta3$ expression compared to blood vessels not undergoing this process. It has been reported that a cyclic peptide or monoclonal antibody antagonist of integrin $\alpha_v\beta3$ blocks cytokine- or tumor-induced angiogenesis on the chick chorioallantoic membrane. Therefore, inhibition of integrin $\alpha_v\beta3$ expression provides an approach to block tumor-induced angiogenesis.

ErbB-2 Receptor Tyrosine Kinases as a Target for Cancer Gene Therapy

Members of the ErbB receptor family play an important role in the development of human malignancies. In particular, ErbB-2 is overexpressed as a result of gene amplification and/or transcriptional deregulation in a high percentage of human adenocarcinomas arising at numerous sites, including breast, ovary, lung, stomach, and salivary gland. Increased expression of ErbB-2 per se leads to constitutive activation of its intrinsic tyrosine kinase. Many clinical studies have shown that patients with tumors showing elevated expression of ErbB-2 have poorer prognosis. Thus, the high occurrence of its aberrant expression in human cancer, as well as the aggressive behavior of overexpressing tumors, make ErbB-2 an attractive target for therapy.

Generation and construction of zinc fingers and fusion proteins targeted to erbB-2 and integrin $\beta_3$ are described in the EXAMPLES.

B. Regulatable Cassette

In embodiments in which the targeted gene is an exogenous gene, particularly a gene that encodes a therapeutic product, the gene is provided as in an expression cassette operatively linked to a promoter and regulatory region with which the fusion protein specifically interacts. The cassette includes at least one polynucleotide domain recognized by the corresponding zinc finger domain present in the fusion protein and a suitable promoter to direct transcription of the exogenous gene. Typically, the regulatable expression cassette contains three to six response elements and interacts with nucleic acid binding domain of the ligand activated transcriptional regulatory fusion protein.

Typically the exogenous gene encodes a therapeutic product, such as a growth factor, that can supplement peptides, polypeptides or proteins encoded by endogenous expressed genes, thereby providing an effective therapy. In several embodiments the gene encodes a suitable reporter molecule that can be detected by suitable direct or indirect means. The cassette can be inserted into a suitable delivery vehicle for introduction into cells. Such vehicles include, but are not limited to, human adenovirus vectors, adeno-associated vectors, murine or lenti virus derived retroviral vectors, and a variety of non-viral compositions including liposomes, polymers, and other DNA containing conjugates.

C. Use of the Fusion Proteins for Gene Regulation

1. Delivery of the Nucleic Acids

There are available to one skilled in the art multiple viral and non-viral methods suitable for introduction of a nucleic acid molecule into a target cell. Genetic modification of a cell may be accomplished using one or more techniques well known in the gene therapy field (*Human Gene Therapy*, April 1994, Vol. 5, p. 543-563; Mulligan, R. C. 1993).

The ability to regulate transgene expression, as defined in the examples herein, can be applied to a wide variety of applications for gene therapy. The ability to control expression of an exogenously introduced transgene is important for the safety and efficacy of most or all envisioned cell and gene therapies. Control of transgene expression can be used to accomplish regulation of a therapeutic protein level, ablation of a desired cell population, either the vector containing cells or others, or activation of a recombinase or other function resulting in control of vector function within the transduced cells. Further, such control permits termination of a gene therapy treatment if necessary.

A number of vector systems useful for gene therapy have been described previously in this application. Vectors for gene therapy include any known to those of skill in the art, and include any vectors derived from animal viruses and artificial chromosomes. The vectors may be designed for integration into the host cell's chromosomes or to remain as extrachromosomal elements. Such vectors include, but are not limited to human adenovirus vectors, adeno-associated viral vectors, retroviral vectors, such as murine retroviral vectors and lentivirus-derived retroviral vectors. Also contemplated herein are any of the variety of non-viral compositions for targeting and/or delivery of genetic material, including, but are not limited to, liposomes, polymers, and other DNA containing compositions, and targeted conjugates, such as nucleic acids linked to antibodies and growth factors. Any delivery system is intended for use of delivery of the nucleic acid constructs encoding the fusion polypeptide and also targeted exogenous genes. Such vector systems can be used to deliver the ZFP-LBD fusion proteins and the inducible transgene cassette either in vitro or in vivo, depending on the vector system. With adenovirus, for instance, vectors can be administered intravenously to transduce the liver and other organs, introduced directly into the lung, or into vascular compartments temporarily localized by ligation or other methods. Methods for constructing such vectors, and methods and uses thereof are known to those skilled in the field of gene therapy.

In one embodiment, one vector encodes the fusion protein regulator and a second vector encodes the inducible transgene cassette. Vectors can be mixed or delivered sequentially to incorporate into cells the regulator and transgene at the appropriate amounts. Subsequent administration of and effective amount of the ligand by standard routes would result in activation of the transgene.

In another embodiment, the nucleic acid encoding the fusion protein and the inducible transgene can be included in the same vector construction. In this instance, the nucleic acid encoding the fusion protein would be positioned within the vector and expressed from a promoter in such a way that it did not interfere with the basal expression and inducibilty of the transgene cassette. Further, the use of cell or tissue specific promoters to express the fusion protein confers an additional level of specificity on the system. Dual component vectors and use for gene therapy are known (see, e.g., Burcin et al. (1999) *Proc. Natl. Acad. Sci. USA* 96: 335-360, which describes an adenovirus vector fully deleted of viral backbone genes).

In another embodiment, gene therapy can be accomplished using a combination of the vectors described above. For example, a retroviral vector can deliver a stably integrated, inducible transgene cassette into a population of cells either in vitro (ex vivo) or in vivo. Subsequently, the integrated transgene can be activated by transducing this same cell population with a second vector, such as an adenovirus vector capable of expressing the fusion protein, followed by the administration of the specific ligand inducing agent. This is particularly useful where "one time" activation of the transgene is desired, for example as a cellular suicide mechanism. An example of this application is the stable integration of an inducible transgene cassette containing the herpes simplex virus thymidine kinase gene (HSV Tk). Subsequent activation of this gene confers sensitivity to ganciclovir and allows ablation of this modified cell.

a. Viral Delivery Systems

Viral transduction methods for delivering nucleic acid constructs to cells are contemplated herein. Suitable DNA viral vectors for use herein includes, but are not limited to an adenovirus (Ad), adeno-associated virus (AAV), herpes virus, vaccinia virus or a polio virus. A suitable RNA virus for use herein includes but is not limited to a retrovirus or Sindbis virus. It is to be understood by those skilled in the art that several such DNA and RNA viruses exist that may be suitable for use herein. Adenoviral vectors have proven especially useful for gene transfer into eukaryotic cells and are widely available to one skilled in the art and is suitable for use herein.

Adeno-associated virus (AAV) has recently been introduced as a gene transfer system with potential applications in gene therapy. Wild-type AAV demonstrates high-level infectivity, broad host range and specificity in integrating into the host cell genome. Herpes simplex virus type-1 (HSV-1) vectors are available and are especially useful in the nervous system because of its neurotropic property. Vaccinia viruses, of the poxvirus family, have also been developed as expression vectors. Each of the above-described vectors is widely available and is suitable for use herein.

Retroviral vectors are capable of infecting a large percentage of the target cells and integrating into the cell genome. Preferred retroviruses include lentiviruses, such as but are not limited to, HIV, BIV and SIV.

Various viral vectors that can be used for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector is made target specific. Retroviral vectors can be made target specific by inserting, for example, a polynucleotide encoding a protein. Preferred targeting is accomplished by using an antibody to target the retroviral vector. Those of skill in the art know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

b. Nonviral Delivery Systems

"Non-viral" delivery techniques for gene therapy include DNA-ligand complexes, adenovirus-ligand-DNA complexes, direct injection of DNA, $CaPO_4$ precipitation, gene gun techniques, electroporation, liposomes and lipofection. Any of these methods are available to one skilled in the art and would be suitable for use herein. Other suitable methods are available to one skilled in the art, and it is to be understood that the methods herein may be accomplished using any of the available methods of transfection.

Another targeted delivery system is a colloidal dispersion system. Colloidal dispersion systems include macromolecule complexes, nanocapsules, microspheres, beads, and lipid-based systems including oil-in-water emulsions, micelles, mixed micelles, and liposomes, which are preferred. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981).

Lipofection may be accomplished by encapsulating an isolated nucleic acid molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as provide herein, an isolated nucleic acid molecule.

Liposomes have been used for delivery of polynucleotides in plant, yeast and bacterial cells as well as mammalian cells. In order for a liposome to be an efficient gene transfer vehicle, characteristics among the following should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting uses the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system are ligands and receptors permitting the targeted delivery system to find and "home in" on the desired cells. A ligand may be any compound of interest that interacts with another compound, such as a receptor.

In general, surface membrane proteins that bind to specific effector molecules are referred to as receptors. Antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting antibody-zinc finger-nucleotide binding protein-containing liposomes directly to the malignant tumor. Since the zinc finger-nucleotide binding protein gene product may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or $F(ab')_2$, as long as they bind efficiently to an the antigenic epitope on the target cells. Liposomes may also be targeted to cells expressing receptors for hormones or other serum factors.

2. Administration a. Delivery of Constructs to Cells

The cells may be transfected in vivo, ex vivo or in vitro. The cells may be transfected as primary cells isolated from a patient or a cell line derived from primary cells, and are not necessarily autologous to the patient to whom the cells are ultimately administered. Following ex vivo or in vitro transfection, the cells may be implanted into a host. Genetic modification of the cells may be accomplished using one or more techniques well known in the gene therapy field (see, e.g., (1994) *Human Gene Therapy* 5:543-563).

Administration of nucleic acid molecules provided herein to a target cell in vivo may be accomplished using any of a variety of techniques well known to those skilled in the art. The vectors of the methods herein may be administered orally, parentally, by inhalation spray, rectally, or topically in dosage unit formulations containing conventional pharmaceutically acceptable carriers, adjuvants, and vehicles. Suppositories for rectal administration of the drug can be prepared by mixing the drug with a suitable non-irritating excipient such as cocoa butter and polyethylene glycols that are solid at ordinary temperatures but liquid at the rectal temperature and therefore melt in the rectum and release the drug.

The dosage regimen for treating a disorder or a disease with the vectors and/or compositions provided is based on a variety of factors, including the type of disease, the age, weight, sex, medical condition of the patient, the severity of the condition, the route of administration, and the particular compound employed. Thus, the dosage regimen may vary widely, but can be determined empirically using standard methods.

The pharmaceutically active compounds (i.e., vectors) can be processed in accordance with conventional methods of pharmacy to produce medicinal agents for administration to patients, including humans and other mammals. For oral administration, the pharmaceutical composition may be in the form of, for example, a capsule, a tablet, a suspension, or liquid. The pharmaceutical composition is preferably made in the form of a dosage unit containing a given amount of DNA or viral vector particles (collectively referred to as "vector"). For example, these may contain an amount of vector from about $10^3$-$10^{15}$ viral vector particles, preferably from about $10^6$-$10^{12}$ viral particles. A suitable daily dose for a human or other mammal may vary widely depending on the condition of the patient and other factors, but, once again, can be determined using routine methods. The vector may also be administered by injection as a composition with suitable carriers including saline, dextrose, or water.

While the nucleic acids and/or vectors herein can be administered as the sole active pharmaceutical agent, they can also be used in combination with one or more vectors or other agents. When administered as a combination, the therapeutic agents can be formulated as separate compositions that are given at the same time or different times, or the therapeutic agents can be given as a single composition.

b. Deliver Ligand

Ligands similarly may be delivered by any suitable mode of administration, including by oral, parenteral, intravenous, intramuscular and other known routes. Any known pharmaceutical formulations is contemplated.

3. Ligands

As noted, the ligands may be naturally-occurring ligands, but are preferentially non-natural ligands with which the LBD is modified to specifically interact. Methods for modifying the LBD are known, as are methods for screening for such ligands.

Ligands include, non-natural ligands, hormones, anti-hormones, synthetic hormones, and other such compounds. Examples of non-natural ligands, anti-hormones and non-native ligands include, but are not limited to, the following: 11β-4-dimethylaminophenyl)-17α-hydroxy-17α-propinyl-4,9-estradiene-3-one (RU38486 or Mifepestone); 11β-(4-dimethylaminophenyl)-17α-hydroxy-17β-(3-hydroxypropyl)-13α-methyl-4,9-gonadiene-3-one (ZK98299 or Onapristone); 11β-(4-acetylphenyl)-17β-hydroxy-17α-(1 -propinyl)-4,9-estradiene-3-one (ZK112993); 11β-(4-dimethylaminophenyl)-17β-hydroxy-17α-(3-hydroxy-1 (Z) -propenyl-estra-4,9-diene-3-one (ZK98734); (7β11β, 17β)-11-(4-dimethylaminophenyl)-7-methyl-4',5'-dihydrospiroy'ester-4,9-diene-17,2' (3'H) -furan!-3-one (Org31806); (11β, 14β, 17α)-4',5'-dihydro-11-(4-dimethylamino -phenyl)y'spi roestra-4,9-diene-17,2'(3'H)-furan !-3-one (Org31376); 5-alpha -pregnane-3,2-dione. Additional non-natural ligands include, in general, synthetic non-steroidal estrogenic or anti-estrogenic compounds, broadly defined as selective estrogen receptor modulators (SERMS). Exemplary compounds include, but are not limited to, tamoxifen and raloxifen.

4. Pharmaceutical Compositions and Combinations

Also provided is a pharmaceutical composition containing a therapeutically effective amount of the fusion protein, or a nucleic acid molecule encoding the fusion protein in a pharmaceutically acceptable carrier. Pharmaceutical compositions containing one or more fusion proteins with different zinc finger-nucleotide binding domains are contemplated.

Also provided are pharmaceutical compositions containing the expression cassettes, and also compositions containing the ligands. Combinations containing a plurality of compositions are also provided.

Preparation of the Compositions

The preparation of a pharmacological composition that contains active ingredients dissolved or dispersed therein is well known. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Tablets and other solid forms are contemplated.

The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and others.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

D. Methods of Gene Regulation

Methods of regulating expression of endogenous and exogenous genes are provided. In particular, ligand-dependent methods are provided. In practicing the methods, a target nucleic acid molecule containing a sequence that interacts with the nucleic acid binding domain of the fusion protein exposed to an effective amount of the fusion protein in the presence of an effective binding amount of a ligand, which can be added simultaneous with or subsequent to the fusion protein. The nucleic acid binding domain of the fusion protein binds to a portion of the target nucleic acid molecule and the ligand binds to the ligand binding domain of the fusion protein. Exposure can occur in vitro, in situ or in vivo.

The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or “contacting” the cellular nucleotide sequence containing the zinc finger-nucleotide binding protein motif, can be accomplished by one of the mechanisms described herein, such as by retroviral vectors or liposomes, or other methods well known in the art.

In one embodiment, a method for inhibiting or suppressing the function of a cellular gene or regulatory sequence that includes a zinc finger-nucleotide binding motif. This is effected by contacting the zinc finger-nucleotide binding motif with an effective amount of a fusion protein that includes zinc finger-nucleotide binding polypeptide derivative that binds to the motif. In instances in which the cellular nucleotide sequence is a promoter, the method includes inhibiting the transcriptional transactivation of a promoter containing a zinc finger-DNA binding motif. The zinc finger-nucleotide binding polypeptide derivative may bind to a motif within a structural gene or within an RNA sequence.

Treatments

Methods for gene therapy are provided. The fusion proteins are administered either as a protein or as a nucleic acid encoding the protein and delivered to cells or tissues in a mammal, such as a human. The fusion protein is targeted either to a specific sequence in the genome (an endogenous gene) or to an exogenously added gene, which is administered as part of an expression cassette. Prior to, simultaneous with or subsequent to administration of the fusion protein, a ligand that specifically interacts with the LBD in the fusion protein is administered. In embodiments, in which the targeted gene is exogenous, the expression cassette, which can be present in a vector, is administered, simultaneous with or subsequent to administration of the fusion protein. These methods are intended for treatment of any genetic disease, for treatment of acquired disease and any other conditions. Diseases include, cell proliferative disorders, such as cancer. Such therapy achieves its therapeutic effect by introduction of the fusion protein that includes the zinc finger-nucleotide binding polypeptide, either as the fusion protein or encoded by a nucleic acid molecule that is expressed in the cells, into cells of animals having the disorder. Delivery of the fusion protein or nucleic acid molecule can be effected by any method known to those of skill in the art, including methods described herein. For example, it can be effected using a recombinant expression vector such as a chimeric virus or a colloidal dispersion system.

The fusion proteins provided herein can be used for treating a variety of disorders. For example the proteins can be used for treating malignancies of the various organ systems, including but are not limited to, lung, breast, lymphoid, gastrointestinal, and genito-urinary tract adenocarcinomas, and other malignancies such as most colon cancers, renal-cell carcinoma, prostate cancer, non-small cell carcinoma of the lung, cancer of the small intestine, and cancer of the esophagus. A polynucleotide encoding the zinc finger-nucleotide binding polypeptide is also useful in treating non-malignant cell-proliferative diseases such as psoriasis, pemphigus vulgaris, Behcet’s syndrome, and lipid histiocytosis. Essentially, any disorder that is etiologically linked to the activation of a zinc finger-nucleotide binding motif containing promoter, structural gene, or RNA, would be considered susceptible to treatment with a polynucleotide encoding a derivative or variant zinc finger derived-nucleotide binding polypeptide.

The following examples are included for illustrative purposes only and are not intended to limit the scope of the invention.

EXAMPLE 1

Construction and Testing of Designed Specific Zinc Finger Domains

Variant zinc finger proteins have been designed and constructed to selectively bind to specific DNA sequences (Table 1). Table 1, below, summarizes the sequences (SEQ ID NO: 77-92) showing the highest selectivity for the sixteen embodiment of GNN target triplets.

TABLE 1

| Target | Amino acids positions | | | | | | | |
|---|---|---|---|---|---|---|---|---|
| Specificity | −1 | 1 | 2 | 3 | 4 | 5 | 6 | SEQ ID NO: |
| GAA | Q | S | S | N | L | V | R | 77 |
| GAC | D | P | G | N | L | V | R | 78 |
| GAG | R | S | D | N | L | V | R | 79 |
| GAT | T | S | G | N | L | V | R | 80 |
| GCA | Q | S | G | D | L | R | R | 81 |
| GCC | D | C | R | D | L | A | R | 82 |
| GCG | R | S | D | D | L | V | K | 83 |
| GCT | T | S | G | E | L | V | R | 84 |
| GGA | Q | R | A | H | L | E | R | 85 |
| GGC | D | P | G | H | L | V | R | 86 |
| GGG | R | S | D | K | L | V | R | 87 |
| GGT | T | S | G | H | L | V | R | 88 |
| GTA | Q | S | S | S | L | V | R | 89 |
| GTC | D | P | G | A | L | V | R | 90 |
| GTG | R | S | D | E | L | V | R | 91 |
| GTT | T | S | G | S | L | V | R | 92 |

Oligonucleotides for Zinc Finger Library Panning

Biotinylated, hairpin-structured target site oligos for panning of finger 2 ("F2") libraries had the following sequence:

F2XXX:

5'-Biotin-GGA CGC N'N'N' CGC GGG TTTT CCC GCG NNN GCG TCC-3' (SEQ ID NO: 25) where NNN=either of the 16 triplets of the GNN set, or TGA and N'N'N'=its complement.

Non-biotinylated, hairpin structured specific competitor oligos had the following sequence:

F2NNN:

5'-GGA CGC N'N'N' CGC GGG TTTT CCC GCG NNN GCG TCC-3' (SEQ ID NO: 25) where NNN=a mixture of all 64 existing triplets and N'N'N'=its complement.

Panning of Zinc Finger Libraries

Panning of zinc finger phage display libraries was carried out in solution using biotinylated target site hairpin oligos. Seven rounds of panning were carried out as follows: Phage prepared from an overnight culture was allowed to pre-bind to varying amounts of non-biotinylated specific competitor hairpin oligo prior to the addition of the target site oligo. The pre-binding was carried out in 400 μl Zinc buffer A containing 1% Blotto, 5 mM DTT, 4 μg sheared herring sperm DNA and 100 μl phage preparation. Typically, 10 times less specific competitor than target oligo was used for the first round of panning. For the subsequent panning rounds, the amount of specific competitor was gradually increased, up to a maximum of 12 μg in the last panning round(s). Following 30 minutes at room temperature, 100 μl Zinc buffer A containing 0.4 μg biotinylated target hairpin oligo were added. After 2.5 to 3.5 hours at RT, phage bound to the target oligo was collected by the addition of 50 μl Dynabeads M-280 suspension (Dynal) and incubation for one hour at RT. The beads were collected with a magnet, washed 10 times with Zinc buffer A (10 mM Tris, pH 7.5/90 mM KCl/1 mM $MgCl_2$/90 μM $ZnCl_2$) containing 2% Tween-20 and 5 mM DTT, and once with Zinc buffer A containing 5 mM DTT. Phage was eluted for 30 minutes at RT with 25 μl of TBS containing 10 mg/ml trypsin. Following the addition of 75 μl Super Broth, eluted phage was allowed to infect 5 ml of *E. coli* ER2537 culture for 30 minutes in a 37 degrees Celsius shaker. The volume was increased to 10 ml and Carbenicillin was added to a concentration of 20 μg/ml. At this stage, the number of output phage was determined by plating aliquots of the infected bacteria onto Carbenicillin-containing LB-agar plates. After one hour shaking at 37 degrees Celsius, the Carbenicillin concentration was increased to 50 μg/ml. After one more hour shaking at 37 degrees Celsius, $10^{13}$ pfu helper phage was added and the culture was incubated for a few minutes at RT. Then, 90 ml of Super Broth containing Carbenicillin (50 μg/ml) and $ZnCl_2$ (90 μM) were added and the culture was incubated at 37 degrees Celsius for two hours. Upon addition of Kanamycin to a final concentration of 70 μg/ml, the culture was incubated in a 37 degrees Celsius shaker overnight. Phage was purified from culture supernatants by PEG precipitation and resuspended in 2 ml Zinc buffer A containing 1% BSA and 5 mM DTT for further rounds of panning. The number of phage was determined by using various dilutions of the phage prep for infection of *E. coli* ER2537, followed by plating onto Carbenicillin-containing LB-agar plates. Following seven rounds of panning, zinc finger cDNAs were subcloned into the bacterial expression vector pMal-CSS, a derivative of pMal-C2 (New England Biolabs), allowing for expression of the zinc finger proteins as maltose binding protein (MBP) fusions.

Generation of Proteins with Desired DNA Binding Specificity

To generate DNA encoding three-finger proteins, F2 coding regions were PCR amplified from selected or designed F2 variants and assembled by PCR overlap extension. Alternatively, DNAs encoding three-finger proteins with a Zif268 or Sp1C framework were synthesized from 8 or 6 overlapping oligonucleotides, respectively. Sp1C framework constructs were generated as follows.

In the case of E2C-HS1 (Sp1), 0.4 pmole each of oligonucleotides SPE2-3 (5'-GCG AGC AAG GTC GCG GCA GTC ACT AAA AGA TTT GCC GCA CTC TGG GCA TTT ATA CGG TTT TTC ACC-3' (SEQ ID NO: 26) and SPE2-4 (5'GTG ACT GCC GCG ACC TTG CTC GCC ATC AAC GCA CTC ATA CTG GCG AGA AGC CAT ACA AAT GTC CAG AAT GTG GC-3') (SEQ ID NO: 27) were mixed with 40 pmole each of oligonucleotides SPE2-2 (5'-GGT AAG TCC TTC TCT CAG AGC TCT CAC CTG GTG CGC CAC CAG CGT ACC CAC ACG GGT GAA AAA CCG TAT AAA TGC CCA GAG-3') (SEQ ID NO: 28) and SPE2-5 (5'-ACG CAC CAG CTT GTC AGA GCG GCT GAA AGA CTT GCC ACA TTC TGG ACA TTT GTA TGG C-3') (SEQ ID NO:29) in a standard PCR mixture and cycled 25 times (30 seconds at 94 degrees Celsius, 30 seconds at 60 degrees Celsius, 30 seconds at 72 degrees Celsius). An aliquot of this pre-assembly reaction was then amplified with 40 pmole each of the primers SPE2-1 (5'-GAG GAG GAG GAG GTG GCC CAG GCG GCC CTC GAG CCC GGG GAG AAG CCC TAT GCT TGT CCG GAA TGT GGT AAG TCC TTC TCT CAG AGC-3') (SEQ ID NO: 30) and SPE2-6 (5'-GAG GAG GAG GAG CTG GCC GGC CTG GCC ACT AGT TTT TTT ACC GGT GTG AGT ACG TTG GTG ACG CAC CAG CTT GTC AGA GCG-3') (SEQ ID NO: 31) using the same cycling conditions.

The E2C-HS2(Sp1), B3B-HS1(Sp1), B3B-HS2(Sp1), B3C2-HS1 (Sp1), and B3C2-HS2(Sp1) DNAs were generated in the same way, using analogous sets of oligonucleotides differing only in the recognition helix coding regions. All assembled three-finger coding regions were digested with the restriction endonuclease Sfi1 and cloned into pMal-CSS, a derivative of the bacterial expression vector pMal-C2 (New England Biolabs), allowing for expression of the zinc finger proteins as MBP fusions. DNAs encoding six-finger proteins with each of the different frameworks were assembled in pMal-CSS using Xma1 and BsrF1 restriction sites included in the sequences flanking the three-finger coding regions (Beerli et al. (1998) *Proc. Natl. Acad. Sci. U.S.A.* 95:14628-14633).

Preparation of MBP-zinc Finger Fusion Proteins for ELISA Assays

Plasmid pMal constructs containing the zinc-finger coding sequences were transformed into the *E. coli* strain XL1-Blue by electroporation. Three milliliters of Super Broth were inoculated and grown overnight at 37 degrees Celsius. The next day, the cultures were diluted 1:20 in 50 ml conical tubes and grown at 37 degrees Celsius until $OD_{600}$=0.5. IPTG was added to a final concentration of 0.3 mM, and incubation was continued for 2 hours. The cultures were centrifuged for 20 minutes, then the pellets resuspended in 400 μl of Zinc Buffer A containing 5 mM fresh DTT. The samples were then frozen in dry ice/ethanol and thawed in 37 degrees Celsius water 6 times, then finally centrifuged for 30 seconds and left on ice for 30 minutes before use of the supernatants.

ELISA Assays

Streptavidin at a concentration of 0.2 μg/25 μl in PBS was added to each well of a 96 well plate, then incubated for 1 hour at 37 degrees Celsius. The plate was washed 2× with water, then biotinylated oligo at 0.1 μg/25 μl in PBS, or just PBS, was added to the appropriate wells and incubated for 1 hour at 37 degrees Celsius. The plate was washed 2× with water, then each well was filled with 3% BSA in PBS and incubated for 1 hour at 37 degrees Celsius. The BSA was removed without washing, and 25 μl of the appropriate extract diluted in Zinc buffer A containing 5 mM DTT was added to the appropriate wells. The binding reaction was allowed to proceed for 1 hour at room temperature. The plate was washed 8× with water, then α-MBP mAb in Zinc buffer A and 1% BSA was added to the wells followed by incubation for 30 minutes at room temperature. The plate was washed 8× with water, then anti-mouse mAb conjugated to alkaline phosphatase in Zinc buffer A was added, and the plate was incubated for 30 minutes at room temperature. After 8 final washes with water, 25 μl of alkaline phosphatase substrate and developer was added to each well. Incubation was performed at room temperature, and the $OD_{405}$ of each well was determined at 30 minute and 1 hour time points.

Construction of Zinc Finger-transcription Regulating Domain Fusion Proteins cDNA encoding amino acids 473 to 530 of the ets repressor factor (ERF) repressor domain (ERD) (Sgouras et al. (1995) *EMBO J.* 14:4781-4793) was generated from four overlapping oligonucleotides using Taq DNA polymerase; a cDNA encoding amino acids 1 to 97 of the KRAB domain of KOX1 (Margolin et al. (1994) *Proc. Natl. Acad. Sci. USA* 91:4509-4513) was assembled from 6 overlapping oligonucleotides; a cDNA encoding amino acids 1 to 36 of the Mad sin3 interaction domain (SID) (Ayer et al. (1996) *Mol. Cell. Biol.* 16:5772-5781) was assembled from 3 overlapping oligonucleotides. The coding region for amino acids 413 to 489 of the VP16 transcriptional activation domain (Sadowski et al., (1988) *Nature* 335:563-564) was PCR amplified from pcDNA3/C7-C7-VP16 (Liu et al. (1997) *Proc. Natl. Acad. Sci. U.S.A.* 94:5525-5530). The VP64 DNA, encoding a tetrameric repeat of VP16's minimal activation domain, comprising amino acids 437 to 447 (Seipel et al. (1992) *EMBO* 13:4961), was generated from two pairs of complementary oligonucleotides. All resulting effector domain-encoding fragments were fused to zinc finger coding regions by standard cloning procedures, such that each resulting construct contained an internal SV40 nuclear localization signal, as well as a C-terminal HA decapeptide tag. Fusion constructs were cloned into pcDNA3 for expression in mammalian cells.

Construction of Integrin β3 and erbB-2 Luciferase Reporter Plasmids

An integrin β3 promoter fragment encompassing nucleotides −584 to −1 (with respect to the ATG codon) was PCR amplified from human genomic DNA, using the primers b3p (Nhe1)-f (5'-GAG GAG GAG GCT AGC GGG ATG TGG TCT TGC CCT CAA CAG GTA GG-3') (SEQ ID NO: 32) and b3p(Hind3)-b (5'-GAG GAG GAG AAG CTT CTC GTC CGC CTC CCG CGG CGC TCC GC-3') (SEQ ID NO: 33), and Taq Expand DNA Polymerase mix (Boehringer). The cycling conditions were: 30 minutes at 94 degrees Celsius; 40× (one minute at 94 degrees Celsius—30 minutes at 62 degrees Celsius—2.5 minutes at 72 degrees Celsius); 10 minutes at 72 degrees Celsius. 10% DMSO was present in the reaction mix.

An erbB-2 promoter fragment (Ishii et al. (1987) *Proc. Natl. Acad. Sci. U.S.A.* 84:4374-4378) encompassing nucleotides −751 to −1 was PCR amplified under the same conditions, using the primers e2p(Nhe1)-f (5'-GAG GAG GAG GCT AGC CGA TGT GAC TGT CTC CTC CCA AAT TTG TAG ACC-3') (SEQ ID NO: 34) and e2p(Hind3)-b (5'-GAG GAG GAG AAG CTT GGT GCT CAC TGC GGC TCC GGC CCC ATG-3') (SEQ ID NO: 35). PCR products were purified with the Qiagen PCR prep kit, digested with the restriction endonucleases Nhe1 and Hind3, and cloned into pGL3basic (Promega).

An erbB-2 promoter fragment encompassing nucleotides −1571 to −24 was excised from pSVOALΔ5'/erbB-2(N-N) by Hind3 digestion and subcloned into pGL3basic. pSVOALΔ5'/erbB-2(N-N) was a gift from Gordon Gill.

Luciferase Assays

For all transfections, HeLa cells were plated in 24 well dishes and used at a confluency of 40-60%. Typically, 200 ng reporter plasmid (pGL3-promoter constructs or, as negative control, pGL3basic) and 20 ng effector plasmid (zinc finger constructs in pcDNA3 or, as negative control, empty pcDNA3) were transfected using the lipofectamine reagent (Gibco BRL). Cell extracts were prepared approximately 48 hours after transfection. Luciferase activity was measured with the Promega luciferase assay reagent, in a MicroLumat LB96P luminometer (EG&G Berthold).

Selection Strategy for the Generation of Six-finger Proteins with DNA Binding Specificity Based on the modular nature of zinc finger domains, as well as the fact that each zinc finger recognizes 3 bp of DNA sequence, several strategies can be employed to generate zinc finger proteins, with preferably one to three fingers, with desired DNA binding specificity. For instance, in vitro evolution of a six-finger protein binding an 18 bp target sequence can follow the strategy outlined in FIG. 1. The target sequence is divided into six 3 bp sub-sites, A-F. In the first step, a Zif268-based zinc finger phage display library in which the central finger 2 is randomized is selected against all 6 subsites in the context of the 2 wild type fingers. After successful generation of all the finger 2 variants required for a given target, cDNAs encoding three-finger proteins recognizing either half-site 1 (ABC) or half-site 2 (DEF) are constructed via PCR overlap extension. Finally, standard cloning procedures are used to construct a gene encoding a six-finger protein recognizing the whole 18 bp target site.

As an alternative to the serial connection of F2 domain variants, three-and six-finger proteins can be produced by "helix grafting". The framework residues of the zinc finger domains, those residues that support the presentation of the recognition helix, vary between proteins. The framework residues play a role in affinity and specificity. Thus, amino acid positions −2 to 6 of the DNA recognition helices are either grafted into a Zif268 (Pavletich et al. (1991) *Science* 252:809-817) or an Sp1C framework (Desjarlais et al. (1993) *Proc. Natl. Acad. Sci. U.S.A.* 90:2256-2260).

Integrin β3 target sequences B and C2 were chosen at various distances from the transcription start site, to allow for a comparison of the efficacy of transcriptional regulation. Since the selected zinc finger proteins are fused to transcriptional effector domains (Sadowski et al., (1988) *Nature* 335: 563-564; Margolin et al. (1994) *Proc. Natl. Acad. Sci. USA* 91:4509-4513); Sgouras et al. (1995) *EMBO* 14:4781-4793; Ayer et al. (1996) *Mol. Cell. Biol.* 16:5772-5781), binding of a zinc finger protein per se have an effect on the level of transcription.

A list of chosen target sequences for the selection of zinc finger proteins is given in Table 2, below. Since zinc finger proteins make base contacts predominantly with one strand of the DNA double helix, only the relevant strand of the target sequence is listed and designated +/− with respect to the coding strand. The location of the target sequences and position relative to the major transcription start site(s) is given.

TABLE 2

Chosen Target Sequences For The Selection Of Zinc Finger Proteins

| | | LOCATION | SEQ ID |
|---|---|---|---|
| | Integrin β3 (B3) target sequences | | |
| B3B | GCC TGA GAG GGA GCG GTG | − strand, promoter region, −160 bp | 72 |
| B3C2 | GGA GGG GAC GCG GTG GGT | − strand, promoter region, −70 bp | 73 |
| | ErbB-2 (E2) target sequences | | |
| E2B2 | GTG TGA GAA(CG)GCT GCA GGC | + strand, promoter, −150/−220 bp | 74 |
| E2B2 | GTG TGA GAA(CG)GGT GCA GGC | + strand, promoter, −150/−220 bp | 74 |
| E2C | GGG GCG GGA GCC GCA GTG | + strand, 5' UTR, +160/+230 bp | 75 |
| E2D | GCA GTT GGA GGG GGC GAG | + strand, promoter, −30/−100 bp | 76 |

CHoice of Human Integrin $\beta_3$ and erbB-2 Target Sequences

Panning experiments carried out previously indicated that zinc fingers binding to G-containing triplets, with a G or a T in 5'-position, are more readily obtained than zinc fingers binding other triplets. The zinc finger target sequences were selected such that they contained one or more G's in each triplet of the 18 bp sequence, and that each triplet started with a G or a T (Table 2). To conform with these requirements, erbB-2 target B2 was split into two halves separated by two bases. A longer linker peptide between the appropriate zinc fingers may also for recognition of such a split site. Blast sequence similarity searches were carried out with each of the target sequences and confirmed that each 18 bp sequence specifies a unique site in the human genome (maximal similarity tolerated: 16/18 bp identity).

Since transcription factor AP-2 is involved in deregulated expression of erbB-2 in a significant fraction of ErbB-2 overexpressing tumor cell lines, erbB-2 target site B2 was designed to overlap with the AP-2 binding site GCTG-CAGGC, with the intention of inhibiting expression of ErbB-2 not only as a result of active transcriptional repression, but also by competition with an important transcription factor. In contrast, zinc finger proteins binding the other erbB-2 target sites (i.e. erbB-2 target sites C and D), affect transcription as a result of their effector domains.

Construction and Panning of a Finger 2 Library

The amino acid residues implicated in contacting DNA in finger 2 of the Zif268-C7 ("C7") (Wu et al. (1995) *Proc. Natl. Acad. Sci. U.S.A.* 92:344-348) have been extensively randomized using the PCR overlap extension mutagenesis strategy. Using two different randomization strategies, two sublibraries have been constructed using the pComb3 phage display vector (Barbas et al. (1991) *Proc. Natl. Acad. Sci. U.S.A.* 88:7978-7982). The sublibraries contain approximately $4\times10^9$ independent clones each.

The mutagenesis strategy for randomization of finger 2 of Zif268-C7, showing helix positions −3 to 7, is summarized in Table 3, below. The top line shows the wild type sequence of finger 2. The lower two lines show the two mutagenesis strategies used, where N=G, A, T, C; K=G, T; V=G, A, C; S=G, C. The NNK randomized codon provides all 20 amino acids in 32 codons. The VNS randomized codon provides 16 amino acids in 24 codons, excluding Phe, Trp, Tyr, Cys and all stops. Note that in the strategy shown in the bottom line, the use of less complex codons allows for the mutagenesis of an additional codon.

TABLE 3

Mutagenesis strategy for randomization of finger 2 of Zif268-C7, showing helix positions −3 to 7.

| −3 | −2 | −1 | 1 | 2 | 3 | 4 | 5 | 6 | 7 |
|---|---|---|---|---|---|---|---|---|---|
| F | S | R | S | D | H | L | T | I | H |
| F | S | (NNK) | (NNK) | (NNK) | (NNK) | L | (NNK) | (NNK) | H |
| F | (VNS) | (VNS) | (VNS) | (VNS) | (VNS) | L | (VNS) | (VNS) | H |

Finger 2 variants recognizing each of the 16 triplets of the GXX set (Segal et al. (1999) *Proc. Natl. Acad. Sci. U.S.A.* 96:2758-2763; and Table 1), as well as one variant recognizing TGA, have been successfully selected. In extension of previous observations, comparison of the zinc finger sequences revealed a code for zinc finger recognition of DNA. Thus, a 5'- and 3'-G selected an arginine at helix positions 6 and −1, respectively, while a central G selected an a histidine or lysine at position 3 of the recognition helix. In contrast, a central A selected an asparagine, a 3'-A a glutamine, a central T a serine or alanine, a 3'-T a threonine or serine, a central C an aspartate or threonine, and a 3'-C an aspartate or glutamate at the corresponding helix positions. An extensive characterization of the specificities and affinities of selected zinc finger variants has been carried out and indicates that many of the zinc finger peptides recognize their targets in a highly specific manner (Segal et al. (1999) *Proc. Natl. Acad. Sci. U.S.A.* 96:2758-2763 and Table 1).

Refinement of Finger 2 Specificities by Site-directed Mutagenesis

Attempts were made to improve binding specificity of some of the zinc finger domains by modifying the recognition helices by using site-directed mutagenesis. Data from the phage display selections and structural information guided the design of the mutants. Although helix positions 1 and 5 were not expected to play a direct role in recognition, the best improvements in specificity always involved modifications in these positions (Segal et al. (1999) *Proc. Natl. Acad. Sci. U.S.A.* 96:2758-2763 and Table 1). These residues have been observed to make phosphate backbone contacts, which contribute to affinity in a nonsequence-specific manner. Thus, removal of nonspecific contacts can increase the importance of the specific contacts to the overall stability of the complex, thereby enhancing specificity.

Generation of Three Finger Proteins Binding erbB-2 and Integrin β3 Target Sequences Two different strategies for generating three-finger proteins recognizing 9 bp of DNA sequence were used. Each strategy is based on the modular nature of the zinc finger domain, and takes advantage of a family of zinc finger domains recognizing triplets of the 5'-GNN-3' type defined in Table 1. Two three-finger proteins recognizing half sites (HS) 1 and 2 of the 5'-$(GNN)_6$-3' erbB-2 target site e2c were generated in the first strategy by fusing the pre-defined finger 2 (F2) domain variants together using a PCR assembly strategy.

To examine the generality of this approach, three additional three-finger proteins recognizing sequences of the 5'-$(GNN)_3$-3' type, were prepared using the same approach. Purified zinc finger proteins were prepared as fusions with the maltose binding protein (MBP). ELISA analysis revealed that serially connected F2 proteins were able to act in concert to specifically recognize the desired 9-bp DNA target sequences (Beerli et al. (1998) *Proc. Natl. Acad. Sci. U.S.A.*95:14628-14633). Each of the 5 proteins shown was able to discriminate between target and non-target 5'-$(GNN)_3$-3' sequence. The affinity of each of the proteins for its target was determined by electrophoretic mobility-shift assays. These studies demonstrated that the zinc finger peptides have affinities comparable to Zif268 and other natural transcription factors with $K_d$ values that ranged from 3 to 70 nM (Table 4, below).

As an alternative to the serial connection of F2 domain variants, in the second strategy, three-finger proteins specific for the two halfsites of the erbB-2 target site e2c (Table 4, below), were produced by "helix grafting." The framework residues may play-a role in affinity and specificity. For helix grafting, amino acid positions −2 to 6 of the DNA recognition helices were either grafted into a Zif268 (Pavietich et al. (1991) *Science* 252:809-817) or an Sp1C framework (Desjarlais et al. (1993) *Proc. Natl. Acad. Sci. U.S.A.* 90:2256-2260). The Sp1C protein is a designed consensus protein shown to have enhanced stability towards chelating agents. The proteins were expressed from DNA templates prepared by a rapid PCR-based gene assembly strategy. In each case, ELISA analysis of MBP fusion proteins showed that the DNA binding specificities and affinities (Table 4, below) observed with the F2 framework constructs were retained. Three finger proteins recognizing HS1 and HS2 of the integrin β3 target sites b3b and b3c2 have also been generated, using the Sp1C backbone. Preliminary ELISA data showed that these proteins bind their respective targets with good specificity. Further characterization of proteins can be made, such as determination of their affinities by gel shift analysis. See Table 4, below.

Generation of Six-finger Proteins for Specific Targeting of the erbB-2 and Integrin β3 Promoter Regions The recognition of 9 bp of DNA sequence is not sufficient to specify a unique site within a complex genome. In contrast, a six-finger protein recognizing 18 bp of contiguous DNA sequence could define a single site in the human genome, thus fulfilling an important prerequisite for the generation of a gene-specific transcriptional switch. Six-finger proteins binding the erbB-2 target sequence e2c were generated from three-finger constructs by simple restriction enzyme digestion and cloning with F2, Zif268, and Sp1C framework template DNAs (for sequences of these proteins, see Beerli et al. (1998) *Proc. Natl. Acad. Sci. U.S.A.*95:14628-14633). Six finger proteins binding the integrin β3 target sequences b3b and b3c2 were only generated using the Sp1C backbone. ELISA analysis of purified MBP fusion proteins showed that each of the six-finger proteins was able to recognize the specific target sequence, with little cross reactivity to non-target 5'-$(GNN)_6$-3' sites or a tandem repeat of the Zif268 target site.

In Table 4, below, the affinities of three- and six-finger proteins for various target sequences as determined by gel shift analysis is summarized. Proteins are named with upper case letters, DNA target sequences with lower case letters. Abbreviations used are: F2=finger 2 framework; Zif=Zif268 framework; Sp1=Sp1C framework; mut=mutant; HS=half-site. With respect to the target site overlap phenomenon, the base following each target sequence is given in lower case letter (see Beerli et al. (1998) *Proc. Natl. Acad. Sci. U.S.A.* 95: 14628-14633). The affinity of the Zif268-DNA interaction was determined to be 10 nM (Segal et al. (1999) *Proc. Natl. Acad. Sci. U.S.A.* 96:2758-2763). $K_d$ values are averages from 2 independent experiments, with standard deviations of 50% or less.

TABLE 4

AFFINITIES OF THREE AND SIX FINGER PROTEINS

| Protein | Target | Target Sequence (5'-3') | $K_d$, nM |
|---|---|---|---|
| B3(F2) | b3 | GGA GGG GAG g | 4 |
| E2(F2) | e2 | GGG GGC GAG g | 3 |
| C5(F2) | c5 | GGA GGC GGG g | 30 |
| E2C-HS1(F2) | e2c-hs1 | GGG GCC GGA g | 45 |
| E2C-HS1(Zif) | e2c-hs1 | GGG GCC GGA g | 70 |
| E2C-HS1(Sp1) | e2c-hs1 | GGG GCC GGA g | 35 |
| E2C-HS2(F2) | e2c-hs2 | GCC GCA GTG g | 70 |
| E2C-HS2(Zif) | e2c-hs2 | GCC GCA GTG g | 75 |
| E2C-HS2(Sp1) | e2c-hs2 | GCC GCA GTG g | 25 |

TABLE 4-continued

AFFINITIES OF THREE AND SIX FINGER PROTEINS

| Protein | Target | Target Sequence (5'-3') | $K_d$, nM |
|---|---|---|---|
| E2C(F2) | e2c-g | GGG GCC GGA GCC GCA GTG g | 25 |
| E2C(Zif) | e2c-g | GGG GCC GGA GCC GCA GTG g | 1.6 |
| E2C(Zif) | e2c-a | GGG GCC GGA GCC GCA GTG a | 2.3 |
| E2C(Zif) | e2c-muths1 | AGT CTG AAT GCC GCA GTG g | 200 |
| E2C(Zif) | e2c-muths2 | GGG GCC GGA AGT CTG AAT g | 200 |
| E2C(Sp1) | e2c-g | GGG GCC GGA GCC GCA GTG g | 0.5 |
| E2C(Sp1) | e2c-a | GGG GCC GGA GCC GCA GTG a | 0.75 |
| E2C(Sp1) | e2c-muths1 | AGT CTG AAT GCC GCA GTG g | 65 |
| E2C(Sp1) | e2c-muths2 | GGG GCC GGA AGT CTG AAT g | 100 |

In Table 5, below, the finger 2 variants generated by phage display selection and refined by site-directed mutagenesis are summarized. Protein designations are in the form pXXX, for clones derived from panning; pmXXX refers to clones refined by mutagenesis. Helix positions −1, 3, and 6 are shown in bold, altered nucleotides are underlined. The values represent the results of at least two independent experiments. The standard error was ±50% or less.

TABLE 5

SUMMARY OF FINGER 2 VARIANTS GENERATED BY PHAGE DISPLAY SELECTION AND REFINED BY SITE-DIRECTED MUTAGENESIS

| Protein | Finger-2 Helix | Finger-2 Subsite | $K_D$ (nM) | $K_{D,Prot}/K_{D,Zif268}$ |
|---|---|---|---|---|
| pGGG | SRSDHLTR | GGG | 0.4 | 0.04 |
| pmGGG | SRSDKLVR | GGG | 6 | 0.6 |
| " | " | GTG | >1,400 | |
| pGGA | SQRAHLER | GGA | 3 | 0.3 |
| pmGGT | STSGHLVR | GGT | 15 | 1.5 |
| " | " | GGC | >2,400 | |
| pmGGC | SDPGHLVR | GGC | 40 | 4.0 |
| pmGAG | SRSDNLVR | GAG | 1 | 0.1 |
| " | " | GGG | 45 | 4.5 |
| pmGAA | SQSSNLVR | GAA | 0.5 | 0.05 |
| pGAT | STSGNLVR | GAT | 3 | 0.3 |
| pmGAC | SDPGNLVR | GAC | 3 | 0.3 |
| " | " | GCC | 90 | 9.0 |
| pGTG | SRKDSLVR | GTG | 3 | 0.3 |
| pmGTG | SRSDELVR | GTG | 15 | 1.5 |
| " | " | GAG | 30 | 3.0 |

TABLE 5-continued

SUMMARY OF FINGER 2 VARIANTS GENERATED BY PHAGE DISPLAY SELECTION AND REFINED BY SITE-DIRECTED MUTAGENESIS

| Protein | Finger-2 Helix | Finger-2 Subsite | $K_D$ (nM) | $K_{D,Prot}/K_{D,Zif268}$ |
|---|---|---|---|---|
| pGTA | SQSSSLVR | GTA | 25 | 2.5 |
| " | " | GTG | >1,000 | |
| pmGTT | STSGSLVR | GTT | 5 | 0.5 |
| pGTC | SDPGALVR | GTC | 40 | 4.0 |
| " | " | GCC | >4,400 | |
| pmGCG | SRSDDLVR | GCG | 9 | 0.9 |
| " | " | GAG | 6 | 0.6 |
| pGCA | SQSGDLRR | GCA | 2 | 0.2 |
| " | " | GCT | 10 | 1 |
| pmGCT | STSGELVR | GCT | 65 | 6.5 |
| pGCC | SDCRDLAR | GCC | 80 | 8.0 |
| pTGA | SQAGHLAS | TGA | nd | nd |
| C7 | SRSDHLTT | TGG | 0.5 | 0.05 |
| Zif268 | SRSDHLTT | TGG | 10 | 1 |

The affinity of each of the E2C proteins for the e2c DNA target site was determined by gel-shift analysis. A modest $K_d$ value of 25 nM was observed with the E2C(F2) six-finger protein constructed from the F2 framework (Table 5, above; Beerli et al.(1998) *Proc. Natl. Acad. Sci. U.S.A.*95:14628-14633), a value that is only 2 to 3 times better than its constituent three-finger proteins. In previous studies of six-finger proteins, an approximately 70-fold enhanced affinity of the six-finger proteins for their DNA ligand compared to their three-finger constituents was observed (Liu et al. (1997) *Proc. Natl. Acad. Sci. U.S.A.* 94:5525-5530). The absence of a substantial increase in the affinity of the E2C(F2) peptide suggested that serial connection of F2 domains is not optimal. It is possible that the periodicity of the F2 domains of the six-finger protein does not match that of the DNA over this extended sequence, and that a significant fraction of the binding energy of this protein is spent in unwinding DNA. In contrast to the F2 domain protein, the E2C(Zif) and E2C(Sp1) six-finger proteins displayed 40- to 70-fold increased affinity as compared to their original three-finger protein constituents, with $K_d$ values of 1.6 nM and 0.5 nM, respectively. Significantly, both three-finger components of these proteins were involved in binding, since mutation of either half-site led to a roughly 100-fold decrease in affinity (Table 4, above; Beerli et al. (1998) *Proc. Natl. Acad. Sci. U.S.A.*95:14628-14633). The preponderance of known transcription factors bind their specific DNA ligands with nanomolar affinity, suggesting that the control of gene expression is governed by protein/DNA complexes of unexceptional life times. Thus, zinc finger proteins of increased affinity should not be required and could be disadvantageous, especially if binding to non-specific DNA is also increased. The affinities of the B3B(Sp1) and B3C2(Sp1) six finger proteins for their respective targets can be determined by one skilled in the art using well-known methods as well as those described herein.

EXAMPLE 2

Construction of Fusion Proteins Containing Zinc Finger Domains and Transcriptional Repressors and Activators In order to demonstrate use of zinc finger proteins as gene-specific transcriptional regulators, the E2C(Sp1), B3B(Sp1), and B3C2(Sp1) six-finger proteins were fused to a number of effector domains (Beerli et al. (1998) *Proc. Natl. Acad. Sci. U.S.A.*95:14628-14633). Transcriptional repressors were generated by attaching either of three human-derived repressor domains to the zinc finger protein. The first repressor protein was prepared using the ERF repressor domain (ERD) (Sgouras et al. (1995) *EMBO J.* 14:4781-4793), defined by amino acids 473 to 530 of the ets2 repressor factor (ERF). This domain mediates the antagonistic effect of ERF on the activity of transcription factors of the ets family. A synthetic repressor was constructed by fusion of this domain to the C-terminus of the zinc finger protein.

The second repressor protein was prepared using the Krüppel-associated box (KRAB) domain (Margolin et al. (1994) *Proc. Natl. Acad. Sci. USA* 91:4509-4513). This repressor domain is commonly found at the N-terminus of zinc finger proteins and presumably exerts its repressive activity on TATA-dependent transcription in a distance- and orientation-independent manner, by interacting with the RING finger protein KAP-1. The KRAB domain found between amino acids 1 and 97 of the zinc finger protein KOX1 was used. In this case an N-terminal fusion with the six-finger protein was constructed. Finally, to demonstrate the utility of histone deacetylation for repression, amino acids 1 to 36 of the Mad mSIN3 interaction domain (SID) were fused to the N-terminus of the zinc finger protein (Ayer et al., (1996) *Mol. Cell. Biol.* 16:5772-5781). This small domain is found at the N-terminus of the transcription factor Mad and is responsible for mediating its transcriptional repression by interacting with mSIN3, which in turn interacts the co-repressor N-CoR and with the histone deacetylase mRPD1.

To examine gene-specific activation, transcriptional activators were generated by fusing the zinc finger protein to amino acids 413 to 489 of the herpes simplex virus VP16 protein (Sadowski et al. (1988) *Nature* 335:563-564), or to an artificial tetrameric repeat of VP16's minimal activation domain, DALDDFDLDML (SEQ ID NO: 36) (Seipel et al. (1992) *EMBO* 13:4961), designated VP64.

Specific Regulation of erbB-2 Promoter Activity

Reporter constructs containing fragments of the erbB-2 promoter coupled to a luciferase reporter gene were generated to test the specific activities of the erbB-2 specific synthetic transcriptional regulators. The target reporter plasmid contained nucleotides −758 to −1 with respect to the ATG initiation codon, whereas the control reporter plasmid contained nucleotides −1571 to −24, thus lacking all but one nucleotide of the E2C binding site encompassed in positions −24 to −7. Both promoter fragments displayed similar activities when transfected transiently into HeLa cells, in agreement with previous observations. To test the effect of zinc finger-repressor domain fusion constructs on erbB-2 promoter activity, HeLa cells were transiently co-transfected with each of the zinc finger expression vectors and the luciferase reporter constructs (Beerli et al., (1998) *Proc. Natl. Acad. Sci. U.S.A.* 95:14628-14633). Significant repression was observed with each construct. The ERD and SID fusion proteins produced approximately 50% and 80% repression, respectively. The most potent repressor was the KRAB fusion protein. This protein caused complete repression of erbB-2 promoter activity. The observed residual activity was at the background level of the promoter-less pGL3 reporter. In contrast, none of the proteins caused significant repression of the control erbB-2 reporter construct lacking the E2C target site, demonstrating that repression is indeed mediated by specific binding of the E2C(Sp1) protein to its target site. Expression of a zinc finger protein lacking any effector domain resulted in weak repression, approximately 30%, indicating that most of the repression observed with the SID and KRAB constructs is caused by their effector domains, rather than by DNA-binding alone. This observation strongly suggests that the mechanism of repression is active inhibition of transcription initiation rather than of elongation. Once initiation of transcription by RNA polymerase II has occurred, the zinc finger protein appears to be readily displaced from the DNA by the action of the polymerase.

The use of erbB-2 specific zinc finger proteins to mediate activation of transcription was demonstrated using the same two reporter constructs. The VP16 fusion protein was found to stimulate transcription approximately 5-fold, whereas the VP64 fusion protein produced a 27-fold activation. This dramatic stimulation of promoter activity caused by a single VP16-based transcriptional activator is exceptional in view of the fact that the zinc finger protein binds in the transcribed region of the gene. This again demonstrates that mere binding of a zinc finger protein, even with one with sub-nanomolar affinity, in the path of RNA polymerase 11 need not necessarily negatively affect gene expression.

Based on the efficient and specific regulation of a reporter construct driven by the erbB-2 promoter, the effect of transiently transfected zinc finger expression plasmids on activity of the endogenous erbB-2 promoter was analyzed. As a read-out of erbB-2 promoter activity, ErbB-2 protein levels were analyzed by Western blotting. Significantly, E2C(Sp1)-VP64 lead to an upregulation of ErbB-2 protein levels, while E2C (Sp1)-SKD lead to its downregulation. This regulation was specific, since no effect was observed on expression of EGFR.

It is important to note that the observations made in these experiments drastically underestimate the efficacy of the zinc finger peptides, since the transfection efficiency of HeLa cells is no more than 50%. To ascertain that 100% of the cells express the zinc finger proteins stable cell lines need to be generated. Production of stable cell lines expressing the zinc finger constructs under control of a tetracycline-inducible promoter is known (Gossen et al. (1992) *Proc. Natl. Acad. Sci. U.S.A.* 89:5547-5551). Inducible expression of zinc finger proteins in stable cell lines allows for detailed analysis of the degree of specificity of such proteins.

Specific Regulation of Integrin β3 Promoter Activity

To test the activity of transcriptional regulators specific for the integrin β3 promoter, a reporter plasmid was constructed containing the luciferase open reading frame under control of the integrin β3 promoter. When compared to the two erbB-2 promoter fragments described above, the integrin β3 promoter fragment had a very low activity. In fact, in some experiments no activation of luciferase expression over background was detected, preventing an analysis of the effects of the KRAB fusion proteins. However, when the VP64 fusion proteins were tested an efficient activation of the integrin β3 promoter was observed. B3B(Sp1)-VP64 and B3C2(Sp1)-VP64 stimulated transcription 12 and 22-fold, respectively. Activation of transcription was specific, since no effect on the activity of the erbB-2 promoter was detected.

EXAMPLE 3

Fusion Protein Construct Comprising Progesterone Receptor Variant

Amino acid sequence comparisons of steroid receptor family members indicates that they generally comprise a number of defined domains, including an N-terminal DNA binding domain and a more C-terminally located ligand binding domain. Importantly, these domains are modular and the DNA binding domain of progesterone receptor (PR) has been successfully exchanged for the Gal4 DNA binding domain. The addition of a VP16 activation or a KRAB repressor domain to the N- or C-terminus of this construct yielded proteins that could regulate a Gal4 responsive reporter in a ligand dependent manner. An important feature of the ligand binding domain used in these studies is that it is derived from a mutant PR with a small C-terminal deletion. This mutant fails to respond to progesterone and is responsive only to progesterone antagonists such as RU486, making this system suitable for in vivo applications.

The original PR DNA binding domain can be replaced by engineered zinc finger proteins. For example, the three finger protein Zif268(C7) was fused to the N-terminus of the PR ligand binding domain (PBD) (aa 640 to 914), and the VP16 activation domain to its C-terminus. It was found that this fusion protein was able to regulate an SV40 promoter luciferase construct with ten upstream Zif268(C7) binding sites in an RU486-dependent manner.

An RU486 dose response curve showed that optimal induction occurs at about 1 nM to about 10 nM RU486. A time course study was carried out with 10 nM RU486 and showed that optimal induction of C7-PBD-VP16 activity occurs at about 24 hours.

Since naturally occurring steroid receptors bind DNA as dimers, an important prerequisite for the application of this approach is the presence of suitable target sequences in the promoter of interest. Fortunately, the spacing and orientation of the two half-sites targeted by steroid receptor dimers is flexible. While a steroid response element usually includes an inverted repeat, or palindrome, also direct repeats or even everted repeats of the half-sites in variable spacing are tolerated (Aumais et al. (1996) *J. Biol. Chem.* 272:12229-12235). A search of the erbB-2 and integrin β3 promoters revealed that direct and inverted repeats of 5'-$(GNN)_3$-3' sequence motifs occur quite frequently. An example of a sequence motif suitable for targeting by a heterodimeric RU486-regulatable zinc finger protein is 5' GAG GAG GGC TGCTT GAG GAA GTA-3' (SEQ ID NO: 37), which was found in the erbB-2 promoter and overlaps with the TATA box (underlined above). In some instances, promoter targeting is possible using a homodimer, for example by targeting the sequence 5'-GCC GGA GCC ATGGGGCCGGAGCC-3' (SEQ ID NO: 38), which is also found in the erbB-2 promoter and overlaps with the target sequence e2c (underlined).

EXAMPLE 4

Figure 2:
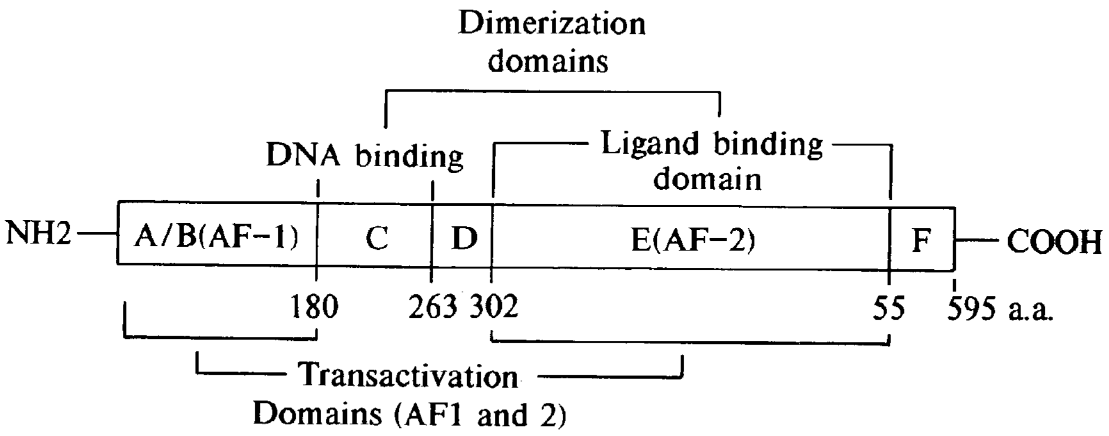
FIG. 2 is a schematic depiction of the functional domains (A-F) of the human estrogen receptor.
Figure 3:
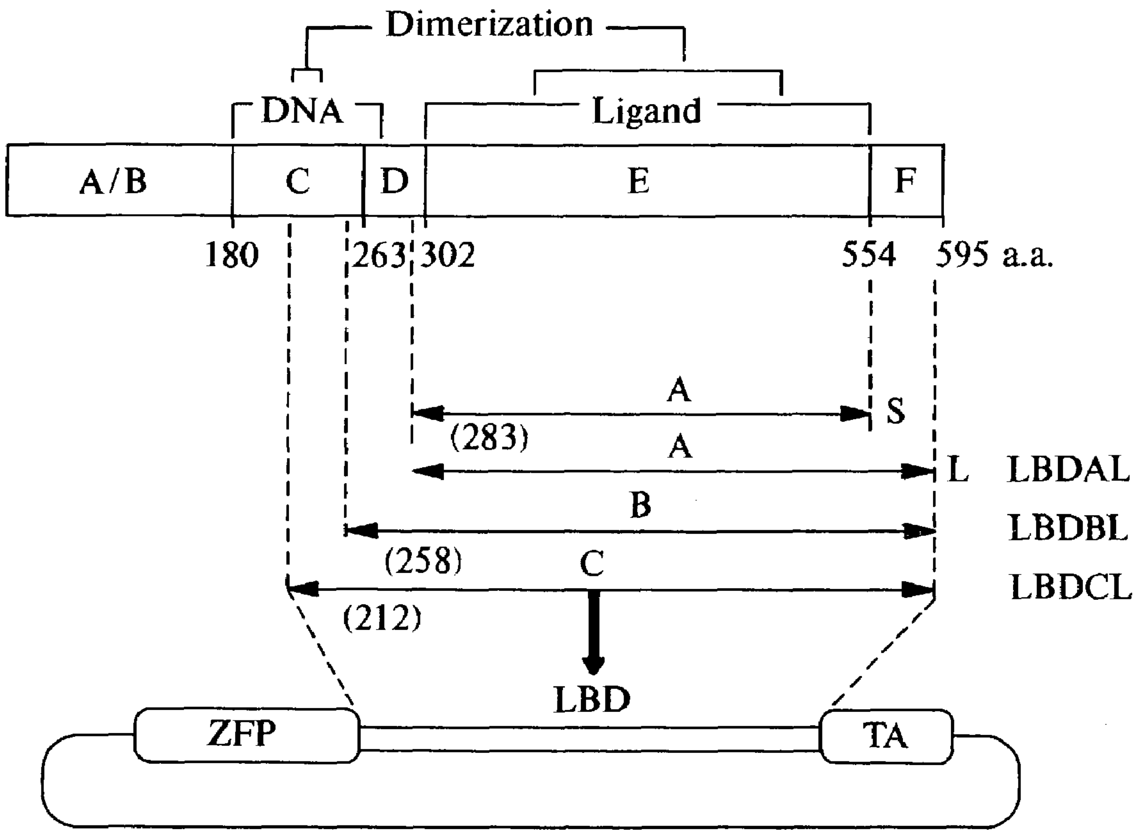
FIG. 3 is a schematic depiction of the cloning strategy for the construction of the recombinant molecular constructs.

Recombinant Ligand Activated Transcriptional Regulator Fusion Proteins Containing Human Estrogen Receptor Ligand Binding Domains The human estrogen receptor is shown in FIG. 2 as an example of a steroid receptor protein. The numbers below the rectangle indicate the position of the amino acid residues defining the borders of each domain. A/B is the domain of the amino terminus activation function 1 (AF-1), C is the DNA binding domain, D is called the hinge region, E is the ligand binding domain, which also contains the activation function 2 (AF-2) and F is the portion closest the carboxyl terminal, a domain whose function has not been fully established. The regions of the protein that participate and stabilize the homodimerized complex are distributed in the C, D and E domains. Regions throughout the steroid receptor ligand binding domain (region E in FIG. 2) as well as regions in the native DBD and hinge region (regions C and D respectively) contribute to homodimerization of the receptor. To demonstrate the importance of these regions to the function of the C2H2-containing receptors, proteins containing three different length LBD fragments were constructed. These differing length LBD constructs are designated A, B, and C (FIG. 3). LBD fragment A represents what is generally referred to as the "minimal" LBD fragment. Some studies have suggested the hinge region plays an important role in steroid receptor LBD—chimeric proteins; fragment B represents the LBD plus hinge. The native C or DNA binding region of estrogen receptor contains two zinc fingers of the C4-C4 class. The 5' or amino terminus finger contributes to DNA specific contacts; the 3' finger contributes to stabilizing the DNA binding domain dimer complex. To take advantage of this contribution of the 3' native zinc finger, LBD fragment C, where the 3' native zinc finger is retained and fused directly to the C2H2 zinc finger array, was included.

In order to optimize the ability of the fusion proteins to regulate gene expression, it may be necessary to add additional heterologous transactivating domains to the receptor. To facilitate these studies, fusion proteins were constructed either with the full length LBD extending to estrogen receptor residue 595, or with LBD fragments truncated at amino acid (aa) 554 to remove the F region. The full-length constructs are referred to as long (L), the truncated versions as short (S). All constructs contain a heterologous transactivation domain (TA) comprised of a VP16 minimal domain, unless otherwise noted, fused to the carboxy terminus of the ligand binding domain. VP16 minimal domain trimer has the amino acid residue sequence 3×(PADALDDFDLDML) (SEQ ID NO: 47), and is the tetracycline controlled transactivator (tTA) TA2 (Baron et al. (1997) *Nucleic Acids Research* 25:2723-2729).

Figure 4:
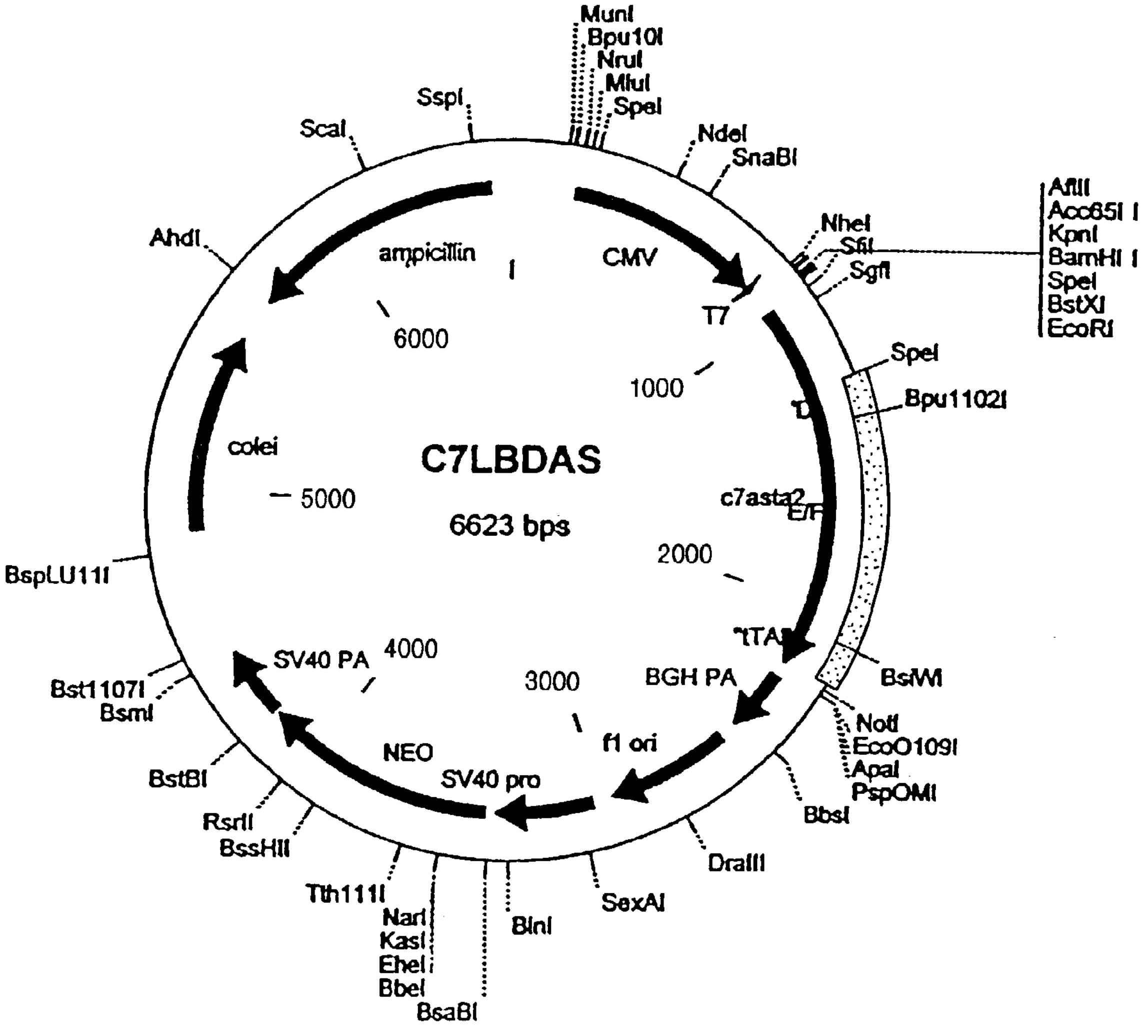
FIG. 4 is a schematic map of the expression vector for C7LBDAS based on the plasmid pCDNA3.1.
Figure 5:
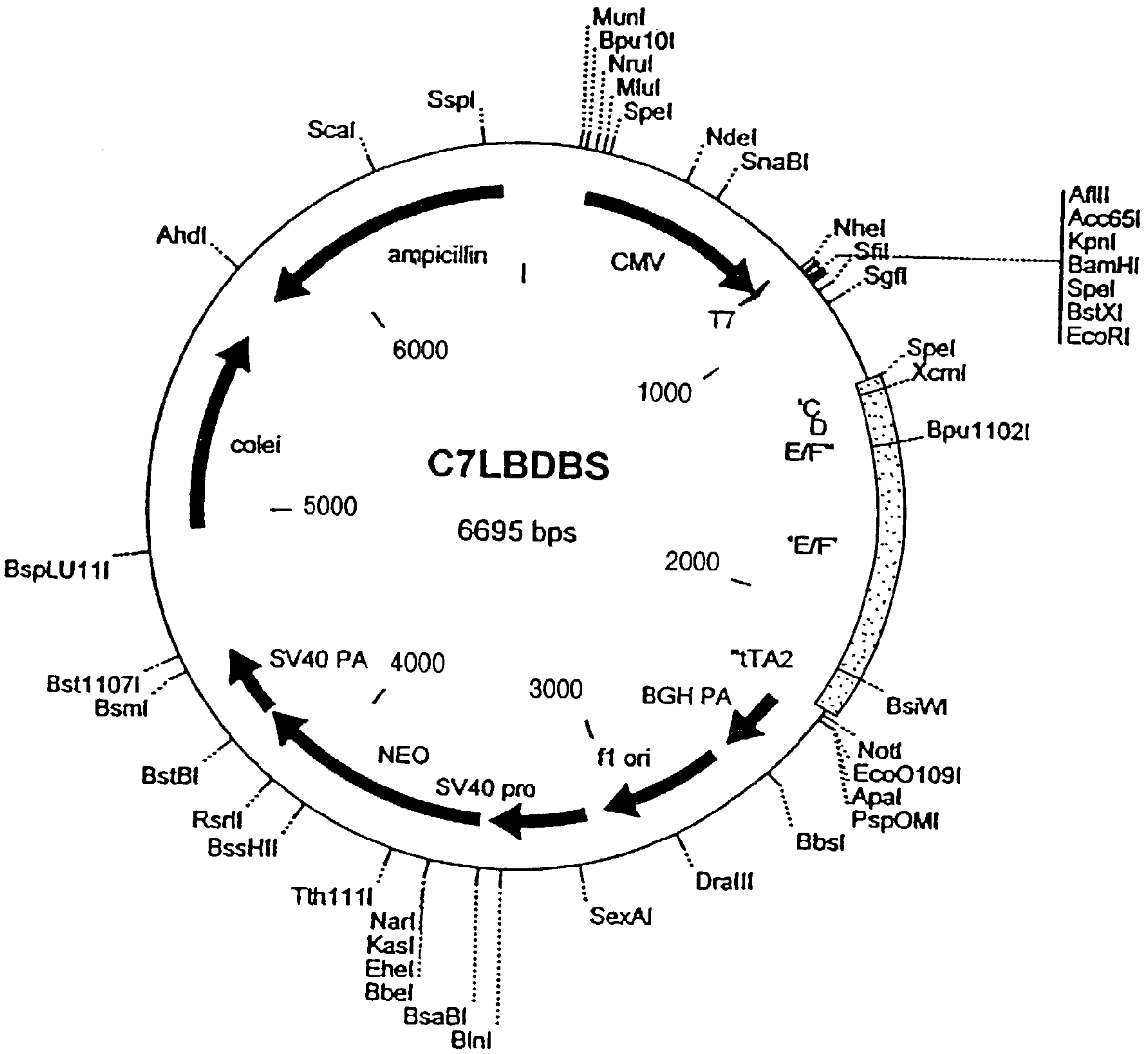
FIG. 5 is a schematic map of the expression vector for C7LBDBS based on the plasmid pCDNA3.1.
Figure 6:
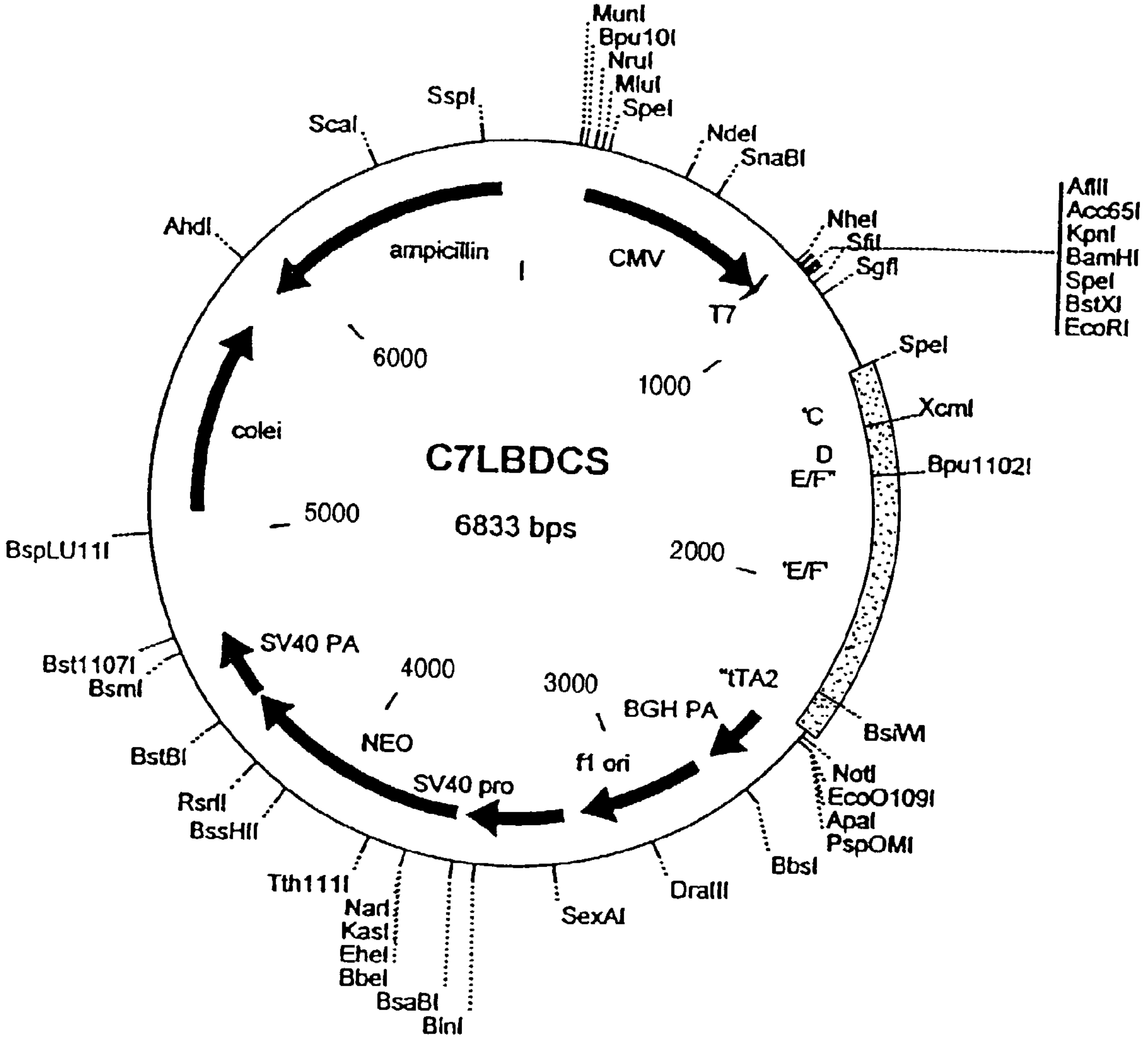
FIG. 6 is a schematic map of the expression vector for C7LBDCS based on the plasmid pCDNA3.1.
Figure 7:
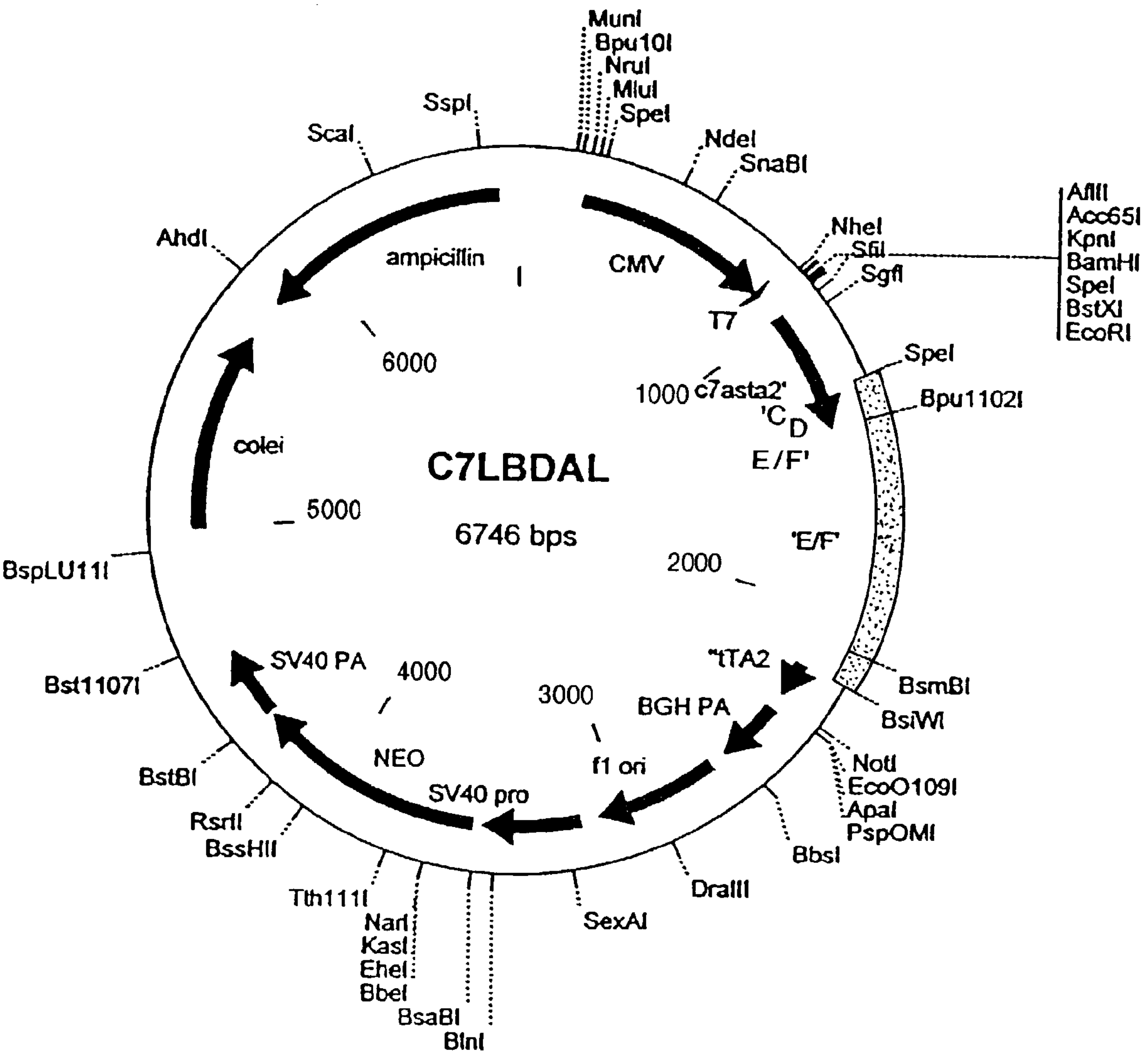
FIG. 7 is a schematic map of the expression vector for C7LBDAL based on the plasmid pCDNA3.1.
Figure 8:
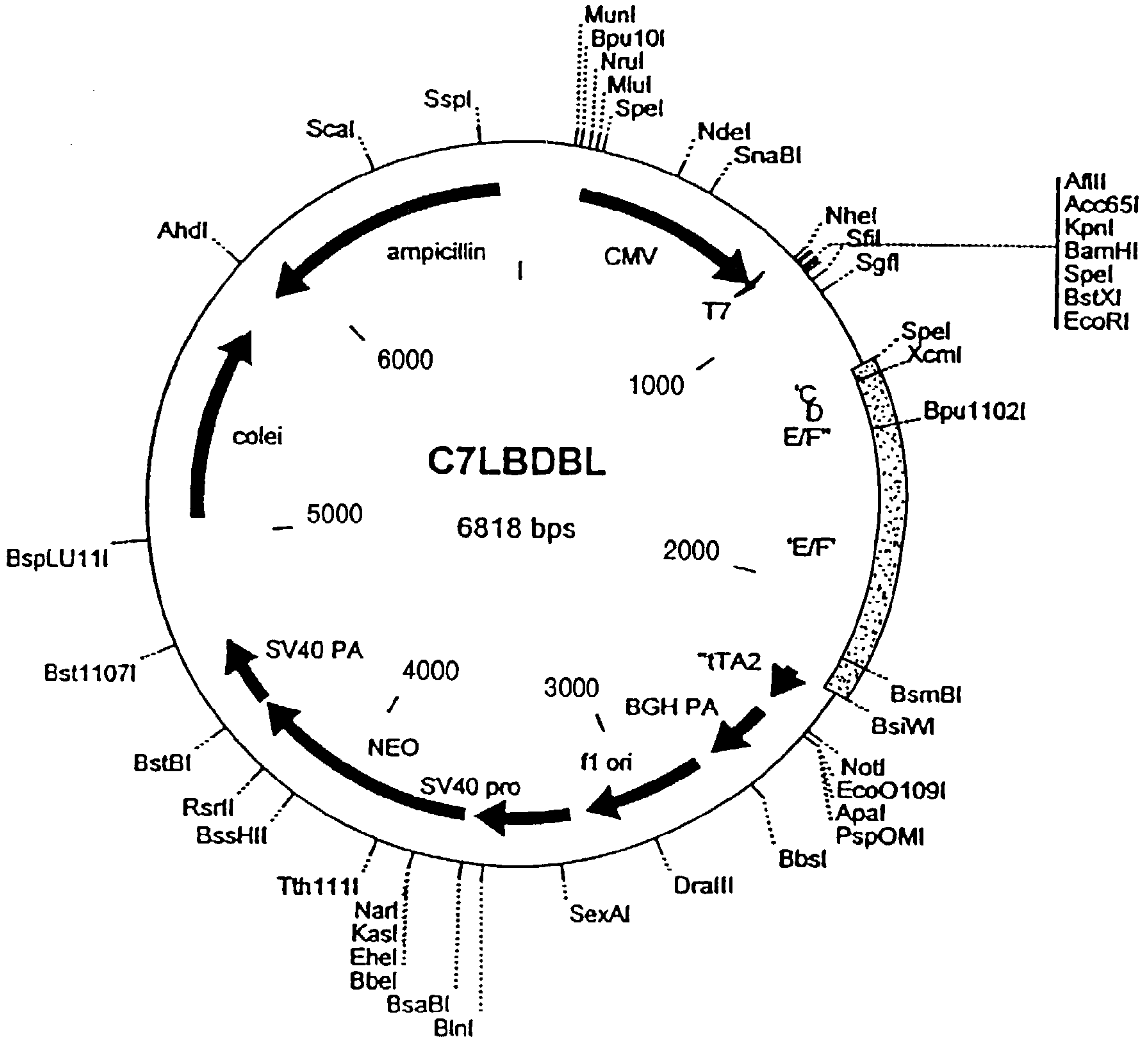
FIG. 8 is a schematic map of the expression vector for C7LBDBL based on the plasmid pCDNA3.1.
Figure 9:
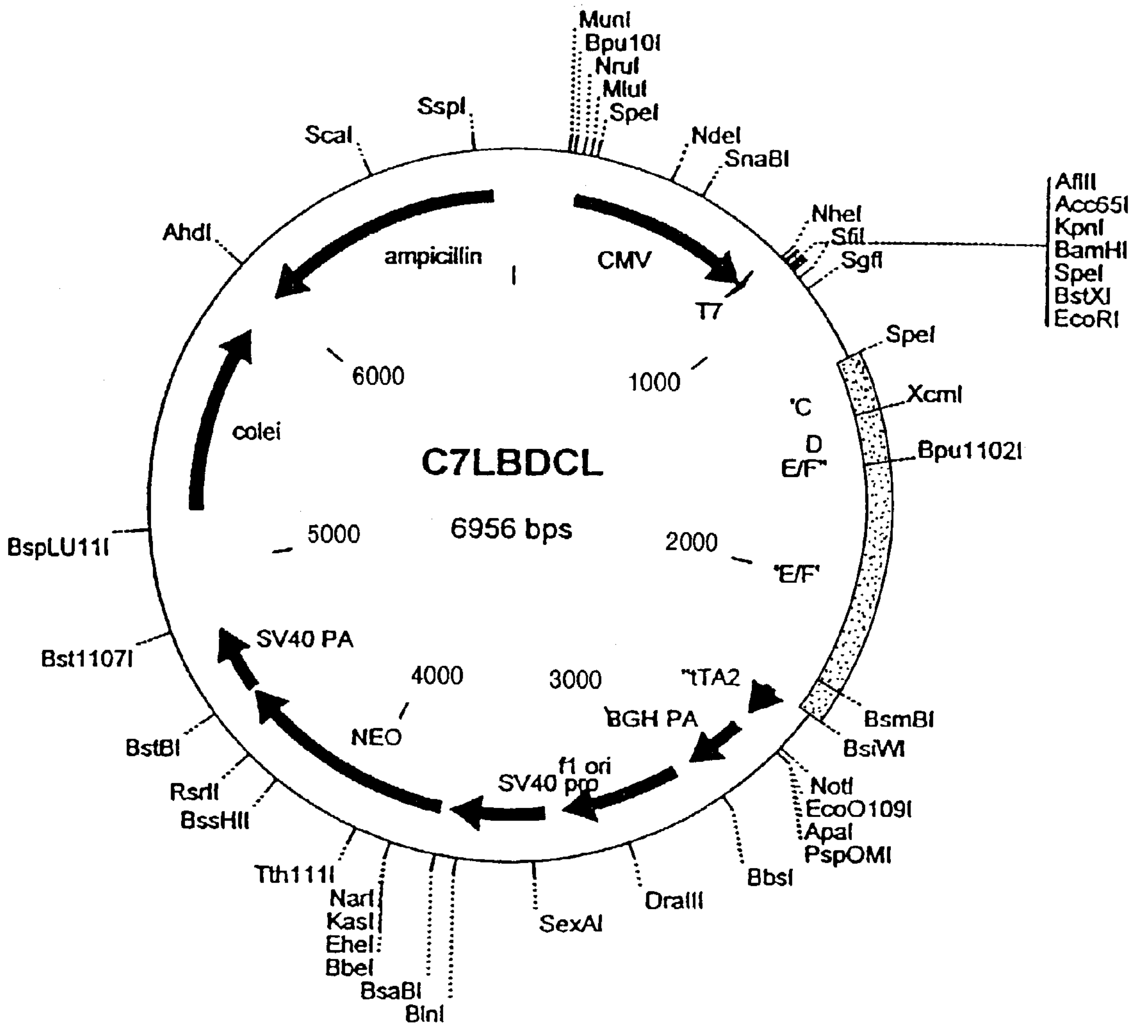
FIG. 9 is a schematic map of the expression vector for C7LBDCL based on the plasmid pCDNA3.1.
Figure 10:
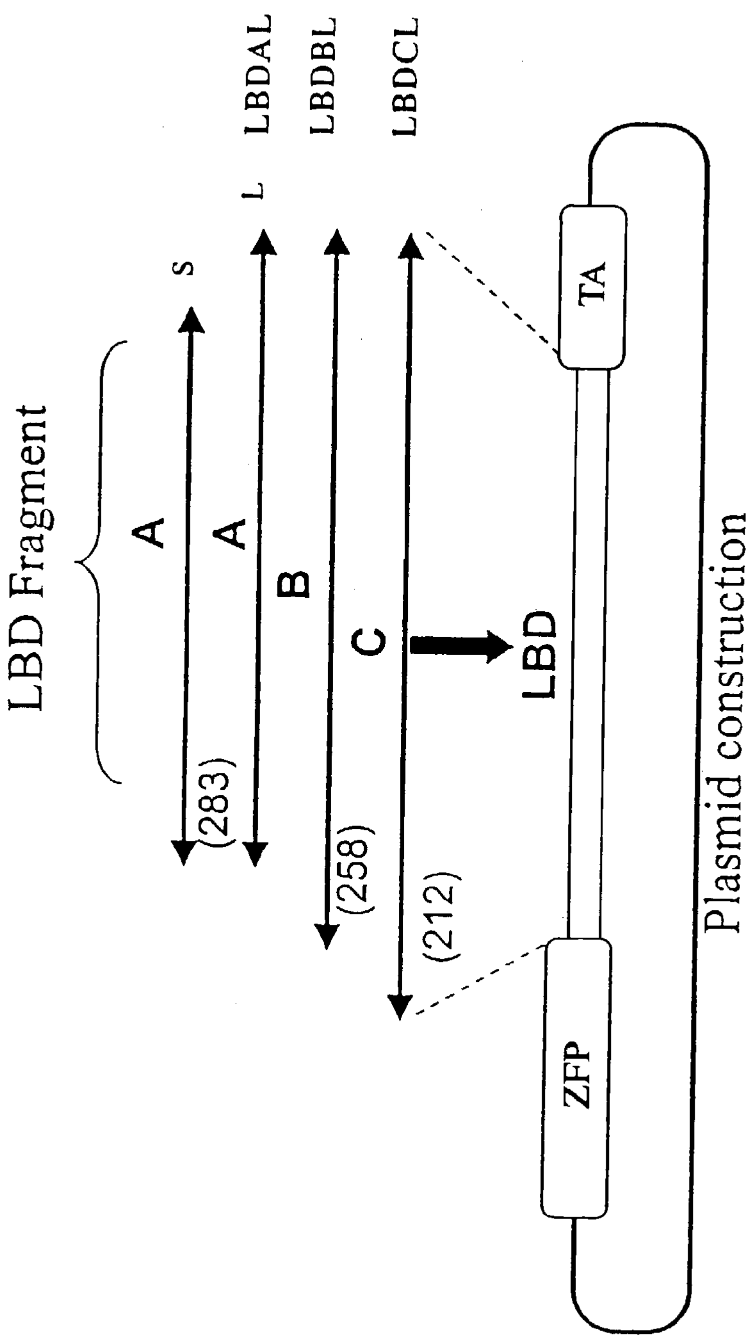
FIG. 10 is a schematic summary of the structure of several embodiments of the recombinant molecular construct and the nucleotide sequences of the DNA binding regions of zinc finger domains C7, E2C and 2C7.

These constructs are summarized in FIG. 3, which provides a schematic summary of the cloning strategy and nomenclature related to the C2H2 DNA binding domain—ER ligand binding domain fusion proteins. As shown in the plasmid construct at the bottom, the final construct contains three components: a C2H2 zinc finger domain (ZFP) at the amino end, a steroid receptor ligand binding domain (LBD) fragment in the middle, and a heterologous transactivation domain (TA) appended onto the carboxyl end. LBD fragments A, B, or C were defined by the position of the amino terminus border of the LBD; amino acid number for A (283), B (258) and C (212) correspond to the residue numbers in wild type ER. LBD fragments were further defined as long (L) or short (S) depending on their carboxy terminus junction. Long constructs fuse the heterologous TA to the wt ER amino acid residue 595, short constructs fuse TA to an LBD fragment truncated at ER amino acid 554. Thus, six fusion proteins in all were constructed, ZFP-LBD-TA A, B and C, each in a long and short form. Maps of specific examples constructed in the expression vector pcDNA3.1 are shown in FIG. 4 (C7LBDAS) (SEQ ID NO: 6), FIG. 5 (C7LBDBS) (SEQ ID NO: 8), FIG. 6 (C7LBDCS) (SEQ ID NO: 10), FIG. 7 (C7LBDAL) (SEQ ID NO: 7), FIG. 8 (C7LBDBL) (SEQ ID NO: 1), and FIG. 9 (C7LBDCL) (SEQ ID NO: 9).

Figure 16:
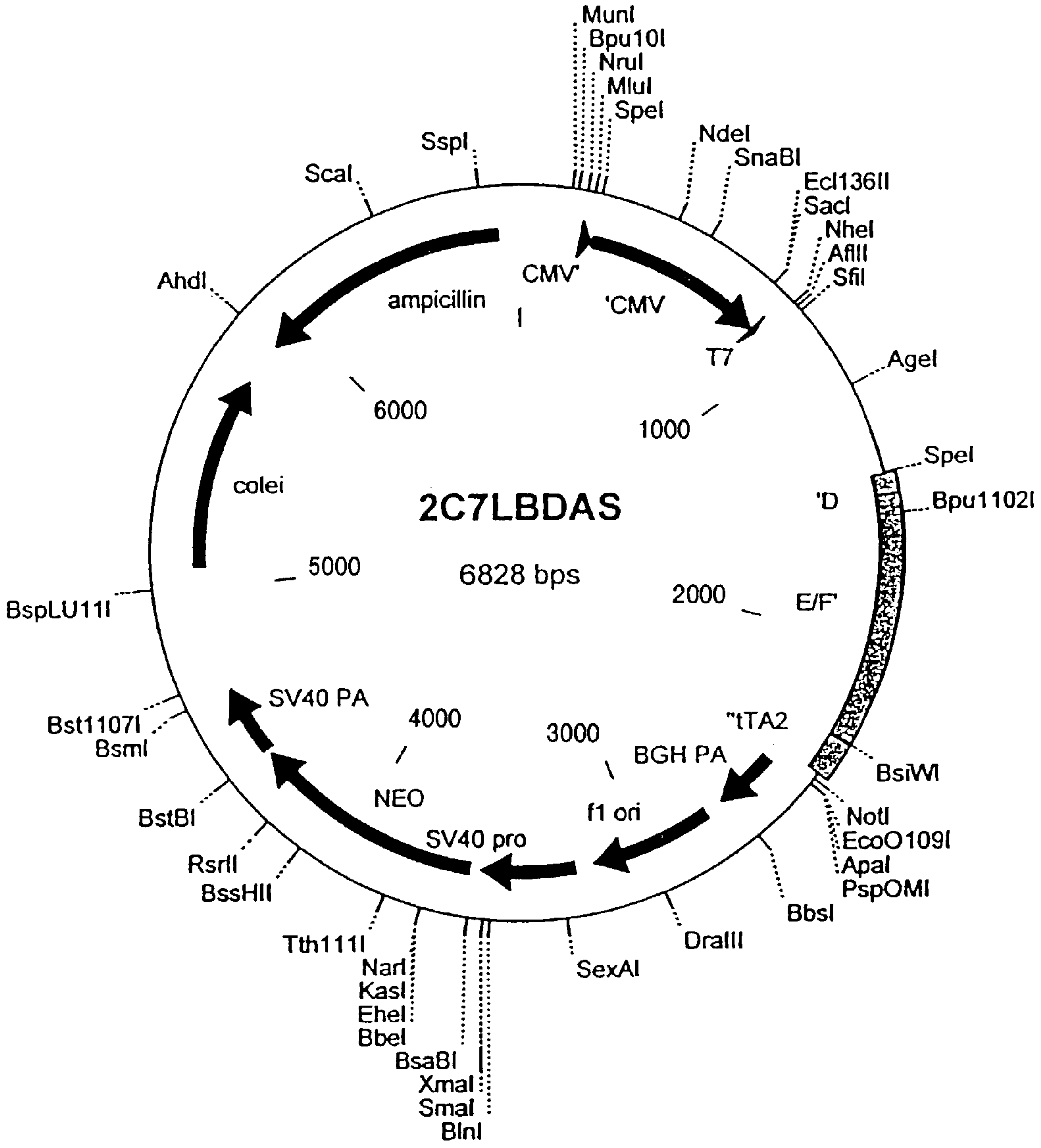
FIG. 16 is a schematic map of the expression vector for 2C7LBDAS based on the plasmid pCDNA3.1.
Figure 17:
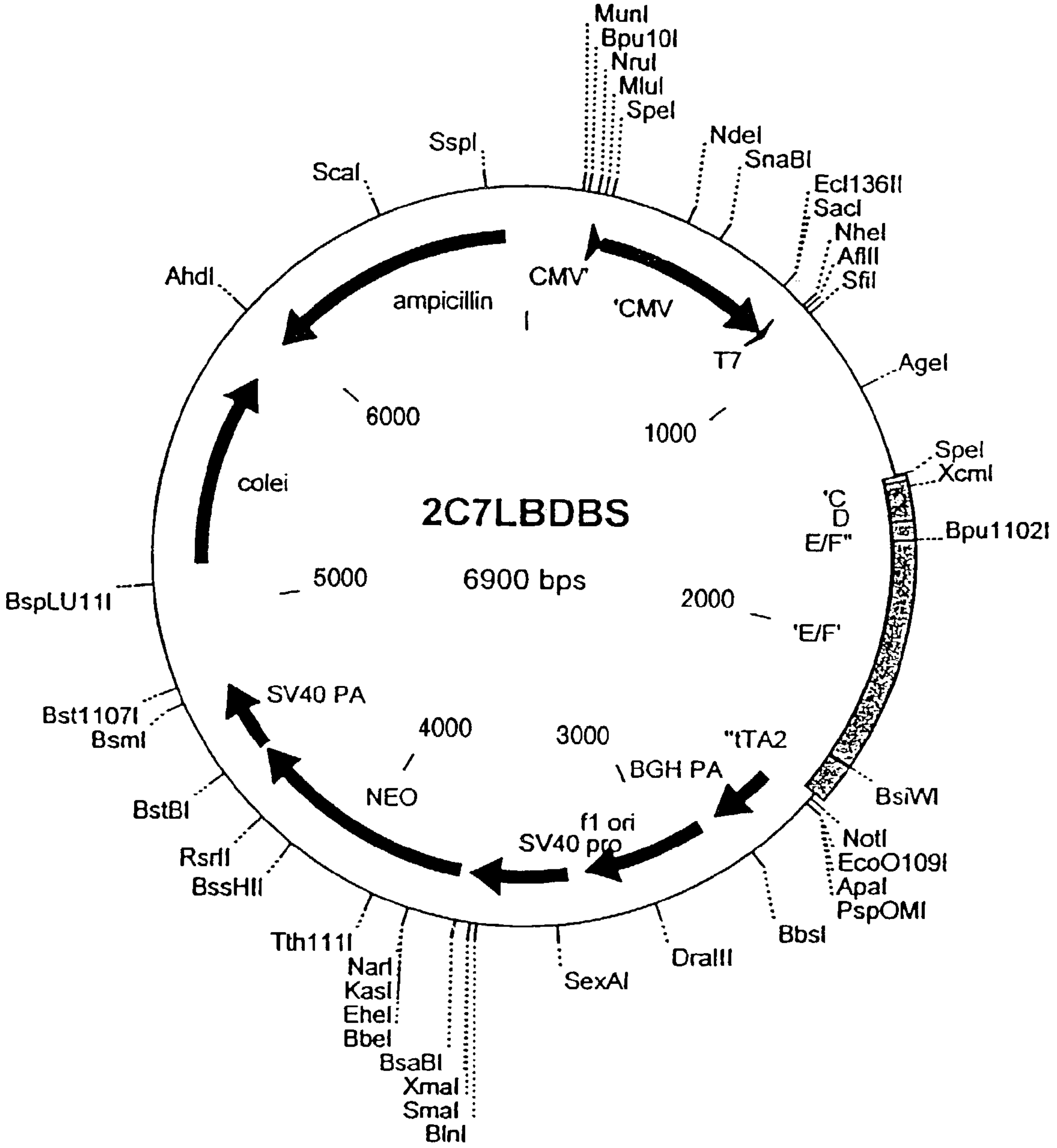
FIG. 17 is a schematic map of the expression vector for 2C7LBDBS based on the plasmid pCDNA3.1.
Figure 18:
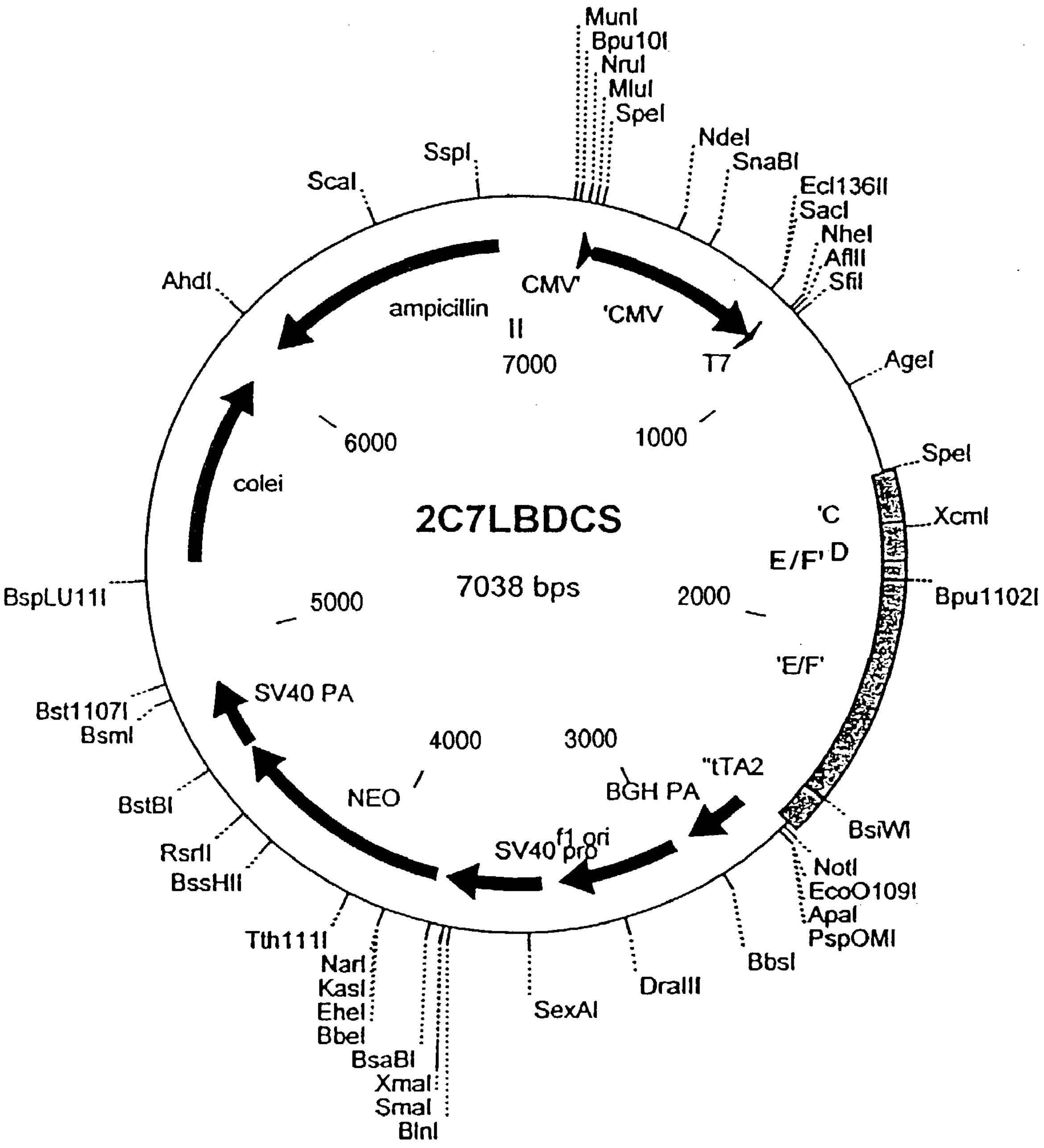
FIG. 18 is a schematic map of the expression vector for 2C7LBDCS based on the plasmid pCDNA3.1.
Figure 19:
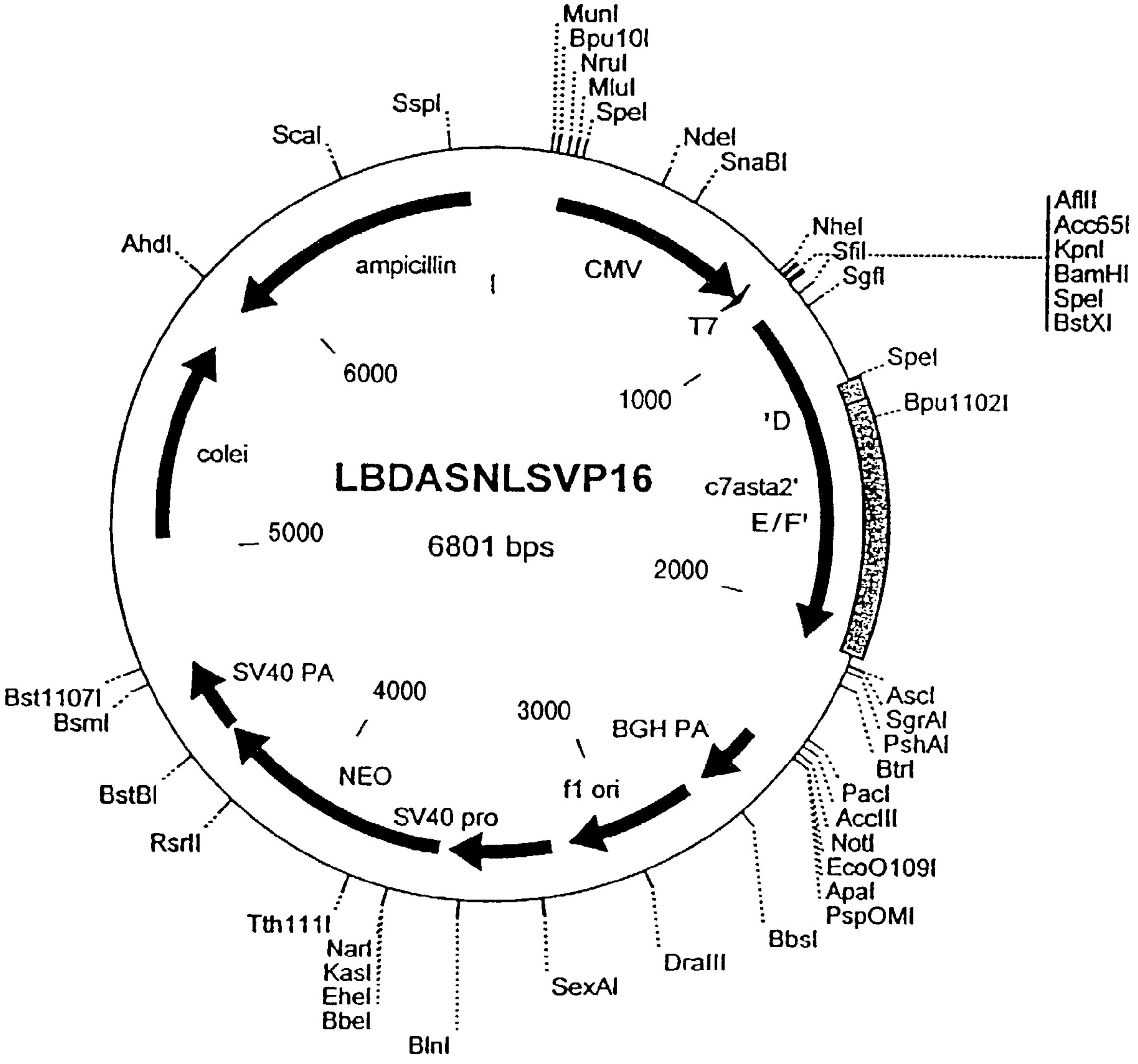
FIG. 19 is a schematic map of the expression vector for LBDASNLSVP16 (SEQ ID NO: 13), based on the plasmid pCDNA3.1.
Figure 20:
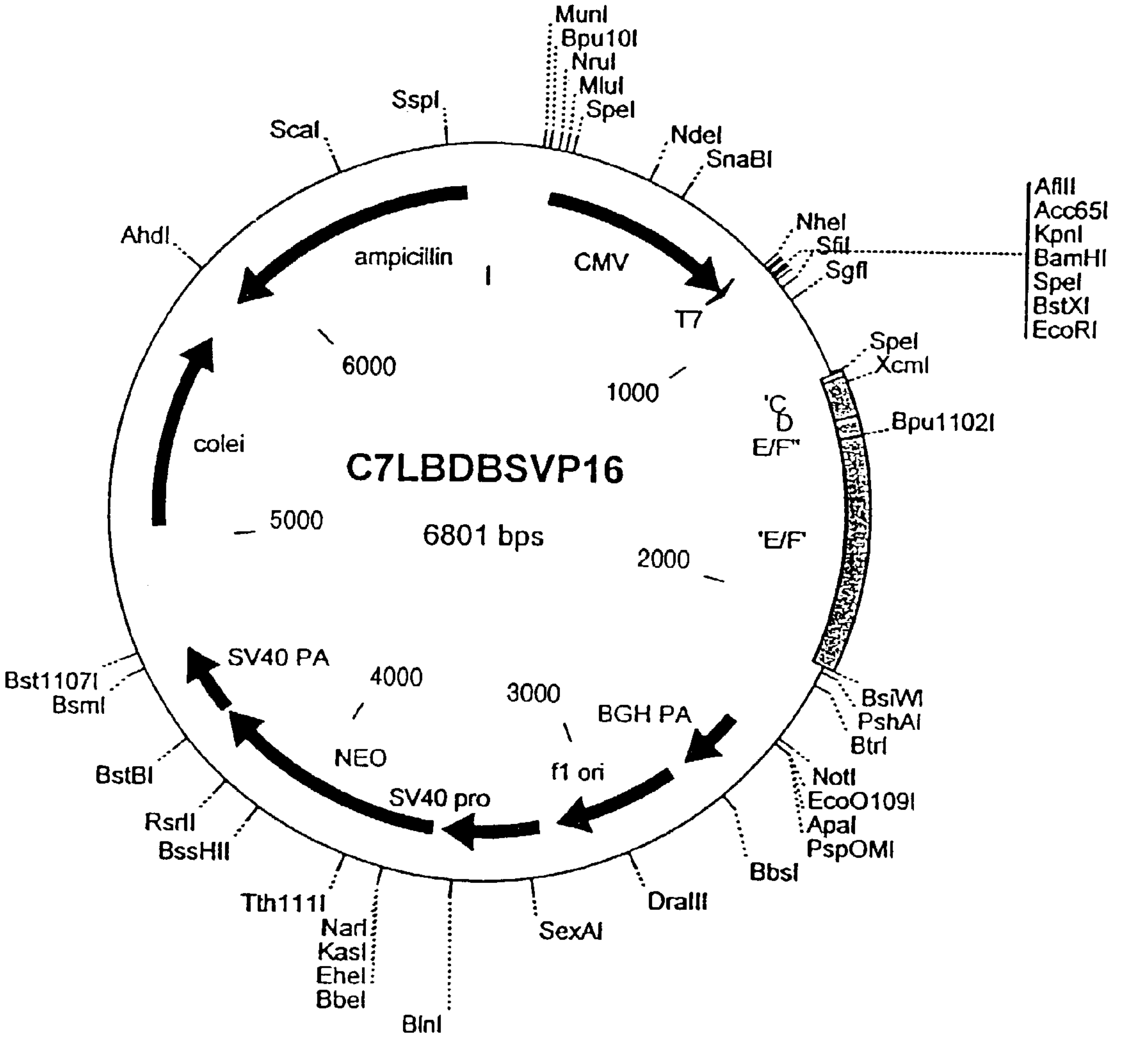
FIG. 20 is a schematic map of the expression vector for C7LBDBSVP16 based on the plasmid pCDNA3.1.
Figure 21:
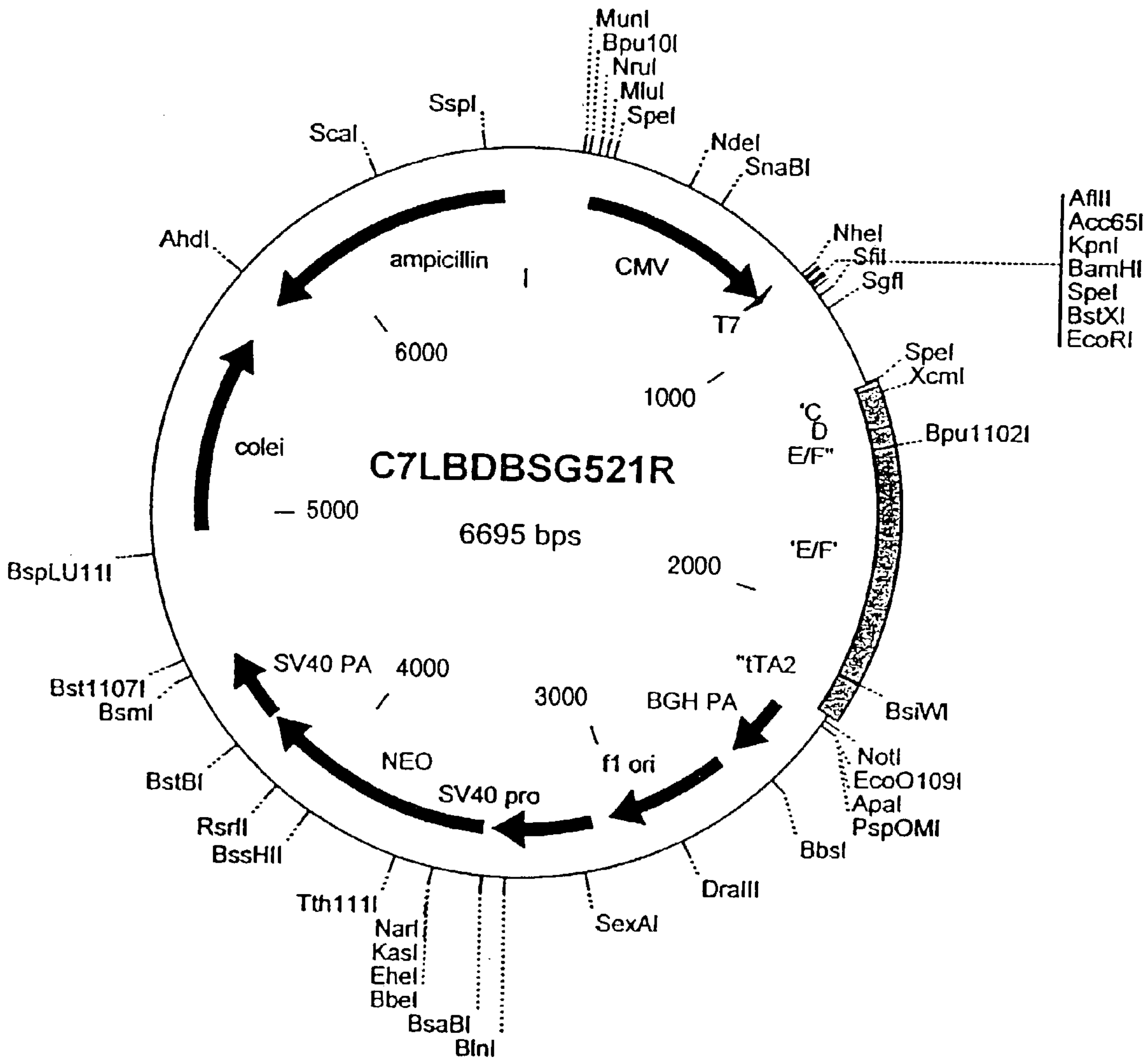
FIG. 21 is a schematic map of the expression vector for C7LBDBSG521R (SEQ ID NO: 15), based on the plasmid pCDNA3.1.
Figure 22:
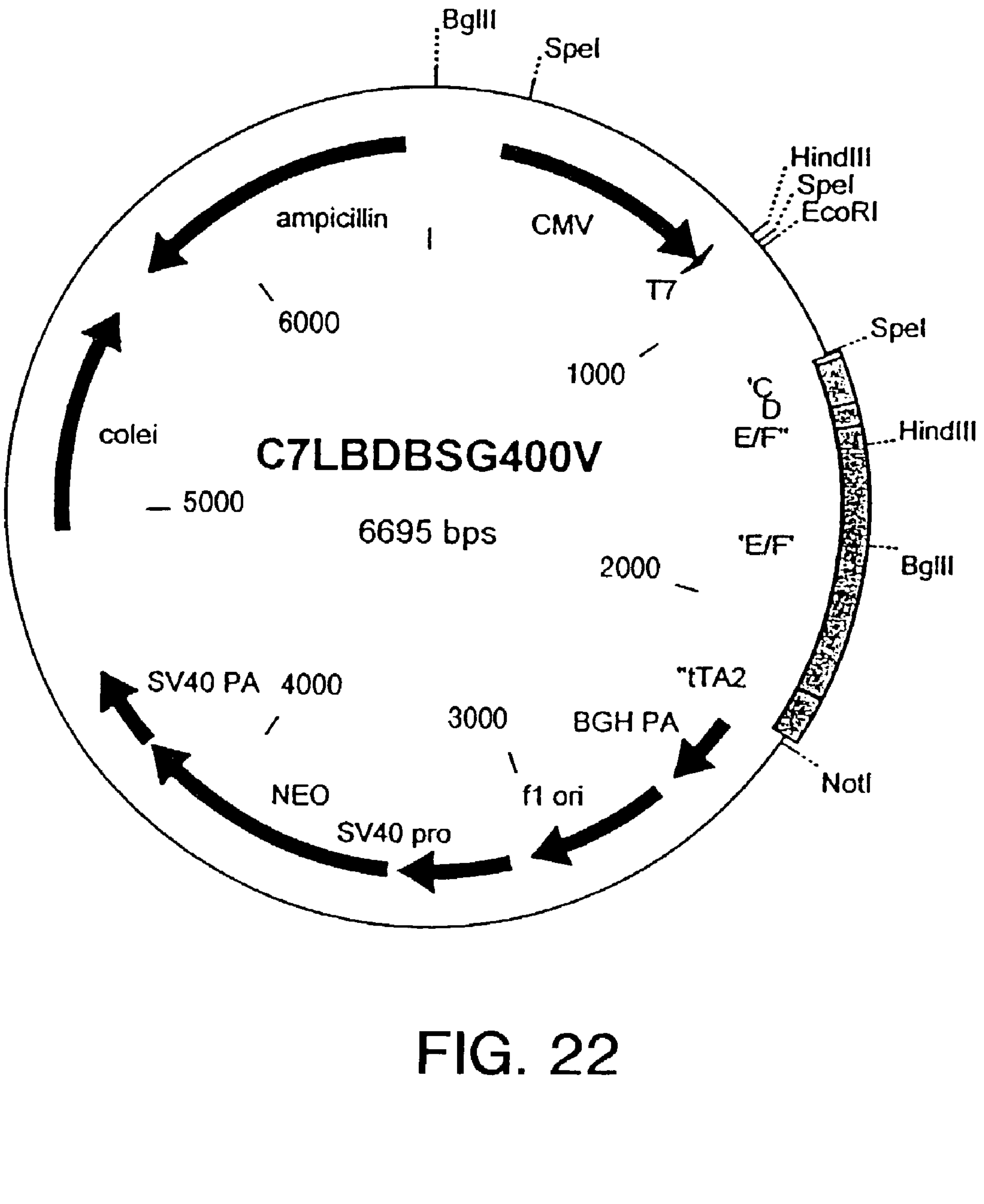
FIG. 22 is a schematic map of the expression vector for C7LBDBSG400V (SEQ ID NO: 14), based on the plasmid pCDNA3.1.

As discussed in detail above, zinc fingers of the C2H2 class each contribute to about 3 bp of DNA sequence contacts. C2H2 zinc finger arrays can be "stitched together" to assemble DNA binding domains having 6, 9, 12, 15, 18 bp or more of specific sequence to which they bind. In order to evaluate the size of the zinc finger array that can be used in these C2H2 Zn finger (ZFP)—steroid receptor fusion proteins, proteins containing 3 finger and 6 finger arrays were constructed. The composition of the various proteins assembled, and their DNA binding site specificity is listed in FIG. 16.

The general cloning strategy was as follows. Three fragments (A, B, and C with reference to FIG. 3) of human estrogen receptor ligand binding domain (LBD) with or without the F region were built into the pcDNA3.1 (Invitrogen) vector backbone through a series of PCR amplification and cloning steps. Initially the LBD fragment A without F region (i.e. short form; LBDAS) and with F region (i.e. long form; LBDAL) were PCR amplified from a plasmid clone of the human wild type estrogen receptor, pHEGO (Tora et al. *EMBO J.* 8:1981-1986) with primer pairs NR1/NR2 and NR1/NR3 respectively (Table 1). Convenient restriction sites were incorporated into primers (Table 1) as needed. The PCR amplified LBDAS and LBDAL fragments were first cloned into the Srf I site of pCR-ScriptAmpSK(+) vector (Stratagene), resulting in constructs pLBDAS and pLBDAL. The VP16 minimal domain trimer (TA2; Baron et al. (1997) *Nucleic Acids Research* 25:2723-2729) was PCR amplified from plasmid pTTA2 (Clontech) with primer pairs NR4 and NR9 and cloned into the SplI and NotI site of pLBDAS and pLBDAL to generate pLBDASTA2 and pLBDALTA2. To generate LBD fragment B without the F region (LBDBS) and LBD fragment C without the F region (LBDCS), PCR primers NR7 and NR8, which represent the 5' boundary of the LBD region fragment in chimerics B and C respectively were designed (Table 6, below). These primers were paired with the 3' end primer NR6, which incorporates a unique BlpI site in ER. PCR fragments from pHEGO with primer pair NR6/

NR7 and PCR fragment with NR6/NR8 were then cloned into the SpeI and BlpI site of pLBDC7ASTA2 backbone. This resulted in plasmid pLBDBSTA2 and pLBDCSTA2.

TABLE 6

PCR Primers Used For Cloning

| NAME/ (SEQ ID NO:) | SEQUENCE |
|---|---|
| NR1 (39) | cct act gcc ggc act agt tct gct gga gac atg aga gct gcc aac ctt |
| NR2 (40) | cct aaa cgt acg gct agt ggg cgc atg tag gcg gtg ggc gtc |
| NR3 (41) | cct aaa cgt acg gac tgt ggc agg gaa acc ctc tgc ctc |
| NR4 (42) | cca ctt aaa tgt gaa agt cgt acg ccg gcc |
| NR6 (43) | tat ggg ggg ctc agc atc caa caa ggc act |
| NR7 (44) | cct act act agt gac cga aga gga ggg aga atg ttg aaa cac aag cgc |
| NR8 (45) | cct act act agt agt att caa gga cat aac gac tat atg tgt |
| NR9 (46) | tat cat gtg cgg ccg ctt act tag tta ccc cgg cag cat |

Having completed cloning of the three LBD fragments fused to the TA2 region, the C2H2 DNA binding protein C7 was then excised from pcDNAC7VP16 by BglII and SpeI digestion and ligated into the BamHI and SpeI site of each of the 3 constructions (pLBDASTA2, pLBDBSTA2 and pLBDCSTA2), which resulted in pC7LBDASTA2, pC7LBDBSTA2 and pC7LBDCSTA2. Cassettes of C7LBDASTA2, C7LBDBSTA2 and C7LBDCSTA2 were then removed from the pCR-Script vector by EcoRI-NotI digestion and cloned into the same sites of the expression cassette vector pcDNA3.1(+), resulting in constructs pCDNAC7ASTA2, pCDNAC7BSTA2 and CDNAC7CSTA2. In order to reconstruct these three ZFP-LBD fusion proteins with an LBD fragment including the estrogen receptor F region fused to TA2, the BlpI to NotI fragment was excised from pLBDALTA2 construct and substituted for the BlpI-NotI fragment in pCDNAC7LBDASTA2, pCDNAC7LBDBSTA2 and pCDNAC7LBDCSTA2 to generate pCDNAC7LBDALTA2, pCDNAC7LBDBLTA2 and pCDNAC7LBDCLTA2.

Cloning for Replacement of DNA Binding Domain C7 with E2C

An intermediate construct pcDNAE2CVP16 was first constructed by replacing the SfiI fragment containing C7 in pcDNAC7VP16 with the E2C(hs1) fragment isolated from pMal/E2C(hs1) after SfiI digestion. Next, pcDNAE2CVP16 was digested with SpeI and a 1 kb fragment was isolated. This SpeI fragment was ligated to the large SpeI fragment of pcDNAC7LBDASTA2, which created pcDNA-E2CLBDASTA2. Similar steps were performed to construct pcDNAE2CLBDBSTA2.

Analysis of Recombinant Construct Protein Binding to DNA

In order to demonstrate that the fusion proteins bind to DNA in a sequence specific manner, and to evaluate the stoichiometry of protein:DNA binding, standard electrophoretic mobility shift or gel retardation assays were performed.

First, fusion proteins were produced by in vitro transcription and translation using the TNT Coupled Reticulocyte Lysate System (Promega, Cat #L4610) according to the manufacturer's instructions. Briefly, each expression reaction was set up in a total volume of 50 μl which contained 25 μl of TNT rabbit reticulocyte lysate, 2 μl of TNT Reaction Buffer, 2 μl of RNasin ribonuclease inhibitor (20 U/μl), 1 μl each of amino acid mixture minus leucine, amino acid mixture minus methionine and TNT T7 RNA polymerase, 2 μl of expression plasmid (1 μg/μl) and water. The reaction mixture was incubated at 30° C. for 90 minutes.

Binding of the expressed protein to duplex oligonucleotides was performed as follows, using the gel shift assay systems (Promega, Cat #E3050): 5 μl of in vitro translation product was co-incubated with 4 μl of 5× gel shift binding buffer and 7 μl of water at room temperature for 20 min, then 2 μl of E2 (10 nM final concentration) and 2 μl of $^{32}$P-labeled probe were added to the mixture. The probe had been labeled using standard protocol as described in the kit. After incubated at room temperature for about 20 minutes, the mixture was loaded onto a 6% DNA retardation gel and run in 0.5× TBE buffer at 150-200 volts for about 30-60 minutes. The gel was then dried and exposed to X-ray film.

A DNA oligonucleotide containing two inverted binding sites for the C2H2 domain known as C7, each half site separated by 3 bp, was used for the initial assessment of DNA binding. This palindromic configuration mimics the composition of the native estrogen receptor response element (ERE), except that the natural 6 bp half site of ERE is replaced by the 9 bp half site specified by C7. Binding of the C7-LBD fusion proteins A, B, and C, all in the short form, were tested and compared to the control proteins C7VP16 and 2C7VP16 (see, Liu, et al. (1997) *Proc. Natl. Acad. Sci. U.S.A* 94:5525-5530, which describes the control proteins). For each protein, binding was tested in the absence or presence of 100 fold excess of unlabeled oligonucleotide (1.75 μM) as a competitor. Competition of the gel shift product by the unlabeled oligonucleotide indicates the band is a specific protein:DNA interaction. The results demonstrated that C7VP16 can bind once or twice to the oligonucleotide, creating two specific gel shift bands. 2C7VP16 binds only once to the oligonucleotide containing two inverted C7 sites. Notably, C7LBDA and C7LBDB bind strongly to yield one major species, which runs higher than any of the control bands. Although true molecular mass cannot be determined from this type of mobility assay, the relative size of the complexes suggest the protein bound for C7LBD is larger than for C7VP or 2C7VP. The size of the band and presence of only one major species indicate that the fusion protein ZFP-LBD is binding to the oligonucleotide as a dimer. No significant gel shift product was detected for C7LBD chimeric C, suggesting that the addition of the additional native zinc finger from the estrogen receptor may have reduced the affinity of the fusion protein for its C2H2-specific DNA binding site. Finally, the reduction of binding for each of the gel shift products by the addition of the unlabeled oligonucleotide indicates that these fusion proteins are binding to DNA in a sequence specific manner.

To further demonstrate that the chimera ZFP-LBD binds to DNA as a dimer, the binding of C7LBD A, B, and C to oligonucleotides containing one or two C7 binding sites was tested. Three fusion proteins (C7LBDAS, C7LBDBS and C7LBDCS) were tested against three different target oligonucleotide sequences, which contained one C7 half site or two C7 half sites either in palindromic or direct repeat orientation.

Oligo 1: gat cca aag tcg cgt ggg cgc agc gcc cac gcg atc aaa ga (SEQ ID NO: 48)

Oligo 2: gat cca aag tcc agg cga gcg cgt ggg cgg cag atc aaa ga (SEQ ID NO: 49) Oligo 3:gat cca aag tcg cgt ggg cgc agg cgc gag cgt ggg cgg atc aaa ga (SEQ ID NO: 50)

Gel shift assay conditions were the same as the standard protocol described above. The results showed that C7LBDAS and C7LBDBS were able to bind to both oligonucleotides containing two C7 half sites, but not to the oligo containing only one half site. C7LBDCS bound weakly or not at all to all three targets.

with 9 intervening spaces, respectively. These data indicate that the ZFP-LBD fusion proteins dimerize and bind preferentially to DNA containing two C7 half sites, but that the exact orientation and spacing of the half sites is not critical. This flexibility in DNA binding site orientation may reflect the lack of a dimerization function in the C2H2 domains, but it is noteworthy that wild type estrogen receptor has also been shown to bind a variety of response elements differing from the consensus ERE, including inverted and direct repeats.

Figure 11:
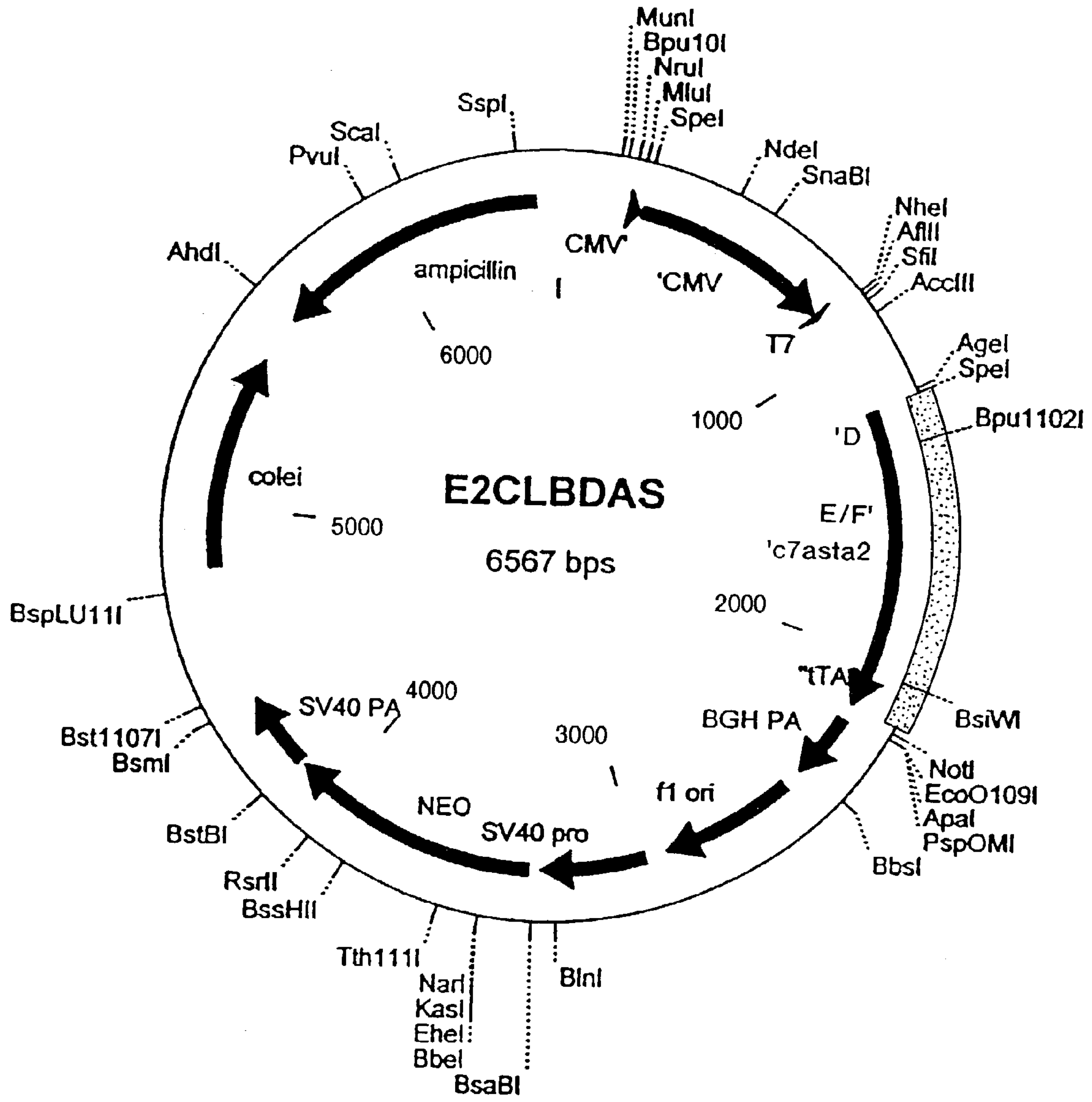
FIG. 11 is a schematic map of the expression vector for E2CLBDAS based on the plasmid pCDNA3.1.
Figure 12:
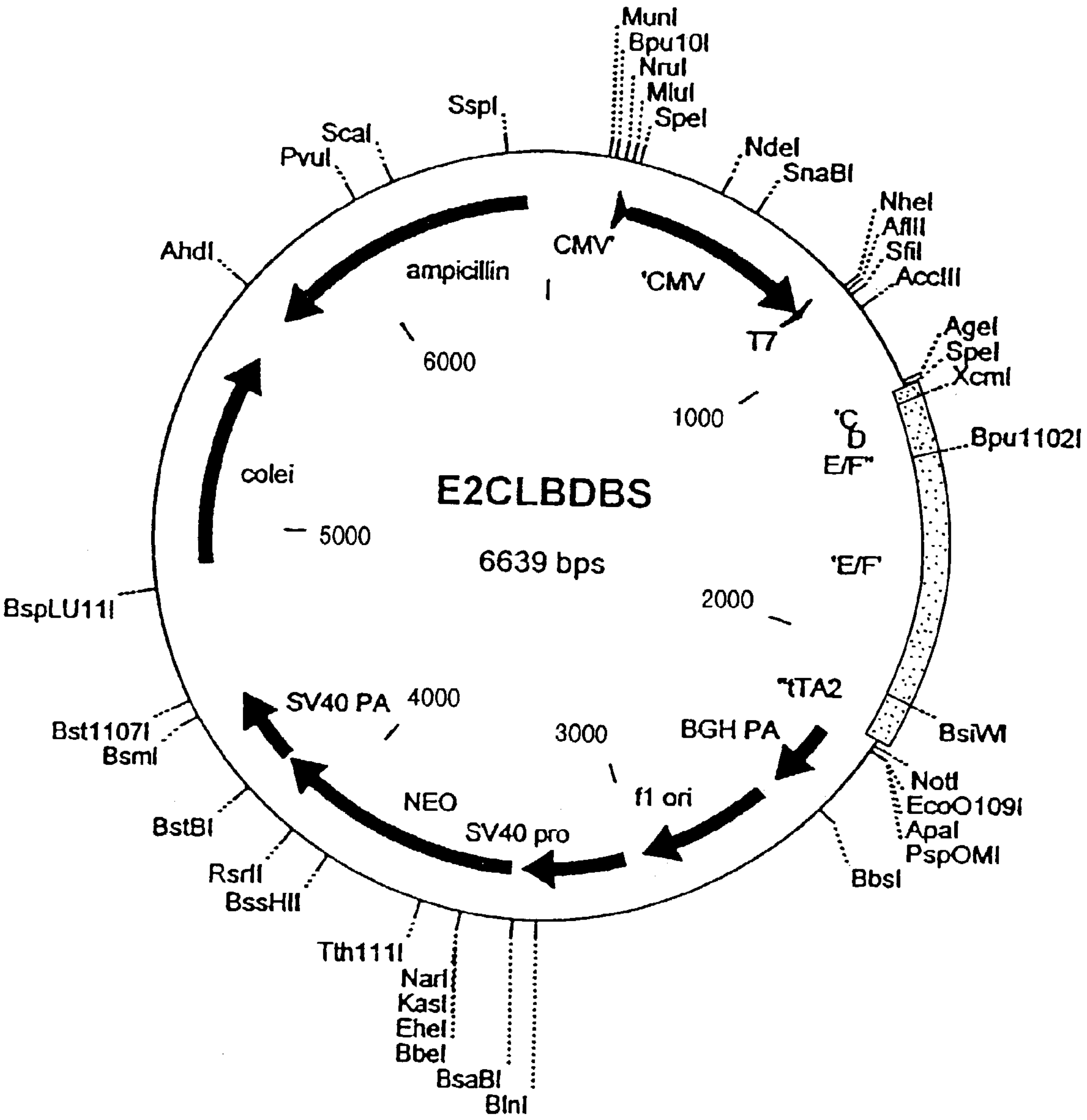
FIG. 12 is a schematic map of the expression vector for E2CLBDBS based on the plasmid pCDNA3.1.

To further confirm the homodimer binding stoichiometry of the ZFP-LBD fusion proteins and to demonstrate their DNA sequence specificity, the following experiment was conducted. A second ZFP-LBD fusion protein was constructed using the C2H2 zinc finger domain E2C(HS1), which binds to a recognition sequence 5'-GGG GCC GGA g 3' that differs in six out of nine base pairs from the C7 binding site. (Note that the lower case g denotes a $10^{th}$ base that makes a minor contribution to the protein:DNA contact affinity.) Maps of specific examples constructed in the expression vector pcDNA3.1 are shown in FIG. 11 (E2CLBDAS) (SEQ ID NO: 11) and FIG. 12 (E2CLBDBS) (SEQ ID NO: 12).

Oligonucleotides were prepared containing an inverted repeat of two C7 sites, two E2C sites, or a mixed heterodimeric site of one C7 and one E2C half site. Two fusion proteins having different DNA binding domains (C7 or E2C) were tested for their DNA binding specificity against three oligonucleotides containing palindromic binding sites specific for C7, E2C or the combination of the two.

```
C7 oligo:       gat cca aag tcg cgt ggg cgc agc gcc cac gcg atc aaa ga (SEQ ID NO:51)

C7/E2C oligo:   gat cca aag tcg cgt ggg cgc act ccg gcc ccg atc aaa ga (SEQ ID NO:52)

E2C oligo:      gat cca aag tcg ggg ccg gag act ccg gcc ccg atc aaa ga (SEQ ID NO:53)
```

To further demonstrate that the chimera ZFP-LBD binds to DNA as a dimer, the binding of C7LBD A, B, and C to oligonucleotides containing one or two C7 binding sites was tested. Three fusion proteins (C7LBDAS, C7LBDBS and C7LBDCS) were tested against three different target oligonucleotide sequences, which contained one C7 half site or two C7 half sites either in palindromic or direct repeat orientation.

Gel shift assays were performed according to the standard protocol described above.

The results showed that C7LBD fusion protein only binds strongly to the oligonucleotide containing two C7 sites, but not to either the 2×E2C probe or the C7/E2C probe. Likewise, the E2C-LBD chimeric protein only binds strongly to the 2×E2C probe. Finally, neither ZFP-LBD construct binds to the oligonucleotide with the heterodimeric site. When the two

```
Oligo 1: gat cca aag tcg cgt ggg cgc agc gcc cac gcg atc aaa ga          (SEQ ID NO:48)

Oligo 2: gat cca aag tcc agg cga gcg cgt ggg cgg cag atc aaa ga          (SEQ ID NO:49)

Oligo 3: gat cca aag tcg cgt ggg cgc agg cgc gag cgt ggg cgg atc aaa ga  (SEQ ID NO:50)
```

(SEQ ID NO: 50 Gel shift assay conditions were the same as the standard procotol described above. The results showed that C7LBDAS and C7LBDBS were able to bind to both oligonucleotides containing two C7 half sites, but not to the oligo containing only one half site. C7LBDCS bound weakly or not at all to all three targets.

Fusion proteins C7LBDA and C7LBDB bound to the probe containing a palindrome (two inverted half sites) as a single form and in equal amount to the C7VP control, while C7LBDC showed no detectable binding. In contrast, the fusion proteins C7LBDA and C7LBDB did not bind to the oligonucleotide containing only one C7 site, while C7VP bound only once, as expected. C7LBDA and C7LBDB bound equally to the oligo 1 and oligo 3, which contain two sites as inverted repeats with 3 intervening spaces or direct repeats proteins were mixed in equal amount, a C7LBD and E2CLBD heterodimer was formed. The heterodimer binds to the heterodimeric probe. These results confirm that the ZFP-LBD fusion proteins are binding DNA preferentially as dimers. Furthermore, these data demonstrate good DNA binding specificity between fusion proteins with different C2H2 binding site preferences.

EXAMPLE 5

Ligand-dependent Regulation of Transgene Expression by ZFP-LBD Fusion Proteins In order to evaluate the ability of the fusion proteins C7LBD A, B, and C to regulate transgene expression, a standard co-transfection reporter assay was performed. A reporter construct, henceforth known as 6×2C7pGL3Luc, containing six copies of a directly repeated C7 binding site (6×2C7) inserted upstream of an SV40 promoter fragment and reporter gene encoding firefly luciferase (pGL3Pro; Promega) was transfected along with the designated fusion protein and assayed as described below.

Cultured cells (HeLa, Cos, Hep3B or other) were seeded at $5\times10^4$ cells/well in a 24 well plate prior to the day of transfection in DMEM Phenol-free media, supplemented with L-glutamine and 5% (v/v) charcoal-dextran stripped Fetal Bovine serum (sFBS). Cells were transfected using the Qiagen Superfect Transfection method. For each well 1 μg of total DNA, containing 0.5 μg luciferase reporter plasmid (6×2C7pGL3proluc), 0.1 μg of chimeric activator DNA (e.g., C7LBDA, C7LBDB, or C7LBDC) unless otherwise indicated, and 0.4 μg of an inert carrier plasmid DNA (p3Kpn), was mixed with 60 μL of DMEM phenol-free/serum free media, and 5 μL of Superfect reagent. In general, about 10 ng to about 0.5 μg of chimeric activator DNA was used for each well.

The mixture was vortexed for 10 seconds and incubated at room temperature for 10 minutes, followed by the addition of 350 μL of DMEM phenol-free 5% sFBS media. Cells were washed once with Dulbecco's phosphate buffered saline (DPBS) and the transfection mixture placed on the cells. Cells were washed once with DPBS following a 2.5 hour incubation at 37 degrees Celsius, and re-fed with DMEM Phenol-free 5% sFBS media.

At approximately 24 hours post-transfection, cells were treated with an inducing agent, 17 β-Estradiol or 4 OH-Tamoxifen as indicated, each at 100 nM final concentration in DMEM Phenol-free 5% sFBS. Cells were harvested 24 hours later by washing once with DPBS and adding 200 μL 1× reporter lysis buffer (Promega). Plates were frozen at −80° C. and thawed at room temperature for 1.5 hours on an orbital shaker at 100 RPM. After allowing for cellular debris to settle, lysate was diluted 1:10 with 1× reporter lysis buffer, and 10 μl transferred to 96 well opaque plates. Plates were analyzed with a Tropix TR717 Microplate Luminometer using firefly luciferase substrate (Promega).

The ability of C7LBD short form chimeric proteins A, B, and C to regulate reporter gene expression in an estrogen-dependent manner was studied in Cos and HeLa cells. The constitutive activators C7VP16 and 2C7VP16 were used as positive controls. The results show that the three ZFP-LBD fusion proteins gave a similar profile in Cos and HeLa cells. All three ZFP-LBD fusion proteins had an estrogen dependent effect on the luciferase reporter gene. The characteristic pattern is that A has greater total activity than B and B has greater total activity than C. Likewise, the basal or ligand-independent effect of these proteins on the reporter gene follows a similar pattern: A>B>C. The estrogen dependent effect on gene expression ranged from two-fold to nine-fold in these experiments.

The regulation of luciferase reporter gene by the C7LBD long and short form fusion proteins was compared in Cos cells. The results indicate that the long form fusion proteins, which contain the estrogen receptor F region, have a higher basal and ligand-independent effect on the reporter gene than the short form. As a result, the long fusion proteins give lower fold induction. This result may be due to an enhanced, but ligand-independent, transactivation activity in the F region that works synergistically with the heterologous VP minimal domain trimer. Alternatively, this result could be due to the difference in spacing, as a result of the intervening F region, between the VP activation domain and the estrogen receptor ligand binding domain of the recombinant proteins.

Figure 13:
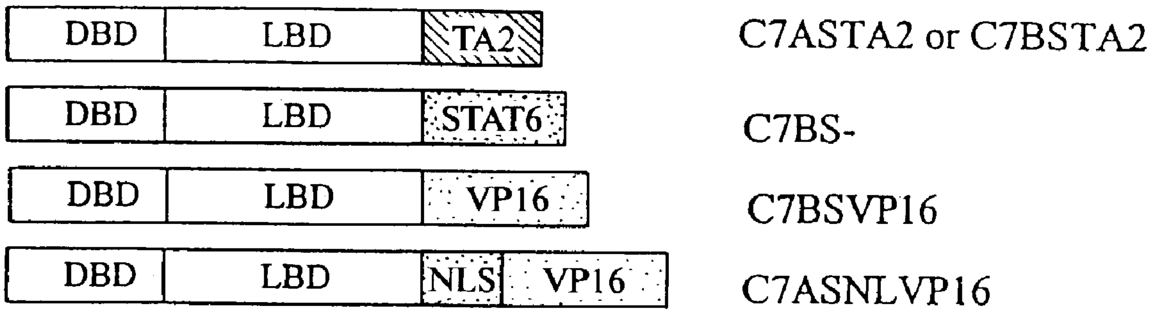
FIG. 13 is a schematic diagram of the constructs C7LBDASTA2, C7LBDBSTA2, C7LBDBS-STAT6, C7LBDBSVP16 (SEQ ID NO: 16), AND C7LBDBSNLSVP16.

In order to evaluate the role of the composition of the heterologous transactivation domain on the activity of the C7LBD fusion proteins, the VP minimal domain trimer was replaced with either the carboxy terminal activation domain from human STAT-6 (amino acids 660-847) or the full length VP16 activation domain of approximately 77 amino acids (residues 413-490) (FIG. 13). In constructs with full length VP16, the transactivation domain was added either native, or in conjunction with an SV40 nuclear localization peptide sequence at the amino terminus of the VP16. C7LBD fusion proteins A or B containing different transactivation domains (TA2, STAT6C, VP16 and NLSVP16) were constructed and evaluated for their effects on gene activation and ligand induction. The construct, shown schematically and abbreviated above, includes the following:

1. C7ASTA2, C7BSTA2: C7LBD A or B short form with the VP16 minimal domain trimer.
2. C7BS-STAT: C7LBDB short form with the STAT6 carboxy activation domain.
3. C7BS VP16: C7LBDB short form with full length VP16 activation domain.
4. C7AS nlsVP16: C7LBDA short with full length VP16 preceded by a nls.

Assays were performed with HeLa cells transfected with 0.5 ug of 6x2C7pGL3Luc reporter and 0.1 μg regulator, Luc activity was determined as previously described. When the human STAT6 transactivation domain was used to replace the TA2 VP minimal domain trimer, the same low basal activity and 9 fold ligand dependent induction of transgene, two-fold less than with the TA2 domain, was obtained.

The incorporation of NLS upstream of the full length VP16 (FIG. 24, C7ASnlsVP16) greatly increased the folding induction compared to TA2 or VP16 without the NLS, but the total activity was significantly decreased. When the full length VP16 domain was used, it gave about 2 fold higher total activity, but high basal activity resulting in weaker ligand dependent induction (3-fold).

EXAMPLE 6

Ligand-Independent Activity of C7-PBD-VP16 Constructs Depends on the Structure of the Reporter Constructs In initial tests, the C7-PBD-VP16 construct showed the high basal (i.e. ligand-independent) activity. Thus, C7-PBD-VP16 was compared to the original, Gal4-based construct GL914VPc', which reportedly had a very low basal activity. When the GL914VPc' protein was tested on a 6xGal4-SV40 promoter-luciferase reporter, it displayed even higher basal activity than C7-PBD-VP16. Variation of effector/reporter ratios had no effect on the basal activities in both systems. It was discovered, however, that the ratios for optimal induction were different for GL914VPc' and C7-PBD-VP16, namely 1/30 and 1/10, respectively.

Other possible sources of ligand-independent activity were examined. Commercially available fetal calf serum (FCS) batches are known to contain estrogen or estrogen-like activities. Since it was possible that the presence of progesterone-agonistic activities in the serum was the cause for the high basal activities, the FCS was "stripped" of steroids using dextran-coated charcoal. However, side-by-side comparison of stripped and non-stripped serum showed no detectable difference in the basal activity of the switch constructs. Lipid-based transfection reagents such as Lipofectamine™ can also have significant agonistic activity on steroid receptors. Thus, the non-lipid transfection reagent Superfect™ from Qiagen was used as an alternative, and compared to Lipofectamine™. No reduction of the basal activities was observed. For all the assays described above, HeLa cells were used. However, the use of HepG2 cells, which were used in the original study with GL914VPc', brought no improvement.

The reporter p17x4TATA-luc, used in the original studies on Gal4, contains four Gal4 dimer binding sites upstream of a TATA box. GL914VPc' had a very low basal activity on this reporter, and was inducible by RU486. An equivalent reporter, pGL3TATA/10xC7, was therefore constructed to test C7-PBD-VP16. While the basal activity using a reporter construct having TATA reporter was still higher than in the Gal4 system, basal activity was clearly lower than using the SV40 promoter-containing pGL3prom/10xC7. Two additional reporters with minimal CMV promoters, pGL3minCMV/6xGal4 and pGL3minCMV/10xC7, were also constructed. The basal activity of the corresponding switch proteins was as high on these reporters as on the SV40 promoter containing reporters.

These results indicate that GL914VPc' and C7-PBD-VP16 were constitutively located in the nucleus and able to bind to their target sites, either as monomers or as dimers. However, unless bound to ligand the fusion proteins are only able to activate transcription in the context of more than a TATA box, i.e. a SV40 promoter or a minimal CMV promoter. If there is only a TATA box, ligand binding presumably associated with a conformational change is required for efficient activation of transcription.

It was found that ligand-independent basal activity is also cell type specific. C7-PBD-VP16 had an even lower basal activity on the TATA reporter in NIH/3T3 cells than it had in HeLa cells.

Since C7-PBD-VP16 appears to be constitutively translocated to the nucleus, the SV40 nuclear localization signal (NLS) between PBD and VP16 domains was removed in the hope of making nuclear translocation more ligand dependent. The resulting construct, C7-PBD-VP16noNLS, was then tested on the pGL3prom/10xC7 reporter. However, transcriptional activation was no more RU486-dependent than in the case of C7-PBD-VP16 as shown by an unchanged basal activity. The construct C7-PBDANLS-VP16noNLS was made in which the small remaining part of a natural SV40-like NLS at the N-terminus of the PBD (aa 640-644) is also removed.

EXAMPLE 7

Optimizing Spacing and Orientation of the DNA Binding Domain Half-Sites

Naturally occurring steroid hormone receptors typically bind to an inverted repeat, or palindromic SRE. However, it has been shown in several cases that there is some flexibility in binding. Direct repeats and everted repeats can also serve as response elements. To determine the optimal spacing and orientation of the two half-sites for binding of a steroid receptor-based switch construct a total of eighteen C7 dimer TATA-luciferase reporter constructs were prepared. Six C7 dimers each in direct, inverted and everted repeat orientation, with spacers of 0 to 5 intervening bases. A test of the RU486-responsive C7-PBD-VP64 protein on each of these reporter constructs revealed that indeed there was quite some flexibility, since RU486 inducible activation was observed with each of the reporters (Tables 7-9, below; values listed are means of two determinations and the standard deviation). There were clear differences in the degree of responsiveness of each of the reporters.

A direct repeat of two C7 sites without any spacing displayed the most favorable properties. This is particularly important, indicating the ability to target $(GNN)_6$ sites using homodimeric and heterodimeric recombinant ligand-responsive transcription factors.

Further tests on the RU486-responsive VP64-C7-PR protein and the tamoxifen-responsive VP64-C7-ER protein, on each of these reporter constructs also revealed some flexibility, since ligand-inducible activation was observed with each of the proteins on each of the reporters. However, the most favorable properties were observed with the VP64-C7-ER protein on the direct and everted repeats with a spacing of 3 bp. Direct repeat with a spacing of 5 bp was also more or less reasonable, permitting targeting of the erbB-2 promoter with a 3 finger construct (see below).

Further studies have shown that binding of a C7/Cf2-PBD-VP64 heterodimer to a C7-Cf2 TATA reporter, with one binding site each for C7 and Cf2 without spacing, provides about a two-fold ligand-dependent change in transcription.

TABLE 7

| | Direct Repeats | |
|---|---|---|
| C7-PBD-VP64 | Mean | STD DEV |
| C7c7 | 4081 | 511 |
| C7c7 + RU486 | 20018 | 2090 |
| C7ac7 | 3383 | 396 |
| C7ac7 + RU486 | 8205 | 2064 |
| C72ac7 | 3417 | 348 |
| C72ac7 + RU486 | 8169 | 634 |
| C73ac7 | 3269 | 1550 |
| C73ac7 + RU486 | 5138 | 2319 |
| C74ac7 | 3966 | 298 |
| C74ac7 + RU486 | 6945 | 1377 |
| C75ac7 | 2597 | 416 |
| C75ac7 + RU486 | 5460 | 207 |

TABLE 8

| | Inverted Repeats | |
|---|---|---|
| C7-PBD-VP64 | Mean | STD DEV |
| C77c | 2921 | 1368 |
| C77c + RU486 | 10811 | 1596 |
| C7a7c | 4342 | 153 |
| C7a7c + RU486 | 9534 | 2943 |
| C72a7c | 6964 | 573 |
| C72ac7 + RU486 | 19186 | 3284 |
| C73a7c | 7132 | 5208 |
| C73a7c + RU486 | 12844 | 171 |
| C74a7c | 3502 | 416 |
| C74a7c + RU486 | 8855 | 2379 |
| C75a7c | 4704 | 105 |
| C75a7c + RU486 | 12444 | 2117 |

TABLE 9

| | Everted Repeats | |
|---|---|---|
| C7-PBD-VP64 | Mean | STD Dev |
| 7cc7 | 8750 | 1839 |
| 7cc7 + RU486 | 17377 | 1335 |
| 7cac7 | 6029 | 613 |
| 7cac7 + RU486 | 13599 | 2014 |
| 7c2ac7 | 7880 | 1720 |
| 7c2ac7 + RU486 | 20825 | 8197 |
| 7c3ac7 | 9670 | 1187 |
| 7c3ac7 + RU486 | 21491 | 274 |

TABLE 9-continued

| C7-PBD-VP64 | Everted Repeats | |
|---|---|---|
| | Mean | STD Dev |
| 7c4ac7 | 6974 | 441 |
| 7c4ac7 + RU486 | 8896 | 2455 |
| 7c5ac7 | 6892 | 388 |
| 7c5ac7 + RU486 | 13124 | 3490 |

EXAMPLE 8

C7-PBD-Repressor Domain Fusion Constructs

To evaluate the use of PBD fusion proteins as regulatable transcriptional repressors, C7-PBD was fused to a number of repressor domains (Table 10, below). When tested in luciferase reporter assays, many repressor constructs had no significant activity. C7-PBD-KK (containing a dimer of two KRAB-A boxes) reproducibly led to a 25-50% repression, which was largely RU486-dependent. A much stronger repression which, however, was largely RU486-independent was observed with a C7-PBD-SKD construct.

EXAMPLE 9

Regulation of erbB-2 Promoter Activity With Three Finger-PBD-VP64 Homo-/Hetero-Dimers The C7-PBD-VP16 switch protein was able to regulate 10xC7 reporter constructs, which contain 10 direct repeats of C7 sites with a spacing of 5 bp (see above), indicating that a switch dimer can bind to direct repeats with this specific spacing. To evaluate the potential use of homo- and hetero-dimeric three finger-PBD fusion proteins for the ligand-dependent regulation of erbB-2 promoter activity, the promoter region was screened for the presence of $(GNN)_3N_5(GNN)_3$ motifs. Four dimer target sites (E2E, E2F, E2G, and E2H) were identified. E2E overlaps with the 18 bp E2C target sequence and could serve as a binding site for a homodimer. The other three sites have the potential to serve as heterodimer binding sites. The seven required three finger proteins were generated by F2 stitchery and analyzed for binding by ELISA (Table 11, below). erbB-2-specific switch constructs were then generated by fusion of each three finger protein to PBD-VP64, and tested for their ability to regulate erbB-2 promoter activity. The values are mean and standard deviation of duplicate measurements. Only the heterodimeric E2F-PBD-VP64 switch led to a detectable regulation of the erbB-2 promoter. This regulation was not RU486-dependent, consistent with the high basal activities of C7-PBD-VP16 and C7-PBD-VP64 proteins.

TABLE 10

Progesterone Receptor Based Ligand-Responsive Transcription Factors

| DNA Binding Domain | Ligand Binding Domain | Transcription Effector Domain |
|---|---|---|
| C7 | hPR (aa 640-914) | VP16 |
| C7 | hPR (aa 640-914) | VP64 |
| C7 | hPR (aa 640-914) | KRABa |
| C7 | hPR (aa 640-914) | Mad |
| C7 | hPR (aa 640-914) | Mad-Mad |
| C7 | hPR (aa 640-914) | KRABa-Mad |
| C7 | hPR (aa 640-914) | Mad-KRABa |

TABLE 10-continued

Progesterone Receptor Based Ligand-Responsive Transcription Factors

| DNA Binding Domain | Ligand Binding Domain | Transcription Effector Domain |
|---|---|---|
| C7 | hPR (aa 640-914) | Deactylase |
| C7 | hPR (aa 640-914) | SKD |
| 2C7 | hPR (aa 640-914) | VP16 |
| 2C7 | hPR (aa 640-914) | VP64 |
| E2E 3F | hPR (aa 640-914) | VP64 |
| E2F 3F | hPR (aa 640-914) | VP64 |
| E2G 3F | hPR (aa 640-914) | VP64 |
| E2H 3F | hPR (aa 640-914) | VP64 |
| E2C(SP1) 6F | hPR (aa 640-914) | VP16 |
| E2C(SP1) 6F | hPR (aa 640-914) | VP64 |
| E2C(SP1) 6F | hPR (aa 640-914) | KRABa |
| E2C(SP1) 6F | hPR (aa 640-914) | Mad |
| E2C(SP1) 6F | hPR (aa 640-914) | KRABa-KRABa |
| E2C(SP1) 6F | hPR (aa 640-914) | Mad-Mad |
| E2C(SP1) 6F | hPR (aa 640-914) | KRABa-Mad |
| E2C(SP1) 6F | hPR (aa 640-914) | Mad-KRABa |

TABLE 11

| Target | Target Sequence | Binding | Mean Basal Activity | STD DEV Basal Activity | Mean RU486 Activity | STD DEV RU486 Activity |
|---|---|---|---|---|---|---|
| Control pcDNA 3.1 | | | 17209 | 1878 | | |
| E2C-HS1 | ggg-gcc-gga | good | | | | |
| E2C-HS2 | gcc-gca-gtg | good | | | | |
| E2E | gcc-gga-ggc | none | 18259 | 140 | 15893 | 2083 |
| E2F-HS1 | gag-gag-ggc | good | 61401 | 25291 | 54986 | 19240 |
| E2F-HS2 | gag-gaa-gta | ? | | | | |
| E2G-HS1 | ggg-gcc-ggg | weak | 25982 | 5444 | 12394 | 139 |
| E2G-HS2 | ggc-gca-gta | weak | | | | |
| E2H-HS1 | ggc-gcg-ggg | weak | 15374 | 844 | 15374 | 537 |
| E2H-HS2 | ggt-gct-gcg | none | | | | |

EXAMPLE 10

Estrogen and Progesterone Receptor Fusion Proteins With N-Terminal Effector Domains Recombinant ligand-responsive polypeptides were constructed using an estrogen receptor (ER) ligand binding domain (EBD). A Myc-ER fusion construct was obtained from Eliane Muller and used as a source of the EBD coding region. Rather than containing the human wild type amino acid sequence, Myc-ER contains a point mutation (aa 282-599, G525R) mouse EBD which has been shown to no longer bind estrogen, but bind the estrogen antagonist 4-OH tamoxifen, and paradoxically becomes activated by it. This has advantages for in vivo applications and for tissue culture experiments, not only because serum contains estrogen but also because phenol red present in all tissue culture media acts as an estrogen agonist.

The VP16-C7-ER, VP16-NLS-C7-ER, and VP16-C7-NLS-ER fusion constructs were prepared as described above. In parallel, an analogous set of progesterone receptor (PR) variants was also prepared (VP16-C7-PR, VP16-NLS-C7-PR, and VP16-C7-NLS-PR. The PBD in these constructs encompasses aa 640-914 and therefore lacks the partial natural NLS (aa 640-644).

Each of these constructs was tested in a luciferase assay and compared to C7-PBD-VP16, using pGL3prom/10xC7 as a reporter. Not only did all these PR constructs have a higher activity in the presence of RU486 than C7-PBD-VP16, but the completely NLS-free VP16-C7-PR also had a significantly lower basal activity. This resulted in a dramatically improved ligand-dependent induction, 26-fold vs. 6-fold in this particular experiment. Tamoxifen-induced activity of the ER constructs was roughly four times higher than RU486-induced activity of the PR variants. Ligand-dependent induction was better; 43 fold for VP16-C7-ER.

The VP16 domain in VP16-C7-PR and VP16-C7-ER has been replaced by the following effector domains: the activator VP64, and the repressors KK (KRAB-A box dimer), MM (dimer of the Mad sin3 interaction domain) and SKD. The VP64 variants are useful, for example, in studies to determine the optimal spacing and orientation of the two half-sites, using the above-mentioned C7 dimer-TATA luciferase reporters

EXAMPLE 11

Targeting Natural Promoters Using 3 Finger Proteins Fused to Nuclear Hormone LBDs The following target sequences for 3 Finger switch homo- and hetero-dimers have been identified in the human erbB-2 (E2) and integrin β3 (B3) promoters:

```
E2E  GCCGGAGCC ATGGG GCC GGA GCC   (SEQ ID NO:54)
direct repeat, 5bp spacing homodimer
```

-continued

```
B3D  CGC TCC CTC TCA GGC GCA GGG   (SEQ ID NO:55)
everted repeat, 3bp spacing, heterodimer

B3E  GGC GCC CAC TGT GGG GCG GGC   (SEQ ID NO:56)
everted repeat, 3bp spacing, heterodimer.
```

EXAMPLE 12

Targeting Natural Promoters Using Six Finger Proteins Fused to Nuclear Hormone Ligand Binding Domains The "6 Finger Heterodimer"

Regulation of a 6 finger protein binding to a single 18 bp site using any of the formats described have been unsuccessful. Similarly, a C7-PBD-VP64 protein did not activate a TATA reporter containing only a single C7 site. As an alternative, heterodimer constructs were prepared in which only one of the dimerization partners contains a DNA binding domain, while the other contains an effector domain.

The formats were as follows:

(1) E2C-PR//PR-VP64

(2) E2C-ER//ER-VP64

All four fusion constructs were fully sequenced and tested in a luciferase assay for their ability to regulate the erbB-2 promoter in a ligand-dependent manner. It was found that the PR 6 Finger heterodimer was inactive; a similar observation was made with an C7-RxR//EcR-VP16 heterodimer. In contrast, the E2C-ER//ER-VP64 heterodimer had some activity, and the addition of Tamoxifen lead to a roughly three-fold upregulation of promoter activity. Variations in the ratio of the two heterodimerization partners led to an increased inducibility, up to total of 5.3-fold.

Figure 14:
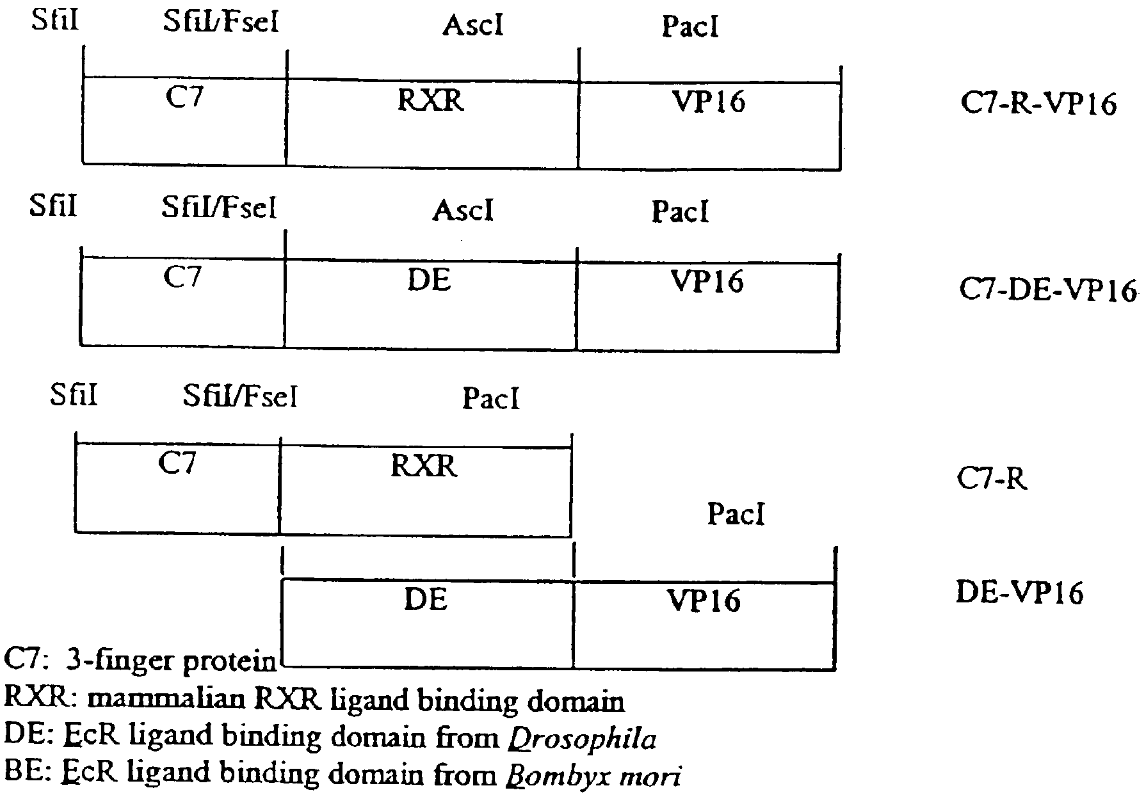
FIG. 14 is a schematic restriction map of constructs comprising RXR and ecdysone (EcR) ligand binding domains used in heterodimers.

The coding region for RXR (mammalian) and EcR (*Drosophila*) were PCR amplified from pVgRXR (Invitrogen) using the primers listed below and AmpliTaq DNA Polymerase (Hoffmann-LaRoche). Forward and backward primers were chosen to allow construction of the constructs. The cycling conditions were 2'/94° C. C; 25×(30"/94° C.-30"/60° C.—2'/72° C.); 10'/72° C. The PCR product was purified with the Quiagen PCR prep kit, cut with the indicated restriction endonucleases and ligated into a modified eukaryotic expression vector pcDNA3 (Invitrogen; see, also, Beerli et al. (1998) *Proc. Natl. Acad. Sci. U.S.A.* 95:14628-14633) to yield the constructs in FIG. 14.

```
Primers:
(Fsel)-RXR: GAGGAGGAGGGCCGGCCGGGAAGCCGTGCAGGAGGAGCGGC          (SEQ ID NO:57)

RXR-(Ascl): GAGGAGGAGGGCGCGCCCAGTCATTTGGTGCGGCGCCTCCAGC        (SEQ ID NO:58)

RXR-(Pacl): GAGGAGGAGTTAATTAAAGTCATTTGGTGCGGCGCCTCCAGC         (SEQ ID NO:59)

(Fsel)-EcR: GAGGAGGAGGGCCGGCCGGGGTGGCGGCCAAGACTTTGTTAAGAAGG    (SEQ ID NO:60)

(Sfil)-EcR: GAGGAGGAGGGCCCAGGCGGCCGGTGGCGGCCAAGACTTTGTTAAGAAGG (SEQ ID NO:61)

EcR-(Ascl): GAGGAGGAGGGCGCGCCCGGCATGAACGTCCCAGATCTCCTCGAG      (SEQ ID NO:62)
```

Exchange of Zinc Finger and Effector Domains

After digestion with the restriction endonuclease SfiI the C7 3-finger protein was replaced with the 6-finger proteins E2C, B3B, B3C2 and 2C7 by standard cloning procedures. After digestion with the restriction endonucleases AscI and PacI the activation domain VP16 was replaced with the activation domain VP64 and the repression domains KK and SKD.

Luciferase Assays

For all transfections, HeLa cells were plated in 24-well dishes and used at a confluency of 40-60%. Typically, 175 ng reporter plasmid (pGL3-promoter constructs or, as negative control, pGL3basic) and 25 ng effector plasmid (zinc finger constructs in pcDNA3 or, as negative control, empty pcDNA3.1) were transfected using the Lipofectamine reagent (Gibco BRL). Cell extracts were prepared approximately 48 hours after transfection. Luciferase activity was measured with the Promega luciferase assay reagent in a MicroLumat LB96P luminometer (EG&G Berthold).

*Bombyx mori* EcR

A plasmid (LNCVBE) containing the coding region for *Bombyx mori* EcR was obtained from F. Gage. *Bombyx mori* EcR is PCR amplified from this plasmid using the primers listed below and AmpliTaq DNA Polymerase (Hoffmann-LaRoche). Forward and backward primers were chosen to allow construction of the constructs corresponding to FIG. 14 but replacing *Drosophila* EcR by *Bombyx mori* EcR.

```
(Fsel)-BE:  GAGGAGGAGGGCCGGCCGGAGGCCTGAATGTGTCATACAGGAGCCC    (SEQ ID NO:63)

(Sfil)-BE:  GAGGAGGAGGGCCCAGGCGGCCAGGCCTGAATGTGTCATACAGGAGCCC (SEQ ID NO:64)

BE-(Ascl):  GAGGAGGAGGGCGCGCCCCTCCGCCACGTCCCAGATCTCCTCGAG     (SEQ ID NO:65)
```

C7-R-VP16//C7-E-VP16

This heterodimer was examined on two reporters, one containing 10 C7 sites and one containing 6 2C7 sites, and in two cell lines, HeLa and NIH. In all cases the C7-R-VP16 construct alone showed a high activation of transcription (840-fold) that did not depend on the presence of Ponasterone A. However the C7-E-VP16 construct showed a very little activation of transcription on its own. C7-R-VP16//C7-E-VP16 together showed the same behavior as C7-R-VP16 alone.

C7-R//E-VP16

In this heterodimer, the activation domain on RXR is dropped to eliminate the basal activation observed above. EcR has no DNA-binding domain to render activation dependent on the presence of DNA-bound RXR. This heterodimer was tested with the 3-finger protein C7 on the 10C7 reporter and with the 6-finger protein E2C on the E2P reporter that contains a single E2P binding site. In both cases no significant activation could be observed.

C7-R//C7-E-VP16

To combine the low basal activity of C7-R//E-VP16 with the high activation seen with C7-R-VP16//C7-E-VP16, the activation domain on RXR was dropped but the zinc finger protein on EcR was retained. In this set-up, on a 6x2G7 reporter, a 5-fold activation with very low basal activity was observed. Similar constructs using the more powerful VP64 activation domain have also been made.

E2C-ER//ER-VP64

This heterodimeric construct showed 5.3 fold tamoxifen-dependent activation at ratios of 6.7/60 and 2.2/60 of the erbB-2 promoter.

E2C-ER//ER-KRAB

This heterodimeric construct showed 2.9 fold tamoxifen-dependent repression of the erbB-2 promoter at a ratio of 1/10.

B3B/B3C2-ER//ER-VP64

This six finger heterodimeric construct showed 4.5-7.8 fold tamoxifen-dependent activation of the β3 promoter.

EXAMPLE 13

Regulation of Endogenous ErbB-2 Gene Expression Using Adenovirus-Mediated Delivery of E2C-KRAB Adenovirus vectors can be produced at very high titers, which makes them useful for gene therapy applications. To demonstrate the use of the E2C-KRAB repressor protein in animal models, E2C-KRAB (and, as a control, 2C7-KRAB) encoding adenoviruses were generated. The method for adenovirus production is described in detail, for example, in He et al. (1998) *Proc. Natl. Acad. Sci. U.S.A.* 95:2509-2514.

Briefly, the zinc finger coding regions were excised from the pMX/E2C-KRAB and pMX/2C7-KRAB bicistronic retrovirus plasmids by BamH1-Not1 digest. The resulting fragments were then subcloned into the Bgl2-Not1 sites of pAdTrack-CMV. After linearization with Pme1, pAdTrack plasmids were co-electroporated with circular pAdEasy-1 into BJ5183 cells. This bacterial strain is not recA and therefore allows homologous recombination between the 2 plasmids. Electroporated cells were then plated onto Kan plates. Only plasmids that have recombined together provide Kanamycin resistance, because this marker is only present on pAdTrack. After screening to distinguish recombinants from background (due to incomplete linearization of pAdTrack plasmids), the linear adenovirus vector genomes were released from the recombinant pAdEasy/E2C-KRAB and pAdEasy/2C7-KRAB plasmids by Pac1 digest.

The linearized vectors were then transfected into 293 cells. This cell line makes the Adeno E1A and E1B proteins, which have been deleted from the vector and are required for replication.

EXAMPLE 14

Modifications to the Estrogen Receptor Ligand Binding Domain Improve Ligand Dependent Induction and Ligand Selectivity Single amino acid mutations in the estrogen receptor ligand binding domain can have a significant effect on the basal and ligand dependent level of gene activation. For example, a glycine to valine substitution at estrogen receptor residue 400, has been described as a destabilizing or temperature sensitive mutation (White (1997) *Adv. Pharmacol.* 40:339-367; Aumais et al. (1996) *J. Biol. Chem.* 272:12229-12235). The effect of this mutation on the properties of the fusion proteins was tested. The general methods for constructing fusion proteins with altered amino acids is described below.

Mutagenesis of the fusion proteins C7LBDa and C7LBDb was performed using oligonucleotide mediated site directed mutagenesis (Stratagene; Quikchange Site-Directed Mutagenesis Kit) to either substitute arginine for glycine at amino acid 521 (G521R-human estrogen receptor nomenclature) or a valine residue for glycine at amino acid 400 (G400V). The sequences of the oligonucleotides used for G521R mutagenesis were GTACAGATGCTCCATGCGTTTGTTACTCATGTGCC (SEQ ID NO: 66) for the noncoding strand and GGCACATGAGTAACAAACGCATGGAGCATCTGTAC (SEQ ID NO: 67) for the coding strand, where the nucleotide in bold represents the change from the wild type sequence.

The sequences of the oligonucleotides used for G400V mutagenesis were CCATGGAGCACCCAGTGAAGCTACTGTTTGC (SEQ ID NO: 68) for the coding strand, and GCAAACAGTAGCTTCACTGGGTGCTCCATGG (SEQ ID NO: 69) for the noncoding strand, where the nucleotide in bold represents the change in sequence from wild type.

Templates were added at 10 ng to 50 ng per reaction with 125 ng of each primer in 10 mM KCl, 10 mM $(NH_4)_2SO_4$, 20 mM Tris-HCl (pH 8.8), 2 mM $MgSO_4$, 0.1% Triton X-100, 0.1 mg/ml BSA, dNTP mix, and 2.5U PfuTurbo™ DNA polymerase. The reactions were carried out on a Perkin Elmer GeneAmp PCR system 9600 thermal-cycle using an initial temperature of 94 degrees Celsius for 30 seconds to denature the template, followed by 12 cycles at 95 degrees Celsius for 30 seconds, 55 degrees Celsius for 1 minute, and 68 degrees Celsius for 4 minutes, with a single round of extension at 72 degrees Celsius for 2.5 minutes. PCR samples were treated with 10U DpnI for 1 hr at 37 degrees Celsius to digest the non-mutagenized parent template.

DH5α supercompetent Epicurean Coli® XL-1 cells were transformed by combining 1 μl of the DpnI treated PCR samples with 50 μL of the cells in chilled Falcon 2059 tubes, incubated on ice for 30 minutes, heat shocked at 42 degrees Celsius for 45 seconds and chilled on ice for 2 minutes. A 500 μL aliquot of SOC media pre-warmed to 42 degrees Celsius was added to the transformation reaction and incubated for 1 hour at 37 degrees Celsius with shaking. The transformed cells were plated onto LB plates containing 100 μg/ml ampicillin and incubated for at least 16 hours.

Mutation efficiency was determined by altering a nonsense codon in a β-galactosidase expression plasmid to glutamine and determining expression of β-galactosidase, as evidenced by IPTG/X-Gal plates. Approximately three clones for each mutation were selected for restriction enzyme digestion to check for template integrity, followed by dideoxynucleotide sequencing of the entire coding frame to confirm the desired mutation.

C7LBD (short) chimeric regulators A, B, and C with and without the G400V mutation in the estrogen receptor LBD were compared for their ability to induce expression of the 6x2C7pGL3Luc. As observed previously, the total activity of the three fusion proteins has the relationship A>B>C; this relationship was maintained with and without the G400V mutation. The pattern of basal expression was dramatically altered by the G400V mutation. The basal or ligand independent effect of the three C7LBD regulators with the G400V mutation is reduced to nearly the level of the reporter plasmid alone. As a result, the fold ligand dependent induction dramatically increases, for example from 10 fold to 420 fold for C7LBDA.

It has previously been observed with fusion proteins containing an estrogen receptor ligand binding domain, that activity could be induced by use of not only the natural agonist estrogen (E2) but also synthetic anti-estrogens such as 4-OH tamoxifen (Littlewood et al. (1995) *Nucl. Acids Res.* 23:1686-1690; Danielian et al. (1993) *Mol. Endocrinol.* 7:234-240). The ability of the C7LBD fusion to be induced by 4-OH-tamoxifen was demonstrated.

The results of the study showed the ligand-dependent regulation of a luciferase reporter gene construct in HeLa cells using three recombinant molecular constructs, C7LBDAS, C7LBDBS, C7LBDCS with and without a G400V mutation in response to estrogen (E2) and 4 hydroxytamoxifen (OHT). In particular, the results showed that fusion proteins C7LBD B and C are induced equally well by 100 nM tamoxifen or estrogen. For C7LBDA, tamoxifen appears to be approximately two-fold more active than estrogen itself.

Another mutation of interest in estrogen receptor LBD is a glycine to arginine substitution at amino acid 521 of human estrogen receptor. This mutation has also been described in the mouse estrogen receptor homolog at the equivalent site of residue 525. This mutation ablates responsiveness of the mutated LBD to estrogen, but still allows the binding of the anti-estrogen tamoxifen (Littlewood et al. (1995) *Nucl. Acids Res.* 23: 1686-1690; Danielian et al. (1993) *Mol. Endocrinol.* 7:234-240). The effect of the G521R mutation on the activity of the C7LBD regulators was tested. C7LBDB was compared to C7LBDB (G400V) and C7LBDB (G521R).

The results of the study showed the ligand-dependent regulation of a luciferase reporter gene construct in HeLa cells using three recombinant molecular constructs: C7LBDBS, C7LBDBS with a G521R mutation and C7LBDBS with a G400V mutation in response to estrogen (E2) and 4 hydroxytamoxifen (OHT). Similar to the effect observed with the G400V mutation, G521R significantly reduces the basal activity of the fusion protein regulator. But most importantly, now the C7LBDB(G521R) regulator is fully activated by 100 nM 4-OH-tamoxifen, but completely inactive in response to estrogen. Note that the G400V mutant is still fully activated by estrogen and tamoxifen.

To further investigate the effect of the G521R mutation, a series of different estrogenic compounds were evaluated for their ability to induce the C7LBD regulators. The activity of 100 nM for four compounds: estrogen (E2) and diethyl-stilbesterol (DES) are estrogenic agonists, 4-OH-tamoxifen and raloxifen (Ral) are non-steroidal anti-estrogens, or so-called SERMS (selective estrogen receptor modulators) were compared.

The study tested ligand-dependent regulation of a luciferase reporter gene construct in Hep3BL liver cells using recombinant molecular constructs C7LBDBS with a G521R mutation and C7LBDBS with a G400V mutation in response to estrogen (E2) diethylstilbesterol (DES), 4-hydroxytamoxifen (4-OHT) and raloxifen (Ralox). The results showed that the G521R mutation selectively eliminates response to the agonists, but the non-steroidal synthetic ligands tamoxifen and raloxifen are still fully active.

EXAMPLE 15

Effect of the Minimal Promoter Composition on Regulation of Transgenes by ZFP-LBD Fusion Proteins The composition of the minimal promoter used in reporter assays can dramatically effect the level of gene expression. Likewise, the activity of natural steroid receptors varies on different gene targets depending on the composition of their promoters. Reporter constructs containing 6x2C7 binding sites upstream of a minimal TATA box promoter fragment derived from the c-fos gene, referred to here as TATA were constructed to show the effect on the level of regulation. C7LBD A and B fusions without or with the G400V or G521R mutations were compared. As observed previously on the pGL3 SV40 promoter, the G400V and G521R mutations significantly decrease the basal activity of the chimeras compared to those without these mutations. Further, the G521R mutant is selectively activated by tamoxifen. On this weaker minimal promoter, estrogen is only a weak inducer, while 4-OH-tamoxifen is significantly better. This effect is even more pronounced on C7LBD A compared to B; on chimera C7LBDA (G400V), tamoxifen is at least 10 fold more active than estrogen.

An experiment was done to directly compare the relative activity of the C7LBD chimeras on reporter constructs containing the stronger pGL3 SV40 promoter or the weaker c-fos TATA box promoter.

The results of the study show that the ligand-dependent regulation of a luciferase reporter gene construct expressed from a minimal TATA promoter in Hep3BL liver cells using recombinant molecular constructs C7LBDAS and C7LBDBS with a G400V mutation and C7LBDBS with a G521R mutation in response to estrogen (E2) and 4-hydroxytamoxifen (OHT). Three important observations can be made: 1) the absolute level of induced activity is about 10 fold higher on the SV40 than the TATA promoter 2) the basal activity of the fusions is also about 10 fold higher on the SV40 than on the TATA promoter, 3) while both promoters show strong fold induction by tamoxifen (492 X on SV40 and 132 X on TATA), estrogen is only a strong inducer of the SV40 but not the TATA promoter (177X vs 14X). These results indication that a gene regulation system using these fusion proteins can be "tuned" by choice of an appropriate minimal promoter.

Target Selectivity of Different C2H2 DNA Binding Domains

Reporter constructs with 3 copies of direct repeats of the C7 binding site (GCG TGG GCG) or E2C binding site (GGG GCC GGA g) inserted upstream of the promoter region in pGL3Luc were used to evaluate target specificity two different ZFP-LBDBs fusion protein regulators. ZFP-LBDB short fusions were constructed containing either the C7 DNA binding domain or the E2C DNA binding domain and tested on the two different reporter constructs. The study was designed to show the effect of three direct repeats of either C7 or E2C binding sites inserted upstream of the promoter of a luciferase reporter gene construct in HeLa cells on estrogen-dependent gene expression using recombinant molecular constructs C7LBDBS and E2CLBDBS. Estrogen-dependent induction only occurs when the chimera's DNA binding domain (DBD) matches the binding sites in the reporter. The E2CLBD chimera shows no increase of luciferase activity on the 3x2C7 Luc reporter and visa versa for C7LBD on the 3xE2C reporter.

It was previously determined from DNA binding studies that the fusion protein regulators have an absolute dependence on the presence of two half sites within a "response element" in order to bind DNA. In order to determine the optimal orientation and spacing of the binding sites for gene activation, a series of different reporter constructs were assembled. In order to determine the optimal target DNA spacing and orientation of the C2H2 binding sites for transgene induction, C7LBDBS was transfected into HeLa cells and assayed for basal and tamoxifen induced activity on a series of reporter constructs.

A series of different reporter constructs assembled in order to determine the optimal target DNA spacing and orientation of the C2H2 binding sites for transgene induction, C7LBDBS was transfected into HeLa cells and assayed for basal and tamoxifen induced activity on a series of reporter constructs diagrammed above. Reporter constructs were constructed by cloning double stranded oligonucleotides containing the various binding sites into the multiple cloning site of the pGL3Luc reporter. "Response elements" composed of direct, inverted (palindromic), and everted repeats of two C7 binding sites were compared; each response element was separated by two (2) bp except in the control 6X2C7, where spacing was 5 bp. Several arrays of directly repeated single C7 sites were tested with various spacing. The data show that direct repeats and everted repeats are preferred over palindromic binding sites. Further, 6 C7 sites, each separated by 2 bp is comparable to the control element of 6x2C7, even though it contains only half the number of individual C7 binding sites.

EXAMPLE 16

Figures 15A, 15B:
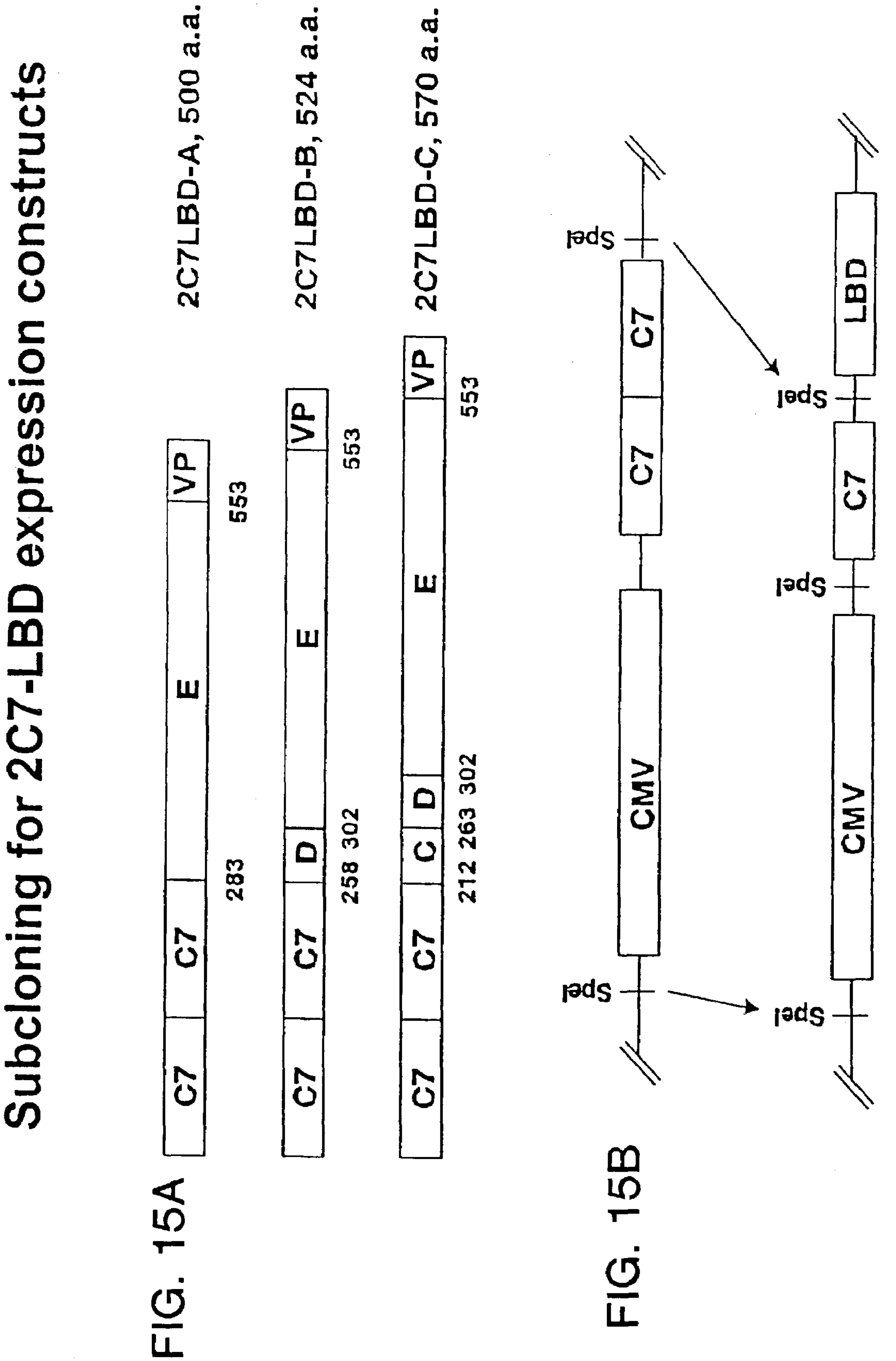
FIG. 15 is a schematic depiction of the cloning strategy for the construction of the 2C7LBD recombinant molecular constructs.

Construction and Evaluation of ZFP-LBD Fusion Protein Regulators Containing Arrays of Six C2H2 Zinc Fingers Studies were performed to determine if DNA binding domains comprised of zinc finger arrays binding up to 18 bp of DNA could be substituted for the normal estrogen receptor DBD. The previous constructs, containing three finger arrays that bind nine bp are a fairly conservative replacement of the wild type estrogen receptor ligand binding domain that binds six bp for each receptor monomer. The possibility exists that if large DNA binding domains are fused to an LBD fragment, that these domains may prevent dimerization via the LBD dimerization domain due to steric interference. However, since the six finger arrays already provide high DNA specificity and affinity, dimerization may be unnecessary for the DNA binding and activity of these fusions proteins. Fusion protein regulators were prepared by fusing the 2C7 six finger array to the three LBD fragments A, B, and C described above. FIG. 15 provides a schematic and description of the cloning step required to assemble 2C7LBDshort A, B, and C.

Protein binding to DNA was analyzed by gel shift assay. The electrophoretic studies used 2C7 recombinant molecular constructs using native PAGE and SDS PAGE analysis of binding to a DNA probe containing six 2C7 binding sites. In this experiment, the 2C7VP16 protein was used as a control and the P32-labeled DNA probe was the 6x2C7 fragment excised from the 6X2C7pGL3Luc. Sufficient 2C7VP protein was added to yield three distinct gel shifted products. When a similar level of protein for the 2C7LBD A, B, and C were applied, only a single weak band was observed. By comparison to the one and two copies bound bands for the 2C7VP16 control, the 2C7LBD band position suggests it is binding as a monomer. Furthermore, the weak level of binding compared to the 2C7VP16 control suggests the DNA binding affinity of the 2C7 domain is significantly reduced in the context of the LBD fusion protein. Results of in vitro expressed proteins by SDS-PAGE, indicated equal amounts of proteins expressed and the expected relative increase in size for the LBD A, B, and C forms.

The ability of the 2C7LBD A, B, and C fusion protein chimeric regulators to activate expression of the 6X2C7Luc reporter gene were evaluated essentially as described previously for the C7LBD studies. The results of the study show the ligand-dependent regulation of a 2C7 SV40 luciferase reporter gene construct in Cos cells using three recombinant molecular constructs, 2C7LBDAS (SEQ ID NO: 1), 2C7LBDBS (SEQ ID NO: 2), 2C7LBDCS (SEQ ID NO: 3), and a positive control, 2C7-Vp16. The results are similar to the data evaluating C7LBD in Cos cells. The 2C7LBD regulators give about two fold estrogen dependent induction over basal, with 2C7LBDA>B>C for both the total activation activity and the increased basal activity relative to reporter plasmid alone. Maps of the additional constructs are depicted in FIG. 16-FIG. 22.

EXAMPLE 17

Construction and Evaluation of Additional Reporter Transgene Constructs

Figure 23A:
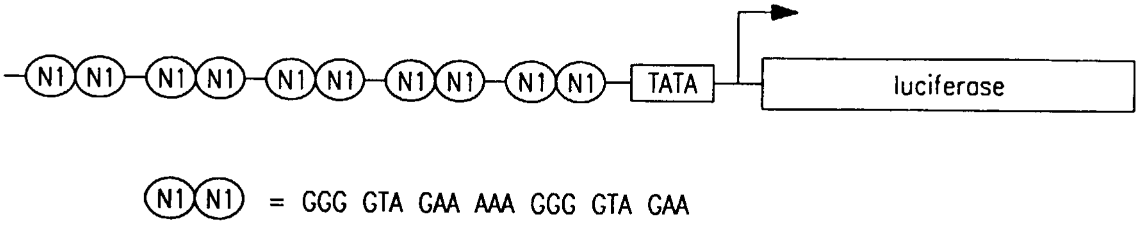
FIG. 23 shows A: an inducible promoter based on binding sites for the 3 Finger protein N1. The promoter contains 5 direct repeats of N1 sites spaced by 3 bp; the spacing between the 5 repeats is 6 bp. Bottom: Luciferase assay. HeLa cells were cotransfected with plasmids encoding the indicated fusion proteins and the N1 reporter construct. Twenty four hours later, the cells were treated with 10 nM RU486 (B) or 100 nM Tamoxifen, C respectively. Forty-eight hours post-transfection, cell extracts were assayed for luciferase activity.

An inducible promoter was constructed based on binding sites for the 3 Finger protein N1. The promoter contains 5 direct repeats of N1 sites spaced by 3 bp; the spacing between the 5 repeats is 6 bp. (FIG. 23A)

Figure 23B:
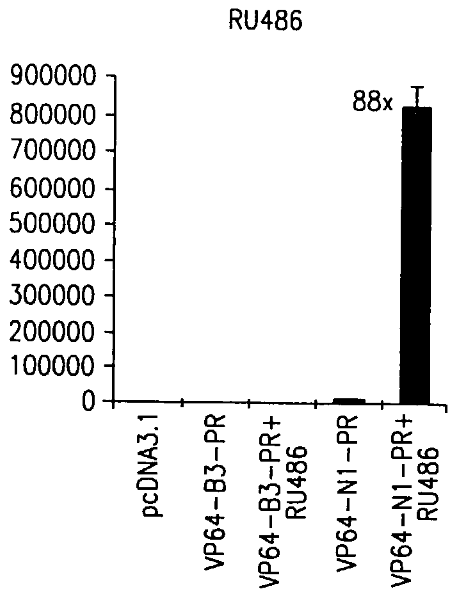
Figure 23C:
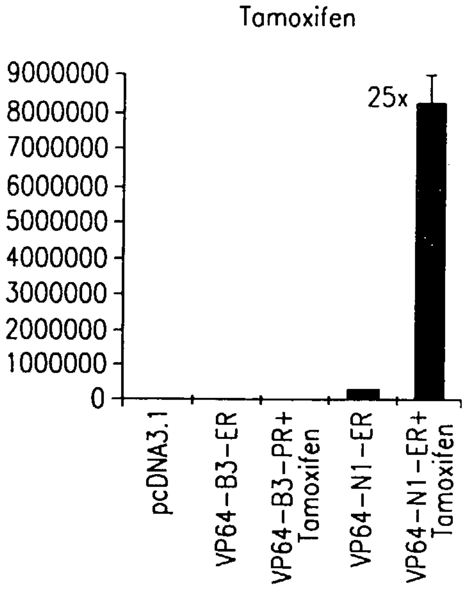

Luciferase assay. HeLa cells were cotransfected with plasmids encoding the indicated fusion proteins and the N1 reporter construct. At 24 h later, the cells were treated with 10 nM RU486 (FIG. 23B) or 100 nM Tamoxifen (FIG. 23C), respectively. At 48 h post transfection, cell extracts were assayed for luciferase activity.

Figure 24A:
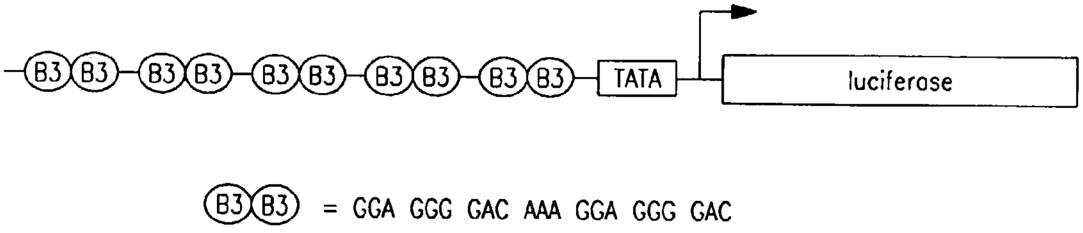
FIG. 24 shows an inducible promoter based on binding sites for the 3 Finger protein B3. A: The promoter contains 5 direct repeats of B3 sites spaced by 3 bp; the spacing between the 5 repeats is 6 bp. Bottom: Luciferase assay. HeLa cells were cotransfected with plasmids encoding the indicated fusion proteins and the B3 reporter construct. At 24 h later, the cells were treated with 10 nM RU486 (B), or 100 nM Tamoxifen (C), respectively. At 48 h post transfection, cell extracts were assayed for luciferase activity.
Figure 24B:
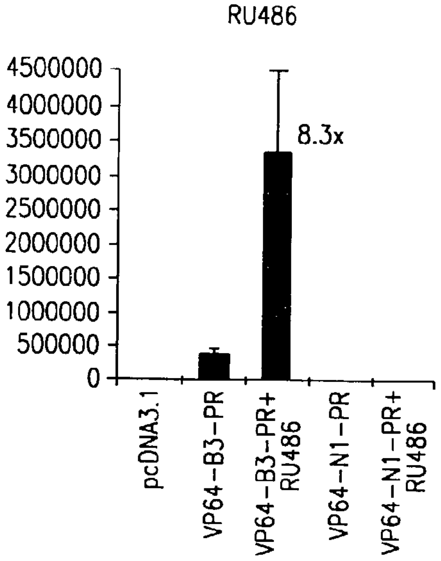
Figure 24C:
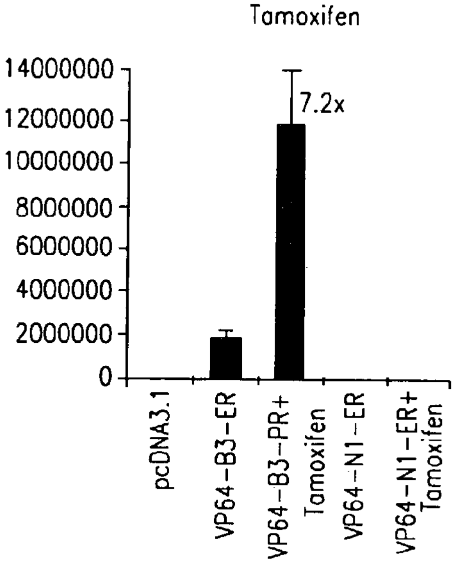

Another inducible promoter based on binding sites for the 3 Finger protein B3. The promoter contains 5 direct repeats of B3 sites spaced by 3 bp; the spacing between the 5 repeats is 6 bp (FIG. 24A).

Luciferase assay. HeLa cells were cotransfected with plasmids encoding the indicated fusion proteins and the B3 reporter construct. At 24 h later, the cells were treated with 10 nM RU486 (FIG. 24B), or 100 nM Tamoxifen (FIG. 24C), respectively. At 48 h post transfection, cell extracts were assayed for luciferase activity.

EXAMPLE 18

Heterodimer Formation in Presence of Ligand

Figure 25A:
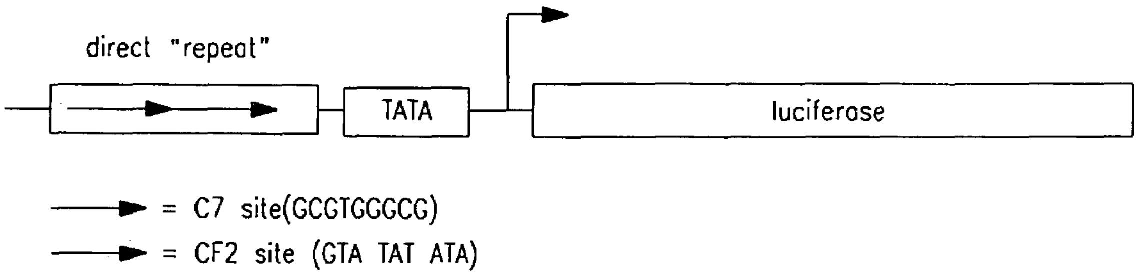
FIG. 25 is a graphical depiction of the results of luciferase assay showing the RU486-induced formation of functional VP64-C7-PR/VP64-CF2-PR heterodimers. HeLa cells were cotransfected with the corresponding effector plasmids and TATA reporter plasmids (C7/CF2-dr0, C7 site 5' to a CF2 site, direct "repeat", no spacing; C7/C7-dr0, 2 C7 sites, direct repeat, no spacing). At 24 h later, the cells were treated with 10 nM RU486. At 48 h post transfection, cell extracts were assayed for luciferase activity.
Figure 25B:
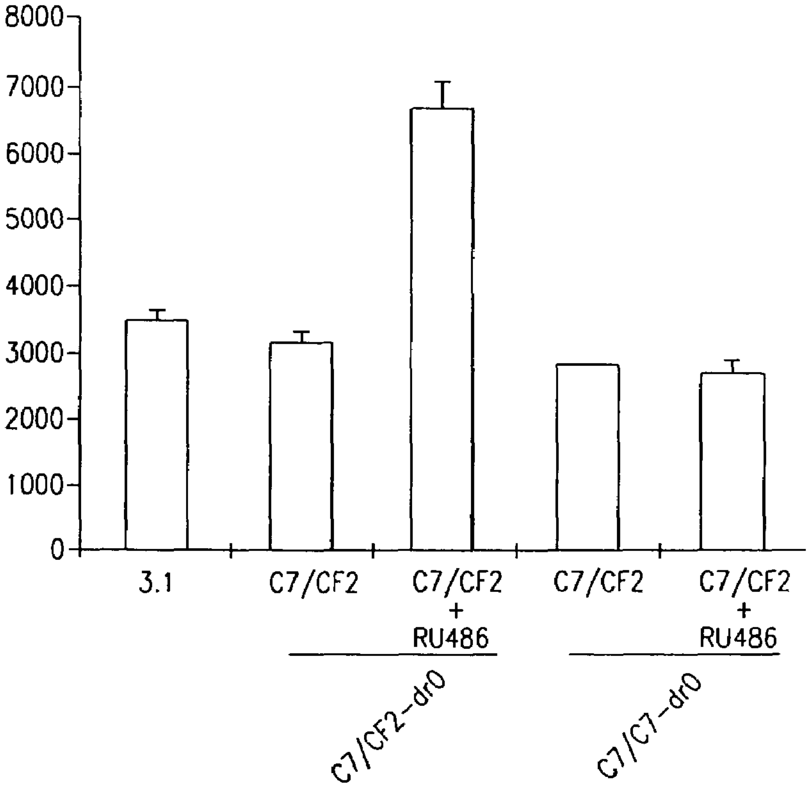

FIG. 25 shows the results of a luciferase assay showing RU486-induced formation of functional VP64-C7-PR/VP64-CF2-PR heterodimers. HeLa cells were cotransfected with the corresponding effector plasmids and TATA reporter plasmids (C7/CF2-dr0, C7 site 5' to a CF2 site, direct "repeat", no spacing; C7/C7-dr0, 2 C7 sites, direct repeat, no spacing). At 24 h later, the cells were treated with 10 nM RU486. At 48 h post transfection, cell extracts were assayed for luciferase activity.

EXAMPLE 19

Construction and Evaluation of the $Cys_2$-$His_2$ Zinc Finger DBD-ER LBD Regulators in Adenoviral Vectors In order to efficiently deliver the two components of the regulatory system to mammalian cells, either ex vivo or in vivo, a series of adenoviral vectors were constructed. These vectors contained either the ZFP-LBD fusion protein regulator linked to the immediate early CMV promoter or the regulatable transgene, linked to the 6x2C7 array of C7 binding sites and the minimal promoter from SV40 or c-fos TATA as described previously. The fusion protein regulator vector and regulatable transgene vector are then be mixed at various ratios and delivered to cells or animals by standard methods.

Construction of an adenovirus vector is routine and generally, the procedure involves three main steps: first a shuttle plasmid containing the viral left ITR, viral packaging signal, a promoter element, a transgene of interest linked to the promoter element and followed by a poly adenylation sequence, and some additional DNA sequences, viral or non-viral, required for recombination is prepared. Second, this left end shuttle plasmid, along with the remainder of the viral genome (i.e. the right end of the vector) are transfected into a host cell and joined through DNA recombination to form a complete vector genome. This recombination step may result from sequence homology between the two vector halves or may be aided by the use of site specific recombinases such as Cre and their corresponding LoxP recombination sequences. Finally, the newly formed virus is amplified up and purified in a series of steps. The details of the construction of these vectors are briefly described below.

Left End Shuttle Plasmid Construction for ZFP-LBD Fusion Protein Regulators

Figure 26:
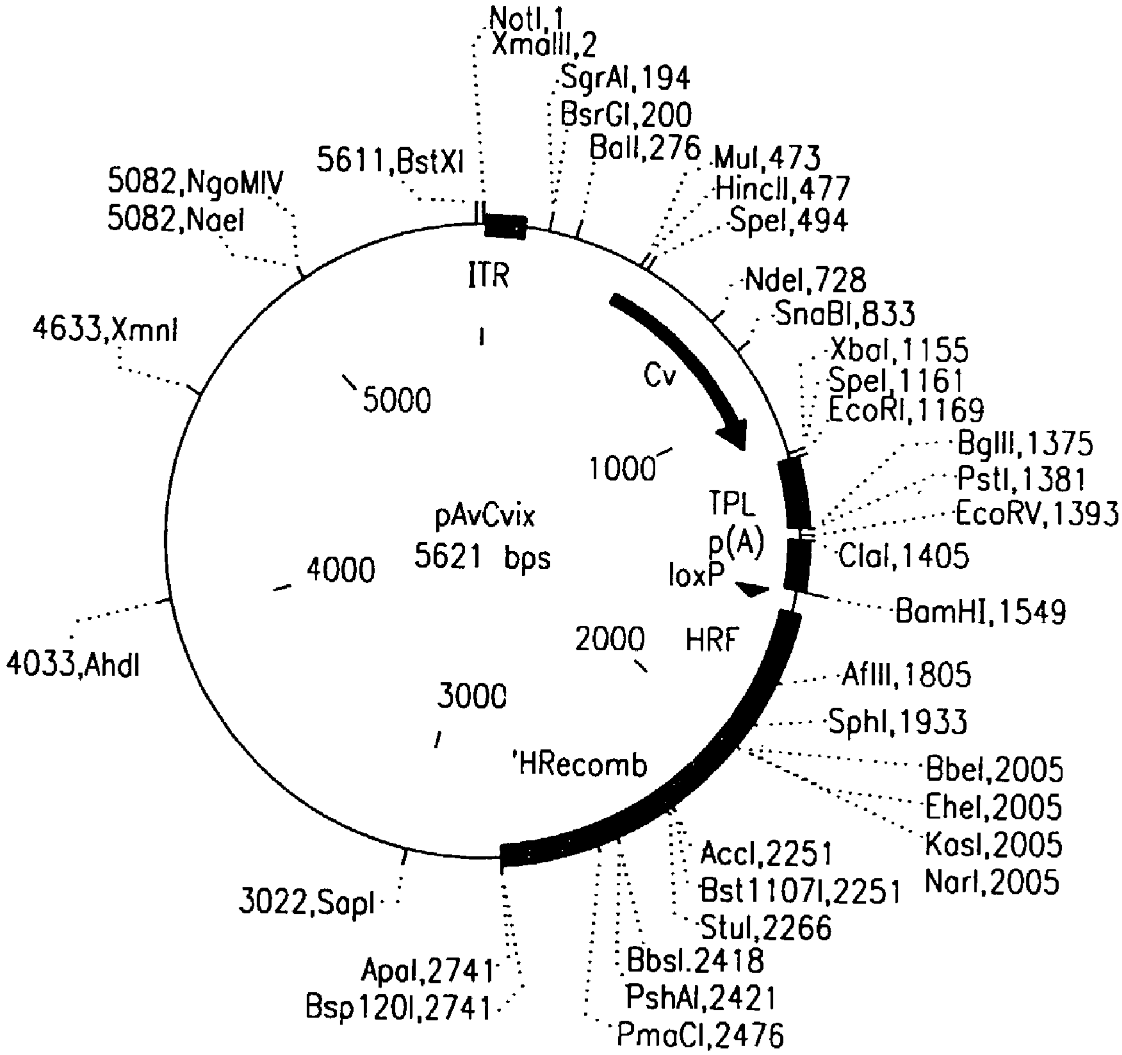
FIG. 26 shows a restriction map for the plasmid designated pAvCVIx.

Shuttle plasmids containing the left viral ITR, CMV immediate early promoter and ZFP-LBD regulator were prepared in the plasmid pAvCVlx (FIG. 26). Note that this vector contains a loxP recombination site just downstream of the poly adenylation sequence. DNA encoding the intact reading frame for the chimeric regulators C7LBD As(G521R), C7LBD Bs(G521R), and C7LBD Bs(G400V) were excised from the appropriate pCDNA constructions, (see FIGS. 4 and 5 for LBD As and LBD Bs constructs respectively) by digestion with restriction enzymes EcoRI and NotI. The ZFP-LBD DNA fragments were modified with Klenow to fill in the restriction site overhangs and blunt end ligated into the EcoRV at bp 1393 site of pAvCvlx to generate pAvGv-C7LBD As(G521R), pAvCv-C7LBD Bs(G521R), and pAvCv-C7LBD Bs(G400V).

Construction of Left End Shuttle Plasmids Containing Regulatable Transgene Cassettes Two regulatable transgene cassettes were prepared. One contained the 6x2C7 binding sites and SV40 minimal promoter fragment linked to the Luciferase transgene as in pGL3 6x2C7-Luc (described in example 5). The second vector contained the 6x2C7 binding sites and c-fos TATA minimal promoter linked to a cDNA encoding murine endostatin fused to an amino terminal secretion signal. The complete sequence of this fusion protein is listed in SEQ ID NOs. 70 and 71.

These vectors were constructed in two steps. First, a fragment containing the CMV promoter and tri-partite leader sequence (TPL) of pAvCvlx (FIG. 26) was excised by digestion with MluI and BglII, which cut at bp 473 and 1375 respectively. The restriction site overhangs were filled in with Klenow. Blunt ended DNA fragments containing the 6x2C7-SV40 or 6x2C7-TATA enhancer/promoter regions of the previously described reporter plasmids were ligated into this backbone to create pAV-6x2C7SV40 and pAV-6x2C7TATA shuttle plasmids. Next, DNA fragments containing the Luciferase or murine endostatin transgenes were ligated into the EcoRV site of the appropriate shuttle plasmids to create pAv6x2C7SV40-Luc (lox) or pAv6x2C7TATA-mEndo (lox).

Construction of a Right End Vector Plasmid

Figure 27:
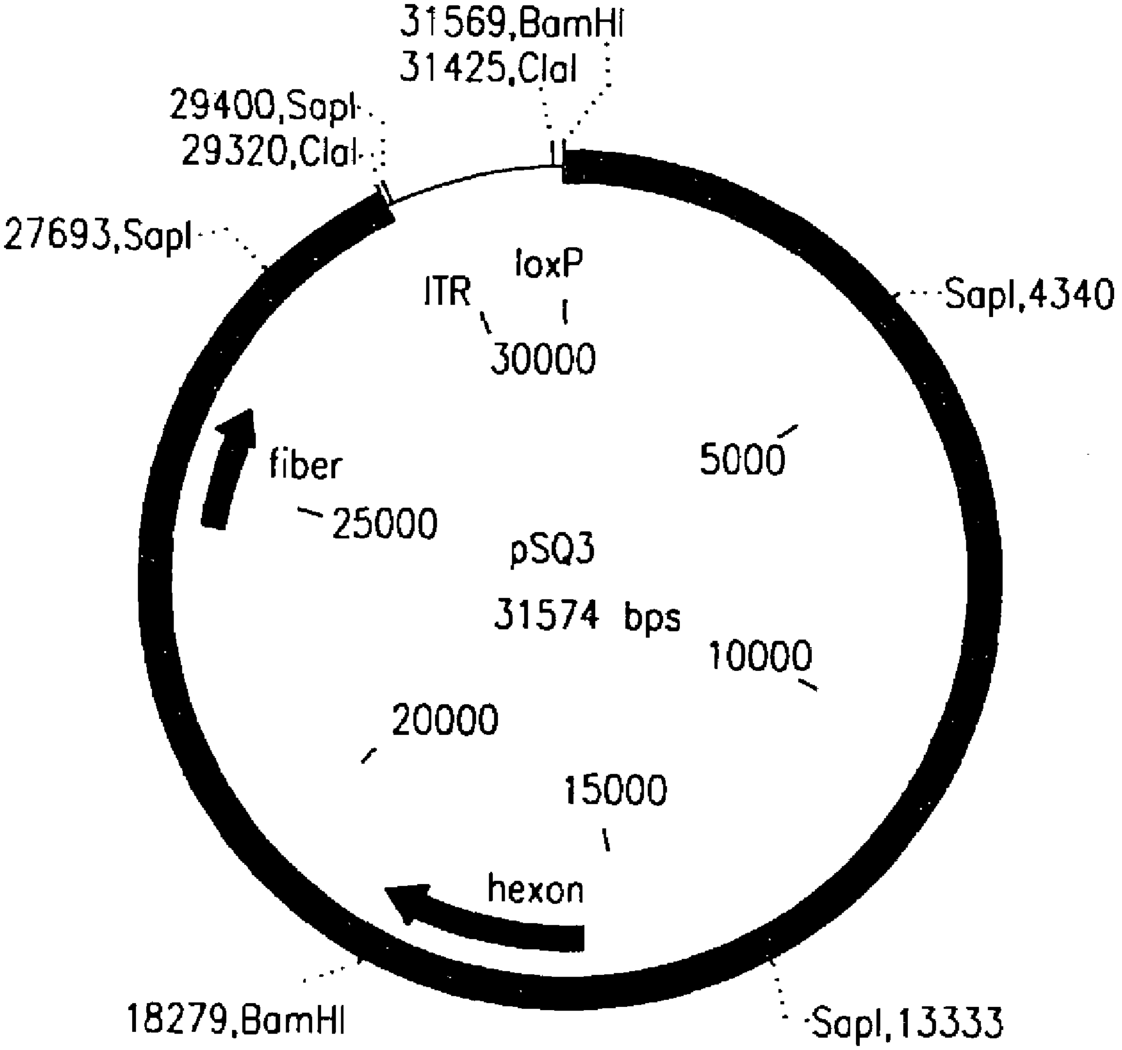
FIG. 27 shows a restriction map for the plasmid designated pSQ3.

To complete the vector construction, a plasmid containing the remainder of the viral vector genome is required. This plasmid, referred to as pSQ3, which is shown in FIG. 27, contains a pBR322-derived backbone, ampicillin resistance gene and the adenovirus serotype 5 genome, beginning at Ad5 bp 3329, through the right ITR, with deletions in the E2a and E3 region as described previously (Gorziglia et al. (1996) *J. Virol.* 70:4173-4178). In addition, this plasmid has two important features, a loxP site inserted at the Bam HI site (bp 31569) just upstream of the Ad5 sequences, and a Cla I site at the end of the viral 5' ITR. This ClaI site is used to linearize the plasmid and expose the right ITR during vector construction.

Vector Assembly and Propagation

Three adenoviral vectors encoding fusion protein regulators, Av3CV-C7LBDAS(G521R), Av3CV-C7LBDBS (G521R), and Av3CV-C7LBDBS(G400V) and two vectors containing regulatable transgenes, Av3SV-LUC and Av3TATA-Endo were constructed. Each vector was generated by a standard procedure. Briefly, for each vector construct, three plasmids, pSQ3 (pre digested with ClaI), the appropriate left end shuttle plasmid (e.g. pAvCv-C7LBD As(G521R), or pAv6x2C7SV40-Luc (lox), pre-digested with NotI and AflII, and an expression plasmid for the Cre recombinase, pCMV-CRE, were cotransfected at a weight ratio of 3:1:1 into dexamethasone induced AE1-2a cells (Gorziglia et al.) using Promega's Profection Kit. About 1 week after transfection, cells were harvested and lysed by 4 cycles of freeze/thaw. The resulting cell lysate was passed onto fresh dexamethasone induced AE1-2a cells and the culture maintained about a week until cytopathic effect (CPE) was observed. This process was repeated several cycles until sufficient material was obtained to purify the vector by CsCl equilibrium density centrifugation. Once purified, vectors are quantitated by lysing in buffer containing 10 mM Tris, 1 mM EDTA, 0.1% SDS for 15 minutes at 56° C., cooling and reading the absorbance at 260 nm wavelength (OD260). The OD260 reading is converted to a virus particle concentration using 1 OD260 unit=$1.1\times10^{12}$ particles/ml.

Results

In Vitro Regulation with Adenovirus Vectors

The ability to regulate expression of a transgene delivered by an adenovirus vector was demonstrated by the following experiment. HeLa cells were infected with a mixture of two adenovirus vectors, one containing a fusion protein regulator either (Av3-C7LBD-A(G521R) or Av3-C7LBD-B(G52R), the other containing the 6x2C7SV40-luc cassette. To determine the optimal ratio of target vector to effector vector, two different doses of the transgene or target vector (50 or 250 viral particles per cell) at three different ratios of effector vector (50, 250, 750 particles per cell for each target dose) were tested. Twenty four hours after vector transduction, the cells were treated where appropriate with 100 nM 4-OH-tamoxifen. Following an additional 24 hrs incubation, the cells were lysed and assayed for luciferase activity. For the Av3GV-C7LBD A(G521R) vector, the data indicate relatively low levels of luc expression in the absence of 4-OHT, a strong 4-OHT dependent induction and a dose dependent increase in luc activity as more fusion protein regulator vector is used. At the highest doses (750 particles per cell) of chimeric regulator vector tested, tamoxifen-specific induction of 460 to 560 fold over basal was achieved at target vector doses of 250 and 50 particles per cell, respectively.

The same experiment carried out using the LBD B version of the chimeric regulator; Av3CV-C7LBD B(G521R). For this vector, the fold induction and absolute luciferase activity were about two fold lower than obtained with the As-based regulator. These results are consistent with all the previous transient transfection experiments performed with plasmids. Notably, a first generation of Av3-chimeric regulator vectors constructed with the RSV promoter driving the expression of the C7LBD gene did not yield good transgene upregulation of the Av3SV40-Luc vector. Apparently, the expression level from the weaker RSV promoter was not adequate to produce the necessary levels of fusion protein.

In Vivo Regulation with Adenovirus Vectors

To demonstrate the effectiveness of the C7LBD regulators to control transgene expression in vivo, a study was designed to evaluate three important variables: 1) the effectiveness of regulators containing either the G400V or G521R mutations, 2) the ratio of target and effector vector, and 3) the dose of 4-OHT. The importance of the G400V and G521R mutations are as follows. While the G521R mutation is selectively responsive to 4-OHT and is not affected by endogenous estrogen, it requires about a 10-fold higher drug concentration than the G400V mutation to achieve maximum activity. While the G400V is active at a lower dose of 4-OHT, it is also subject to induction by estrogen and could show higher basal activity in vivo.

Details of the animal study are as follows. On study day 1, C57Bl/6 male mice were given a total adenovirus vector dose of $2\times10^{11}$ particles via tail vein injection. On day two blood samples were collected, then animals were injected i.p. with 200 μl of sunflower seed oil containing 5% DMSO and either no, 50 μg, or 500 μg of tamoxifen (Sigma # T56448). Blood samples were collected daily for three days following drug administration, and on study days 8 and 10. At the completion of the study, murine endostatin levels were determined by ELISA (Accucyte Kit, Cytimmune Sciences, Maryland).

The study groups included the following:

Negative Control—$2\times10^{11}$ particles Av3Null, Ad vector with no transgene Positive Control—$2\times10^{11}$ particles Av3RSV-mEndo, constitutively expresses endostatin from the RSV promoter.

1:1 As521—Received $1\times10^{11}$ particles of Av3TATA-mEndo and $1\times10^{11}$ particles of Av3Cv-C7LBDAs (G521R); no treatment (basal) or +50 μg tamoxifen.

1:1 Bs400—Received $1\times10^{11}$ particles of Av3TATA-mEndo and $1\times10^{11}$ particles of Av3Cv-C7LBDBs (G400V); no treatment (basal) or +50 μg tamoxifen.

In addition, groups 5 and 6 were similar to groups 3 and 4, but animals received $0.5\times10^{11}$ of the Av3TATA-mEndo vector and $1.5\times10^{11}$ of the C7LBD regulator vector, for a 1:3 ratio of target to effector. Groups 3-6 each contained no drug, 50 μg, and 500 μg tamoxifen treatment sub-groups.

The results showed a dramatic induction of murine endostatin following the day 2 administration of 50 μg of tamoxifen. The highest level of induction was observed on day 3, the day immediately following drug administration. Compared to the basal level observed on day 3 in the no tamoxifen groups, the C7LBDAs(G521R) and C7LBDBs (G400V) regulators gave comparable fold induction, approximately 17 fold, and comparable absolute levels of expression, around 1500 ng/ml. In this study, the endogenous murine endostatin levels in an untreated mouse cohort was 20±7 ng/ml. The drug-induced endostatin expression rapidly declines by day 5, three days after drug administration, which is presumably due to the clearance of the tamoxifen and biological half life of the endostatin protein. In contrast, expression in the Av3RSV-mEndo treatment group persists at 200 ng/ml through day 15. In the 1:3 target to effector ratio groups, tamoxifen-induced expression reached 600-900 ng/ml, approximately ½ the level in the 1:1 ratio cohorts. This result indicates that in vivo, the transgene-containing vector, not the fusion protein-encoding vector, is limiting for absolute protein expression. Furthermore, endostatin expression in the animals treated with 500 μg tamoxifen was comparable to the animals treated with only 50 μg, indicating that the lower dose of tamoxifen is sufficient to fully activate the As(G521R) and Bs(G400V) regulators. Finally, the comparable low basal level of endostatin observed in the As(G521R) and Bs(G400V) groups suggests that the endogenous level of estrogen in the C57Bl/6 mice is not sufficient to induce the estrogen-responsive Bs(G400V) regulator. An elevation in basal endostatin levels observed at days 3-5 appeared to be a non-specific effect resulting from adenovirus vector administration, since the Av3Null vector has an effect similar to the Av3TATA-mEndo containing groups.

Conclusions

The in vitro and in vivo results shown in this Example, demonstrate that the ZFP-LBD fusion proteins can be efficiently delivered via an adenovirus vector and can be expressed in sufficient amounts to provide high levels of drug-dependent control of a transgene in animals. Furthermore, the data show that the basal level of expression from the 6x2C7-minimal promoter constructs tested in an adenovirus vector give relatively low levels of expression, even when the fusion protein is expressed in the same cell. Thus, the system is highly drug dependent and allows for substantial regulation of the vector-delivered transgene. Taken together, these data evidence the effectiveness of this system for gene therapy applications.

EXAMPLE 20

Construction and Evaluation of the $Cys_2$-$His_2$ Zinc Finger DBD-ERLBD Regulators in Lentiviral Vectors In order to demonstrate controlled gene expression in an integrated vector system, the regulatory system described in Example 19 with the adenoviral vectors were used to develop a series of lentiviral vectors. These vectors contained either the ZFP-LBD fusion protein linked to the immediate early CMV promoter or a regulatable transgene (either eGFP or luciferase) linked to the 6X2C7 array of C7 binding sites and either the minimal promoter from SV40 or C-fos TATA. The fusion protein-encoding vector and the regulatable transgene vector can then be used to generate lentiviral vector supernatant. The supernatant can be used to stably transduced human cells either singly or in parallel. Stable cell lines containing the integrated vectors can then be induced with the appropriate activating drug (e.g., 4-OH-tamoxifen) and gene expression is measured as fold induction in the presence and absence of drug.

Construction of Lentiviral Vectors Encoding the ZFP-LBD Fusion Protein or the Regulatable Transgene The generation of lentiviral vectors and vector supernatant involves 3 main steps: first a gene or region of interest is inserted into shuttle vector backbone plasmid containing all of the viral cis-elements for transcription, packaging, reverse transcription, and integration. Second, the lentiviral vector shuttle plasmid is co-transfected into human 293 cells along with plasmids providing the packaging functions (gag, pol, and env). Typically the transfections include 10 μg of vector plasmid, 10 μg of packaging plasmid and 1 μg envelope plasmid (Vesicular Stomatitis virus G envelope) using a Profection Calcium Phosphate transfection kit. Third, the culture supernatant containing the lentiviral vector is harvested (between 24 and 48 hours post transfection) and used to transduce naive human target cells.

Construction of HIV-1 Based Vectors

An HIV-1-based vector system containing an internal CMV promoter was constructed from an infectious HIV-$1_{IIIB}$ provirus cDNA (pHIV-IIIB) The infectious proviral cDNA was generated by PCR from DNA isolated from H-9 cells chronically infected with HIV-$1_{IIIB}$. The gag/pol and env sequences of pHIVIIIB were removed by digestion and excision of a PstI-KpnI fragment. Replacing the gag/pol and env sequences was a PstI/Kpn polylinker containing unique multiple cloning sites to form the intermediate vector p2XLTR. The Rev response element (RRE) fragment from HIVIIIB, required for proper vector RNA processing, was inserted downstream of the truncated gag sequences of p2XTR to form the construct pHIVec. An AseI-XbaI CMV-eGFP reporter fragment derived from pEGFP-N1 (Clontech, Palo Alto, Calif.) was cloned into the Ndel-Xba site of pHIVec to generate pHIVCMVGFP. pHIVCMV-X was generated by removal of the eGFP fragment by KpnI digestion and religation.

Construction of pHIVCMV-C7LBD/A(G521R)

The AS521R (C7LBD/A(G521R) coding fragment derived from C7LBDAS by digestion with NotI, T4 DNA polymerase fill-in, and EcoRI site was cloned into pHIVCMV-X cloned downstream of the CMV promoter into a EcoRI/SmaI restriction site. As a control for induction, an HIV vector containing a constitutive transactivator and DBD chimera was generated, pHIVCMV-C7VP16. A HindIII-NotI restriction fragment from pCDNA3-C7VP16 containing the C7VP16 coding fragment was inserted downstream of the CMV promoter at the Sma site of pHIVecCMV-X.

Construction of pHIV6x2C7Sv and pHIV6x2C7TATA Luciferase Vectors

A BamHI-XbaI restriction fragment containing the 6x2C7TATA luciferase fragment was isolated from pTATA6x2C7Luc and cloned downstream of the RRE at the SpeI-XbaI restriction sites. A MluI-BstBI restriction fragment containing the 6x2C7Sv luciferase fragment was isolated from pGL3-6x2C7SvLuc and cloned downstream of the RRE at the Spe-XbaI restriction sites.

Evaluation of the ZFP-LBD Fusion Proteins and Regulatable Lentiviral Vectors

Transduction of HeLa Cells by Inducible Lentiviral Vectors

Subconfluent HeLa cells were transduced with either HIV6x2C7SvLuc or HIV6x2C7TATALuc vector supernatant for 24 hours followed by transduction with HIVAS521R lentiviral vector supernatant. Cells were allowed to recover from infection for 24 hours in fresh culture medium after which 4-OH-tamoxifen (100 or 1000 nm) was added to the culture for an additional 24 hours. Cells were lysed in a standard luciferase lysis buffer, subjected to freeze thaw and analyzed for luciferase activity using a luciferase assay kit (Promega). The results showed that cells infected with either HIV6x2C7SvLuc or HIV6x2C7TATALuc followed by transduction with HIVCMVAS521R resulted in a 13.1 and 11.7 fold stimulation in luciferase activity respectively, when given 4-OH-tamoxifen.

Lentiviral Transduction of Lentiviral Integrated Target Vector Populations

HeLa cells that had been previously transduced with either HIV6x2C7SvLuc or HIV6x2C7TATALuc were carried in culture for 9 passages without exposure to any ZFP-LBD fusion protein. On passage 10, cells were transduced with HIVCMVAS521R for 24 hours followed by the addition of 100 nm tamoxifen for an additional 24 hours. The results show that HeLa cell lines containing an integrated HIV6x2C7SvLuc or HIV6x2C7TATALuc vector can be induced for luciferase expression by transduction of a LV containing AS521R+tamoxifen 31.4- and 22.5-fold, respectively.

These data demonstrate the effectiveness of the C2H2-LBD regulator for controlling expression of a transgene that is stably integrated into the host cell chromosome.

Since modifications will be apparent to those of skill in this art, it is intended that this invention be limited only by the scope of the appended claims.

What is claimed is:

1. A nucleic acid molecule, comprising a sequence of nucleotides encoding the fusion protein, wherein:

the fusion protein comprises a nucleotide binding domain (DBD) operatively linked to a modified ligand binding domain (LBD) from an intracellular receptor:

the fusion protein is a ligand activated transcriptional regulator;

the nucleotide binding domain is a polydactyl zinc-finger domain that contains at least three modular portions thereof;

each modular portion of the nucleotide binding domain interacts with a contiguous sequence of nucleotides of at least 3 nucleotides; and the ligand specificity of the LBD for endogenous and exogenous ligands is modified to change its ligand specificity compared to the ligand specificity of the ligand binding domain of the native intracellular receptor, whereby ligands that activate the fusion protein are not the ligands that activate the receptor from which the LBD was derived.

2. A nucleic acid molecule of claim 1, wherein the fusion protein further comprises an operatively linked transcription regulating domain.

3. A vector, comprising a nucleic acid molecule of claim 1.

4. A vector of claim 3, wherein the fusion protein further comprises an operatively linked transcription regulating domain.

5. An isolated cell, comprising the expression vector of claim 3.

6. An isolated cell, comprising the expression vector of claim 4.

7. The cell of claim 5 that is a eukaryotic cell.

8. The cell of claim 6 that is a eukaryotic cell.

9. The vector of claim 3 that is a viral vector.

10. The vector of claim 4 that is a viral vector.

11. The vector of claim 9, wherein the viral vector is derived from a DNA virus or a retrovirus.

12. The vector of claim 11 that is selected from the group consisting of an adenoviral vector, and adeno-associated viral vector, a herpes virus vector, a vaccinia virus vector and a lentiviral vector.

13. The vector of claim 12 that is an adenoviral vector.

14. The vector of claim 10, wherein the viral vector is derived from a DNA virus or a retrovirus.

15. The vector of claim 14 that is selected from the group consisting of an adenoviral vector, and adeno-associated viral vector, a herpes virus vector, a vaccinia virus vector and a lentiviral vector.

16. A combination, comprising:

a nucleic acid molecule of claim 1; and a regulatable expression cassette that comprises at least one response element recognized by the nucleic acid binding domain of the fusion protein, wherein the nucleic acid molecule and regulatable expression cassette are in separate compositions or in a single composition.

17. The combination of claim 16, wherein the cassette comprises a gene that encodes a protein.

18. The combination of claim 16 that comprises a single composition that contains the nucleic acid molecule that encodes the fusion protein, and the regulatable expression cassette in a pharmaceutically acceptable excipient.

19. The combination of claim 16, wherein the nucleic acid molecule comprising a sequence of nucleotides that encodes the fusion protein, and the regulatable expression cassette are in separate compositions.

20. A composition for regulating gene expression comprising:

an effective amount of a nucleic acid molecule of claim 1, wherein the amount is effective, upon translation into the encoded fusion polypeptide, for regulating gene expression; and a pharmaceutically acceptable excipient.

21. The combination of claim 16, wherein the regulatable expression cassette comprises 3 to 6 response elements.

22. The nucleic acid molecule of claim 1, wherein the polydactyl zinc-finger domain peptide or a modular portion thereof specifically binds to a contiguous nucleotide sequence of at least 18 nucleotides.

23. A non-viral delivery system, comprising:

a nucleic acid molecule of claim 1; and reagents for effecting non-viral delivery of the nucleic acid molecule.

24. The non-viral delivery system of claim 23, further comprising a nucleic acid molecule that comprises an expression cassette containing a sequence of nucleotides with which the nucleic acid binding domain of the fusion protein interacts.

25. The non-viral delivery system of claim 23, wherein the reagent for effecting non-viral delivery is selected from the group consisting of a DNA-ligand complex, an adenovirus-ligand-DNA complex, a reagent for direct injection of DNA, a reagent for $CaPO_4$ precipitation, a reagent for gene gun techniques, a reagent for electroporation, liposomes and a reagent for lipofection.

26. The nucleic acid molecule of claim 1, wherein the intracellular receptor is a nuclear hormone receptor.

27. The nucleic acid molecule of claim 1, wherein a module of the zinc-finger peptide binds to a sequence of nucleotides of the formula $(GNN)_n$, where G is guanidine, N is any nucleotide and n is an integer from 3 to 6.

28. The nucleic acid molecule of claim 1, wherein:

the nucleotide binding domain of the encoded fusion protein comprises at least 6 modular portions of a polydactyl zinc-finger domain peptide, wherein each modular portion thereof interacts with a contiguous nucleotide sequence of at least 3 nucleotides;

the zinc-finger peptide is comprised of modular units from a C2H2 zinc-finger; and the fusion protein is a gene-specific ligand activated transcriptional regulator.

29. The nucleic acid molecule of claim 1, wherein the encoded fusion protein comprises at least four zinc fingers or zinc finger variants.

30. The nucleic acid molecule of claim 1, wherein the intracellular receptor is a steroid receptor.

31. The nucleic acid molecule of claim 2, wherein the transcription regulating domain comprises a transcription activation domain.

32. The nucleic acid molecule of claim 2, wherein the transcription regulating domain comprises a transcription activation domain selected from the group consisting of VP16, VP64, TA2, STAT-6, p65 and derivatives, multimers and combinations thereof that have transcription activation activity.

33. The nucleic acid molecule of claim 1, wherein the intracellular receptor is a nuclear hormone receptor selected from the group consisting of estrogen receptors, progesterone receptors, glucocorticoid-α receptors, glucocorticoid-β receptors, mineralocorticoid receptors, androgen receptors, thyroid hormone receptors, retinoic acid receptors, retinoid X receptors, Vitamin D receptors, COUP-TF receptors, ecdysone receptors, Nurr-1 receptors and orphan receptors.

34. The combination of claim 16 that is packaged as a kit.

* * * * *

UNITED STATES PATENT AND TRADEMARK OFFICE

CERTIFICATE OF CORRECTION

PATENT NO. : 7,442,784 B2 
APPLICATION NO. : 10/422934
DATED : October 28, 2008
INVENTOR(S) : Barbas, III et al.

It is certified that error appears in the above-identified patent and that said Letters Patent is hereby corrected as shown below:

IN THE SPECIFICATION:

At column 3, line 6, please replace "Ligan" with --Ligand-- at column 5, line 17, please insert

--Compositions, particularly pharmaceutical compositions containing the fusion polypeptides in a pharmaceutically acceptable carrier are also provided.

Combinations of the expression cassette and fusion polypeptide or nucleic acid molecules, particularly expression vectors that encode the fusion polypeptide are provided. The combinations may include separate compositions or a single composition containing both elements. Kits containing the combinations and optionally instructions for administration thereof and other reagents used in preparing and administering the combinations are also provided.

Hence compositions suitable for gene therapy that contain nucleic acid encoding the fusion protein, typically in a vector suitable for gene therapy are provided. Preferred vectors include viral vectors, preferably adenoviral vectors, and lentiviral vectors. In other embodiments, non-viral delivery systems, including DNA-ligand complexes, adenovirus-ligand-DNA complexes, direct injection of DNA, $CaPO_4$ precipitation, gene gun techniques, electroporation, liposomes and lipofection are provided.

The compositions suitable for regulating gene expression contain an effective amount of the fusion protein or a polynucleotide encoding the ligand activated transcriptional regulatory fusion protein and a pharmaceutically acceptable excipient. Such compositions can further include a regulatable expression cassette encoding a gene and at least one response element for the gene recognized by the nucleotide binding domain of the fusion polypeptide.

The regulatable expression cassette is designed to include a sequence of nucleic acids with which the nucleic acid binding domain of the ligand activated transcriptional regulatory fusion protein interacts. It also preferably includes operatively linked transcriptional regulatory sequences that are regulatable by the TRD of the fusion protein. Typically, the regulatable expression cassette includes 3 to 6 response elements.-- at column 6, line 26, please delete

"Methods for treating a cellular proliferative disorder by the *ex vivo* introduction of a recombinant expression vector encoding the fusion protein are provided. Cellular proliferative disorders include disorders associated with transcription of a gene at reduced or increased levels.

UNITED STATES PATENT AND TRADEMARK OFFICE
CERTIFICATE OF CORRECTION

PATENT NO. : 7,442,784 B2
APPLICATION NO. : 10/422934
DATED : October 28, 2008
INVENTOR(S) : Barbas, III et al.

It is certified that error appears in the above-identified patent and that said Letters Patent is hereby corrected as shown below:

Administration of the composition(s) can be effected *in vitro, in vivo* or *ex vivo*. One such method includes the removal of a tissue sample from a subject with a disorder, such as a cell proliferative disorder, isolating hematopoietic or other cells from the tissue sample, and contacting isolated cells with the fusion protein or a nucleic acid molecule encoding the fusion protein, and, optionally, a target specific gene. Optionally, the cells can be treated with a growth factor, such as interleukin-2 for example, to stimulate cell growth, before reintroducing the cells into the subject. When reintroduced, the cells specifically target the cell population from which they were originally isolated. In this way, the trans-repressing activity of the zinc finger-nucleotide binding polypeptide may be used to inhibit or suppress undesirable cell proliferation in a subject. Preferably, the subject is a human."

at column 10, line 43, please replace "identify." with --identity.-- at column 16, line 44, please delete

"As used herein, non-natural ligands or non-native ligands refer to compounds that are normally not found in mammals, such as humans, that bind to or interact with the ligand binding domain of a receptor. Hence, the term "non-native ligands" refers to those ligands that are not naturally found in the specific organism (man or animal) in which gene therapy is contemplated. For example, certain insect hormones such as ecdysone are not found in humans. As such ecdysone is non-native hormone to an animal, such as a human."

at column 34, lines 43-44, please replace "11$\beta$-4-dimethylaminophenyl)-17$\alpha$-hydroxy-17$\alpha$-propinyl-4,9-estradiene-3-one (RU38486 or Mifepestone);" with --11$\beta$-(4-dimethylaminophenyl)-17$\beta$-hydroxy-17$\alpha$-propinyl-4,9-estradiene-3-one (RU38486 or Mifepristone);-- at column 34, lines 50-53, please replace "(7$\beta$11$\beta$,17$\beta$)-l l-(4-dimethylaminophenyl)-7-methyl-4',5'-dihydrospiroy' ester-4,9-diene-17,2' (3'H)-furan!-3-one (Org31806);" with --(7$\beta$,11$\beta$,17$\beta$)-11-(4-dimethylaminophenyl)-7-methyl-4',5'-dihydrospiro[ester-4,9-diene-17,2' (3'H)-furan]-3-one (Org31806);-- at column 34, line 53-55, please replace "(11$\beta$,14$\beta$,17$\alpha$)- 4',5'-dihydro-l l-(4-dimethylaminophenyl)y'spi roestra-4,9-diene-17,2' (3'H)-furan!-3-one (Org31376);" with --(11$\beta$,14$\beta$,17$\alpha$)-4',5'-dihydro-11-(4-dimethylaminophenyl)-[spiroestra-4,9-diene-17,2' (3'H)-furan]-3-one (Org31376);-- at column 34, line 55, please replace "5-alpha-pregnane-3,2-dione." with --5-alpha-pregnane-3,20-dione.--

UNITED STATES PATENT AND TRADEMARK OFFICE

CERTIFICATE OF CORRECTION

PATENT NO. : 7,442,784 B2
APPLICATION NO. : 10/422934
DATED : October 28, 2008
INVENTOR(S) : Barbas, III et al.

It is certified that error appears in the above-identified patent and that said Letters Patent is hereby corrected as shown below:

IN THE CLAIMS:

Please replace Claim 12 with the following amended Claim:

Column 201, lines 4-7

12. The vector of claim 11 that is selected from the group consisting of an adenoviral vector, an adeno-associated viral vector, a herpes virus vector, a vaccinia virus vector and a lentiviral vector.

Please replace Claim 15 with the following amended Claim:

Column 201, lines 11-14

15. The vector of claim 14 that is selected from the group consisting of an adenoviral vector, an adeno-associated viral vector, a herpes virus vector, a vaccinia virus vector and a lentiviral vector.

Signed and Sealed this

Seventh Day of April, 2009

JOHN DOLL

*Acting Director of the United States Patent and Trademark Office*

SEQUENCE LISTING

<160> NUMBER OF SEQ ID NOS: 92

<210> SEQ ID NO 1
<211> LENGTH: 6828
<212> TYPE: DNA
<213> ORGANISM: Artificial Sequence
<220> FEATURE:
<223> OTHER INFORMATION: Description of Artificial Sequence: Construct
2C7LBDAS

<400> SEQUENCE: 1
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttagat ctatggccca ggcggccctc gagccctatg cttgccctgt 960
cgagtcctgc gatcgccgct tttctaagtc ggctgatctg aagcgccata tccgcatcca 1020
cacaggccag aagcctttcc agtgtcgaat atgcatgcgt aacttcagtc gtagtgacca 1080
ccttaccacc cacatccgca cccacacagg cgagaagcct tttgcctgtg acatttgtgg 1140
gaggaagttt gccaggagtg atgaacgcaa gaggcatacc aaaatccata ccggtgagaa 1200
gccctatgct tgccctgtcg agtcctgcga tcgccgcttt tctaagtcgg ctgatctgaa 1260
gcgccatatc cgcatccaca caggccagaa gcccttccag tgtcgaatat gcatgcgtaa 1320
cttcagtcgt agtgaccacc ttaccaccca catccgcacc cacacaggcg agaagccttt 1380
tgcctgtgac atttgtggga ggaagtttgc caggagtgat gaacgcaaga ggcataccaa 1440
aatccattta agacagaggg actctagaac tagttctgct ggagacatga gagctgccaa 1500
cctttggcca agcccgctca tgatcaaacg ctctaagaag aacagcctgg ccttgtccct 1560
gacggccgac cagatggtca gtgccttgtt ggatgctgag ccccccatac tctattccga 1620
gtatgatcct accagaccct tcagtgaagc ttcgatgatg ggcttactga ccaacctggc 1680
agacagggag ctggttcaca tgatcaactg ggcgaagagg gtgccaggct ttgtggattt 1740
gaccctccat gatcaggtcc accttctaga atgtgcctgg ctagagatcc tgatgattgg 1800
tctcgtctgg cgctccatgg agcacccagg gaagctactg tttgctccta acttgctctt 1860
ggacaggaac cagggaaaat gtgtagaggg catggtggag atcttcgaca tgctgctggc 1920

-continued

```
tacatcatct cggttccgca tgatgaatct gcagggagag gagtttgtgt gcctcaaatc   1980
tattattttg cttaattctg gagtgtacac atttctgtcc agcaccctga agtctctgga   2040
agagaaggac catatccacc gagtcctgga caagatcaca gacactttga tccacctgat   2100
ggccaaggca ggcctgaccc tgcagcagca gcaccagcgg ctggcccagc tcctcctcat   2160
cctctcccac atcaggcaca tgagtaacaa aggcatggag catctgtaca gcatgaagtg   2220
caagaacgtg gtgcccctct atgacctgct gctggagatg ctggacgccc accgcctaca   2280
tgcgcccact agccgtacgc cggccgacgc cctggacgac ttcgacctgg acatgctgcc   2340
ggccgacgcc ctggacgact tcgacctgga catgctgccg gccgacgccc tggacgactt   2400
cgacctggac atgctgccgg ggtaactaag taagcggccg ctcgagtcta gagggcccgt   2460
ttaaacccgc tgatcagcct cgactgtgcc ttctagttgc cagccatctg ttgtttgccc   2520
ctcccccgtg ccttccttga ccctggaagg tgccactccc actgtccttt cctaataaaa   2580
tgaggaaatt gcatcgcatt gtctgagtag gtgtcattct attctggggg gtggggtggg   2640
gcaggacagc aagggggagg attgggaaga caatagcagg catgctgggg atgcggtggg   2700
ctctatggct tctgaggcgg aaagaaccag ctggggctct agggggtatc cccacgcgcc   2760
ctgtagcggc gcattaagcg cggcgggtgt ggtggttacg cgcagcgtga ccgctacact   2820
tgccagcgcc ctagcgcccg ctcctttcgc tttcttccct tcctttctcg ccacgttcgc   2880
cggctttccc cgtcaagctc taaatcgggg catcccttta gggttccgat ttagtgcttt   2940
acggcacctc gaccccaaaa aacttgatta gggtgatggt tcacgtagtg ggccatcgcc   3000
ctgatagacg gtttttcgcc ctttgacgtt ggagtccacg ttctttaata gtggactctt   3060
gttccaaact ggaacaacac tcaaccctat ctcggtctat tcttttgatt tataagggat   3120
tttggggatt tcggcctatt ggttaaaaaa tgagctgatt taacaaaaat ttaacgcgaa   3180
ttaattctgt ggaatgtgtg tcagttaggg tgtggaaagt ccccaggctc cccaggcagg   3240
cagaagtatg caaagcatgc atctcaatta gtcagcaacc aggtgtggaa agtccccagg   3300
ctccccagca ggcagaagta tgcaaagcat gcatctcaat tagtcagcaa ccatagtccc   3360
gcccctaact ccgcccatcc cgcccctaac tccgcccagt tccgcccatt ctccgcccca   3420
tggctgacta attttttta tttatgcaga ggccgaggcc gcctctgcct ctgagctatt   3480
ccagaagtag tgaggaggct tttttggagg cctaggcttt tgcaaaaagc tcccgggagc   3540
ttgtatatcc attttcggat ctgatcaaga gacaggatga ggatcgtttc gcatgattga   3600
acaagatgga ttgcacgcag gttctccggc cgcttgggtg gagaggctat tcggctatga   3660
ctgggcacaa cagacaatcg gctgctctga tgccgccgtg ttccggctgt cagcgcaggg   3720
gcgcccggtt ctttttgtca agaccgacct gtccggtgcc ctgaatgaac tgcaggacga   3780
ggcagcgcgg ctatcgtggc tggccacgac gggcgttcct tgcgcagctg tgctcgacgt   3840
tgtcactgaa gcgggaaggg actggctgct attgggcgaa gtgccggggc aggatctcct   3900
gtcatctcac cttgctcctg ccgagaaagt atccatcatg gctgatgcaa tgcggcggct   3960
gcatacgctt gatccggcta cctgcccatt cgaccaccaa gcgaaacatc gcatcgagcg   4020
agcacgtact cggatggaag ccggtcttgt cgatcaggat gatctggacg aagagcatca   4080
ggggctcgcg ccagccgaac tgttcgccag gctcaaggcg cgcatgcccg acggcgagga   4140
tctcgtcgtg acccatggcg atgcctgctt gccgaatatc atggtggaaa atggccgctt   4200
ttctggattc atcgactgtg gccggctggg tgtggcggac cgctatcagg acatagcgtt   4260
```

-continued

```
ggctacccgt gatattgctg aagagcttgg cggcgaatgg gctgaccgct tcctcgtgct   4320
ttacggtatc gccgctcccg attcgcagcg catcgccttc tatcgccttc ttgacgagtt   4380
cttctgagcg ggactctggg gttcgaaatg accgaccaag cgacgcccaa cctgccatca   4440
cgagatttcg attccaccgc cgccttctat gaaaggttgg gcttcggaat cgttttccgg   4500
gacgccggct ggatgatcct ccagcgcggg gatctcatgc tggagttctt cgcccacccc   4560
aacttgttta ttgcagctta taatggttac aaataaagca atagcatcac aaatttcaca   4620
aataaagcat ttttttcact gcattctagt tgtggtttgt ccaaactcat caatgtatct   4680
tatcatgtct gtataccgtc gacctctagc tagagcttgg cgtaatcatg gtcatagctg   4740
tttcctgtgt gaaattgtta tccgctcaca attccacaca acatacgagc cggaagcata   4800
aagtgtaaag cctggggtgc ctaatgagtg agctaactca cattaattgc gttgcgctca   4860
ctgcccgctt tccagtcggg aaacctgtcg tgccagctgc attaatgaat cggccaacgc   4920
gcggggagag gcggtttgcg gcgagcggta tcagctcact caaaggcggt aatacggtta   4980
tccacagaat caggggataa cgcaggaaag aacatgtgag caaaaggcca gcaaaaggcc   5040
aggaaccgta aaaaggccgc gttgctggcg tttttccata ggctccgccc ccctgacgag   5100
catcacaaaa atcgacgctc aagtcagagg tggcgaaacc cgacaggact ataaagatac   5160
caggcgtttc cccctggaag ctccctcgtg cgctctcctg ttccgaccct gccgcttacc   5220
ggatacctgt ccgcctttct cccttcggga agcgtggcgc tttctcaatg ctcacgctgt   5280
aggtatctca gttcggtgta ggtcgttcgc tccaagctgg gctgtgtgca cgaacccccc   5340
gttcagcccg accgctgcgc cttatccggt aactatcgtc ttgagtccaa cccggtaaga   5400
cacgacttat cgccactggc agcagccact ggtaacagga ttagcagagc gaggtatgta   5460
ggcggtgcta cagagttctt gaagtggtgg cctaactacg gctacactag aaggacagta   5520
tttggtatct gcgctctgct gaagccagtt accttcggaa aaagagttgg tagctcttga   5580
tccggcaaac aaaccaccgc tggtagcggt ggtttttttg tttgcaagca gcagattacg   5640
cgcagaaaaa aaggatctca agaagatcct ttgatctttt ctacggggtc tgacgctcag   5700
tggaacgaaa actcacgtta agggattttg gtcatgagat tatcaaaaag gatcttcacc   5760
tagatccttt taaattaaaa atgaagtttt aaatcaatct aaagtatata tgagtaaact   5820
tggtctgaca gttaccaatg cttaatcagt gaggcaccta tctcagcgat ctgtctattt   5880
cgttcatcca tagttgcctg actccccgtc gtgtagataa ctacgatacg ggagggctta   5940
ccatctggcc ccagtgctgc aatgataccg cgagacccac gctcaccggc tccagattta   6000
tcagcaataa accagccagc cggaagggcc gagcgcagaa gtggtcctgc aactttatcc   6060
gcctccatcc agtctattaa ttgttgccgg gaagctagag taagtagttc gccagttaat   6120
agtttgcgca acgttgttgc cattgctaca ggcatcgtgg tgtcacgctc gtcgtttggt   6180
atggcttcat tcagctccgg ttcccaacga tcaaggcgag ttacatgatc ccccatgttg   6240
tgcaaaaaag cggttagctc cttcggtcct ccgatcgttg tcagaagtaa gttggccgca   6300
gtgttatcac tcatggttat ggcagcactg cataattctc ttactgtcat gccatccgta   6360
agatgctttt ctgtgactgg tgagtactca accaagtcat tctgagaata gtgtatgcgg   6420
cgaccgagtt gctcttgccc ggcgtcaata cgggataata ccgcgccaca tagcagaact   6480
ttaaaagtgc tcatcattgg aaaacgttct tcggggcgaa aactctcaag gatcttaccg   6540
ctgttgagat ccagttcgat gtaacccact cgtgcaccca actgatcttc agcatctttt   6600
actttcacca gcgtttctgg gtgagcaaaa acaggaaggc aaaatgccgc aaaaaaggga   6660
```

-continued

```
ataagggcga cacggaaatg ttgaatactc atactcttcc tttttcaata ttattgaagc   6720

atttatcagg gttattgtct catgagcgga tacatatttg aatgtattta gaaaaataaa   6780

caaatagggg ttccgcgcac atttccccga aaagtgccac ctgacgtc                6828
```

```
<210> SEQ ID NO 2
<211> LENGTH: 6900
<212> TYPE: DNA
<213> ORGANISM: Artificial Sequence
<220> FEATURE:
<220> FEATURE:
<223> OTHER INFORMATION: Description of Artificial Sequence: Construct
      2C7LBDBS

<400> SEQUENCE: 2

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttagat ctatggccca ggcggccctc gagccctatg cttgccctgt    960

cgagtcctgc gatcgccgct ttctaagtc ggctgatctg aagcgccata tccgcatcca    1020

cacaggccag aagcctttcc agtgtcgaat atgcatgcgt aacttcagtc gtagtgacca   1080

ccttaccacc cacatccgca cccacacagg cgagaagcct tttgcctgtg acatttgtgg   1140

gaggaagttt gccaggagtg atgaacgcaa gaggcatacc aaaatccata ccggtgagaa   1200

gccctatgct tgccctgtcg agtcctgcga tcgccgcttt tctaagtcgg ctgatctgaa   1260

gcgccatatc cgcatccaca caggccagaa gcccttccag tgtcgaatat gcatgcgtaa   1320

cttcagtcgt agtgaccacc ttaccaccca catccgcacc cacacaggcg agaagccttt   1380

tgcctgtgac atttgtggga ggaagtttgc caggagtgat gaacgcaaga ggcataccaa   1440

aatccattta agacagaggg actctagaac tagtgaccga agaggaggga gaatgttgaa   1500

acacaagcgc cagagagatg atggggaggg caggggtgaa gtggggtctg ctggagacat   1560

gagagctgcc aacctttggc caagcccgct catgatcaaa cgctctaaga agaacagcct   1620

ggccttgtcc ctgacggccg accagatggt cagtgccttg ttggatgctg agccccccat   1680

actctattcc gagtatgatc ctaccagacc cttcagtgaa gcttcgatga tgggcttact   1740

gaccaacctg gcagacaggg agctggttca catgatcaac tgggcgaaga gggtgccagg   1800
```

-continued

```
ctttgtggat ttgaccctcc atgatcaggt ccaccttcta gaatgtgcct ggctagagat   1860
cctgatgatt ggtctcgtct ggcgctccat ggagcaccca gggaagctac tgtttgctcc   1920
taacttgctc ttggacagga accagggaaa atgtgtagag ggcatggtgg agatcttcga   1980
catgctgctg gctacatcat ctcggttccg catgatgaat ctgcagggag aggagtttgt   2040
gtgcctcaaa tctattattt tgcttaattc tggagtgtac acatttctgt ccagcaccct   2100
gaagtctctg gaagagaagg accatatcca ccgagtcctg gacaagatca cagacacttt   2160
gatccacctg atggccaagg caggcctgac cctgcagcag cagcaccagc ggctggccca   2220
gctcctcctc atcctctccc acatcaggca catgagtaac aaaggcatgg agcatctgta   2280
cagcatgaag tgcaagaacg tggtgcccct ctatgacctg ctgctggaga tgctggacgc   2340
ccaccgccta catgcgccca ctagccgtac gccggccgac gccctggacg acttcgacct   2400
ggacatgctg ccggccgacg ccctggacga cttcgacctg gacatgctgc cggccgacgc   2460
cctggacgac ttcgacctgg acatgctgcc ggggtaacta agtaagcggc cgctcgagtc   2520
tagagggccc gtttaaaccc gctgatcagc ctcgactgtg ccttctagtt gccagccatc   2580
tgttgtttgc ccctcccccg tgccttcctt gaccctggaa ggtgccactc ccactgtcct   2640
ttcctaataa aatgaggaaa ttgcatcgca ttgtctgagt aggtgtcatt ctattctggg   2700
gggtggggtg gggcaggaca gcaaggggga ggattgggaa gacaatagca ggcatgctgg   2760
ggatgcggtg ggctctatgg cttctgaggc ggaaagaacc agctggggct ctagggggta   2820
tccccacgcg ccctgtagcg gcgcattaag cgcggcgggt gtggtggtta cgcgcagcgt   2880
gaccgctaca cttgccagcg ccctagcgcc cgctcctttc gctttcttcc cttcctttct   2940
cgccacgttc gccggctttc cccgtcaagc tctaaatcgg ggcatccctt tagggttccg   3000
atttagtgct ttacggcacc tcgaccccaa aaaacttgat tagggtgatg gttcacgtag   3060
tgggccatcg ccctgataga cggtttttcg ccctttgacg ttggagtcca cgttctttaa   3120
tagtggactc ttgttccaaa ctggaacaac actcaaccct atctcggtct attcttttga   3180
tttataaggg attttgggga tttcggccta ttggttaaaa aatgagctga tttaacaaaa   3240
atttaacgcg aattaattct gtggaatgtg tgtcagttag ggtgtggaaa gtccccaggc   3300
tccccaggca ggcagaagta tgcaaagcat gcatctcaat tagtcagcaa ccaggtgtgg   3360
aaagtcccca ggctccccag caggcagaag tatgcaaagc atgcatctca attagtcagc   3420
aaccatagtc ccgcccctaa ctccgcccat cccgccccta actccgccca gttccgccca   3480
ttctccgccc catggctgac taattttttt tatttatgca gaggccgagg ccgcctctgc   3540
ctctgagcta ttccagaagt agtgaggagg cttttttgga ggcctaggct tttgcaaaaa   3600
gctcccggga gcttgtatat ccattttcgg atctgatcaa gagacaggat gaggatcgtt   3660
tcgcatgatt gaacaagatg gattgcacgc aggttctccg gccgcttggg tggagaggct   3720
attcggctat gactgggcac aacagacaat cggctgctct gatgccgccg tgttccggct   3780
gtcagcgcag gggcgcccgg ttctttttgt caagaccgac ctgtccggtg ccctgaatga   3840
actgcaggac gaggcagcgc ggctatcgtg gctggccacg acgggcgttc cttgcgcagc   3900
tgtgctcgac gttgtcactg aagcgggaag ggactggctg ctattgggcg aagtgccggg   3960
gcaggatctc ctgtcatctc accttgctcc tgccgagaaa gtatccatca tggctgatgc   4020
aatgcggcgg ctgcatacgc ttgatccggc tacctgccca ttcgaccacc aagcgaaaca   4080
tcgcatcgag cgagcacgta ctcggatgga agccggtctt gtcgatcagg atgatctgga   4140
cgaagagcat caggggctcg cgccagccga actgttcgcc aggctcaagg cgcgcatgcc   4200
```

-continued

```
cgacggcgag gatctcgtcg tgacccatgg cgatgcctgc ttgccgaata tcatggtgga   4260
aaatggccgc ttttctggat tcatcgactg tggccggctg ggtgtggcgg accgctatca   4320
ggacatagcg ttggctaccc gtgatattgc tgaagagctt ggcggcgaat gggctgaccg   4380
cttcctcgtg ctttacggta tcgccgctcc cgattcgcag cgcatcgcct tctatcgcct   4440
tcttgacgag ttcttctgag cgggactctg gggttcgaaa tgaccgacca agcgacgccc   4500
aacctgccat cacgagattt cgattccacc gccgccttct atgaaaggtt gggcttcgga   4560
atcgttttcc gggacgccgg ctggatgatc ctccagcgcg gggatctcat gctggagttc   4620
ttcgcccacc ccaacttgtt tattgcagct tataatggtt acaaataaag caatagcatc   4680
acaaatttca caaataaagc atttttttca ctgcattcta gttgtggttt gtccaaactc   4740
atcaatgtat cttatcatgt ctgtataccg tcgacctcta gctagagctt ggcgtaatca   4800
tggtcatagc tgtttcctgt gtgaaattgt tatccgctca caattccaca caacatacga   4860
gccggaagca taaagtgtaa agcctggggt gcctaatgag tgagctaact cacattaatt   4920
gcgttgcgct cactgcccgc tttccagtcg ggaaacctgt cgtgccagct gcattaatga   4980
atcggccaac gcgcggggag aggcggtttg cggcgagcgg tatcagctca ctcaaaggcg   5040
gtaatacggt tatccacaga atcaggggat aacgcaggaa agaacatgtg agcaaaaggc   5100
cagcaaaagg ccaggaaccg taaaaaggcc gcgttgctgg cgtttttcca taggctccgc   5160
ccccctgacg agcatcacaa aaatcgacgc tcaagtcaga ggtggcgaaa cccgacagga   5220
ctataaagat accaggcgtt tccccctgga agctccctcg tgcgctctcc tgttccgacc   5280
ctgccgctta ccggatacct gtccgccttt ctcccttcgg gaagcgtggc gctttctcaa   5340
tgctcacgct gtaggtatct cagttcggtg taggtcgttc gctccaagct gggctgtgtg   5400
cacgaacccc ccgttcagcc cgaccgctgc gccttatccg gtaactatcg tcttgagtcc   5460
aacccggtaa gacacgactt atcgccactg gcagcagcca ctggtaacag gattagcaga   5520
gcgaggtatg taggcggtgc tacagagttc ttgaagtggt ggcctaacta cggctacact   5580
agaaggacag tatttggtat ctgcgctctg ctgaagccag ttaccttcgg aaaaagagtt   5640
ggtagctctt gatccggcaa acaaaccacc gctggtagcg gtggtttttt tgtttgcaag   5700
cagcagatta cgcgcagaaa aaaaggatct caagaagatc ctttgatctt ttctacgggg   5760
tctgacgctc agtggaacga aaactcacgt taagggattt tggtcatgag attatcaaaa   5820
aggatcttca cctagatcct tttaaattaa aaatgaagtt ttaaatcaat ctaaagtata   5880
tatgagtaaa cttggtctga cagttaccaa tgcttaatca gtgaggcacc tatctcagcg   5940
atctgtctat ttcgttcatc catagttgcc tgactccccg tcgtgtagat aactacgata   6000
cgggagggct taccatctgg ccccagtgct gcaatgatac cgcgagaccc acgctcaccg   6060
gctccagatt tatcagcaat aaaccagcca gccggaaggg ccgagcgcag aagtggtcct   6120
gcaactttat ccgcctccat ccagtctatt aattgttgcc gggaagctag agtaagtagt   6180
tcgccagtta atagtttgcg caacgttgtt gccattgcta caggcatcgt ggtgtcacgc   6240
tcgtcgtttg gtatggcttc attcagctcc ggttcccaac gatcaaggcg agttacatga   6300
tcccccatgt tgtgcaaaaa agcggttagc tccttcggtc ctccgatcgt tgtcagaagt   6360
aagttggccg cagtgttatc actcatggtt atggcagcac tgcataattc tcttactgtc   6420
atgccatccg taagatgctt ttctgtgact ggtgagtact caaccaagtc attctgagaa   6480
tagtgtatgc ggcgaccgag ttgctcttgc ccggcgtcaa tacgggataa taccgcgcca   6540
```

-continued

```
catagcagaa ctttaaaagt gctcatcatt ggaaaacgtt cttcggggcg aaaactctca   6600

aggatcttac cgctgttgag atccagttcg atgtaaccca ctcgtgcacc caactgatct   6660

tcagcatctt ttactttcac cagcgtttct gggtgagcaa aaacaggaag gcaaaatgcc   6720

gcaaaaaagg gaataagggc gacacggaaa tgttgaatac tcatactctt cctttttcaa   6780

tattattgaa gcatttatca gggttattgt ctcatgagcg gatacatatt tgaatgtatt   6840

tagaaaaata aacaaatagg ggttccgcgc acatttcccc gaaaagtgcc acctgacgtc   6900
```

<210> SEQ ID NO 3
<211> LENGTH: 7038
<212> TYPE: DNA
<213> ORGANISM: Artificial Sequence
<220> FEATURE:
<220> FEATURE:
<223> OTHER INFORMATION: Description of Artificial Sequence: Construct 2C7LBDCS

<400> SEQUENCE: 3

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttagat ctatggccca ggcggccctc gagccctatg cttgccctgt    960

cgagtcctgc gatcgccgct tttctaagtc ggctgatctg aagcgccata tccgcatcca   1020

cacaggccag aagcctttcc agtgtcgaat atgcatgcgt aacttcagtc gtagtgacca   1080

ccttaccacc cacatccgca cccacacagg cgagaagcct tttgcctgtg acatttgtgg   1140

gaggaagttt gccaggagtg atgaacgcaa gaggcatacc aaaatccata ccggtgagaa   1200

gccctatgct tgccctgtcg agtcctgcga tcgccgcttt tctaagtcgg ctgatctgaa   1260

gcgccatatc cgcatccaca caggccagaa gcccttccag tgtcgaatat gcatgcgtaa   1320

cttcagtcgt agtgaccacc ttaccaccca catccgcacc cacacaggcg agaagccttt   1380

tgcctgtgac atttgtggga ggaagtttgc caggagtgat gaacgcaaga ggcataccaa   1440

aatccattta agacagaggg actctagaac tagtagtatt caaggacata acgactatat   1500

gtgtccagcc accaaccagt gcaccattga taaaaacagg aggaagagct gccaggcctg   1560

ccggctccgc aaatgctacg aagtgggaat gatgaaaggt gggatacgaa aagaccgaag   1620

aggagggaga atgttgaaac acaagcgcca gagagatgat ggggagggca ggggtgaagt   1680
```

-continued

```
ggggtctgct ggagacatga gagctgccaa cctttggcca agcccgctca tgatcaaacg   1740
ctctaagaag aacagcctgg ccttgtccct gacggccgac cagatggtca gtgccttgtt   1800
ggatgctgag ccccccatac tctattccga gtatgatcct accagaccct tcagtgaagc   1860
ttcgatgatg ggcttactga ccaacctggc agacagggag ctggttcaca tgatcaactg   1920
ggcgaagagg gtgccaggct ttgtggattt gaccctccat gatcaggtcc accttctaga   1980
atgtgcctgg ctagagatcc tgatgattgg tctcgtctgg cgctccatgg agcacccagg   2040
gaagctactg tttgctccta acttgctctt ggacaggaac cagggaaaat gtgtagaggg   2100
catggtggag atcttcgaca tgctgctggc tacatcatct cggttccgca tgatgaatct   2160
gcagggagag gagtttgtgt gcctcaaatc tattattttg cttaattctg gagtgtacac   2220
atttctgtcc agcaccctga agtctctgga agagaaggac catatccacc gagtcctgga   2280
caagatcaca gacactttga tccacctgat ggccaaggca ggcctgaccc tgcagcagca   2340
gcaccagcgg ctggcccagc tcctcctcat cctctcccac atcaggcaca tgagtaacaa   2400
aggcatggag catctgtaca gcatgaagtg caagaacgtg gtgcccctct atgacctgct   2460
gctggagatg ctggacgccc accgcctaca tgcgcccact agccgtacgc cggccgacgc   2520
cctggacgac ttcgacctgg acatgctgcc ggccgacgcc ctggacgact tcgacctgga   2580
catgctgccg gccgacgccc tggacgactt cgacctggac atgctgccgg ggtaactaag   2640
taagcggccg ctcgagtcta gagggcccgt ttaaacccgc tgatcagcct cgactgtgcc   2700
ttctagttgc cagccatctg ttgtttgccc ctcccccgtg ccttccttga ccctggaagg   2760
tgccactccc actgtccttt cctaataaaa tgaggaaatt gcatcgcatt gtctgagtag   2820
gtgtcattct attctggggg gtggggtggg gcaggacagc aagggggagg attgggaaga   2880
caatagcagg catgctgggg atgcggtggg ctctatggct tctgaggcgg aaagaaccag   2940
ctggggctct agggggtatc cccacgcgcc ctgtagcggc gcattaagcg cggcgggtgt   3000
ggtggttacg cgcagcgtga ccgctacact tgccagcgcc ctagcgcccg ctcctttcgc   3060
tttcttccct tcctttctcg ccacgttcgc cggctttccc cgtcaagctc taaatcgggg   3120
catcccttta gggttccgat ttagtgcttt acggcacctc gaccccaaaa aacttgatta   3180
gggtgatggt tcacgtagtg ggccatcgcc ctgatagacg gtttttcgcc ctttgacgtt   3240
ggagtccacg ttctttaata gtggactctt gttccaaact ggaacaacac tcaaccctat   3300
ctcggtctat tcttttgatt tataagggat tttggggatt tcggcctatt ggttaaaaaa   3360
tgagctgatt taacaaaaat ttaacgcgaa ttaattctgt ggaatgtgtg tcagttaggg   3420
tgtggaaagt ccccaggctc cccaggcagg cagaagtatg caaagcatgc atctcaatta   3480
gtcagcaacc aggtgtggaa agtccccagg ctccccagca ggcagaagta tgcaaagcat   3540
gcatctcaat tagtcagcaa ccatagtccc gcccctaact ccgcccatcc cgcccctaac   3600
tccgcccagt tccgcccatt ctccgcccca tggctgacta atttttttta tttatgcaga   3660
ggccgaggcc gcctctgcct ctgagctatt ccagaagtag tgaggaggct tttttggagg   3720
cctaggcttt tgcaaaaagc tcccgggagc ttgtatatcc attttcggat ctgatcaaga   3780
gacaggatga ggatcgtttc gcatgattga acaagatgga ttgcacgcag gttctccggc   3840
cgcttgggtg gagaggctat tcggctatga ctgggcacaa cagacaatcg gctgctctga   3900
tgccgccgtg ttccggctgt cagcgcaggg gcgcccggtt ctttttgtca agaccgacct   3960
gtccggtgcc ctgaatgaac tgcaggacga ggcagcgcgg ctatcgtggc tggccacgac   4020
```

-continued

```
gggcgttcct tgcgcagctg tgctcgacgt tgtcactgaa gcgggaaggg actggctgct   4080
attgggcgaa gtgccggggc aggatctcct gtcatctcac cttgctcctg ccgagaaagt   4140
atccatcatg gctgatgcaa tgcggcggct gcatacgctt gatccggcta cctgcccatt   4200
cgaccaccaa gcgaaacatc gcatcgagcg agcacgtact cggatggaag ccggtcttgt   4260
cgatcaggat gatctggacg aagagcatca ggggctcgcg ccagccgaac tgttcgccag   4320
gctcaaggcg cgcatgcccg acggcgagga tctcgtcgtg acccatggcg atgcctgctt   4380
gccgaatatc atggtggaaa atggccgctt ttctggattc atcgactgtg gccggctggg   4440
tgtggcggac cgctatcagg acatagcgtt ggctacccgt gatattgctg aagagcttgg   4500
cggcgaatgg gctgaccgct tcctcgtgct ttacggtatc gccgctcccg attcgcagcg   4560
catcgccttc tatcgccttc ttgacgagtt cttctgagcg ggactctggg gttcgaaatg   4620
accgaccaag cgacgcccaa cctgccatca cgagatttcg attccaccgc cgccttctat   4680
gaaaggttgg gcttcggaat cgttttccgg gacgccggct ggatgatcct ccagcgcggg   4740
gatctcatgc tggagttctt cgcccacccc aacttgttta ttgcagctta taatggttac   4800
aaataaagca atagcatcac aaatttcaca aataaagcat ttttttcact gcattctagt   4860
tgtggtttgt ccaaactcat caatgtatct tatcatgtct gtataccgtc gacctctagc   4920
tagagcttgg cgtaatcatg gtcatagctg tttcctgtgt gaaattgtta tccgctcaca   4980
attccacaca acatacgagc cggaagcata aagtgtaaag cctggggtgc ctaatgagtg   5040
agctaactca cattaattgc gttgcgctca ctgcccgctt tccagtcggg aaacctgtcg   5100
tgccagctgc attaatgaat cggccaacgc gcggggagag gcggtttgcg gcgagcggta   5160
tcagctcact caaaggcggt aatacggtta tccacagaat caggggataa cgcaggaaag   5220
aacatgtgag caaaaggcca gcaaaaggcc aggaaccgta aaaaggccgc gttgctggcg   5280
tttttccata ggctccgccc ccctgacgag catcacaaaa atcgacgctc aagtcagagg   5340
tggcgaaacc cgacaggact ataaagatac caggcgtttc cccctggaag ctccctcgtg   5400
cgctctcctg ttccgaccct gccgcttacc ggatacctgt ccgcctttct cccttcggga   5460
agcgtggcgc tttctcaatg ctcacgctgt aggtatctca gttcggtgta ggtcgttcgc   5520
tccaagctgg gctgtgtgca cgaacccccc gttcagcccg accgctgcgc cttatccggt   5580
aactatcgtc ttgagtccaa cccggtaaga cacgacttat cgccactggc agcagccact   5640
ggtaacagga ttagcagagc gaggtatgta ggcggtgcta cagagttctt gaagtggtgg   5700
cctaactacg gctacactag aaggacagta tttggtatct gcgctctgct gaagccagtt   5760
accttcggaa aaagagttgg tagctcttga tccggcaaac aaaccaccgc tggtagcggt   5820
ggtttttttg tttgcaagca gcagattacg cgcagaaaaa aaggatctca agaagatcct   5880
ttgatctttt ctacggggtc tgacgctcag tggaacgaaa actcacgtta agggattttg   5940
gtcatgagat tatcaaaaag gatcttcacc tagatccttt taaattaaaa atgaagtttt   6000
aaatcaatct aaagtatata tgagtaaact tggtctgaca gttaccaatg cttaatcagt   6060
gaggcaccta tctcagcgat ctgtctattt cgttcatcca tagttgcctg actccccgtc   6120
gtgtagataa ctacgatacg ggagggctta ccatctggcc ccagtgctgc aatgataccg   6180
cgagacccac gctcaccggc tccagattta tcagcaataa accagccagc cggaagggcc   6240
gagcgcagaa gtggtcctgc aactttatcc gcctccatcc agtctattaa ttgttgccgg   6300
gaagctagag taagtagttc gccagttaat agtttgcgca acgttgttgc cattgctaca   6360
ggcatcgtgg tgtcacgctc gtcgtttggt atggcttcat tcagctccgg ttcccaacga   6420
```

-continued

```
tcaaggcgag ttacatgatc ccccatgttg tgcaaaaaag cggttagctc cttcggtcct   6480

ccgatcgttg tcagaagtaa gttggccgca gtgttatcac tcatggttat ggcagcactg   6540

cataattctc ttactgtcat gccatccgta agatgctttt ctgtgactgg tgagtactca   6600

accaagtcat tctgagaata gtgtatgcgg cgaccgagtt gctcttgccc ggcgtcaata   6660

cgggataata ccgcgccaca tagcagaact ttaaaagtgc tcatcattgg aaaacgttct   6720

tcggggcgaa aactctcaag gatcttaccg ctgttgagat ccagttcgat gtaacccact   6780

cgtgcaccca actgatcttc agcatctttt actttcacca gcgtttctgg gtgagcaaaa   6840

acaggaaggc aaaatgccgc aaaaaaggga ataagggcga cacggaaatg ttgaatactc   6900

atactcttcc tttttcaata ttattgaagc atttatcagg gttattgtct catgagcgga   6960

tacatatttg aatgtattta gaaaaataaa caaatagggg ttccgcgcac atttccccga   7020

aaagtgccac ctgacgtc                                                 7038
```

<210> SEQ ID NO 4
<211> LENGTH: 1496
<212> TYPE: DNA
<213> ORGANISM: Artificial Sequence
<220> FEATURE:
<220> FEATURE:
<223> OTHER INFORMATION: Description of Artificial Sequence: Construct
C7PBDVP16

<400> SEQUENCE: 4

```
ggtaccggat ccgccaccat ggcccaggcg gccctcgagc cctatgcttg ccctgtcgag     60

tcctgcgatc gccgcttttc taagtcggct gatctgaagc gccatatccg catccacaca    120

ggccagaagc ccttccagtg tcgaatatgc atgcgtaact tcagtcgtag tgaccacctt    180

accacccaca tccgcaccca cacaggcgag aagccttttg cctgtgacat ttgtgggagg    240

aagtttgcca ggagtgatga acgcaagagg cataccaaaa tccatttaag acagaaggac    300

tctagaacta gtggccaggc cggccgcgtc gaccagaaaa agttcaataa agtcagagtt    360

gtgagagcac tggatgctgt tgctctccca cagccagtgg gcgttccaaa tgaaagccaa    420

gccctaagcc agagattcac tttttcacca ggtcaagaca tacagttgat tccaccactg    480

atcaacctgt taatgagcat tgaaccagat gtgatctatg caggacatga caacacaaaa    540

cctgacacct ccagttcttt gctgacaagt cttaatcaac taggcgagag gcaacttctt    600

tcagtagtca agtggtctaa atcattgcca ggttttcgaa acttacatat tgatgaccag    660

ataactctca ttcagtattc ttggatgagc ttaatggtgt ttggtctagg atggagatcc    720

tacaaacacg tcagtgggca gatgctgtat tttgcacctg atctaatact aaatgaacag    780

cggatgaaag aatcatcatt ctattcatta tgccttacca tgtggcagat cccacaggag    840

tttgtcaagc ttcaagttag ccaagaagag ttcctctgta tgaaagtatt gttacttctt    900

aatacaattc ctttggaagg gctacgaagt caaacccagt ttgaggagat gaggtcaagc    960

tacattagag agctcatcaa ggcaattggt ttgaggcaaa aaggagttgt gtcgagctca   1020

cagcgtttct atcaacttac aaaacttctt gataacttgc atgatcttgt caaacaactt   1080

catctgtact gcttgaatac atttatccag tcccgggcac tgagtgttga atttccagaa   1140

atgatgtctg aagttattgc tgggtcgacg gctagcccga aaaagaaacg caaagttggg   1200

cgcgccggcg ctcccccgac cgatgtcagc ctgggggacg agctccactt agacggcgag   1260

gacgtggcga tggcgcatgc cgacgcgcta gacgatttcg atctggacat gttgggggac   1320
```

-continued ggggattccc cgggtccggg atttaccccc cacgactccg ccccctacgg cgctctggat 1380
atggccgact tcgagtttga gcagatgttt accgatgccc ttggaattga cgagtacggt 1440
ttaattaact acccgtacga cgttccggac tacgcttctt gagaattcgc ggccgc 1496

<210> SEQ ID NO 5
<211> LENGTH: 6746
<212> TYPE: DNA
<213> ORGANISM: Artificial Sequence
<220> FEATURE:
<220> FEATURE:
<223> OTHER INFORMATION: Description of Artificial Sequence: Construct C7LBDAL

<400> SEQUENCE: 5
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cagcccgggg gatctatggc ccaggcggcc ctcgagccct atgcttgccc tgtcgagtcc 1020
tgcgatcgcc gcttttctaa gtcggctgat ctgaagcgcc atatccgcat ccacacaggc 1080
cagaagcctt tccagtgtcg aatatgcatg cgtaacttca gtcgtagtga ccaccttacc 1140
acccacatcc gcacccacac aggcgagaag cctttgcct gtgacatttg tgggaggaag 1200
tttgccagga gtgatgaacg caagaggcat accaaaatcc atttaagaca gagggactct 1260
agaactagtt ctgctggaga catgagagct gccaaccttt ggccaagccc gctcatgatc 1320
aaacgctcta agaagaacag cctggccttg tccctgacgg ccgaccagat ggtcagtgcc 1380
ttgttggatg ctgagccccc catactctat tccgagtatg atcctaccag acccttcagt 1440
gaagcttcga tgatgggctt actgaccaac ctggcagaca gggagctggt tcacatgatc 1500
aactgggcga agagggtgcc aggctttgtg gatttgaccc tccatgatca ggtccacctt 1560
ctagaatgtg cctggctaga gatcctgatg attggtctcg tctggcgctc catggagcac 1620
ccagggaagc tactgtttgc tcctaacttg ctcttggaca ggaaccaggg aaaatgtgta 1680
gagggcatgg tggagatctt cgacatgctg ctggctacat catctcggtt ccgcatgatg 1740
aatctgcagg gagaggagtt tgtgtgcctc aaatctatta ttttgcttaa ttctggagtg 1800
tacacatttc tgtccagcac cctgaagtct ctggaagaga aggaccatat ccaccgagtc 1860

-continued

```
ctggacaaga tcacagacac tttgatccac ctgatggcca aggcaggcct gaccctgcag   1920
cagcagcacc agcggctggc ccagctcctc ctcatcctct cccacatcag gcacatgagt   1980
aacaaaggca tggagcatct gtacagcatg aagtgcaaga acgtggtgcc cctctatgac   2040
ctgctgctgg agatgctgga cgcccaccgc ctacatgcgc ccactagccg tggaggggca   2100
tccgtggagg agacggacca aagccacttg gccactgcgg gctctacttc atcgcattcc   2160
ttgcaaaagt attacatcac gggggaggca gagggtttcc ctgccacagt ccgtacgccg   2220
gccgacgccc tggacgactt cgacctggac atgctgccgg ccgacgccct ggacgacttc   2280
gacctggaca tgctgccggc cgacgccctg gacgacttcg acctggacat gctgccgggg   2340
taactaagta agcggccgct cgagtctaga gggcccgttt aaacccgctg atcagcctcg   2400
actgtgcctt ctagttgcca gccatctgtt gtttgcccct cccccgtgcc ttccttgacc   2460
ctggaaggtg ccactcccac tgtcctttcc taataaaatg aggaaattgc atcgcattgt   2520
ctgagtaggt gtcattctat tctggggggt ggggtggggc aggacagcaa gggggaggat   2580
tgggaagaca atagcaggca tgctggggat gcggtgggct ctatggcttc tgaggcggaa   2640
agaaccagct ggggctctag ggggtatccc cacgcgccct gtagcggcgc attaagcgcg   2700
gcgggtgtgg tggttacgcg cagcgtgacc gctacacttg ccagcgccct agcgcccgct   2760
cctttcgctt tcttcccttc ctttctcgcc acgttcgccg gctttccccg tcaagctcta   2820
aatcggggca tccctttagg gttccgattt agtgctttac ggcacctcga ccccaaaaaa   2880
cttgattagg gtgatggttc acgtagtggg ccatcgccct gatagacggt ttttcgccct   2940
ttgacgttgg agtccacgtt ctttaatagt ggactcttgt tccaaactgg aacaacactc   3000
aaccctatct cggtctattc ttttgattta taagggattt tggggatttc ggcctattgg   3060
ttaaaaaatg agctgattta acaaaaattt aacgcgaatt aattctgtgg aatgtgtgtc   3120
agttagggtg tggaaagtcc ccaggctccc caggcaggca gaagtatgca aagcatgcat   3180
ctcaattagt cagcaaccag gtgtggaaag tccccaggct ccccagcagg cagaagtatg   3240
caaagcatgc atctcaatta gtcagcaacc atagtcccgc ccctaactcc gcccatcccg   3300
cccctaactc cgcccagttc cgcccattct ccgccccatg gctgactaat tttttttatt   3360
tatgcagagg ccgaggccgc ctctgcctct gagctattcc agaagtagtg aggaggcttt   3420
tttggaggcc taggcttttg caaaaagctc ccgggagctt gtatatccat tttcggatct   3480
gatcaagaga caggatgagg atcgtttcgc atgattgaac aagatggatt gcacgcaggt   3540
tctccggccg cttgggtgga gaggctattc ggctatgact gggcacaaca gacaatcggc   3600
tgctctgatg ccgccgtgtt ccggctgtca gcgcaggggc gcccggttct ttttgtcaag   3660
accgacctgt ccggtgccct gaatgaactg caggacgagg cagcgcggct atcgtggctg   3720
gccacgacgg gcgttccttg cgcagctgtg ctcgacgttg tcactgaagc gggaagggac   3780
tggctgctat tgggcgaagt gccggggcag gatctcctgt catctcacct tgctcctgcc   3840
gagaaagtat ccatcatggc tgatgcaatg cggcggctgc atacgcttga tccggctacc   3900
tgcccattcg accaccaagc gaaacatcgc atcgagcgag cacgtactcg gatggaagcc   3960
ggtcttgtcg atcaggatga tctggacgaa gagcatcagg ggctcgcgcc agccgaactg   4020
ttcgccaggc tcaaggcgcg catgcccgac ggcgaggatc tcgtcgtgac ccatggcgat   4080
gcctgcttgc cgaatatcat ggtggaaaat ggccgctttt ctggattcat cgactgtggc   4140
cggctgggtg tggcggaccg ctatcaggac atagcgttgg ctacccgtga tattgctgaa   4200
```

-continued

```
gagcttggcg gcgaatgggc tgaccgcttc ctcgtgcttt acggtatcgc cgctcccgat   4260

tcgcagcgca tcgccttcta tcgccttctt gacgagttct tctgagcggg actctggggt   4320

tcgaaatgac cgaccaagcg acgcccaacc tgccatcacg agatttcgat tccaccgccg   4380

ccttctatga aaggttgggc ttcggaatcg ttttccggga cgccggctgg atgatcctcc   4440

agcgcgggga tctcatgctg gagttcttcg cccaccccaa cttgtttatt gcagcttata   4500

atggttacaa ataaagcaat agcatcacaa atttcacaaa taaagcattt ttttcactgc   4560

attctagttg tggtttgtcc aaactcatca atgtatctta tcatgtctgt ataccgtcga   4620

cctctagcta gagcttggcg taatcatggt catagctgtt tcctgtgtga aattgttatc   4680

cgctcacaat tccacacaac atacgagccg gaagcataaa gtgtaaagcc tggggtgcct   4740

aatgagtgag ctaactcaca ttaattgcgt tgcgctcact gcccgctttc cagtcgggaa   4800

acctgtcgtg ccagctgcat taatgaatcg gccaacgcgc ggggagaggc ggtttgcggc   4860

gagcggtatc agctcactca aaggcggtaa tacggttatc cacagaatca ggggataacg   4920

caggaaagaa catgtgagca aaaggccagc aaaaggccag gaaccgtaaa aaggccgcgt   4980

tgctggcgtt tttccatagg ctccgccccc ctgacgagca tcacaaaaat cgacgctcaa   5040

gtcagaggtg gcgaaacccg acaggactat aaagatacca ggcgtttccc cctggaagct   5100

ccctcgtgcg ctctcctgtt ccgaccctgc cgcttaccgg atacctgtcc gcctttctcc   5160

cttcgggaag cgtggcgctt tctcaatgct cacgctgtag gtatctcagt tcggtgtagg   5220

tcgttcgctc caagctgggc tgtgtgcacg aaccccccgt tcagcccgac cgctgcgcct   5280

tatccggtaa ctatcgtctt gagtccaacc cggtaagaca cgacttatcg ccactggcag   5340

cagccactgg taacaggatt agcagagcga ggtatgtagg cggtgctaca gagttcttga   5400

agtggtggcc taactacggc tacactagaa ggacagtatt tggtatctgc gctctgctga   5460

agccagttac cttcggaaaa agagttggta gctcttgatc cggcaaacaa accaccgctg   5520

gtagcggtgg tttttttgtt tgcaagcagc agattacgcg cagaaaaaaa ggatctcaag   5580

aagatccttt gatcttttct acggggtctg acgctcagtg gaacgaaaac tcacgttaag   5640

ggattttggt catgagatta tcaaaaagga tcttcaccta gatcctttta aattaaaaat   5700

gaagttttaa atcaatctaa agtatatatg agtaaacttg gtctgacagt taccaatgct   5760

taatcagtga ggcacctatc tcagcgatct gtctatttcg ttcatccata gttgcctgac   5820

tccccgtcgt gtagataact acgatacggg agggcttacc atctggcccc agtgctgcaa   5880

tgataccgcg agacccacgc tcaccggctc cagatttatc agcaataaac cagccagccg   5940

gaagggccga gcgcagaagt ggtcctgcaa ctttatccgc ctccatccag tctattaatt   6000

gttgccggga agctagagta agtagttcgc cagttaatag tttgcgcaac gttgttgcca   6060

ttgctacagg catcgtggtg tcacgctcgt cgtttggtat ggcttcattc agctccggtt   6120

cccaacgatc aaggcgagtt acatgatccc ccatgttgtg caaaaaagcg gttagctcct   6180

tcggtcctcc gatcgttgtc agaagtaagt tggccgcagt gttatcactc atggttatgg   6240

cagcactgca taattctctt actgtcatgc catccgtaag atgcttttct gtgactggtg   6300

agtactcaac caagtcattc tgagaatagt gtatgcggcg accgagttgc tcttgcccgg   6360

cgtcaatacg ggataatacc gcgccacata gcagaacttt aaaagtgctc atcattggaa   6420

aacgttcttc ggggcgaaaa ctctcaagga tcttaccgct gttgagatcc agttcgatgt   6480

aacccactcg tgcacccaac tgatcttcag catcttttac tttcaccagc gtttctgggt   6540

gagcaaaaac aggaaggcaa aatgccgcaa aaaagggaat aagggcgaca cggaaatgtt   6600
```

```
gaatactcat actcttcctt tttcaatatt attgaagcat ttatcagggt tattgtctca   6660

tgagcggata catatttgaa tgtatttaga aaaataaaca aataggggtt ccgcgcacat   6720

ttccccgaaa agtgccacct gacgtc                                        6746


<210> SEQ ID NO 6
<211> LENGTH: 6623
<212> TYPE: DNA
<213> ORGANISM: Artificial Sequence
<220> FEATURE:
<220> FEATURE:
<223> OTHER INFORMATION: Description of Artificial Sequence: Construct
      C7LBDAS

<400> SEQUENCE: 6

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattcctg    960

cagcccgggg gatctatggc ccaggcggcc ctcgagccct atgcttgccc tgtcgagtcc   1020

tgcgatcgcc gcttttctaa gtcggctgat ctgaagcgcc atatccgcat ccacacaggc   1080

cagaagcctt tccagtgtcg aatatgcatg cgtaacttca gtcgtagtga ccaccttacc   1140

acccacatcc gcacccacac aggcgagaag ccttttgcct gtgacatttg tgggaggaag   1200

tttgccagga gtgatgaacg caagaggcat accaaaatcc atttaagaca gagggactct   1260

agaactagtt ctgctggaga catgagagct gccaaccttt ggccaagccc gctcatgatc   1320

aaacgctcta agaagaacag cctggccttg tccctgacgg ccgaccagat ggtcagtgcc   1380

ttgttggatg ctgagccccc catactctat tccgagtatg atcctaccag acccttcagt   1440

gaagcttcga tgatgggctt actgaccaac ctggcagaca gggagctggt tcacatgatc   1500

aactgggcga agagggtgcc aggctttgtg gatttgaccc tccatgatca ggtccacctt   1560

ctagaatgtg cctggctaga gatcctgatg attggtctcg tctggcgctc catggagcac   1620

ccagggaagc tactgtttgc tcctaacttg ctcttggaca ggaaccaggg aaaatgtgta   1680

gagggcatgg tggagatctt cgacatgctg ctggctacat catctcggtt ccgcatgatg   1740

aatctgcagg gagaggagtt tgtgtgcctc aaatctatta ttttgcttaa ttctggagtg   1800
```

-continued

```
tacacatttc tgtccagcac cctgaagtct ctggaagaga aggaccatat ccaccgagtc   1860
ctggacaaga tcacagacac tttgatccac ctgatggcca aggcaggcct gaccctgcag   1920
cagcagcacc agcggctggc ccagctcctc ctcatcctct cccacatcag gcacatgagt   1980
aacaaaggca tggagcatct gtacagcatg aagtgcaaga acgtggtgcc cctctatgac   2040
ctgctgctgg agatgctgga cgcccaccgc ctacatgcgc ccactagccg tacgccggcc   2100
gacgccctgg acgacttcga cctggacatg ctgccggccg acgccctgga cgacttcgac   2160
ctggacatgc tgccggccga cgccctggac gacttcgacc tggacatgct gccggggtaa   2220
ctaagtaagc ggccgctcga gtctagaggg cccgtttaaa cccgctgatc agcctcgact   2280
gtgccttcta gttgccagcc atctgttgtt tgcccctccc ccgtgccttc cttgaccctg   2340
gaaggtgcca ctcccactgt cctttcctaa taaaatgagg aaattgcatc gcattgtctg   2400
agtaggtgtc attctattct ggggggtggg gtggggcagg acagcaaggg ggaggattgg   2460
gaagacaata gcaggcatgc tggggatgcg gtgggctcta tggcttctga ggcggaaaga   2520
accagctggg gctctagggg gtatccccac gcgccctgta gcggcgcatt aagcgcggcg   2580
ggtgtggtgg ttacgcgcag cgtgaccgct acacttgcca gcgccctagc gcccgctcct   2640
ttcgctttct tcccttcctt tctcgccacg ttcgccggct ttccccgtca agctctaaat   2700
cggggcatcc ctttagggtt ccgatttagt gctttacggc acctcgaccc caaaaaactt   2760
gattagggtg atggttcacg tagtgggcca tcgccctgat agacggtttt tcgccctttg   2820
acgttggagt ccacgttctt taatagtgga ctcttgttcc aaactggaac aacactcaac   2880
cctatctcgg tctattcttt tgatttataa gggattttgg ggatttcggc ctattggtta   2940
aaaaatgagc tgatttaaca aaaatttaac gcgaattaat tctgtggaat gtgtgtcagt   3000
tagggtgtgg aaagtcccca ggctccccag gcaggcagaa gtatgcaaag catgcatctc   3060
aattagtcag caaccaggtg tggaaagtcc ccaggctccc cagcaggcag aagtatgcaa   3120
agcatgcatc tcaattagtc agcaaccata gtcccgcccc taactccgcc catcccgccc   3180
ctaactccgc ccagttccgc ccattctccg ccccatggct gactaatttt ttttatttat   3240
gcagaggccg aggccgcctc tgcctctgag ctattccaga agtagtgagg aggctttttt   3300
ggaggcctag gcttttgcaa aaagctcccg ggagcttgta tatccatttt cggatctgat   3360
caagagacag gatgaggatc gtttcgcatg attgaacaag atggattgca cgcaggttct   3420
ccggccgctt gggtggagag gctattcggc tatgactggg cacaacagac aatcggctgc   3480
tctgatgccg ccgtgttccg gctgtcagcg caggggcgcc cggttctttt tgtcaagacc   3540
gacctgtccg gtgccctgaa tgaactgcag gacgaggcag cgcggctatc gtggctggcc   3600
acgacgggcg ttccttgcgc agctgtgctc gacgttgtca ctgaagcggg aagggactgg   3660
ctgctattgg gcgaagtgcc ggggcaggat ctcctgtcat ctcaccttgc tcctgccgag   3720
aaagtatcca tcatggctga tgcaatgcgg cggctgcata cgcttgatcc ggctacctgc   3780
ccattcgacc accaagcgaa acatcgcatc gagcgagcac gtactcggat ggaagccggt   3840
cttgtcgatc aggatgatct ggacgaagag catcaggggc tcgcgccagc cgaactgttc   3900
gccaggctca aggcgcgcat gcccgacggc gaggatctcg tcgtgaccca tggcgatgcc   3960
tgcttgccga atatcatggt ggaaaatggc cgcttttctg gattcatcga ctgtggccgg   4020
ctgggtgtgg cggaccgcta tcaggacata gcgttggcta cccgtgatat tgctgaagag   4080
cttggcggcg aatgggctga ccgcttcctc gtgctttacg gtatcgccgc tcccgattcg   4140
cagcgcatcg ccttctatcg ccttcttgac gagttcttct gagcgggact ctggggttcg   4200
```

-continued

```
aaatgaccga ccaagcgacg cccaacctgc catcacgaga tttcgattcc accgccgcct   4260
tctatgaaag gttgggcttc ggaatcgttt tccgggacgc cggctggatg atcctccagc   4320
gcggggatct catgctggag ttcttcgccc accccaactt gtttattgca gcttataatg   4380
gttacaaata aagcaatagc atcacaaatt tcacaaataa agcatttttt tcactgcatt   4440
ctagttgtgg tttgtccaaa ctcatcaatg tatcttatca tgtctgtata ccgtcgacct   4500
ctagctagag cttggcgtaa tcatggtcat agctgtttcc tgtgtgaaat tgttatccgc   4560
tcacaattcc acacaacata cgagccggaa gcataaagtg taaagcctgg ggtgcctaat   4620
gagtgagcta actcacatta attgcgttgc gctcactgcc cgctttccag tcgggaaacc   4680
tgtcgtgcca gctgcattaa tgaatcggcc aacgcgcggg gagaggcggt ttgcggcgag   4740
cggtatcagc tcactcaaag gcggtaatac ggttatccac agaatcaggg gataacgcag   4800
gaaagaacat gtgagcaaaa ggccagcaaa aggccaggaa ccgtaaaaag gccgcgttgc   4860
tggcgttttt ccataggctc cgcccccctg acgagcatca caaaaatcga cgctcaagtc   4920
agaggtggcg aaacccgaca ggactataaa gataccaggc gtttccccct ggaagctccc   4980
tcgtgcgctc tcctgttccg accctgccgc ttaccggata cctgtccgcc tttctccctt   5040
cgggaagcgt ggcgctttct caatgctcac gctgtaggta tctcagttcg gtgtaggtcg   5100
ttcgctccaa gctgggctgt gtgcacgaac cccccgttca gcccgaccgc tgcgccttat   5160
ccggtaacta tcgtcttgag tccaacccgg taagacacga cttatcgcca ctggcagcag   5220
ccactggtaa caggattagc agagcgaggt atgtaggcgg tgctacagag ttcttgaagt   5280
ggtggcctaa ctacggctac actagaagga cagtatttgg tatctgcgct ctgctgaagc   5340
cagttacctt cggaaaaaga gttggtagct cttgatccgg caaacaaacc accgctggta   5400
gcggtggttt ttttgtttgc aagcagcaga ttacgcgcag aaaaaaagga tctcaagaag   5460
atcctttgat cttttctacg gggtctgacg ctcagtggaa cgaaaactca cgttaaggga   5520
ttttggtcat gagattatca aaaaggatct tcacctagat ccttttaaat taaaaatgaa   5580
gttttaaatc aatctaaagt atatatgagt aaacttggtc tgacagttac caatgcttaa   5640
tcagtgaggc acctatctca gcgatctgtc tatttcgttc atccatagtt gcctgactcc   5700
ccgtcgtgta gataactacg atacgggagg gcttaccatc tggccccagt gctgcaatga   5760
taccgcgaga cccacgctca ccggctccag atttatcagc aataaaccag ccagccggaa   5820
gggccgagcg cagaagtggt cctgcaactt tatccgcctc catccagtct attaattgtt   5880
gccgggaagc tagagtaagt agttcgccag ttaatagttt gcgcaacgtt gttgccattg   5940
ctacaggcat cgtggtgtca cgctcgtcgt ttggtatggc ttcattcagc tccggttccc   6000
aacgatcaag gcgagttaca tgatccccca tgttgtgcaa aaaagcggtt agctccttcg   6060
gtcctccgat cgttgtcaga agtaagttgg ccgcagtgtt atcactcatg gttatggcag   6120
cactgcataa ttctcttact gtcatgccat ccgtaagatg cttttctgtg actggtgagt   6180
actcaaccaa gtcattctga gaatagtgta tgcggcgacc gagttgctct tgcccggcgt   6240
caatacggga taataccgcg ccacatagca gaactttaaa agtgctcatc attggaaaac   6300
gttcttcggg gcgaaaactc tcaaggatct taccgctgtt gagatccagt tcgatgtaac   6360
ccactcgtgc acccaactga tcttcagcat cttttacttt caccagcgtt tctgggtgag   6420
caaaaacagg aaggcaaaat gccgcaaaaa agggaataag ggcgacacgg aaatgttgaa   6480
tactcatact cttccttttt caatattatt gaagcattta tcagggttat tgtctcatga   6540
```

-continued gcggatacat atttgaatgt atttagaaaa ataaacaaat aggggttccg cgcacatttc 6600
cccgaaaagt gccacctgac gtc 6623

<210> SEQ ID NO 7
<211> LENGTH: 6818
<212> TYPE: DNA
<213> ORGANISM: Artificial Sequence
<220> FEATURE:
<220> FEATURE:
<223> OTHER INFORMATION: Description of Artificial Sequence: Construct
C7LBDBL

<400> SEQUENCE: 7
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cagcccgggg gatctatggc ccaggcggcc ctcgagccct atgcttgccc tgtcgagtcc 1020
tgcgatcgcc gcttttctaa gtcggctgat ctgaagcgcc atatccgcat ccacacaggc 1080
cagaagcctt tccagtgtcg aatatgcatg cgtaacttca gtcgtagtga ccaccttacc 1140
acccacatcc gcacccacac aggcgagaag cctttttgcct gtgacatttg tgggaggaag 1200
tttgccagga gtgatgaacg caagaggcat accaaaatcc atttaagaca gagggactct 1260
agaactagtg accgaagagg agggagaatg ttgaaacaca agcgccagag agatgatggg 1320
gagggcaggg gtgaagtggg gtctgctgga gacatgagag ctgccaacct ttggccaagc 1380
ccgctcatga tcaaacgctc taagaagaac agcctggcct tgtccctgac ggccgaccag 1440
atggtcagtg ccttgttgga tgctgagccc cccatactct attccgagta tgatcctacc 1500
agacccttca gtgaagcttc gatgatgggc ttactgacca acctggcaga cagggagctg 1560
gttcacatga tcaactgggc gaagagggtg ccaggctttg tggatttgac cctccatgat 1620
caggtccacc ttctagaatg tgcctggcta gagatcctga tgattggtct cgtctggcgc 1680
tccatggagc acccagggaa gctactgttt gctcctaact tgctcttgga caggaaccag 1740
ggaaaatgtg tagagggcat ggtggagatc ttcgacatgc tgctggctac atcatctcgg 1800
ttccgcatga tgaatctgca gggagaggag tttgtgtgcc tcaaatctat tattttgctt 1860
aattctggag tgtacacatt tctgtccagc accctgaagt ctctggaaga gaaggaccat 1920

-continued

```
atccaccgag tcctggacaa gatcacagac actttgatcc acctgatggc caaggcaggc   1980
ctgaccctgc agcagcagca ccagcggctg gcccagctcc tcctcatcct ctcccacatc   2040
aggcacatga gtaacaaagg catggagcat ctgtacagca tgaagtgcaa gaacgtggtg   2100
cccctctatg acctgctgct ggagatgctg gacgcccacc gcctacatgc gcccactagc   2160
cgtggagggg catccgtgga ggagacggac caaagccact tggccactgc gggctctact   2220
tcatcgcatt ccttgcaaaa gtattacatc acgggggagg cagagggttt ccctgccaca   2280
gtccgtacgc cggccgacgc cctggacgac ttcgacctgg acatgctgcc ggccgacgcc   2340
ctggacgact tcgacctgga catgctgccg gccgacgccc tggacgactt cgacctggac   2400
atgctgccgg ggtaactaag taagcggccg ctcgagtcta gagggcccgt ttaaacccgc   2460
tgatcagcct cgactgtgcc ttctagttgc cagccatctg ttgtttgccc ctcccccgtg   2520
ccttccttga ccctggaagg tgccactccc actgtccttt cctaataaaa tgaggaaatt   2580
gcatcgcatt gtctgagtag gtgtcattct attctggggg gtggggtggg gcaggacagc   2640
aagggggagg attgggaaga caatagcagg catgctgggg atgcggtggg ctctatggct   2700
tctgaggcgg aaagaaccag ctggggctct agggggtatc cccacgcgcc ctgtagcggc   2760
gcattaagcg cggcgggtgt ggtggttacg cgcagcgtga ccgctacact tgccagcgcc   2820
ctagcgcccg ctcctttcgc tttcttccct tcctttctcg ccacgttcgc cggctttccc   2880
cgtcaagctc taaatcgggg catcccttta gggttccgat ttagtgcttt acggcacctc   2940
gaccccaaaa aacttgatta gggtgatggt tcacgtagtg ggccatcgcc ctgatagacg   3000
gtttttcgcc ctttgacgtt ggagtccacg ttctttaata gtggactctt gttccaaact   3060
ggaacaacac tcaaccctat ctcggtctat tcttttgatt tataagggat tttggggatt   3120
tcggcctatt ggttaaaaaa tgagctgatt taacaaaaat ttaacgcgaa ttaattctgt   3180
ggaatgtgtg tcagttaggg tgtggaaagt ccccaggctc cccaggcagg cagaagtatg   3240
caaagcatgc atctcaatta gtcagcaacc aggtgtggaa agtccccagg ctccccagca   3300
ggcagaagta tgcaaagcat gcatctcaat tagtcagcaa ccatagtccc gcccctaact   3360
ccgcccatcc cgcccctaac tccgcccagt tccgcccatt ctccgcccca tggctgacta   3420
atttttttta tttatgcaga ggccgaggcc gcctctgcct ctgagctatt ccagaagtag   3480
tgaggaggct tttttggagg cctaggcttt tgcaaaaagc tcccgggagc ttgtatatcc   3540
attttcggat ctgatcaaga gacaggatga ggatcgtttc gcatgattga acaagatgga   3600
ttgcacgcag gttctccggc cgcttgggtg gagaggctat tcggctatga ctgggcacaa   3660
cagacaatcg gctgctctga tgccgccgtg ttccggctgt cagcgcaggg gcgcccggtt   3720
ctttttgtca agaccgacct gtccggtgcc ctgaatgaac tgcaggacga ggcagcgcgg   3780
ctatcgtggc tggccacgac gggcgttcct tgcgcagctg tgctcgacgt tgtcactgaa   3840
gcgggaaggg actggctgct attgggcgaa gtgccggggc aggatctcct gtcatctcac   3900
cttgctcctg ccgagaaagt atccatcatg gctgatgcaa tgcggcggct gcatacgctt   3960
gatccggcta cctgcccatt cgaccaccaa gcgaaacatc gcatcgagcg agcacgtact   4020
cggatggaag ccggtcttgt cgatcaggat gatctggacg aagagcatca ggggctcgcg   4080
ccagccgaac tgttcgccag gctcaaggcg cgcatgcccg acggcgagga tctcgtcgtg   4140
acccatggcg atgcctgctt gccgaatatc atggtggaaa atggccgctt ttctggattc   4200
atcgactgtg gccggctggg tgtggcggac cgctatcagg acatagcgtt ggctacccgt   4260
```

-continued

```
gatattgctg aagagcttgg cggcgaatgg gctgaccgct tcctcgtgct ttacggtatc   4320
gccgctcccg attcgcagcg catcgccttc tatcgccttc ttgacgagtt cttctgagcg   4380
ggactctggg gttcgaaatg accgaccaag cgacgcccaa cctgccatca cgagatttcg   4440
attccaccgc cgccttctat gaaaggttgg gcttcggaat cgttttccgg gacgccggct   4500
ggatgatcct ccagcgcggg gatctcatgc tggagttctt cgcccacccc aacttgttta   4560
ttgcagctta taatggttac aaataaagca atagcatcac aaatttcaca aataaagcat   4620
ttttttcact gcattctagt tgtggtttgt ccaaactcat caatgtatct tatcatgtct   4680
gtataccgtc gacctctagc tagagcttgg cgtaatcatg gtcatagctg tttcctgtgt   4740
gaaattgtta tccgctcaca attccacaca acatacgagc cggaagcata aagtgtaaag   4800
cctggggtgc ctaatgagtg agctaactca cattaattgc gttgcgctca ctgcccgctt   4860
tccagtcggg aaacctgtcg tgccagctgc attaatgaat cggccaacgc gcggggagag   4920
gcggtttgcg gcgagcggta tcagctcact caaaggcggt aatacggtta tccacagaat   4980
caggggataa cgcaggaaag aacatgtgag caaaaggcca gcaaaaggcc aggaaccgta   5040
aaaaggccgc gttgctggcg tttttccata ggctccgccc ccctgacgag catcacaaaa   5100
atcgacgctc aagtcagagg tggcgaaacc cgacaggact ataaagatac caggcgtttc   5160
cccctggaag ctccctcgtg cgctctcctg ttccgaccct gccgcttacc ggatacctgt   5220
ccgcctttct cccttcggga agcgtggcgc tttctcaatg ctcacgctgt aggtatctca   5280
gttcggtgta ggtcgttcgc tccaagctgg gctgtgtgca cgaacccccc gttcagcccg   5340
accgctgcgc cttatccggt aactatcgtc ttgagtccaa cccggtaaga cacgacttat   5400
cgccactggc agcagccact ggtaacagga ttagcagagc gaggtatgta ggcggtgcta   5460
cagagttctt gaagtggtgg cctaactacg gctacactag aaggacagta tttggtatct   5520
gcgctctgct gaagccagtt accttcggaa aaagagttgg tagctcttga tccggcaaac   5580
aaaccaccgc tggtagcggt ggtttttttg tttgcaagca gcagattacg cgcagaaaaa   5640
aaggatctca agaagatcct ttgatctttt ctacggggtc tgacgctcag tggaacgaaa   5700
actcacgtta agggattttg gtcatgagat tatcaaaaag gatcttcacc tagatccttt   5760
taaattaaaa atgaagtttt aaatcaatct aaagtatata tgagtaaact tggtctgaca   5820
gttaccaatg cttaatcagt gaggcaccta tctcagcgat ctgtctattt cgttcatcca   5880
tagttgcctg actccccgtc gtgtagataa ctacgatacg ggagggctta ccatctggcc   5940
ccagtgctgc aatgataccg cgagacccac gctcaccggc tccagattta tcagcaataa   6000
accagccagc cggaagggcc gagcgcagaa gtggtcctgc aactttatcc gcctccatcc   6060
agtctattaa ttgttgccgg gaagctagag taagtagttc gccagttaat agtttgcgca   6120
acgttgttgc cattgctaca ggcatcgtgg tgtcacgctc gtcgtttggt atggcttcat   6180
tcagctccgg ttcccaacga tcaaggcgag ttacatgatc ccccatgttg tgcaaaaaag   6240
cggttagctc cttcggtcct ccgatcgttg tcagaagtaa gttggccgca gtgttatcac   6300
tcatggttat ggcagcactg cataattctc ttactgtcat gccatccgta agatgctttt   6360
ctgtgactgg tgagtactca accaagtcat tctgagaata gtgtatgcgg cgaccgagtt   6420
gctcttgccc ggcgtcaata cgggataata ccgcgccaca tagcagaact ttaaaagtgc   6480
tcatcattgg aaaacgttct tcggggcgaa aactctcaag gatcttaccg ctgttgagat   6540
ccagttcgat gtaacccact cgtgcaccca actgatcttc agcatctttt actttcacca   6600
gcgtttctgg gtgagcaaaa acaggaaggc aaaatgccgc aaaaaaggga ataagggcga   6660
```

-continued

```
cacggaaatg ttgaatactc atactcttcc tttttcaata ttattgaagc atttatcagg   6720

gttattgtct catgagcgga tacatatttg aatgtattta gaaaaataaa caaatagggg   6780

ttccgcgcac atttccccga aaagtgccac ctgacgtc                           6818


<210> SEQ ID NO 8
<211> LENGTH: 6695
<212> TYPE: DNA
<213> ORGANISM: Artificial Sequence
<220> FEATURE:
<220> FEATURE:
<223> OTHER INFORMATION: Description of Artificial Sequence: Construct
      C7LBDBS

<400> SEQUENCE: 8

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattcctg    960

cagcccgggg gatctatggc ccaggcggcc ctcgagccct atgcttgccc tgtcgagtcc   1020

tgcgatcgcc gcttttctaa gtcggctgat ctgaagcgcc atatccgcat ccacacaggc   1080

cagaagcctt tccagtgtcg aatatgcatg cgtaacttca gtcgtagtga ccaccttacc   1140

acccacatcc gcacccacac aggcgagaag ccttttgcct gtgacatttg tgggaggaag   1200

tttgccagga gtgatgaacg caagaggcat accaaaatcc atttaagaca gagggactct   1260

agaactagtg accgaagagg agggagaatg ttgaaacaca agcgccagag agatgatggg   1320

gagggcaggg gtgaagtggg gtctgctgga gacatgagag ctgccaacct ttggccaagc   1380

ccgctcatga tcaaacgctc taagaagaac agcctggcct tgtccctgac ggccgaccag   1440

atggtcagtg ccttgttgga tgctgagccc cccatactct attccgagta tgatcctacc   1500

agacccttca gtgaagcttc gatgatgggc ttactgacca acctggcaga cagggagctg   1560

gttcacatga tcaactgggc gaagagggtg ccaggctttg tggatttgac cctccatgat   1620

caggtccacc ttctagaatg tgcctggcta gagatcctga tgattggtct cgtctggcgc   1680

tccatggagc acccagggaa gctactgttt gctcctaact tgctcttgga caggaaccag   1740

ggaaaatgtg tagagggcat ggtggagatc ttcgacatgc tgctggctac atcatctcgg   1800
```

-continued

```
ttccgcatga tgaatctgca gggagaggag tttgtgtgcc tcaaatctat tattttgctt   1860
aattctggag tgtacacatt tctgtccagc accctgaagt ctctggaaga gaaggaccat   1920
atccaccgag tcctggacaa gatcacagac actttgatcc acctgatggc caaggcaggc   1980
ctgaccctgc agcagcagca ccagcggctg gcccagctcc tcctcatcct ctcccacatc   2040
aggcacatga gtaacaaagg catggagcat ctgtacagca tgaagtgcaa gaacgtggtg   2100
cccctctatg acctgctgct ggagatgctg gacgcccacc gcctacatgc gcccactagc   2160
cgtacgccgg ccgacgccct ggacgacttc gacctggaca tgctgccggc cgacgccctg   2220
gacgacttcg acctggacat gctgccggcc gacgccctgg acgacttcga cctggacatg   2280
ctgccggggt aactaagtaa gcggccgctc gagtctagag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcaagagac aggatgagga tcgtttcgca tgattgaaca agatggattg   3480
cacgcaggtt ctccggccgc ttgggtggag aggctattcg gctatgactg ggcacaacag   3540
acaatcggct gctctgatgc cgccgtgttc cggctgtcag cgcaggggcg cccggttctt   3600
tttgtcaaga ccgacctgtc cggtgccctg aatgaactgc aggacgaggc agcgcggcta   3660
tcgtggctgg ccacgacggg cgttccttgc gcagctgtgc tcgacgttgt cactgaagcg   3720
ggaagggact ggctgctatt gggcgaagtg ccggggcagg atctcctgtc atctcacctt   3780
gctcctgccg agaaagtatc catcatggct gatgcaatgc ggcggctgca tacgcttgat   3840
ccggctacct gcccattcga ccaccaagcg aaacatcgca tcgagcgagc acgtactcgg   3900
atggaagccg gtcttgtcga tcaggatgat ctggacgaag agcatcaggg gctcgcgcca   3960
gccgaactgt tcgccaggct caaggcgcgc atgcccgacg gcgaggatct cgtcgtgacc   4020
catggcgatg cctgcttgcc gaatatcatg gtggaaaatg gccgcttttc tggattcatc   4080
gactgtggcc ggctgggtgt ggcggaccgc tatcaggaca tagcgttggc tacccgtgat   4140
attgctgaag agcttggcgg cgaatgggct gaccgcttcc tcgtgcttta cggtatcgcc   4200
```

-continued

```
gctcccgatt cgcagcgcat cgccttctat cgccttcttg acgagttctt ctgagcggga   4260
ctctggggtt cgaaatgacc gaccaagcga cgcccaacct gccatcacga gatttcgatt   4320
ccaccgccgc cttctatgaa aggttgggct tcggaatcgt tttccgggac gccggctgga   4380
tgatcctcca gcgcggggat ctcatgctgg agttcttcgc ccaccccaac ttgtttattg   4440
cagcttataa tggttacaaa taaagcaata gcatcacaaa tttcacaaat aaagcatttt   4500
tttcactgca ttctagttgt ggtttgtcca aactcatcaa tgtatcttat catgtctgta   4560
taccgtcgac ctctagctag agcttggcgt aatcatggtc atagctgttt cctgtgtgaa   4620
attgttatcc gctcacaatt ccacacaaca tacgagccgg aagcataaag tgtaaagcct   4680
ggggtgccta atgagtgagc taactcacat taattgcgtt gcgctcactg cccgctttcc   4740
agtcgggaaa cctgtcgtgc cagctgcatt aatgaatcgg ccaacgcgcg gggagaggcg   4800
gtttgcggcg agcggtatca gctcactcaa aggcggtaat acggttatcc acagaatcag   4860
gggataacgc aggaaagaac atgtgagcaa aaggccagca aaaggccagg aaccgtaaaa   4920
aggccgcgtt gctggcgttt ttccataggc tccgcccccc tgacgagcat cacaaaaatc   4980
gacgctcaag tcagaggtgg cgaaacccga caggactata aagataccag gcgtttcccc   5040
ctggaagctc cctcgtgcgc tctcctgttc cgaccctgcc gcttaccgga tacctgtccg   5100
cctttctccc ttcgggaagc gtggcgcttt ctcaatgctc acgctgtagg tatctcagtt   5160
cggtgtaggt cgttcgctcc aagctgggct gtgtgcacga accccccgtt cagcccgacc   5220
gctgcgcctt atccggtaac tatcgtcttg agtccaaccc ggtaagacac gacttatcgc   5280
cactggcagc agccactggt aacaggatta gcagagcgag gtatgtaggc ggtgctacag   5340
agttcttgaa gtggtggcct aactacggct acactagaag gacagtattt ggtatctgcg   5400
ctctgctgaa gccagttacc ttcggaaaaa gagttggtag ctcttgatcc ggcaaacaaa   5460
ccaccgctgg tagcggtggt ttttttgttt gcaagcagca gattacgcgc agaaaaaaag   5520
gatctcaaga agatcctttg atcttttcta cggggtctga cgctcagtgg aacgaaaact   5580
cacgttaagg gattttggtc atgagattat caaaaaggat cttcacctag atccttttaa   5640
attaaaaatg aagttttaaa tcaatctaaa gtatatatga gtaaacttgg tctgacagtt   5700
accaatgctt aatcagtgag gcacctatct cagcgatctg tctatttcgt tcatccatag   5760
ttgcctgact ccccgtcgtg tagataacta cgatacggga gggcttacca tctggcccca   5820
gtgctgcaat gataccgcga gacccacgct caccggctcc agatttatca gcaataaacc   5880
agccagccgg aagggccgag cgcagaagtg gtcctgcaac tttatccgcc tccatccagt   5940
ctattaattg ttgccgggaa gctagagtaa gtagttcgcc agttaatagt ttgcgcaacg   6000
ttgttgccat tgctacaggc atcgtggtgt cacgctcgtc gtttggtatg gcttcattca   6060
gctccggttc ccaacgatca aggcgagtta catgatcccc catgttgtgc aaaaaagcgg   6120
ttagctcctt cggtcctccg atcgttgtca gaagtaagtt ggccgcagtg ttatcactca   6180
tggttatggc agcactgcat aattctctta ctgtcatgcc atccgtaaga tgcttttctg   6240
tgactggtga gtactcaacc aagtcattct gagaatagtg tatgcggcga ccgagttgct   6300
cttgcccggc gtcaatacgg gataataccg cgccacatag cagaacttta aaagtgctca   6360
tcattggaaa acgttcttcg gggcgaaaac tctcaaggat cttaccgctg ttgagatcca   6420
gttcgatgta acccactcgt gcacccaact gatcttcagc atcttttact ttcaccagcg   6480
tttctgggtg agcaaaaaca ggaaggcaaa atgccgcaaa aaagggaata agggcgacac   6540
```

-continued

```
ggaaatgttg aatactcata ctcttccttt ttcaatatta ttgaagcatt tatcagggtt   6600

attgtctcat gagcggatac atatttgaat gtatttagaa aaataaacaa ataggggttc   6660

cgcgcacatt tccccgaaaa gtgccacctg acgtc                              6695
```

```
<210> SEQ ID NO 9
<211> LENGTH: 6956
<212> TYPE: DNA
<213> ORGANISM: Artificial Sequence
<220> FEATURE:
<220> FEATURE:
<223> OTHER INFORMATION: Description of Artificial Sequence: Construct
      C7LBDCL

<400> SEQUENCE: 9

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattcctg    960

cagcccgggg gatctatggc ccaggcggcc ctcgagccct atgcttgccc tgtcgagtcc   1020

tgcgatcgcc gcttttctaa gtcggctgat ctgaagcgcc atatccgcat ccacacaggc   1080

cagaagcctt tccagtgtcg aatatgcatg cgtaacttca gtcgtagtga ccaccttacc   1140

acccacatcc gcacccacac aggcgagaag ccttttgcct gtgacatttg tgggaggaag   1200

tttgccagga gtgatgaacg caagaggcat accaaaatcc atttaagaca gagggactct   1260

agaactagta gtattcaagg acataacgac tatatgtgtc cagccaccaa ccagtgcacc   1320

attgataaaa acaggaggaa gagctgccag gcctgccggc tccgcaaatg ctacgaagtg   1380

ggaatgatga aaggtgggat acgaaaagac cgaagaggag ggagaatgtt gaaacacaag   1440

cgccagagag atgatgggga gggcaggggt gaagtggggt ctgctggaga catgagagct   1500

gccaaccttt ggccaagccc gctcatgatc aaacgctcta agaagaacag cctggccttg   1560

tccctgacgg ccgaccagat ggtcagtgcc ttgttggatg ctgagccccc catactctat   1620

tccgagtatg atcctaccag acccttcagt gaagcttcga tgatgggctt actgaccaac   1680

ctggcagaca gggagctggt tcacatgatc aactgggcga agagggtgcc aggctttgtg   1740

gatttgaccc tccatgatca ggtccacctt ctagaatgtg cctggctaga gatcctgatg   1800

attggtctcg tctggcgctc catggagcac ccagggaagc tactgtttgc tcctaacttg   1860
```

-continued

```
ctcttggaca ggaaccaggg aaaatgtgta gagggcatgg tggagatctt cgacatgctg   1920
ctggctacat catctcggtt ccgcatgatg aatctgcagg gagaggagtt tgtgtgcctc   1980
aaatctatta ttttgcttaa ttctggagtg tacacatttc tgtccagcac cctgaagtct   2040
ctggaagaga aggaccatat ccaccgagtc ctggacaaga tcacagacac tttgatccac   2100
ctgatggcca aggcaggcct gaccctgcag cagcagcacc agcggctggc ccagctcctc   2160
ctcatcctct cccacatcag gcacatgagt aacaaaggca tggagcatct gtacagcatg   2220
aagtgcaaga acgtggtgcc cctctatgac ctgctgctgg agatgctgga cgcccaccgc   2280
ctacatgcgc ccactagccg tggaggggca tccgtggagg agacggacca aagccacttg   2340
gccactgcgg gctctacttc atcgcattcc ttgcaaaagt attacatcac gggggaggca   2400
gagggtttcc ctgccacagt ccgtacgccg gccgacgccc tggacgactt cgacctggac   2460
atgctgccgg ccgacgccct ggacgacttc gacctggaca tgctgccggc cgacgccctg   2520
gacgacttcg acctggacat gctgccgggg taactaagta agcggccgct cgagtctaga   2580
gggcccgttt aaacccgctg atcagcctcg actgtgcctt ctagttgcca gccatctgtt   2640
gtttgcccct cccccgtgcc ttccttgacc ctggaaggtg ccactcccac tgtcctttcc   2700
taataaaatg aggaaattgc atcgcattgt ctgagtaggt gtcattctat tctggggggt   2760
ggggtggggc aggacagcaa gggggaggat tgggaagaca atagcaggca tgctggggat   2820
gcggtgggct ctatggcttc tgaggcggaa agaaccagct ggggctctag ggggtatccc   2880
cacgcgccct gtagcggcgc attaagcgcg gcgggtgtgg tggttacgcg cagcgtgacc   2940
gctacacttg ccagcgccct agcgcccgct cctttcgctt tcttcccttc ctttctcgcc   3000
acgttcgccg gctttccccg tcaagctcta aatcggggca tccctttagg gttccgattt   3060
agtgctttac ggcacctcga ccccaaaaaa cttgattagg gtgatggttc acgtagtggg   3120
ccatcgccct gatagacggt ttttcgccct ttgacgttgg agtccacgtt ctttaatagt   3180
ggactcttgt tccaaactgg aacaacactc aaccctatct cggtctattc ttttgattta   3240
taagggattt tggggatttc ggcctattgg ttaaaaaatg agctgattta acaaaaattt   3300
aacgcgaatt aattctgtgg aatgtgtgtc agttagggtg tggaaagtcc ccaggctccc   3360
caggcaggca gaagtatgca aagcatgcat ctcaattagt cagcaaccag gtgtggaaag   3420
tccccaggct ccccagcagg cagaagtatg caaagcatgc atctcaatta gtcagcaacc   3480
atagtcccgc ccctaactcc gcccatcccg cccctaactc cgcccagttc cgcccattct   3540
ccgccccatg gctgactaat tttttttatt tatgcagagg ccgaggccgc ctctgcctct   3600
gagctattcc agaagtagtg aggaggcttt tttggaggcc taggcttttg caaaaagctc   3660
ccgggagctt gtatatccat tttcggatct gatcaagaga caggatgagg atcgtttcgc   3720
atgattgaac aagatggatt gcacgcaggt tctccggccg cttgggtgga gaggctattc   3780
ggctatgact gggcacaaca gacaatcggc tgctctgatg ccgccgtgtt ccggctgtca   3840
gcgcaggggc gcccggttct ttttgtcaag accgacctgt ccggtgccct gaatgaactg   3900
caggacgagg cagcgcggct atcgtggctg gccacgacgg gcgttccttg cgcagctgtg   3960
ctcgacgttg tcactgaagc gggaagggac tggctgctat tgggcgaagt gccggggcag   4020
gatctcctgt catctcacct tgctcctgcc gagaaagtat ccatcatggc tgatgcaatg   4080
cggcggctgc atacgcttga tccggctacc tgcccattcg accaccaagc gaaacatcgc   4140
atcgagcgag cacgtactcg gatggaagcc ggtcttgtcg atcaggatga tctggacgaa   4200
```

-continued

```
gagcatcagg ggctcgcgcc agccgaactg ttcgccaggc tcaaggcgcg catgcccgac   4260
ggcgaggatc tcgtcgtgac ccatggcgat gcctgcttgc cgaatatcat ggtggaaaat   4320
ggccgctttt ctggattcat cgactgtggc cggctgggtg tggcggaccg ctatcaggac   4380
atagcgttgg ctacccgtga tattgctgaa gagcttggcg gcgaatgggc tgaccgcttc   4440
ctcgtgcttt acggtatcgc cgctcccgat tcgcagcgca tcgccttcta tcgccttctt   4500
gacgagttct tctgagcggg actctggggt tcgaaatgac cgaccaagcg acgcccaacc   4560
tgccatcacg agatttcgat tccaccgccg ccttctatga aaggttgggc ttcggaatcg   4620
ttttccggga cgccggctgg atgatcctcc agcgcgggga tctcatgctg gagttcttcg   4680
cccaccccaa cttgtttatt gcagcttata atggttacaa ataaagcaat agcatcacaa   4740
atttcacaaa taaagcattt ttttcactgc attctagttg tggtttgtcc aaactcatca   4800
atgtatctta tcatgtctgt ataccgtcga cctctagcta gagcttggcg taatcatggt   4860
catagctgtt tcctgtgtga aattgttatc cgctcacaat tccacacaac atacgagccg   4920
gaagcataaa gtgtaaagcc tggggtgcct aatgagtgag ctaactcaca ttaattgcgt   4980
tgcgctcact gcccgctttc cagtcgggaa acctgtcgtg ccagctgcat taatgaatcg   5040
gccaacgcgc ggggagaggc ggtttgcggc gagcggtatc agctcactca aaggcggtaa   5100
tacggttatc cacagaatca ggggataacg caggaaagaa catgtgagca aaaggccagc   5160
aaaaggccag gaaccgtaaa aaggccgcgt tgctggcgtt tttccatagg ctccgccccc   5220
ctgacgagca tcacaaaaat cgacgctcaa gtcagaggtg gcgaaacccg acaggactat   5280
aaagatacca ggcgtttccc cctggaagct ccctcgtgcg ctctcctgtt ccgaccctgc   5340
cgcttaccgg atacctgtcc gcctttctcc cttcgggaag cgtggcgctt tctcaatgct   5400
cacgctgtag gtatctcagt tcggtgtagg tcgttcgctc caagctgggc tgtgtgcacg   5460
aaccccccgt tcagcccgac cgctgcgcct tatccggtaa ctatcgtctt gagtccaacc   5520
cggtaagaca cgacttatcg ccactggcag cagccactgg taacaggatt agcagagcga   5580
ggtatgtagg cggtgctaca gagttcttga agtggtggcc taactacggc tacactagaa   5640
ggacagtatt tggtatctgc gctctgctga agccagttac cttcggaaaa agagttggta   5700
gctcttgatc cggcaaacaa accaccgctg gtagcggtgg tttttttgtt tgcaagcagc   5760
agattacgcg cagaaaaaaa ggatctcaag aagatccttt gatcttttct acggggtctg   5820
acgctcagtg gaacgaaaac tcacgttaag ggattttggt catgagatta tcaaaaagga   5880
tcttcaccta gatcctttta aattaaaaat gaagttttaa atcaatctaa agtatatatg   5940
agtaaacttg gtctgacagt taccaatgct taatcagtga ggcacctatc tcagcgatct   6000
gtctatttcg ttcatccata gttgcctgac tccccgtcgt gtagataact acgatacggg   6060
agggcttacc atctggcccc agtgctgcaa tgataccgcg agacccacgc tcaccggctc   6120
cagatttatc agcaataaac cagccagccg gaagggccga gcgcagaagt ggtcctgcaa   6180
ctttatccgc ctccatccag tctattaatt gttgccggga agctagagta agtagttcgc   6240
cagttaatag tttgcgcaac gttgttgcca ttgctacagg catcgtggtg tcacgctcgt   6300
cgtttggtat ggcttcattc agctccggtt cccaacgatc aaggcgagtt acatgatccc   6360
ccatgttgtg caaaaaagcg gttagctcct tcggtcctcc gatcgttgtc agaagtaagt   6420
tggccgcagt gttatcactc atggttatgg cagcactgca taattctctt actgtcatgc   6480
catccgtaag atgcttttct gtgactggtg agtactcaac caagtcattc tgagaatagt   6540
gtatgcggcg accgagttgc tcttgcccgg cgtcaatacg ggataatacc gcgccacata   6600
```

-continued gcagaacttt aaaagtgctc atcattggaa aacgttcttc ggggcgaaaa ctctcaagga 6660
tcttaccgct gttgagatcc agttcgatgt aacccactcg tgcacccaac tgatcttcag 6720
catcttttac tttcaccagc gtttctgggt gagcaaaaac aggaaggcaa aatgccgcaa 6780
aaaagggaat aagggcgaca cggaaatgtt gaatactcat actcttcctt tttcaatatt 6840
attgaagcat ttatcagggt tattgtctca tgagcggata catatttgaa tgtatttaga 6900
aaaataaaca aataggggtt ccgcgcacat ttccccgaaa agtgccacct gacgtc 6956

<210> SEQ ID NO 10
<211> LENGTH: 6833
<212> TYPE: DNA
<213> ORGANISM: Artificial Sequence
<220> FEATURE:
<220> FEATURE:
<223> OTHER INFORMATION: Description of Artificial Sequence: Construct
C7LBDCS

<400> SEQUENCE: 10
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cagcccgggg gatctatggc ccaggcggcc ctcgagccct atgcttgccc tgtcgagtcc 1020
tgcgatcgcc gcttttctaa gtcggctgat ctgaagcgcc atatccgcat ccacacaggc 1080
cagaagcctt tccagtgtcg aatatgcatg cgtaacttca gtcgtagtga ccaccttacc 1140
acccacatcc gcacccacac aggcgagaag ccttttgcct gtgacatttg tgggaggaag 1200
tttgccagga gtgatgaacg caagaggcat accaaaatcc atttaagaca gagggactct 1260
agaactagta gtattcaagg acataacgac tatatgtgtc cagccaccaa ccagtgcacc 1320
attgataaaa acaggaggaa gagctgccag gcctgccggc tccgcaaatg ctacgaagtg 1380
ggaatgatga aaggtgggat acgaaaagac cgaagaggag ggagaatgtt gaaacacaag 1440
cgccagagag atgatgggga gggcaggggt gaagtggggt ctgctggaga catgagagct 1500
gccaaccttt ggccaagccc gctcatgatc aaacgctcta agaagaacag cctggccttg 1560
tccctgacgg ccgaccagat ggtcagtgcc ttgttggatg ctgagccccc catactctat 1620

-continued

```
tccgagtatg atcctaccag acccttcagt gaagcttcga tgatgggctt actgaccaac   1680
ctggcagaca gggagctggt tcacatgatc aactgggcga agagggtgcc aggctttgtg   1740
gatttgaccc tccatgatca ggtccacctt ctagaatgtg cctggctaga gatcctgatg   1800
attggtctcg tctggcgctc catggagcac ccagggaagc tactgtttgc tcctaacttg   1860
ctcttggaca ggaaccaggg aaaatgtgta gagggcatgg tggagatctt cgacatgctg   1920
ctggctacat catctcggtt ccgcatgatg aatctgcagg gagaggagtt tgtgtgcctc   1980
aaatctatta ttttgcttaa ttctggagtg tacacatttc tgtccagcac cctgaagtct   2040
ctggaagaga aggaccatat ccaccgagtc ctggacaaga tcacagacac tttgatccac   2100
ctgatggcca aggcaggcct gaccctgcag cagcagcacc agcggctggc ccagctcctc   2160
ctcatcctct cccacatcag gcacatgagt aacaaaggca tggagcatct gtacagcatg   2220
aagtgcaaga acgtggtgcc cctctatgac ctgctgctgg agatgctgga cgcccaccgc   2280
ctacatgcgc ccactagccg tacgccggcc gacgccctgg acgacttcga cctggacatg   2340
ctgccggccg acgccctgga cgacttcgac ctggacatgc tgccggccga cgccctggac   2400
gacttcgacc tggacatgct gccggggtaa ctaagtaagc ggccgctcga gtctagaggg   2460
cccgtttaaa cccgctgatc agcctcgact gtgccttcta gttgccagcc atctgttgtt   2520
tgcccctccc ccgtgccttc cttgaccctg gaaggtgcca ctcccactgt cctttcctaa   2580
taaaatgagg aaattgcatc gcattgtctg agtaggtgtc attctattct ggggggtggg   2640
gtggggcagg acagcaaggg ggaggattgg gaagacaata gcaggcatgc tggggatgcg   2700
gtgggctcta tggcttctga ggcggaaaga accagctggg gctctagggg gtatccccac   2760
gcgccctgta gcggcgcatt aagcgcggcg ggtgtggtgg ttacgcgcag cgtgaccgct   2820
acacttgcca gcgccctagc gcccgctcct ttcgctttct tcccttcctt tctcgccacg   2880
ttcgccggct ttccccgtca agctctaaat cggggcatcc ctttagggtt ccgatttagt   2940
gctttacggc acctcgaccc caaaaaactt gattagggtg atggttcacg tagtgggcca   3000
tcgccctgat agacggtttt tcgccctttg acgttggagt ccacgttctt taatagtgga   3060
ctcttgttcc aaactggaac aacactcaac cctatctcgg tctattcttt tgatttataa   3120
gggattttgg ggatttcggc ctattggtta aaaaatgagc tgatttaaca aaaatttaac   3180
gcgaattaat tctgtggaat gtgtgtcagt tagggtgtgg aaagtcccca ggctccccag   3240
gcaggcagaa gtatgcaaag catgcatctc aattagtcag caaccaggtg tggaaagtcc   3300
ccaggctccc cagcaggcag aagtatgcaa agcatgcatc tcaattagtc agcaaccata   3360
gtcccgcccc taactccgcc catcccgccc ctaactccgc ccagttccgc ccattctccg   3420
ccccatggct gactaatttt ttttatttat gcagaggccg aggccgcctc tgcctctgag   3480
ctattccaga agtagtgagg aggctttttt ggaggcctag gcttttgcaa aaagctcccg   3540
ggagcttgta tatccatttt cggatctgat caagagacag gatgaggatc gtttcgcatg   3600
attgaacaag atggattgca cgcaggttct ccggccgctt gggtggagag gctattcggc   3660
tatgactggg cacaacagac aatcggctgc tctgatgccg ccgtgttccg gctgtcagcg   3720
caggggcgcc cggttctttt tgtcaagacc gacctgtccg gtgccctgaa tgaactgcag   3780
gacgaggcag cgcggctatc gtggctggcc acgacgggcg ttccttgcgc agctgtgctc   3840
gacgttgtca ctgaagcggg aagggactgg ctgctattgg gcgaagtgcc ggggcaggat   3900
ctcctgtcat ctcaccttgc tcctgccgag aaagtatcca tcatggctga tgcaatgcgg   3960
cggctgcata cgcttgatcc ggctacctgc ccattcgacc accaagcgaa acatcgcatc   4020
```

-continued

```
gagcgagcac gtactcggat ggaagccggt cttgtcgatc aggatgatct ggacgaagag   4080
catcaggggc tcgcgccagc cgaactgttc gccaggctca aggcgcgcat gcccgacggc   4140
gaggatctcg tcgtgaccca tggcgatgcc tgcttgccga atatcatggt ggaaaatggc   4200
cgcttttctg gattcatcga ctgtggccgg ctgggtgtgg cggaccgcta tcaggacata   4260
gcgttggcta cccgtgatat tgctgaagag cttggcggcg aatgggctga ccgcttcctc   4320
gtgctttacg gtatcgccgc tcccgattcg cagcgcatcg ccttctatcg ccttcttgac   4380
gagttcttct gagcgggact ctggggttcg aaatgaccga ccaagcgacg cccaacctgc   4440
catcacgaga tttcgattcc accgccgcct tctatgaaag gttgggcttc ggaatcgttt   4500
tccgggacgc cggctggatg atcctccagc gcggggatct catgctggag ttcttcgccc   4560
accccaactt gtttattgca gcttataatg gttacaaata aagcaatagc atcacaaatt   4620
tcacaaataa agcatttttt tcactgcatt ctagttgtgg tttgtccaaa ctcatcaatg   4680
tatcttatca tgtctgtata ccgtcgacct ctagctagag cttggcgtaa tcatggtcat   4740
agctgtttcc tgtgtgaaat tgttatccgc tcacaattcc acacaacata cgagccggaa   4800
gcataaagtg taaagcctgg ggtgcctaat gagtgagcta actcacatta attgcgttgc   4860
gctcactgcc cgctttccag tcgggaaacc tgtcgtgcca gctgcattaa tgaatcggcc   4920
aacgcgcggg gagaggcggt ttgcggcgag cggtatcagc tcactcaaag gcggtaatac   4980
ggttatccac agaatcaggg gataacgcag gaaagaacat gtgagcaaaa ggccagcaaa   5040
aggccaggaa ccgtaaaaag gccgcgttgc tggcgttttt ccataggctc cgcccccctg   5100
acgagcatca caaaaatcga cgctcaagtc agaggtggcg aaacccgaca ggactataaa   5160
gataccaggc gtttccccct ggaagctccc tcgtgcgctc tcctgttccg accctgccgc   5220
ttaccggata cctgtccgcc tttctccctt cgggaagcgt ggcgctttct caatgctcac   5280
gctgtaggta tctcagttcg gtgtaggtcg ttcgctccaa gctgggctgt gtgcacgaac   5340
cccccgttca gcccgaccgc tgcgccttat ccggtaacta tcgtcttgag tccaacccgg   5400
taagacacga cttatcgcca ctggcagcag ccactggtaa caggattagc agagcgaggt   5460
atgtaggcgg tgctacagag ttcttgaagt ggtggcctaa ctacggctac actagaagga   5520
cagtatttgg tatctgcgct ctgctgaagc cagttacctt cggaaaaaga gttggtagct   5580
cttgatccgg caaacaaacc accgctggta gcggtggttt ttttgtttgc aagcagcaga   5640
ttacgcgcag aaaaaaagga tctcaagaag atcctttgat cttttctacg gggtctgacg   5700
ctcagtggaa cgaaaactca cgttaaggga ttttggtcat gagattatca aaaaggatct   5760
tcacctagat ccttttaaat taaaaatgaa gttttaaatc aatctaaagt atatatgagt   5820
aaacttggtc tgacagttac caatgcttaa tcagtgaggc acctatctca gcgatctgtc   5880
tatttcgttc atccatagtt gcctgactcc ccgtcgtgta gataactacg atacgggagg   5940
gcttaccatc tggccccagt gctgcaatga taccgcgaga cccacgctca ccggctccag   6000
atttatcagc aataaaccag ccagccggaa gggccgagcg cagaagtggt cctgcaactt   6060
tatccgcctc catccagtct attaattgtt gccgggaagc tagagtaagt agttcgccag   6120
ttaatagttt gcgcaacgtt gttgccattg ctacaggcat cgtggtgtca cgctcgtcgt   6180
ttggtatggc ttcattcagc tccggttccc aacgatcaag gcgagttaca tgatccccca   6240
tgttgtgcaa aaaagcggtt agctccttcg gtcctccgat cgttgtcaga agtaagttgg   6300
ccgcagtgtt atcactcatg gttatggcag cactgcataa ttctcttact gtcatgccat   6360
```

-continued

```
ccgtaagatg cttttctgtg actggtgagt actcaaccaa gtcattctga gaatagtgta   6420

tgcggcgacc gagttgctct tgcccggcgt caatacggga taataccgcg ccacatagca   6480

gaactttaaa agtgctcatc attggaaaac gttcttcggg gcgaaaactc tcaaggatct   6540

taccgctgtt gagatccagt tcgatgtaac ccactcgtgc acccaactga tcttcagcat   6600

cttttacttt caccagcgtt tctgggtgag caaaaacagg aaggcaaaat gccgcaaaaa   6660

agggaataag ggcgacacgg aaatgttgaa tactcatact cttccttttt caatattatt   6720

gaagcattta tcagggttat tgtctcatga gcggatacat atttgaatgt atttagaaaa   6780

ataaacaaat aggggttccg cgcacatttc cccgaaaagt gccacctgac gtc          6833
```

<210> SEQ ID NO 11
<211> LENGTH: 6567
<212> TYPE: DNA
<213> ORGANISM: Artificial Sequence
<220> FEATURE:
<220> FEATURE:
<223> OTHER INFORMATION: Description of Artificial Sequence: Construct E2CLBDAS

<400> SEQUENCE: 11

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttagat ctatggccca ggcggccctc gagcccgggg agaagcccta    960

tgcttgtccg gaatgtggta agtccttctc tcagagctct cacctggtgc gccaccagcg   1020

tacccacacg ggtgaaaaac cgtataaatg cccagagtgc ggcaaatctt ttagtgactg   1080

ccgcgacctt gctcgccatc aacgcactca tactggcgag aagccataca aatgtccaga   1140

atgtggcaag tctttcagcc gctctgacaa gctggtgcgt caccaacgta ctcacaccgg   1200

taaaaaaact agttctgctg gagacatgag agctgccaac ctttggccaa gcccgctcat   1260

gatcaaacgc tctaagaaga acagcctggc cttgtccctg acggccgacc agatggtcag   1320

tgccttgttg gatgctgagc cccccatact ctattccgag tatgatccta ccagaccctt   1380

cagtgaagct tcgatgatgg gcttactgac caacctggca gacagggagc tggttcacat   1440

gatcaactgg gcgaagaggg tgccaggctt tgtggatttg accctccatg atcaggtcca   1500

ccttctagaa tgtgcctggc tagagatcct gatgattggt ctcgtctggc gctccatgga   1560
```

-continued

```
gcacccaggg aagctactgt ttgctcctaa cttgctcttg gacaggaacc agggaaaatg   1620
tgtagagggc atggtggaga tcttcgacat gctgctggct acatcatctc ggttccgcat   1680
gatgaatctg cagggagagg agtttgtgtg cctcaaatct attattttgc ttaattctgg   1740
agtgtacaca tttctgtcca gcaccctgaa gtctctggaa gagaaggacc atatccaccg   1800
agtcctggac aagatcacag acactttgat ccacctgatg gccaaggcag gcctgaccct   1860
gcagcagcag caccagcggc tggcccagct cctcctcatc ctctcccaca tcaggcacat   1920
gagtaacaaa ggcatggagc atctgtacag catgaagtgc aagaacgtgg tgcccctcta   1980
tgacctgctg ctggagatgc tggacgccca ccgcctacat gcgcccacta gccgtacgcc   2040
ggccgacgcc ctggacgact tcgacctgga catgctgccg gccgacgccc tggacgactt   2100
cgacctggac atgctgccgg ccgacgccct ggacgacttc gacctggaca tgctgccggg   2160
gtaactaagt aagcggccgc tcgagtctag agggcccgtt taaacccgct gatcagcctc   2220
gactgtgcct tctagttgcc agccatctgt tgtttgcccc tcccccgtgc cttccttgac   2280
cctggaaggt gccactccca ctgtcctttc ctaataaaat gaggaaattg catcgcattg   2340
tctgagtagg tgtcattcta ttctgggggg tggggtgggg caggacagca agggggagga   2400
ttgggaagac aatagcaggc atgctgggga tgcggtgggc tctatggctt ctgaggcgga   2460
aagaaccagc tggggctcta gggggtatcc ccacgcgccc tgtagcggcg cattaagcgc   2520
ggcgggtgtg gtggttacgc gcagcgtgac cgctacactt gccagcgccc tagcgcccgc   2580
tcctttcgct ttcttccctt cctttctcgc cacgttcgcc ggctttcccc gtcaagctct   2640
aaatcggggc atccctttag ggttccgatt tagtgcttta cggcacctcg accccaaaaa   2700
acttgattag ggtgatggtt cacgtagtgg gccatcgccc tgatagacgg tttttcgccc   2760
tttgacgttg gagtccacgt tctttaatag tggactcttg ttccaaactg gaacaacact   2820
caaccctatc tcggtctatt cttttgattt ataagggatt ttggggattt cggcctattg   2880
gttaaaaaat gagctgattt aacaaaaatt taacgcgaat taattctgtg gaatgtgtgt   2940
cagttagggt gtggaaagtc cccaggctcc ccaggcaggc agaagtatgc aaagcatgca   3000
tctcaattag tcagcaacca ggtgtggaaa gtccccaggc tccccagcag gcagaagtat   3060
gcaaagcatg catctcaatt agtcagcaac catagtcccg cccctaactc cgcccatccc   3120
gcccctaact ccgcccagtt ccgcccattc tccgccccat ggctgactaa ttttttttat   3180
ttatgcagag gccgaggccg cctctgcctc tgagctattc cagaagtagt gaggaggctt   3240
ttttggaggc ctaggctttt gcaaaaagct cccgggagct tgtatatcca ttttcggatc   3300
tgatcaagag acaggatgag gatcgtttcg catgattgaa caagatggat tgcacgcagg   3360
ttctccggcc gcttgggtgg agaggctatt cggctatgac tgggcacaac agacaatcgg   3420
ctgctctgat gccgccgtgt tccggctgtc agcgcagggg cgcccggttc tttttgtcaa   3480
gaccgacctg tccggtgccc tgaatgaact gcaggacgag gcagcgcggc tatcgtggct   3540
ggccacgacg ggcgttcctt gcgcagctgt gctcgacgtt gtcactgaag cgggaaggga   3600
ctggctgcta ttgggcgaag tgccggggca ggatctcctg tcatctcacc ttgctcctgc   3660
cgagaaagta tccatcatgg ctgatgcaat gcggcggctg catacgcttg atccggctac   3720
ctgcccattc gaccaccaag cgaaacatcg catcgagcga gcacgtactc ggatggaagc   3780
cggtcttgtc gatcaggatg atctggacga agagcatcag gggctcgcgc cagccgaact   3840
gttcgccagg ctcaaggcgc gcatgcccga cggcgaggat ctcgtcgtga cccatggcga   3900
```

-continued

```
tgcctgcttg ccgaatatca tggtggaaaa tggccgcttt tctggattca tcgactgtgg   3960
ccggctgggt gtggcggacc gctatcagga catagcgttg gctacccgtg atattgctga   4020
agagcttggc ggcgaatggg ctgaccgctt cctcgtgctt tacggtatcg ccgctcccga   4080
ttcgcagcgc atcgccttct atcgccttct tgacgagttc ttctgagcgg gactctgggg   4140
ttcgaaatga ccgaccaagc gacgcccaac ctgccatcac gagatttcga ttccaccgcc   4200
gccttctatg aaaggttggg cttcggaatc gttttccggg acgccggctg gatgatcctc   4260
cagcgcgggg atctcatgct ggagttcttc gcccacccca acttgtttat tgcagcttat   4320
aatggttaca aataaagcaa tagcatcaca aatttcacaa ataaagcatt tttttcactg   4380
cattctagtt gtggtttgtc caaactcatc aatgtatctt atcatgtctg tataccgtcg   4440
acctctagct agagcttggc gtaatcatgg tcatagctgt ttcctgtgtg aaattgttat   4500
ccgctcacaa ttccacacaa catacgagcc ggaagcataa agtgtaaagc ctggggtgcc   4560
taatgagtga gctaactcac attaattgcg ttgcgctcac tgcccgcttt ccagtcggga   4620
aacctgtcgt gccagctgca ttaatgaatc ggccaacgcg cggggagagg cggtttgcgg   4680
cgagcggtat cagctcactc aaaggcggta atacggttat ccacagaatc aggggataac   4740
gcaggaaaga acatgtgagc aaaaggccag caaaaggcca ggaaccgtaa aaaggccgcg   4800
ttgctggcgt ttttccatag gctccgcccc cctgacgagc atcacaaaaa tcgacgctca   4860
agtcagaggt ggcgaaaccc gacaggacta taaagatacc aggcgtttcc ccctggaagc   4920
tccctcgtgc gctctcctgt tccgaccctg ccgcttaccg gatacctgtc cgcctttctc   4980
ccttcgggaa gcgtggcgct ttctcaatgc tcacgctgta ggtatctcag ttcggtgtag   5040
gtcgttcgct ccaagctggg ctgtgtgcac gaaccccccg ttcagcccga ccgctgcgcc   5100
ttatccggta actatcgtct tgagtccaac ccggtaagac acgacttatc gccactggca   5160
gcagccactg gtaacaggat tagcagagcg aggtatgtag gcggtgctac agagttcttg   5220
aagtggtggc ctaactacgg ctacactaga aggacagtat ttggtatctg cgctctgctg   5280
aagccagtta ccttcggaaa aagagttggt agctcttgat ccggcaaaca aaccaccgct   5340
ggtagcggtg gtttttttgt ttgcaagcag cagattacgc gcagaaaaaa aggatctcaa   5400
gaagatcctt tgatcttttc tacggggtct gacgctcagt ggaacgaaaa ctcacgttaa   5460
gggattttgg tcatgagatt atcaaaaagg atcttcacct agatcctttt aaattaaaaa   5520
tgaagtttta aatcaatcta aagtatatat gagtaaactt ggtctgacag ttaccaatgc   5580
ttaatcagtg aggcacctat ctcagcgatc tgtctatttc gttcatccat agttgcctga   5640
ctccccgtcg tgtagataac tacgatacgg gagggcttac catctggccc cagtgctgca   5700
atgataccgc gagacccacg ctcaccggct ccagatttat cagcaataaa ccagccagcc   5760
ggaagggccg agcgcagaag tggtcctgca actttatccg cctccatcca gtctattaat   5820
tgttgccggg aagctagagt aagtagttcg ccagttaata gtttgcgcaa cgttgttgcc   5880
attgctacag gcatcgtggt gtcacgctcg tcgtttggta tggcttcatt cagctccggt   5940
tcccaacgat caaggcgagt tacatgatcc cccatgttgt gcaaaaaagc ggttagctcc   6000
ttcggtcctc cgatcgttgt cagaagtaag ttggccgcag tgttatcact catggttatg   6060
gcagcactgc ataattctct tactgtcatg ccatccgtaa gatgcttttc tgtgactggt   6120
gagtactcaa ccaagtcatt ctgagaatag tgtatgcggc gaccgagttg ctcttgcccg   6180
gcgtcaatac gggataatac cgcgccacat agcagaactt taaaagtgct catcattgga   6240
aaacgttctt cggggcgaaa actctcaagg atcttaccgc tgttgagatc cagttcgatg   6300
```

-continued taacccactc gtgcacccaa ctgatcttca gcatctttta ctttcaccag cgtttctggg 6360
tgagcaaaaa caggaaggca aaatgccgca aaaaagggaa taagggcgac acggaaatgt 6420
tgaatactca tactcttcct ttttcaatat tattgaagca tttatcaggg ttattgtctc 6480
atgagcggat acatatttga atgtatttag aaaaataaac aaataggggt tccgcgcaca 6540
tttccccgaa aagtgccacc tgacgtc 6567

<210> SEQ ID NO 12
<211> LENGTH: 6639
<212> TYPE: DNA
<213> ORGANISM: Artificial Sequence
<220> FEATURE:
<220> FEATURE:
<223> OTHER INFORMATION: Description of Artificial Sequence: Construct
E2CLBDBS

<400> SEQUENCE: 12
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttagat ctatggccca ggcggccctc gagcccgggg agaagcccta 960
tgcttgtccg gaatgtggta agtccttctc tcagagctct cacctggtgc gccaccagcg 1020
tacccacacg ggtgaaaaac cgtataaatg cccagagtgc ggcaaatctt ttagtgactg 1080
ccgcgacctt gctcgccatc aacgcactca tactggcgag aagccataca aatgtccaga 1140
atgtggcaag tctttcagcc gctctgacaa gctggtgcgt caccaacgta ctcacaccgg 1200
taaaaaaact agtgaccgaa gaggagggag aatgttgaaa cacaagcgcc agagagatga 1260
tggggagggc aggggtgaag tggggtctgc tggagacatg agagctgcca acctttggcc 1320
aagcccgctc atgatcaaac gctctaagaa gaacagcctg gccttgtccc tgacggccga 1380
ccagatggtc agtgccttgt tggatgctga gccccccata ctctattccg agtatgatcc 1440
taccagaccc ttcagtgaag cttcgatgat gggcttactg accaacctgg cagacaggga 1500
gctggttcac atgatcaact gggcgaagag ggtgccaggc tttgtggatt tgaccctcca 1560
tgatcaggtc caccttctag aatgtgcctg gctagagatc ctgatgattg gtctcgtctg 1620
gcgctccatg gagcacccag ggaagctact gtttgctcct aacttgctct tggacaggaa 1680

-continued

```
ccagggaaaa tgtgtagagg gcatggtgga gatcttcgac atgctgctgg ctacatcatc   1740
tcggttccgc atgatgaatc tgcagggaga ggagtttgtg tgcctcaaat ctattatttt   1800
gcttaattct ggagtgtaca catttctgtc cagcaccctg aagtctctgg aagagaagga   1860
ccatatccac cgagtcctgg acaagatcac agacactttg atccacctga tggccaaggc   1920
aggcctgacc ctgcagcagc agcaccagcg gctggcccag ctcctcctca tcctctccca   1980
catcaggcac atgagtaaca aaggcatgga gcatctgtac agcatgaagt gcaagaacgt   2040
ggtgcccctc tatgacctgc tgctggagat gctggacgcc caccgcctac atgcgcccac   2100
tagccgtacg ccggccgacg ccctggacga cttcgacctg gacatgctgc cggccgacgc   2160
cctggacgac ttcgacctgg acatgctgcc ggccgacgcc ctggacgact tcgacctgga   2220
catgctgccg ggtaactaa gtaagcggcc gctcgagtct agagggcccg tttaaacccg   2280
ctgatcagcc tcgactgtgc cttctagttg ccagccatct gttgtttgcc cctcccccgt   2340
gccttccttg accctggaag gtgccactcc cactgtcctt tcctaataaa atgaggaaat   2400
tgcatcgcat tgtctgagta ggtgtcattc tattctgggg ggtggggtgg ggcaggacag   2460
caagggggag gattgggaag acaatagcag gcatgctggg gatgcggtgg gctctatggc   2520
ttctgaggcg gaaagaacca gctggggctc tagggggtat ccccacgcgc cctgtagcgg   2580
cgcattaagc gcggcgggtg tggtggttac gcgcagcgtg accgctacac ttgccagcgc   2640
cctagcgccc gctcctttcg ctttcttccc ttcctttctc gccacgttcg ccggctttcc   2700
ccgtcaagct ctaaatcggg gcatcccttt agggttccga tttagtgctt tacggcacct   2760
cgaccccaaa aaacttgatt agggtgatgg ttcacgtagt gggccatcgc cctgatagac   2820
ggtttttcgc cctttgacgt tggagtccac gttctttaat agtggactct tgttccaaac   2880
tggaacaaca ctcaacccta tctcggtcta ttcttttgat ttataaggga ttttggggat   2940
ttcggcctat tggttaaaaa atgagctgat ttaacaaaaa tttaacgcga attaattctg   3000
tggaatgtgt gtcagttagg gtgtggaaag tccccaggct ccccaggcag gcagaagtat   3060
gcaaagcatg catctcaatt agtcagcaac caggtgtgga aagtccccag gctccccagc   3120
aggcagaagt atgcaaagca tgcatctcaa ttagtcagca accatagtcc cgcccctaac   3180
tccgcccatc ccgcccctaa ctccgcccag ttccgcccat tctccgcccc atggctgact   3240
aatttttttt atttatgcag aggccgaggc cgcctctgcc tctgagctat tccagaagta   3300
gtgaggaggc ttttttggag gcctaggctt ttgcaaaaag ctcccgggag cttgtatatc   3360
cattttcgga tctgatcaag agacaggatg aggatcgttt cgcatgattg aacaagatgg   3420
attgcacgca ggttctccgg ccgcttgggt ggagaggcta ttcggctatg actgggcaca   3480
acagacaatc ggctgctctg atgccgccgt gttccggctg tcagcgcagg ggcgcccggt   3540
tctttttgtc aagaccgacc tgtccggtgc cctgaatgaa ctgcaggacg aggcagcgcg   3600
gctatcgtgg ctggccacga cgggcgttcc ttgcgcagct gtgctcgacg ttgtcactga   3660
agcgggaagg gactggctgc tattgggcga agtgccgggg caggatctcc tgtcatctca   3720
ccttgctcct gccgagaaag tatccatcat ggctgatgca atgcggcggc tgcatacgct   3780
tgatccggct acctgcccat tcgaccacca agcgaaacat cgcatcgagc gagcacgtac   3840
tcggatggaa gccggtcttg tcgatcagga tgatctggac gaagagcatc aggggctcgc   3900
gccagccgaa ctgttcgcca ggctcaaggc gcgcatgccc gacggcgagg atctcgtcgt   3960
gacccatggc gatgcctgct tgccgaatat catggtggaa aatggccgct tttctggatt   4020
catcgactgt ggccggctgg gtgtggcgga ccgctatcag gacatagcgt tggctacccg   4080
```

-continued tgatattgct gaagagcttg gcggcgaatg ggctgaccgc ttcctcgtgc tttacggtat 4140
cgccgctccc gattcgcagc gcatcgcctt ctatcgcctt cttgacgagt tcttctgagc 4200
gggactctgg ggttcgaaat gaccgaccaa gcgacgccca acctgccatc acgagatttc 4260
gattccaccg ccgccttcta tgaaaggttg ggcttcggaa tcgttttccg ggacgccggc 4320
tggatgatcc tccagcgcgg ggatctcatg ctggagttct tcgcccaccc caacttgttt 4380
attgcagctt ataatggtta caaataaagc aatagcatca caaatttcac aaataaagca 4440
tttttttcac tgcattctag ttgtggtttg tccaaactca tcaatgtatc ttatcatgtc 4500
tgtataccgt cgacctctag ctagagcttg gcgtaatcat ggtcatagct gtttcctgtg 4560
tgaaattgtt atccgctcac aattccacac aacatacgag ccggaagcat aaagtgtaaa 4620
gcctggggtg cctaatgagt gagctaactc acattaattg cgttgcgctc actgcccgct 4680
ttccagtcgg gaaacctgtc gtgccagctg cattaatgaa tcggccaacg cgcggggaga 4740
ggcggtttgc ggcgagcggt atcagctcac tcaaaggcgg taatacggtt atccacagaa 4800
tcaggggata acgcaggaaa gaacatgtga gcaaaaggcc agcaaaaggc caggaaccgt 4860
aaaaaggccg cgttgctggc gtttttccat aggctccgcc cccctgacga gcatcacaaa 4920
aatcgacgct caagtcagag gtggcgaaac ccgacaggac tataaagata ccaggcgttt 4980
ccccctggaa gctccctcgt gcgctctcct gttccgaccc tgccgcttac cggatacctg 5040
tccgcctttc tcccttcggg aagcgtggcg ctttctcaat gctcacgctg taggtatctc 5100
agttcggtgt aggtcgttcg ctccaagctg ggctgtgtgc acgaaccccc cgttcagccc 5160
gaccgctgcg ccttatccgg taactatcgt cttgagtcca acccggtaag acacgactta 5220
tcgccactgg cagcagccac tggtaacagg attagcagag cgaggtatgt aggcggtgct 5280
acagagttct tgaagtggtg gcctaactac ggctacacta gaaggacagt atttggtatc 5340
tgcgctctgc tgaagccagt taccttcgga aaaagagttg gtagctcttg atccggcaaa 5400
caaaccaccg ctggtagcgg tggttttttt gtttgcaagc agcagattac gcgcagaaaa 5460
aaaggatctc aagaagatcc tttgatcttt tctacggggt ctgacgctca gtggaacgaa 5520
aactcacgtt aagggatttt ggtcatgaga ttatcaaaaa ggatcttcac ctagatcctt 5580
ttaaattaaa aatgaagttt taaatcaatc taaagtatat atgagtaaac ttggtctgac 5640
agttaccaat gcttaatcag tgaggcacct atctcagcga tctgtctatt tcgttcatcc 5700
atagttgcct gactccccgt cgtgtagata actacgatac gggagggctt accatctggc 5760
cccagtgctg caatgatacc gcgagaccca cgctcaccgg ctccagattt atcagcaata 5820
aaccagccag ccggaagggc cgagcgcaga agtggtcctg caactttatc cgcctccatc 5880
cagtctatta attgttgccg ggaagctaga gtaagtagtt cgccagttaa tagtttgcgc 5940
aacgttgttg ccattgctac aggcatcgtg gtgtcacgct cgtcgtttgg tatggcttca 6000
ttcagctccg gttcccaacg atcaaggcga gttacatgat cccccatgtt gtgcaaaaaa 6060
gcggttagct ccttcggtcc tccgatcgtt gtcagaagta agttggccgc agtgttatca 6120
ctcatggtta tggcagcact gcataattct cttactgtca tgccatccgt aagatgcttt 6180
tctgtgactg gtgagtactc aaccaagtca ttctgagaat agtgtatgcg gcgaccgagt 6240
tgctcttgcc cggcgtcaat acgggataat accgcgccac atagcagaac tttaaaagtg 6300
ctcatcattg gaaaacgttc ttcggggcga aaactctcaa ggatcttacc gctgttgaga 6360
tccagttcga tgtaacccac tcgtgcaccc aactgatctt cagcatcttt tactttcacc 6420

-continued

```
agcgtttctg ggtgagcaaa aacaggaagg caaaatgccg caaaaaaggg aataagggcg   6480

acacggaaat gttgaatact catactcttc ctttttcaat attattgaag catttatcag   6540

ggttattgtc tcatgagcgg atacatattt gaatgtattt agaaaaataa acaaataggg   6600

gttccgcgca catttccccg aaaagtgcca cctgacgtc                          6639
```

<210> SEQ ID NO 13
<211> LENGTH: 6801
<212> TYPE: DNA
<213> ORGANISM: Artificial Sequence
<220> FEATURE:
<220> FEATURE:
<223> OTHER INFORMATION: Description of Artificial Sequence: Construct LBDASNLSVP16

<400> SEQUENCE: 13

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattcctg    960

cagcccgggg gatctatggc ccaggcggcc ctcgagccct atgcttgccc tgtcgagtcc   1020

tgcgatcgcc gcttttctaa gtcggctgat ctgaagcgcc atatccgcat ccacacaggc   1080

cagaagcctt tccagtgtcg aatatgcatg cgtaacttca gtcgtagtga ccaccttacc   1140

acccacatcc gcacccacac aggcgagaag ccttttgcct gtgacatttg tgggaggaag   1200

tttgccagga gtgatgaacg caagaggcat accaaaatcc atttaagaca gagggactct   1260

agaactagtt ctgctggaga catgagagct gccaaccttt ggccaagccc gctcatgatc   1320

aaacgctcta agaagaacag cctggccttg tccctgacgg ccgaccagat ggtcagtgcc   1380

ttgttggatg ctgagccccc catactctat tccgagtatg atcctaccag acccttcagt   1440

gaagcttcga tgatgggctt actgaccaac ctggcagaca gggagctggt tcacatgatc   1500

aactgggcga agagggtgcc aggctttgtg gatttgaccc tccatgatca ggtccacctt   1560

ctagaatgtg cctggctaga gatcctgatg attggtctcg tctggcgctc catggagcac   1620

ccagggaagc tactgtttgc tcctaacttg ctcttggaca ggaaccaggg aaaatgtgta   1680

gagggcatgg tggagatctt cgacatgctg ctggctacat catctcggtt ccgcatgatg   1740

aatctgcagg gagaggagtt tgtgtgcctc aaatctatta ttttgcttaa ttctggagtg   1800
```

-continued

```
tacacatttc tgtccagcac cctgaagtct ctggaagaga aggaccatat ccaccgagtc   1860
ctggacaaga tcacagacac tttgatccac ctgatggcca aggcaggcct gaccctgcag   1920
cagcagcacc agcggctggc ccagctcctc ctcatcctct cccacatcag gcacatgagt   1980
aacaaaggca tggagcatct gtacagcatg aagtgcaaga acgtggtgcc cctctatgac   2040
ctgctgctgg agatgctgga cgcccaccgc ctacatgcgc ccactagccg tacgccgaaa   2100
aagaaacgca aagttgggcg cgccggcgct cccccgaccg atgtcagcct gggggacgag   2160
ctccacttag acggcgagga cgtggcgatg gcgcatgccg acgcgctaga cgatttcgat   2220
ctggacatgt tgggggacgg ggattccccg ggtccgggat ttacccccca cgactccgcc   2280
ccctacggcg ctctggatat ggccgacttc gagtttgagc agatgtttac cgatgccctt   2340
ggaattgacg agtacggttt aattaactac ccgtacgacg ttccggacta cgcttcttga   2400
gaattcgcgg ccgctcgagt ctagagggcc cgtttaaacc cgctgatcag cctcgactgt   2460
gccttctagt tgccagccat ctgttgtttg cccctccccc gtgccttcct tgaccctgga   2520
aggtgccact cccactgtcc tttcctaata aaatgaggaa attgcatcgc attgtctgag   2580
taggtgtcat tctattctgg ggggtggggt ggggcaggac agcaaggggg aggattggga   2640
agacaatagc aggcatgctg gggatgcggt gggctctatg gcttctgagg cggaaagaac   2700
cagctggggc tctagggggt atccccacgc gccctgtagc ggcgcattaa gcgcggcggg   2760
tgtggtggtt acgcgcagcg tgaccgctac acttgccagc gccctagcgc ccgctccttt   2820
cgctttcttc ccttcctttc tcgccacgtt cgccggcttt ccccgtcaag ctctaaatcg   2880
gggcatccct ttagggttcc gatttagtgc tttacggcac ctcgacccca aaaaacttga   2940
ttagggtgat ggttcacgta gtgggccatc gccctgatag acggtttttc gccctttgac   3000
gttggagtcc acgttcttta atagtggact cttgttccaa actggaacaa cactcaaccc   3060
tatctcggtc tattcttttg atttataagg gattttgggg atttcggcct attggttaaa   3120
aaatgagctg atttaacaaa aatttaacgc gaattaattc tgtggaatgt gtgtcagtta   3180
gggtgtggaa agtccccagg ctccccaggc aggcagaagt atgcaaagca tgcatctcaa   3240
ttagtcagca accaggtgtg gaaagtcccc aggctcccca gcaggcagaa gtatgcaaag   3300
catgcatctc aattagtcag caaccatagt cccgccccta actccgccca tcccgcccct   3360
aactccgccc agttccgccc attctccgcc ccatggctga ctaatttttt ttatttatgc   3420
agaggccgag gccgcctctg cctctgagct attccagaag tagtgaggag gcttttttgg   3480
aggcctaggc ttttgcaaaa agctcccggg agcttgtata tccattttcg gatctgatca   3540
agagacagga tgaggatcgt ttcgcatgat tgaacaagat ggattgcacg caggttctcc   3600
ggccgcttgg gtggagaggc tattcggcta tgactgggca caacagacaa tcggctgctc   3660
tgatgccgcc gtgttccggc tgtcagcgca ggggcgcccg gttctttttg tcaagaccga   3720
cctgtccggt gccctgaatg aactgcagga cgaggcagcg cggctatcgt ggctggccac   3780
gacgggcgtt ccttgcgcag ctgtgctcga cgttgtcact gaagcgggaa gggactggct   3840
gctattgggc gaagtgccgg ggcaggatct cctgtcatct caccttgctc ctgccgagaa   3900
agtatccatc atggctgatg caatgcggcg gctgcatacg cttgatccgg ctacctgccc   3960
attcgaccac caagcgaaac atcgcatcga gcgagcacgt actcggatgg aagccggtct   4020
tgtcgatcag gatgatctgg acgaagagca tcaggggctc gcgccagccg aactgttcgc   4080
caggctcaag gcgcgcatgc ccgacggcga ggatctcgtc gtgacccatg gcgatgcctg   4140
```

-continued

```
cttgccgaat atcatggtgg aaaatggccg cttttctgga ttcatcgact gtggccggct   4200
gggtgtggcg gaccgctatc aggacatagc gttggctacc cgtgatattg ctgaagagct   4260
tggcggcgaa tgggctgacc gcttcctcgt gctttacggt atcgccgctc ccgattcgca   4320
gcgcatcgcc ttctatcgcc ttcttgacga gttcttctga gcgggactct ggggttcgaa   4380
atgaccgacc aagcgacgcc caacctgcca tcacgagatt tcgattccac cgccgccttc   4440
tatgaaaggt tgggcttcgg aatcgttttc cgggacgccg gctggatgat cctccagcgc   4500
ggggatctca tgctggagtt cttcgcccac cccaacttgt ttattgcagc ttataatggt   4560
tacaaataaa gcaatagcat cacaaatttc acaaataaag catttttttc actgcattct   4620
agttgtggtt tgtccaaact catcaatgta tcttatcatg tctgtatacc gtcgacctct   4680
agctagagct tggcgtaatc atggtcatag ctgtttcctg tgtgaaattg ttatccgctc   4740
acaattccac acaacatacg agccggaagc ataaagtgta aagcctgggg tgcctaatga   4800
gtgagctaac tcacattaat tgcgttgcgc tcactgcccg ctttccagtc gggaaacctg   4860
tcgtgccagc tgcattaatg aatcggccaa cgcgcgggga gaggcggttt gcggcgagcg   4920
gtatcagctc actcaaaggc ggtaatacgg ttatccacag aatcagggga taacgcagga   4980
aagaacatgt gagcaaaagg ccagcaaaag gccaggaacc gtaaaaaggc cgcgttgctg   5040
gcgtttttcc ataggctccg cccccctgac gagcatcaca aaaatcgacg ctcaagtcag   5100
aggtggcgaa acccgacagg actataaaga taccaggcgt ttccccctgg aagctccctc   5160
gtgcgctctc ctgttccgac cctgccgctt accggatacc tgtccgcctt tctcccttcg   5220
ggaagcgtgg cgctttctca atgctcacgc tgtaggtatc tcagttcggt gtaggtcgtt   5280
cgctccaagc tgggctgtgt gcacgaaccc cccgttcagc ccgaccgctg cgccttatcc   5340
ggtaactatc gtcttgagtc caacccggta agacacgact tatcgccact ggcagcagcc   5400
actggtaaca ggattagcag agcgaggtat gtaggcggtg ctacagagtt cttgaagtgg   5460
tggcctaact acggctacac tagaaggaca gtatttggta tctgcgctct gctgaagcca   5520
gttaccttcg gaaaaagagt tggtagctct tgatccggca aacaaaccac cgctggtagc   5580
ggtggttttt ttgtttgcaa gcagcagatt acgcgcagaa aaaaaggatc tcaagaagat   5640
cctttgatct tttctacggg gtctgacgct cagtggaacg aaaactcacg ttaagggatt   5700
ttggtcatga gattatcaaa aaggatcttc acctagatcc ttttaaatta aaaatgaagt   5760
tttaaatcaa tctaaagtat atatgagtaa acttggtctg acagttacca atgcttaatc   5820
agtgaggcac ctatctcagc gatctgtcta tttcgttcat ccatagttgc ctgactcccc   5880
gtcgtgtaga taactacgat acgggagggc ttaccatctg gccccagtgc tgcaatgata   5940
ccgcgagacc cacgctcacc ggctccagat ttatcagcaa taaaccagcc agccggaagg   6000
gccgagcgca gaagtggtcc tgcaacttta tccgcctcca tccagtctat taattgttgc   6060
cgggaagcta gagtaagtag ttcgccagtt aatagtttgc gcaacgttgt tgccattgct   6120
acaggcatcg tggtgtcacg ctcgtcgttt ggtatggctt cattcagctc cggttcccaa   6180
cgatcaaggc gagttacatg atcccccatg ttgtgcaaaa aagcggttag ctccttcggt   6240
cctccgatcg ttgtcagaag taagttggcc gcagtgttat cactcatggt tatggcagca   6300
ctgcataatt ctcttactgt catgccatcc gtaagatgct tttctgtgac tggtgagtac   6360
tcaaccaagt cattctgaga atagtgtatg cggcgaccga gttgctcttg cccggcgtca   6420
atacgggata ataccgcgcc acatagcaga actttaaaag tgctcatcat tggaaaacgt   6480
tcttcggggc gaaaactctc aaggatctta ccgctgttga gatccagttc gatgtaaccc   6540
```

actcgtgcac ccaactgatc ttcagcatct tttactttca ccagcgtttc tgggtgagca 6600
aaaacaggaa ggcaaaatgc cgcaaaaaag ggaataaggg cgacacggaa atgttgaata 6660
ctcatactct tcctttttca atattattga agcatttatc agggttattg tctcatgagc 6720
ggatacatat ttgaatgtat ttagaaaaat aaacaaatag gggttccgcg cacatttccc 6780
cgaaaagtgc cacctgacgt c 6801

<210> SEQ ID NO 14
<211> LENGTH: 6695
<212> TYPE: DNA
<213> ORGANISM: Artificial Sequence
<220> FEATURE:
<220> FEATURE:
<223> OTHER INFORMATION: Description of Artificial Sequence: Construct
LBDBSG400V

<400> SEQUENCE: 14
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cagcccgggg gatctatggc ccaggcggcc ctcgagccct atgcttgccc tgtcgagtcc 1020
tgcgatcgcc gcttttctaa gtcggctgat ctgaagcgcc atatccgcat ccacacaggc 1080
cagaagcctt tccagtgtcg aatatgcatg cgtaacttca gtcgtagtga ccaccttacc 1140
acccacatcc gcacccacac aggcgagaag ccttttgcct gtgacatttg tgggaggaag 1200
tttgccagga gtgatgaacg caagaggcat accaaaatcc atttaagaca gagggactct 1260
agaactagtg accgaagagg agggagaatg ttgaaacaca agcgccagag agatgatggg 1320
gagggcaggg gtgaagtggg gtctgctgga gacatgagag ctgccaacct ttggccaagc 1380
ccgctcatga tcaaacgctc taagaagaac agcctggcct tgtccctgac ggccgaccag 1440
atggtcagtg ccttgttgga tgctgagccc cccatactct attccgagta tgatcctacc 1500
agacccttca gtgaagcttc gatgatgggc ttactgacca acctggcaga cagggagctg 1560
gttcacatga tcaactgggc gaagagggtg ccaggctttg tggatttgac cctccatgat 1620
caggtccacc ttctagaatg tgcctggcta gagatcctga tgattggtct cgtctggcgc 1680

-continued

```
tccatggagc acccagtgaa gctactgttt gctcctaact tgctcttgga caggaaccag   1740
ggaaaatgtg tagagggcat ggtggagatc ttcgacatgc tgctggctac atcatctcgg   1800
ttccgcatga tgaatctgca gggagaggag tttgtgtgcc tcaaatctat tattttgctt   1860
aattctggag tgtacacatt tctgtccagc accctgaagt ctctggaaga gaaggaccat   1920
atccaccgag tcctggacaa gatcacagac actttgatcc acctgatggc caaggcaggc   1980
ctgaccctgc agcagcagca ccagcggctg gcccagctcc tcctcatcct ctcccacatc   2040
aggcacatga gtaacaaagg catggagcat ctgtacagca tgaagtgcaa gaacgtggtg   2100
cccctctatg acctgctgct ggagatgctg gacgcccacc gcctacatgc gcccactagc   2160
cgtacgccgg ccgacgccct ggacgacttc gacctggaca tgctgccggc cgacgccctg   2220
gacgacttcg acctggacat gctgccggcc gacgccctgg acgacttcga cctggacatg   2280
ctgccggggt aactaagtaa gcggccgctc gagtctagag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcaagagac aggatgagga tcgtttcgca tgattgaaca agatggattg   3480
cacgcaggtt ctccggccgc ttgggtggag aggctattcg gctatgactg ggcacaacag   3540
acaatcggct gctctgatgc cgccgtgttc cggctgtcag cgcaggggcg cccggttctt   3600
tttgtcaaga ccgacctgtc cggtgccctg aatgaactgc aggacgaggc agcgcggcta   3660
tcgtggctgg ccacgacggg cgttccttgc gcagctgtgc tcgacgttgt cactgaagcg   3720
ggaagggact ggctgctatt gggcgaagtg ccggggcagg atctcctgtc atctcacctt   3780
gctcctgccg agaaagtatc catcatggct gatgcaatgc ggcggctgca tacgcttgat   3840
ccggctacct gcccattcga ccaccaagcg aaacatcgca tcgagcgagc acgtactcgg   3900
atggaagccg gtcttgtcga tcaggatgat ctggacgaag agcatcaggg gctcgcgcca   3960
gccgaactgt tcgccaggct caaggcgcgc atgcccgacg gcgaggatct cgtcgtgacc   4020
catggcgatg cctgcttgcc gaatatcatg gtggaaaatg gccgcttttc tggattcatc   4080
```

-continued

```
gactgtggcc ggctgggtgt ggcggaccgc tatcaggaca tagcgttggc tacccgtgat   4140
attgctgaag agcttggcgg cgaatgggct gaccgcttcc tcgtgcttta cggtatcgcc   4200
gctcccgatt cgcagcgcat cgccttctat cgccttcttg acgagttctt ctgagcggga   4260
ctctggggtt cgaaatgacc gaccaagcga cgcccaacct gccatcacga gatttcgatt   4320
ccaccgccgc cttctatgaa aggttgggct tcggaatcgt tttccgggac gccggctgga   4380
tgatcctcca gcgcggggat ctcatgctgg agttcttcgc ccaccccaac ttgtttattg   4440
cagcttataa tggttacaaa taaagcaata gcatcacaaa tttcacaaat aaagcatttt   4500
tttcactgca ttctagttgt ggtttgtcca aactcatcaa tgtatcttat catgtctgta   4560
taccgtcgac ctctagctag agcttggcgt aatcatggtc atagctgttt cctgtgtgaa   4620
attgttatcc gctcacaatt ccacacaaca tacgagccgg aagcataaag tgtaaagcct   4680
ggggtgccta atgagtgagc taactcacat taattgcgtt gcgctcactg cccgctttcc   4740
agtcgggaaa cctgtcgtgc cagctgcatt aatgaatcgg ccaacgcgcg gggagaggcg   4800
gtttgcggcg agcggtatca gctcactcaa aggcggtaat acggttatcc acagaatcag   4860
gggataacgc aggaaagaac atgtgagcaa aaggccagca aaaggccagg aaccgtaaaa   4920
aggccgcgtt gctggcgttt ttccataggc tccgcccccc tgacgagcat cacaaaaatc   4980
gacgctcaag tcagaggtgg cgaaacccga caggactata aagataccag gcgtttcccc   5040
ctggaagctc cctcgtgcgc tctcctgttc cgaccctgcc gcttaccgga tacctgtccg   5100
cctttctccc ttcgggaagc gtggcgcttt ctcaatgctc acgctgtagg tatctcagtt   5160
cggtgtaggt cgttcgctcc aagctgggct gtgtgcacga accccccgtt cagcccgacc   5220
gctgcgcctt atccggtaac tatcgtcttg agtccaaccc ggtaagacac gacttatcgc   5280
cactggcagc agccactggt aacaggatta gcagagcgag gtatgtaggc ggtgctacag   5340
agttcttgaa gtggtggcct aactacggct acactagaag gacagtattt ggtatctgcg   5400
ctctgctgaa gccagttacc ttcggaaaaa gagttggtag ctcttgatcc ggcaaacaaa   5460
ccaccgctgg tagcggtggt ttttttgttt gcaagcagca gattacgcgc agaaaaaaag   5520
gatctcaaga agatcctttg atcttttcta cggggtctga cgctcagtgg aacgaaaact   5580
cacgttaagg gattttggtc atgagattat caaaaaggat cttcacctag atccttttaa   5640
attaaaaatg aagttttaaa tcaatctaaa gtatatatga gtaaacttgg tctgacagtt   5700
accaatgctt aatcagtgag gcacctatct cagcgatctg tctatttcgt tcatccatag   5760
ttgcctgact ccccgtcgtg tagataacta cgatacggga gggcttacca tctggcccca   5820
gtgctgcaat gataccgcga gacccacgct caccggctcc agatttatca gcaataaacc   5880
agccagccgg aagggccgag cgcagaagtg gtcctgcaac tttatccgcc tccatccagt   5940
ctattaattg ttgccgggaa gctagagtaa gtagttcgcc agttaatagt ttgcgcaacg   6000
ttgttgccat tgctacaggc atcgtggtgt cacgctcgtc gtttggtatg gcttcattca   6060
gctccggttc ccaacgatca aggcgagtta catgatcccc catgttgtgc aaaaaagcgg   6120
ttagctcctt cggtcctccg atcgttgtca gaagtaagtt ggccgcagtg ttatcactca   6180
tggttatggc agcactgcat aattctctta ctgtcatgcc atccgtaaga tgcttttctg   6240
tgactggtga gtactcaacc aagtcattct gagaatagtg tatgcggcga ccgagttgct   6300
cttgcccggc gtcaatacgg gataataccg cgccacatag cagaacttta aaagtgctca   6360
tcattggaaa acgttcttcg gggcgaaaac tctcaaggat cttaccgctg ttgagatcca   6420
```

-continued gttcgatgta acccactcgt gcacccaact gatcttcagc atcttttact ttcaccagcg 6480
tttctgggtg agcaaaaaca ggaaggcaaa atgccgcaaa aaagggaata agggcgacac 6540
ggaaatgttg aatactcata ctcttccttt ttcaatatta ttgaagcatt tatcagggtt 6600
attgtctcat gagcggatac atatttgaat gtatttagaa aaataaacaa ataggggttc 6660
cgcgcacatt tccccgaaaa gtgccacctg acgtc 6695

<210> SEQ ID NO 15
<211> LENGTH: 6695
<212> TYPE: DNA
<213> ORGANISM: Artificial Sequence
<220> FEATURE:
<220> FEATURE:
<223> OTHER INFORMATION: Description of Artificial Sequence: Construct LBDBSG521R

<400> SEQUENCE: 15
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattcctg 960
cagcccgggg gatctatggc ccaggcggcc ctcgagccct atgcttgccc tgtcgagtcc 1020
tgcgatcgcc gcttttctaa gtcggctgat ctgaagcgcc atatccgcat ccacacaggc 1080
cagaagcctt tccagtgtcg aatatgcatg cgtaacttca gtcgtagtga ccaccttacc 1140
acccacatcc gcacccacac aggcgagaag ccttttgcct gtgacatttg tgggaggaag 1200
tttgccagga gtgatgaacg caagaggcat accaaaatcc atttaagaca gagggactct 1260
agaactagtg accgaagagg agggagaatg ttgaaacaca agcgccagag agatgatggg 1320
gagggcaggg gtgaagtggg gtctgctgga gacatgagag ctgccaacct ttggccaagc 1380
ccgctcatga tcaaacgctc taagaagaac agcctggcct tgtccctgac ggccgaccag 1440
atggtcagtg ccttgttgga tgctgagccc cccatactct attccgagta tgatcctacc 1500
agacccttca gtgaagcttc gatgatgggc ttactgacca acctggcaga cagggagctg 1560
gttcacatga tcaactgggc gaagagggtg ccaggctttg tggatttgac cctccatgat 1620
caggtccacc ttctagaatg tgcctggcta gagatcctga tgattggtct cgtctggcgc 1680
tccatggagc acccagggaa gctactgttt gctcctaact tgctcttgga caggaaccag 1740

-continued

```
ggaaaatgtg tagagggcat ggtggagatc ttcgacatgc tgctggctac atcatctcgg   1800
ttccgcatga tgaatctgca gggagaggag tttgtgtgcc tcaaatctat tattttgctt   1860
aattctggag tgtacacatt tctgtccagc accctgaagt ctctggaaga gaaggaccat   1920
atccaccgag tcctggacaa gatcacagac actttgatcc acctgatggc caaggcaggc   1980
ctgaccctgc agcagcagca ccagcggctg gcccagctcc tcctcatcct ctcccacatc   2040
aggcacatga gtaacaaacg catggagcat ctgtacagca tgaagtgcaa gaacgtggtg   2100
cccctctatg acctgctgct ggagatgctg gacgcccacc gcctacatgc gcccactagc   2160
cgtacgccgg ccgacgccct ggacgacttc gacctggaca tgctgccggc cgacgccctg   2220
gacgacttcg acctggacat gctgccggcc gacgccctgg acgacttcga cctggacatg   2280
ctgccggggt aactaagtaa gcggccgctc gagtctagag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcaagagac aggatgagga tcgtttcgca tgattgaaca agatggattg   3480
cacgcaggtt ctccggccgc ttgggtggag aggctattcg gctatgactg ggcacaacag   3540
acaatcggct gctctgatgc cgccgtgttc cggctgtcag cgcaggggcg cccggttctt   3600
tttgtcaaga ccgacctgtc cggtgccctg aatgaactgc aggacgaggc agcgcggcta   3660
tcgtggctgg ccacgacggg cgttccttgc gcagctgtgc tcgacgttgt cactgaagcg   3720
ggaagggact ggctgctatt gggcgaagtg ccggggcagg atctcctgtc atctcacctt   3780
gctcctgccg agaaagtatc catcatggct gatgcaatgc ggcggctgca tacgcttgat   3840
ccggctacct gcccattcga ccaccaagcg aaacatcgca tcgagcgagc acgtactcgg   3900
atggaagccg gtcttgtcga tcaggatgat ctggacgaag agcatcaggg gctcgcgcca   3960
gccgaactgt tcgccaggct caaggcgcgc atgcccgacg gcgaggatct cgtcgtgacc   4020
catggcgatg cctgcttgcc gaatatcatg gtggaaaatg gccgcttttc tggattcatc   4080
```

-continued

```
gactgtggcc ggctgggtgt ggcggaccgc tatcaggaca tagcgttggc tacccgtgat   4140
attgctgaag agcttggcgg cgaatgggct gaccgcttcc tcgtgcttta cggtatcgcc   4200
gctcccgatt cgcagcgcat cgccttctat cgccttcttg acgagttctt ctgagcggga   4260
ctctggggtt cgaaatgacc gaccaagcga cgcccaacct gccatcacga gatttcgatt   4320
ccaccgccgc cttctatgaa aggttgggct tcggaatcgt tttccgggac gccggctgga   4380
tgatcctcca gcgcggggat ctcatgctgg agttcttcgc ccaccccaac ttgtttattg   4440
cagcttataa tggttacaaa taaagcaata gcatcacaaa tttcacaaat aaagcatttt   4500
tttcactgca ttctagttgt ggtttgtcca aactcatcaa tgtatcttat catgtctgta   4560
taccgtcgac ctctagctag agcttggcgt aatcatggtc atagctgttt cctgtgtgaa   4620
attgttatcc gctcacaatt ccacacaaca tacgagccgg aagcataaag tgtaaagcct   4680
ggggtgccta atgagtgagc taactcacat taattgcgtt gcgctcactg cccgctttcc   4740
agtcgggaaa cctgtcgtgc cagctgcatt aatgaatcgg ccaacgcgcg gggagaggcg   4800
gtttgcggcg agcggtatca gctcactcaa aggcggtaat acggttatcc acagaatcag   4860
gggataacgc aggaaagaac atgtgagcaa aaggccagca aaaggccagg aaccgtaaaa   4920
aggccgcgtt gctggcgttt ttccataggc tccgcccccc tgacgagcat cacaaaaatc   4980
gacgctcaag tcagaggtgg cgaaacccga caggactata aagataccag gcgtttcccc   5040
ctggaagctc cctcgtgcgc tctcctgttc cgaccctgcc gcttaccgga tacctgtccg   5100
cctttctccc ttcgggaagc gtggcgcttt ctcaatgctc acgctgtagg tatctcagtt   5160
cggtgtaggt cgttcgctcc aagctgggct gtgtgcacga accccccgtt cagcccgacc   5220
gctgcgcctt atccggtaac tatcgtcttg agtccaaccc ggtaagacac gacttatcgc   5280
cactggcagc agccactggt aacaggatta gcagagcgag gtatgtaggc ggtgctacag   5340
agttcttgaa gtggtggcct aactacggct acactagaag gacagtattt ggtatctgcg   5400
ctctgctgaa gccagttacc ttcggaaaaa gagttggtag ctcttgatcc ggcaaacaaa   5460
ccaccgctgg tagcggtggt ttttttgttt gcaagcagca gattacgcgc agaaaaaaag   5520
gatctcaaga agatcctttg atcttttcta cggggtctga cgctcagtgg aacgaaaact   5580
cacgttaagg gattttggtc atgagattat caaaaaggat cttcacctag atccttttaa   5640
attaaaaatg aagttttaaa tcaatctaaa gtatatatga gtaaacttgg tctgacagtt   5700
accaatgctt aatcagtgag gcacctatct cagcgatctg tctatttcgt tcatccatag   5760
ttgcctgact ccccgtcgtg tagataacta cgatacggga gggcttacca tctggcccca   5820
gtgctgcaat gataccgcga gacccacgct caccggctcc agatttatca gcaataaacc   5880
agccagccgg aagggccgag cgcagaagtg gtcctgcaac tttatccgcc tccatccagt   5940
ctattaattg ttgccgggaa gctagagtaa gtagttcgcc agttaatagt ttgcgcaacg   6000
ttgttgccat tgctacaggc atcgtggtgt cacgctcgtc gtttggtatg gcttcattca   6060
gctccggttc ccaacgatca aggcgagtta catgatcccc catgttgtgc aaaaaagcgg   6120
ttagctcctt cggtcctccg atcgttgtca gaagtaagtt ggccgcagtg ttatcactca   6180
tggttatggc agcactgcat aattctctta ctgtcatgcc atccgtaaga tgcttttctg   6240
tgactggtga gtactcaacc aagtcattct gagaatagtg tatgcggcga ccgagttgct   6300
cttgcccggc gtcaatacgg gataataccg cgccacatag cagaacttta aaagtgctca   6360
tcattggaaa acgttcttcg gggcgaaaac tctcaaggat cttaccgctg ttgagatcca   6420
gttcgatgta acccactcgt gcacccaact gatcttcagc atcttttact ttcaccagcg   6480
```

-continued

```
tttctgggtg agcaaaaaca ggaaggcaaa atgccgcaaa aaagggaata agggcgacac   6540

ggaaatgttg aatactcata ctcttccttt ttcaatatta ttgaagcatt tatcagggtt   6600

attgtctcat gagcggatac atatttgaat gtatttagaa aaataaacaa ataggggttc   6660

cgcgcacatt tccccgaaaa gtgccacctg acgtc                              6695
```

<210> SEQ ID NO 16
<211> LENGTH: 6801
<212> TYPE: DNA
<213> ORGANISM: Artificial Sequence
<220> FEATURE:
<220> FEATURE:
<223> OTHER INFORMATION: Description of Artificial Sequence: Construct
LBDBSVP16

<400> SEQUENCE: 16

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattcctg    960

cagcccgggg gatctatggc ccaggcggcc ctcgagccct atgcttgccc tgtcgagtcc   1020

tgcgatcgcc gcttttctaa gtcggctgat ctgaagcgcc atatccgcat ccacacaggc   1080

cagaagcctt tccagtgtcg aatatgcatg cgtaacttca gtcgtagtga ccaccttacc   1140

acccacatcc gcacccacac aggcgagaag ccttttgcct gtgacatttg tgggaggaag   1200

tttgccagga gtgatgaacg caagaggcat accaaaatcc atttaagaca gagggactct   1260

agaactagtg accgaagagg agggagaatg ttgaaacaca agcgccagag agatgatggg   1320

gagggcaggg gtgaagtggg gtctgctgga gacatgagag ctgccaacct ttggccaagc   1380

ccgctcatga tcaaacgctc taagaagaac agcctggcct tgtccctgac ggccgaccag   1440

atggtcagtg ccttgttgga tgctgagccc cccatactct attccgagta tgatcctacc   1500

agacccttca gtgaagcttc gatgatgggc ttactgacca acctggcaga cagggagctg   1560

gttcacatga tcaactgggc gaagagggtg ccaggctttg tggatttgac cctccatgat   1620

caggtccacc ttctagaatg tgcctggcta gagatcctga tgattggtct cgtctggcgc   1680

tccatggagc acccagggaa gctactgttt gctcctaact tgctcttgga caggaaccag   1740
```

-continued

```
ggaaaatgtg tagagggcat ggtggagatc ttcgacatgc tgctggctac atcatctcgg   1800
ttccgcatga tgaatctgca gggagaggag tttgtgtgcc tcaaatctat tattttgctt   1860
aattctggag tgtacacatt tctgtccagc accctgaagt ctctggaaga gaaggaccat   1920
atccaccgag tcctggacaa gatcacagac actttgatcc acctgatggc caaggcaggc   1980
ctgaccctgc agcagcagca ccagcggctg gcccagctcc tcctcatcct ctcccacatc   2040
aggcacatga gtaacaaagg catggagcat ctgtacagca tgaagtgcaa gaacgtggtg   2100
cccctctatg acctgctgct ggagatgctg gacgcccacc gcctacatgc gcccactagc   2160
cgtacgggcg ctcccccgac cgatgtcagc ctgggggacg agctccactt agacggcgag   2220
gacgtggcga tggcgcatgc cgacgcgcta gacgatttcg atctggacat gttgggggac   2280
ggggattccc cgggtccggg atttaccccc cacgactccg cccccctacgg cgctctggat   2340
atggccgact tcgagtttga gcagatgttt accgatgccc ttggaattga cgagtacggt   2400
tagggggcgg ccgctcgagt ctagagggcc cgtttaaacc cgctgatcag cctcgactgt   2460
gccttctagt tgccagccat ctgttgtttg cccctccccc gtgccttcct tgaccctgga   2520
aggtgccact cccactgtcc tttcctaata aaatgaggaa attgcatcgc attgtctgag   2580
taggtgtcat tctattctgg ggggtggggt ggggcaggac agcaaggggg aggattggga   2640
agacaatagc aggcatgctg gggatgcggt gggctctatg gcttctgagg cggaaagaac   2700
cagctggggc tctagggggt atccccacgc gccctgtagc ggcgcattaa gcgcggcggg   2760
tgtggtggtt acgcgcagcg tgaccgctac acttgccagc gccctagcgc ccgctccttt   2820
cgctttcttc ccttcctttc tcgccacgtt cgccggcttt ccccgtcaag ctctaaatcg   2880
gggcatccct ttagggttcc gatttagtgc tttacggcac ctcgacccca aaaaacttga   2940
ttagggtgat ggttcacgta gtgggccatc gccctgatag acggtttttc gccctttgac   3000
gttggagtcc acgttcttta atagtggact cttgttccaa actggaacaa cactcaaccc   3060
tatctcggtc tattcttttg atttataagg gattttgggg atttcggcct attggttaaa   3120
aaatgagctg atttaacaaa aatttaacgc gaattaattc tgtggaatgt gtgtcagtta   3180
gggtgtggaa agtccccagg ctccccaggc aggcagaagt atgcaaagca tgcatctcaa   3240
ttagtcagca accaggtgtg gaaagtcccc aggctcccca gcaggcagaa gtatgcaaag   3300
catgcatctc aattagtcag caaccatagt cccgccccta actccgccca tcccgcccct   3360
aactccgccc agttccgccc attctccgcc ccatggctga ctaatttttt ttatttatgc   3420
agaggccgag gccgcctctg cctctgagct attccagaag tagtgaggag gcttttttgg   3480
aggcctaggc ttttgcaaaa agctcccggg agcttgtata tccattttcg gatctgatca   3540
agagacagga tgaggatcgt ttcgcatgat tgaacaagat ggattgcacg caggttctcc   3600
ggccgcttgg gtggagaggc tattcggcta tgactgggca caacagacaa tcggctgctc   3660
tgatgccgcc gtgttccggc tgtcagcgca ggggcgcccg gttctttttg tcaagaccga   3720
cctgtccggt gccctgaatg aactgcagga cgaggcagcg cggctatcgt ggctggccac   3780
gacgggcgtt ccttgcgcag ctgtgctcga cgttgtcact gaagcgggaa gggactggct   3840
gctattgggc gaagtgccgg ggcaggatct cctgtcatct caccttgctc ctgccgagaa   3900
agtatccatc atggctgatg caatgcggcg gctgcatacg cttgatccgg ctacctgccc   3960
attcgaccac caagcgaaac atcgcatcga gcgagcacgt actcggatgg aagccggtct   4020
tgtcgatcag gatgatctgg acgaagagca tcaggggctc gcgccagccg aactgttcgc   4080
caggctcaag gcgcgcatgc ccgacggcga ggatctcgtc gtgacccatg gcgatgcctg   4140
```

-continued cttgccgaat atcatggtgg aaaatggccg cttttctgga ttcatcgact gtggccggct 4200
gggtgtggcg gaccgctatc aggacatagc gttggctacc cgtgatattg ctgaagagct 4260
tggcggcgaa tgggctgacc gcttcctcgt gctttacggt atcgccgctc ccgattcgca 4320
gcgcatcgcc ttctatcgcc ttcttgacga gttcttctga gcgggactct ggggttcgaa 4380
atgaccgacc aagcgacgcc caacctgcca tcacgagatt tcgattccac cgccgccttc 4440
tatgaaaggt tgggcttcgg aatcgttttc cgggacgccg gctggatgat cctccagcgc 4500
ggggatctca tgctggagtt cttcgcccac cccaacttgt ttattgcagc ttataatggt 4560
tacaaataaa gcaatagcat cacaaatttc acaaataaag catttttttc actgcattct 4620
agttgtggtt tgtccaaact catcaatgta tcttatcatg tctgtatacc gtcgacctct 4680
agctagagct tggcgtaatc atggtcatag ctgtttcctg tgtgaaattg ttatccgctc 4740
acaattccac acaacatacg agccggaagc ataaagtgta aagcctgggg tgcctaatga 4800
gtgagctaac tcacattaat tgcgttgcgc tcactgcccg ctttccagtc gggaaacctg 4860
tcgtgccagc tgcattaatg aatcggccaa cgcgcgggga gaggcggttt gcggcgagcg 4920
gtatcagctc actcaaaggc ggtaatacgg ttatccacag aatcagggga taacgcagga 4980
aagaacatgt gagcaaaagg ccagcaaaag gccaggaacc gtaaaaaggc cgcgttgctg 5040
gcgtttttcc ataggctccg cccccctgac gagcatcaca aaaatcgacg ctcaagtcag 5100
aggtggcgaa acccgacagg actataaaga taccaggcgt ttccccctgg aagctccctc 5160
gtgcgctctc ctgttccgac cctgccgctt accggatacc tgtccgcctt tctcccttcg 5220
ggaagcgtgg cgctttctca atgctcacgc tgtaggtatc tcagttcggt gtaggtcgtt 5280
cgctccaagc tgggctgtgt gcacgaaccc cccgttcagc ccgaccgctg cgccttatcc 5340
ggtaactatc gtcttgagtc caacccggta agacacgact tatcgccact ggcagcagcc 5400
actggtaaca ggattagcag agcgaggtat gtaggcggtg ctacagagtt cttgaagtgg 5460
tggcctaact acggctacac tagaaggaca gtatttggta tctgcgctct gctgaagcca 5520
gttaccttcg gaaaaagagt tggtagctct tgatccggca aacaaaccac cgctggtagc 5580
ggtggttttt ttgtttgcaa gcagcagatt acgcgcagaa aaaaaggatc tcaagaagat 5640
cctttgatct tttctacggg gtctgacgct cagtggaacg aaaactcacg ttaagggatt 5700
ttggtcatga gattatcaaa aaggatcttc acctagatcc ttttaaatta aaaatgaagt 5760
tttaaatcaa tctaaagtat atatgagtaa acttggtctg acagttacca atgcttaatc 5820
agtgaggcac ctatctcagc gatctgtcta tttcgttcat ccatagttgc ctgactcccc 5880
gtcgtgtaga taactacgat acgggagggc ttaccatctg gccccagtgc tgcaatgata 5940
ccgcgagacc cacgctcacc ggctccagat ttatcagcaa taaaccagcc agccggaagg 6000
gccgagcgca gaagtggtcc tgcaacttta tccgcctcca tccagtctat taattgttgc 6060
cgggaagcta gagtaagtag ttcgccagtt aatagtttgc gcaacgttgt tgccattgct 6120
acaggcatcg tggtgtcacg ctcgtcgttt ggtatggctt cattcagctc cggttcccaa 6180
cgatcaaggc gagttacatg atcccccatg ttgtgcaaaa aagcggttag ctccttcggt 6240
cctccgatcg ttgtcagaag taagttggcc gcagtgttat cactcatggt tatggcagca 6300
ctgcataatt ctcttactgt catgccatcc gtaagatgct tttctgtgac tggtgagtac 6360
tcaaccaagt cattctgaga atagtgtatg cggcgaccga gttgctcttg cccggcgtca 6420
atacgggata ataccgcgcc acatagcaga actttaaaag tgctcatcat tggaaaacgt 6480

-continued tcttcggggc gaaaactctc aaggatctta ccgctgttga gatccagttc gatgtaaccc 6540
actcgtgcac ccaactgatc ttcagcatct tttactttca ccagcgtttc tgggtgagca 6600
aaaacaggaa ggcaaaatgc cgcaaaaaag ggaataaggg cgacacggaa atgttgaata 6660
ctcatactct tcctttttca atattattga agcatttatc agggttattg tctcatgagc 6720
ggatacatat ttgaatgtat ttagaaaaat aaacaaatag gggttccgcg cacatttccc 6780
cgaaaagtgc cacctgacgt c 6801

<210> SEQ ID NO 17
<211> LENGTH: 1551
<212> TYPE: DNA
<213> ORGANISM: Artificial Sequence
<220> FEATURE:
<220> FEATURE:
<223> OTHER INFORMATION: Description of Artificial Sequence: Construct
VP16C7ER

<400> SEQUENCE: 17
gctagcgcca ccatggggcg cgccggcgct cccccgaccg atgtcagcct gggggacgag 60
ctccacttag acggcgagga cgtggcgatg gcgcatgccg acgcgctaga cgatttcgat 120
ctggacatgt tgggggacgg ggattccccg ggtccgggat ttacccccca cgactccgcc 180
ccctacggcg ctctggatat ggccgacttc gagtttgagc agatgtttac cgatgccctt 240
ggaattgacg agtacggttt aattaacaag cttggggccc aggcggccct cgagccctat 300
gcttgccctg tcgagtcctg cgatcgccgc ttttctaagt cggctgatct gaagcgccat 360
atccgcatcc acacaggcca gaagcccttc cagtgtcgaa tatgcatgcg taacttcagt 420
cgtagtgacc accttaccac ccacatccgc acccacacag gcgagaagcc ttttgcctgt 480
gacatttgtg ggaggaagtt tgccaggagt gatgaacgca agaggcatac caaaatccat 540
ttaagacaga aggactctag aactagtggc caggccggcc agggggatcc acgaaatgaa 600
atgggtgctt caggagacat gagggctgcc aacctttggc caagccctct tgtgattaag 660
cacactaaga agaatagccc tgccttgtcc ttgacagctg accagatggt cagtgccttg 720
ttggatgctg aaccgcccat gatctattct gaatatgatc cttctagacc cttcagtgaa 780
gcctcaatga tgggcttatt gaccaaccta gcagataggg agctggttca tatgatcaac 840
tgggcaaaga gagtgccagg ctttggggac ttgaatctcc atgatcaggt ccaccttctc 900
gagtgtgcct ggctggagat tctgatgatt ggtctcgtct ggcgctccat ggaacacccg 960
gggaagctcc tgtttgctcc taacttgctc ctggacagga atcaaggtaa atgtgtggaa 1020
ggcatggtgg agatctttga catgttgctt gctacgtcaa gtcggttccg catgatgaac 1080
ctgcagggtg aagagtttgt gtgcctcaaa tccatcattt tgcttaattc cggagtgtac 1140
acgtttctgt ccagcacctt gaagtctctg gaagagaagg accacatcca ccgtgtcctg 1200
gacaagatca cagacacttt gatccacctg atggccaaag ctggcctgac tctgcagcag 1260
cagcatcgcc gcctagctca gctccttctc attctttccc atatccggca catgagtaac 1320
aaaggcatgg agcatctcta caacatgaaa tgcaagaacg ttgtgcccct ctatgacctg 1380
ctcctggaga tgttggatgc ccaccgcctt catgccccag ccagtcgcat gggagtgccc 1440
ccagaggagc ccagccagac ccagctggcc accaccagct ccacttcagc acattcctta 1500
caaacctact acatacccc ggaagcagag ggcttcccca acacgatctg a 1551

<210> SEQ ID NO 18
<211> LENGTH: 1404

-continued

<212> TYPE: DNA
<213> ORGANISM: Artificial Sequence
<220> FEATURE:
<220> FEATURE:
<223> OTHER INFORMATION: Description of Artificial Sequence: Construct
VP16C7PR

<400> SEQUENCE: 18
gctagcgcca ccatggggcg cgccggcgct cccccgaccg atgtcagcct gggggacgag 60
ctccacttag acggcgagga cgtggcgatg gcgcatgccg acgcgctaga cgatttcgat 120
ctggacatgt tgggggacgg ggattccccg ggtccgggat ttacccccca cgactccgcc 180
ccctacggcg ctctggatat ggccgacttc gagtttgagc agatgtttac cgatgccctt 240
ggaattgacg agtacggttt aattaacaag cttggggccc aggcggccct cgagccctat 300
gcttgccctg tcgagtcctg cgatcgccgc ttttctaagt cggctgatct gaagcgccat 360
atccgcatcc acacaggcca gaagcccttc cagtgtcgaa tatgcatgcg taacttcagt 420
cgtagtgacc accttaccac ccacatccgc acccacacag gcgagaagcc ttttgcctgt 480
gacatttgtg ggaggaagtt tgccaggagt gatgaacgca agaggcatac caaaatccat 540
ttaagacaga aggactctag aactagtggc caggccggcc agggggatcc agtcagagtt 600
gtgagagcac tggatgctgt tgctctccca cagccagtgg gcgttccaaa tgaaagccaa 660
gccctaagcc agagattcac tttttcacca ggtcaagaca tacagttgat tccaccactg 720
atcaacctgt taatgagcat tgaaccagat gtgatctatg caggacatga caacacaaaa 780
cctgacacct ccagttcttt gctgacaagt cttaatcaac taggcgagag gcaacttctt 840
tcagtagtca agtggtctaa atcattgcca ggttttcgaa acttacatat tgatgaccag 900
ataactctca ttcagtattc ttggatgagc ttaatggtgt ttggtctagg atggagatcc 960
tacaaacacg tcagtgggca gatgctgtat tttgcacctg atctaatact aaatgaacag 1020
cggatgaaag aatcatcatt ctattcatta tgccttacca tgtggcagat cccacaggag 1080
tttgtcaagc ttcaagttag ccaagaagag ttcctctgta tgaaagtatt gttacttctt 1140
aatacaattc ctttggaagg gctacgaagt caaacccagt ttgaggagat gaggtcaagc 1200
tacattagag agctcatcaa ggcaattggt ttgaggcaaa aaggagttgt gtcgagctca 1260
cagcgtttct atcaacttac aaaacttctt gataacttgc atgatcttgt caaacaactt 1320
catctgtact gcttgaatac atttatccag tcccgggcac tgagtgttga atttccagaa 1380
atgatgtctg aagttattgc ttga 1404

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Recombinant
molecule

<400> SEQUENCE: 19

Thr Gly Glu Lys Pro
1 5

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Recombinant
molecule -continued

```
<220> FEATURE:
<221> NAME/KEY: n=
x ; X= any number
<222> LOCATION: 10

<400> SEQUENCE: 20

ggcccacgcn gcgtgggcg                                                    19


<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Recombinant
      molecule
<220> FEATURE:
<221> NAME/KEY: n=
x; X= any number
<222> LOCATION: 19

<400> SEQUENCE: 21

cgccgccgcc gccgccgcng cgtgggcg                                          28


<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 22

Met Lys Leu Leu Glu Pro Tyr Ala Cys Pro Val Glu Ser Cys Asp Arg
  1               5                  10                  15

Arg Phe Ser Lys Ser Ala Asp Leu Lys Arg His Ile Arg His Thr Gly
             20                  25                  30

Glu Lys Pro
         35


<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 23

Tyr Ala Cys Pro Val Glu Ser Cys Asp Arg Arg Phe Ser Lys Ser Ala
  1               5                  10                  15

Asp Leu Lys His Ile Arg Ile His Thr Gly Glu Lys Pro
             20                  25


<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Recombinant
      molecule

<400> SEQUENCE: 24

cctcgccgcc gcgggttttc ccgcgccccc gagg                                   34


<210> SEQ ID NO 25
<211> LENGTH: 34
```

-continued

<212> TYPE: DNA
<213> ORGANISM: Artificial Sequence
<220> FEATURE:
<223> OTHER INFORMATION: Description of Artificial Sequence: Recombinant
molecule
<220> FEATURE:
<221> NAME/KEY: nnn= a mixture of all 64 existing triplets and its
complement
<222> LOCATION: 26-28 and 7-9 respectively

<400> SEQUENCE: 25
ggacgcnnnc gcgggttttc ccgcgnnngc gtcc 34

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 26
gcgagcaagg tcgcggcagt cactaaaaga tttgccgcac tctgggcatt tatacggttt 60
ttcacc 66

<210> SEQ ID NO 27
<211> LENGTH: 74
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 27
gtgactgccg cgaccttgct cgccatcaac gcactcatac tggcgagaag ccatacaaat 60
gtccagaatg tggc 74

<210> SEQ ID NO 28
<211> LENGTH: 81
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 28
ggtaagtcct tctctcagag ctctcacctg gtgcgccacc agcgtaccca cacgggtgaa 60
aaaccgtata aatgcccaga g 81

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 29
acgcaccagc ttgtcagagc ggctgaaaga cttgccacat tctggacatt tgtatggc 58

<210> SEQ ID NO 30
<211> LENGTH: 87
<212> TYPE: DNA
<213> ORGANISM: Artificial Sequence
<220> FEATURE:
<223> OTHER INFORMATION: Description of Artificial Sequence: Recombinant -continued molecule

<400> SEQUENCE: 30
gaggaggagg aggtggccca ggcggccctc gagcccgggg agaagcccta tgcttgtccg 60
gaatgtggta agtccttctc tcagagc 87

<210> SEQ ID NO 31
<211> LENGTH: 81
<212> TYPE: DNA
<213> ORGANISM: Artificial Sequence
<220> FEATURE:
<223> OTHER INFORMATION: Description of Artificial Sequence: Recombinant molecule

<400> SEQUENCE: 31
gaggaggagg agctggccgg cctggccact agttttttta ccggtgtgag tacgttggtg 60
acgcaccagc ttgtcagagc g 81

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: Recombinant molecule

<400> SEQUENCE: 32
gaggaggagg ctagcgggat gtggtcttgc cctcaacagg tagg 44

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 33
gaggaggaga agcttctcgt ccgcctcccg cggcgctccg c 41

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Recombinant molecule

<400> SEQUENCE: 34
gaggaggagg ctagccgatg tgactgtctc ctcccaaatt tgtagacc 48

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Recombinant molecule

<400> SEQUENCE: 35
gaggaggaga agcttggtgc tcactgcggc tccggcccca tg 42

<210> SEQ ID NO 36
<211> LENGTH: 11
<212> TYPE: PRT

-continued

<213> ORGANISM: Artificial Sequence
<220> FEATURE:
<223> OTHER INFORMATION: Description of Artificial Sequence: Recombinant
molecule

<400> SEQUENCE: 36

Asp Ala Leu Asp Asp Phe Asp Leu Asp Met Leu
1 5 10

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 37
gaggagggct gcttgaggaa gta 23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 38
gccggagcca tggggccgga gcc 23

<210> SEQ ID NO 39
<211> LENGTH: 48
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 39
cctactgccg gcactagttc tgctggagac atgagagctg ccaacctt 48

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 40
cctaaacgta cggctagtgg gcgcatgtag gcggtgggcg tc 42

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Recombinant
molecule

<400> SEQUENCE: 41
cctaaacgta cggactgtgg cagggaaacc ctctgcctc 39

<210> SEQ ID NO 42
<211> LENGTH: 30
<212> TYPE: DNA

-continued

```
<213> ORGANISM: Artificial Sequence
<220> FEATURE:
<223> OTHER INFORMATION: Description of Artificial Sequence: Recombinant
      molecule

<400> SEQUENCE: 42

ccacttaaat gtgaaagtcg tacgccggcc                                        30


<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Recombinant
      molecule

<400> SEQUENCE: 43

tatggggggc tcagcatcca acaaggcact                                        30


<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Recombinant
      molecule

<400> SEQUENCE: 44

cctactacta gtgaccgaag aggagggaga atgttgaaac acaagcgc                    48


<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Recombinant
      molecule

<400> SEQUENCE: 45

cctactacta gtagtattca aggacataac gactatatgt gt                          42


<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Recombinant
      molecule

<400> SEQUENCE: 46

tatcatgtgc ggccgcttac ttagttaccc cggcagcat                              39


<210> SEQ ID NO 47
<211> LENGTH: 39
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 47

Pro Ala Asp Ala Leu Asp Asp Phe Asp Leu Asp Met Leu Pro Ala Asp
  1               5                  10                  15

Ala Leu Asp Asp Phe Asp Leu Asp Met Leu Pro Ala Asp Ala Leu Asp
             20                  25                  30

Asp Phe Asp Leu Asp Met Leu
```

-continued

35

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 48
gatccaaagt cgcgtgggcg cagcgcccac gcgatcaaag a 41

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 49
gatccaaagt ccaggcgagc gcgtgggcgg cagatcaaag a 41

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Recombinant molecule

<400> SEQUENCE: 50
gatccaaagt cgcgtgggcg caggcgcgag cgtgggcgga tcaaaga 47

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 51
gatccaaagt cgcgtgggcg cagcgcccac gcgatcaaag a 41

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 52
gatccaaagt cgcgtgggcg cactccggcc ccgatcaaag a 41

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 53
gatccaaagt cggggccgga gactccggcc ccgatcaaag a 41

-continued

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Recombinant molecule

<400> SEQUENCE: 54
gccggagcca tggggccgga gcc 23

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Recombinant molecule

<400> SEQUENCE: 55
cgctccctct caggcgcagg g 21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Recombinant molecule

<400> SEQUENCE: 56
ggcgcccact gtggggcggg c 21

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Recombinant molecule

<400> SEQUENCE: 57
gaggaggagg gccggccggg aagccgtgca ggaggagcgg c 41

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Recombinant molecule

<400> SEQUENCE: 58
gaggaggagg gcgcgcccag tcatttggtg cggcgcctcc agc 43

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Recombinant molecule

<400> SEQUENCE: 59
gaggaggagt taattaaagt catttggtgc ggcgcctcca gc 42

-continued

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Recombinant molecule

<400> SEQUENCE: 60
gaggaggagg gccggccggg gtggcggcca agactttgtt aagaagg 47

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: Recombinant molecule

<400> SEQUENCE: 61
gaggaggagg gcccaggcgg ccggtggcgg ccaagacttt gttaagaagg 50

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Recombinant molecule

<400> SEQUENCE: 62
gaggaggagg gcgcgcccgg catgaacgtc ccagatctcc tcgag 45

<210> SEQ ID NO 63
<211> LENGTH: 46
<212> TYPE: DNA
<213> ORGANISM: Artificial Sequence
<220> FEATURE:
<223> OTHER INFORMATION: Description of Artificial Sequence: Recombinant molecule

<400> SEQUENCE: 63
gaggaggagg gccggccgga ggcctgaatg tgtcatacag gagccc 46

<210> SEQ ID NO 64
<211> LENGTH: 49
<212> TYPE: DNA
<213> ORGANISM: Artificial Sequence
<220> FEATURE:
<223> OTHER INFORMATION: Description of Artificial Sequence: Recombinant molecule

<400> SEQUENCE: 64
gaggaggagg gcccaggcgg ccaggcctga atgtgtcata caggagccc 49

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence:  Recombinant molecule

<400> SEQUENCE: 65
gaggaggagg gcgcgcccct ccgccacgtc ccagatctcc tcgag 45

-continued

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Recombinant molecule

<400> SEQUENCE: 66
gtacagatgc tccatgcgtt tgttactcat gtgcc 35

<210> SEQ ID NO 67
<211> LENGTH: 35
<212> TYPE: DNA
<213> ORGANISM: Artificial Sequence
<220> FEATURE:
<223> OTHER INFORMATION: Description of Artificial Sequence: Recombinant molecule

<400> SEQUENCE: 67
ggcacatgag taacaaacgc atggagcatc tgtac 35

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Recombinant molecule

<400> SEQUENCE: 68
ccatggagca cccagtgaag ctactgtttg c 31

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Recombinant molecule

<400> SEQUENCE: 69
gcaaacagta gcttcactgg gtgctccatg g 31

<210> SEQ ID NO 70
<211> LENGTH: 624
<212> TYPE: DNA
<213> ORGANISM: Muridae
<220> FEATURE:
<221> NAME/KEY: CDS
<222> LOCATION: (1)...(624)
<223> OTHER INFORMATION: cDNA encoding secretion signal and murine endostain protein.

<400> SEQUENCE: 70

```
atg gag aca gac aca ctc ctg cta tgg gta ctg ctg ctc tgg gtt cca       48
Met Glu Thr Asp Thr Leu Leu Leu Trp Val Leu Leu Leu Trp Val Pro
 1               5                  10                  15

ggt tcc act ggt gac gcg gcc cat act cat cag gac ttt cag cca gtg       96
Gly Ser Thr Gly Asp Ala Ala His Thr His Gln Asp Phe Gln Pro Val
            20                  25                  30

ctc cac ctg gtg gca ctg aac acc ccc ctg tct gga ggc atg cgt ggt      144
Leu His Leu Val Ala Leu Asn Thr Pro Leu Ser Gly Gly Met Arg Gly
        35                  40                  45

atc cgt gga gca gat ttc cag tgc ttc cag caa gcc cga gcc gtg ggg      192
Ile Arg Gly Ala Asp Phe Gln Cys Phe Gln Gln Ala Arg Ala Val Gly
    50                  55                  60
```

-continued

```
ctg tcg ggc acc ttc cgg gct ttc ctg tcc tct agg ctg cag gat ctc      240
Leu Ser Gly Thr Phe Arg Ala Phe Leu Ser Ser Arg Leu Gln Asp Leu
 65                  70                  75                  80

tat agc atc gtg cgc cgt gct gac cgg ggg tct gtg ccc atc gtc aac      288
Tyr Ser Ile Val Arg Arg Ala Asp Arg Gly Ser Val Pro Ile Val Asn
                 85                  90                  95

ctg aag gac gag gtg cta tct ccc agc tgg gac tcc ctg ttt tct ggc      336
Leu Lys Asp Glu Val Leu Ser Pro Ser Trp Asp Ser Leu Phe Ser Gly
            100                 105                 110

tcc cag ggt caa gtg caa ccc ggg gcc cgc atc ttt tct ttt gac ggc      384
Ser Gln Gly Gln Val Gln Pro Gly Ala Arg Ile Phe Ser Phe Asp Gly
        115                 120                 125

aga gat gtc ctg aga cac cca gcc tgg ccg cag aag agc gta tgg cac      432
Arg Asp Val Leu Arg His Pro Ala Trp Pro Gln Lys Ser Val Trp His
    130                 135                 140

ggc tcg gac ccc agt ggg cgg agg ctg atg gag agt tac tgt gag aca      480
Gly Ser Asp Pro Ser Gly Arg Arg Leu Met Glu Ser Tyr Cys Glu Thr
145                 150                 155                 160

tgg cga act gaa act act ggg gct aca ggt cag gcc tcc tcc ctg ctg      528
Trp Arg Thr Glu Thr Thr Gly Ala Thr Gly Gln Ala Ser Ser Leu Leu
                165                 170                 175

tca ggc agg ctc ctg gaa cag aaa gct gcg agc tgc cac aac agc tac      576
Ser Gly Arg Leu Leu Glu Gln Lys Ala Ala Ser Cys His Asn Ser Tyr
            180                 185                 190

atc gtc ctg tgc att gag aat agc ttc atg acc tct ttc tcc aaa tag      624
Ile Val Leu Cys Ile Glu Asn Ser Phe Met Thr Ser Phe Ser Lys  *
        195                 200                 205


<210> SEQ ID NO 71
<211> LENGTH: 207
<212> TYPE: PRT
<213> ORGANISM: Muridae

<400> SEQUENCE: 71

Met Glu Thr Asp Thr Leu Leu Leu Trp Val Leu Leu Leu Trp Val Pro
 1               5                  10                  15

Gly Ser Thr Gly Asp Ala Ala His Thr His Gln Asp Phe Gln Pro Val
            20                  25                  30

Leu His Leu Val Ala Leu Asn Thr Pro Leu Ser Gly Gly Met Arg Gly
        35                  40                  45

Ile Arg Gly Ala Asp Phe Gln Cys Phe Gln Gln Ala Arg Ala Val Gly
    50                  55                  60

Leu Ser Gly Thr Phe Arg Ala Phe Leu Ser Ser Arg Leu Gln Asp Leu
65                  70                  75                  80

Tyr Ser Ile Val Arg Arg Ala Asp Arg Gly Ser Val Pro Ile Val Asn
                85                  90                  95

Leu Lys Asp Glu Val Leu Ser Pro Ser Trp Asp Ser Leu Phe Ser Gly
            100                 105                 110

Ser Gln Gly Gln Val Gln Pro Gly Ala Arg Ile Phe Ser Phe Asp Gly
        115                 120                 125

Arg Asp Val Leu Arg His Pro Ala Trp Pro Gln Lys Ser Val Trp His
    130                 135                 140

Gly Ser Asp Pro Ser Gly Arg Arg Leu Met Glu Ser Tyr Cys Glu Thr
145                 150                 155                 160

Trp Arg Thr Glu Thr Thr Gly Ala Thr Gly Gln Ala Ser Ser Leu Leu
                165                 170                 175

Ser Gly Arg Leu Leu Glu Gln Lys Ala Ala Ser Cys His Asn Ser Tyr
```

-continued 180 185 190

Ile Val Leu Cys Ile Glu Asn Ser Phe Met Thr Ser Phe Ser Lys
195 200 205

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Integrin _3
(B3B) target sequence

<400> SEQUENCE: 72
gcctgagagg gagcggtg 18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Integrin _3
(B3C) target sequence

<400> SEQUENCE: 73
ggaggggacg cggtgggt 18

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: ErbB-2
(E2B2) target sequence

<400> SEQUENCE: 74
gtgtgagaac ggctgcaggc 20

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: ErbB-2
(E2C) target sequence

<400> SEQUENCE: 75
ggggccggag ccgcagtg 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: ErbB-2
(E2D) target sequence

<400> SEQUENCE: 76
gcagttggag gggcgag 18

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Recombinant
molecule -continued

<400> SEQUENCE: 77

```
Gln Ser Ser Asn Leu Val Arg
  1               5
```

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 78

```
Asp Pro Gly Asn Leu Val Arg
  1               5
```

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 79

```
Arg Ser Asp Asn Leu Val Arg
  1               5
```

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 80

```
Thr Ser Gly Asn Leu Val Arg
  1               5
```

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 81

```
Gln Ser Gly Asp Leu Arg Arg
  1               5
```

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 82

```
Asp Cys Arg Asp Leu Ala Arg
  1               5
```

<210> SEQ ID NO 83
<211> LENGTH: 7
<212> TYPE: PRT

-continued

<213> ORGANISM: Artificial Sequence
<220> FEATURE:
<223> OTHER INFORMATION: Description of Artificial Sequence: Recombinant molecule

<400> SEQUENCE: 83

Arg Ser Asp Asp Leu Val Lys
1 5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 84

Thr Ser Gly Glu Leu Val Arg
1 5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 85

Gln Arg Ala His Leu Glu Arg
1 5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 86

Asp Pro Gly His Leu Val Arg
1 5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 87

Arg Ser Asp Lys Leu Val Arg
1 5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Recombinant molecule

<400> SEQUENCE: 88

Thr Ser Gly His Leu Val Arg
1 5

-continued

```
<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 89

Gln Ser Ser Ser Leu Val Arg
  1               5


<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 90

Asp Pro Gly Ala Leu Val Arg
  1               5


<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 91

Arg Ser Asp Glu Leu Val Arg
  1               5


<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Recombinant
      molecule

<400> SEQUENCE: 92

Thr Ser Gly Ser Leu Val Arg
  1               5
```